US010004701B2

(12) United States Patent
Dunman et al.

(10) Patent No.: US 10,004,701 B2
(45) Date of Patent: Jun. 26, 2018

(54) METHODS AND COMPOSITIONS FOR TREATING INFECTION

(71) Applicants: UNIVERSITY OF ROCHESTER, Rochester, NY (US); UNIVERSITY OF KANSAS, Lawrence, KS (US)

(72) Inventors: Paul M. Dunman, Pittsford, NY (US); Damian J. Krysan, Pittsford, NY (US); Daniel P. Flaherty, Overland Park, KS (US)

(73) Assignees: UNIVERSITY OF ROCHESTER, Rochester, NY (US); UNIVERSITY OF KANSAS, Lawrence, KS (US)

( * ) Notice: Subject to any disclaimer, the term of this patent is extended or adjusted under 35 U.S.C. 154(b) by 0 days. days.

(21) Appl. No.: 15/356,940

(22) Filed: Nov. 21, 2016

(65) Prior Publication Data
US 2017/0065540 A1    Mar. 9, 2017

Related U.S. Application Data

(62) Division of application No. 14/431,031, filed as application No. PCT/US2013/062309 on Sep. 27, 2013, now abandoned.
(Continued)

(51) Int. Cl.
| A61K 31/135 | (2006.01) |
| A61K 31/138 | (2006.01) |
| A61K 31/4152 | (2006.01) |
| A61K 31/445 | (2006.01) |
| A61K 31/566 | (2006.01) |
| A61K 31/66 | (2006.01) |
| A61K 31/4515 | (2006.01) |
| A61K 31/4525 | (2006.01) |

(Continued)

(52) U.S. Cl.
CPC ........ *A61K 31/138* (2013.01); *A61K 31/4152* (2013.01); *A61K 31/445* (2013.01); *A61K 31/4515* (2013.01); *A61K 31/4525* (2013.01); *A61K 31/4545* (2013.01); *A61K 31/566* (2013.01); *A61K 31/66* (2013.01); *C12Q 1/18* (2013.01); *C12Q 1/485* (2013.01)

(58) Field of Classification Search
CPC .................................................... A61K 31/138
USPC ......................................................... 514/651
See application file for complete search history.

(56) References Cited

U.S. PATENT DOCUMENTS

| 3,689,646 A | 9/1972 | Sevag |
| 5,261,896 A | 11/1993 | Conway et al. |

(Continued)

FOREIGN PATENT DOCUMENTS

| EP | 1214937 | 6/2002 |
| WO | 03020274 | 3/2003 |

(Continued)

OTHER PUBLICATIONS

Atroshi et al. "Effects of tamoxifen, Melatonin, Coenzyme Q10, and L-carnitine supplementation on bacterial Growth in presence of mycotoxins," Pharmacological Research, 1998, vol. 38, No. 4, pp. 289-295.*

(Continued)

*Primary Examiner* — Shengjun Wang
(74) *Attorney, Agent, or Firm* — Kilpatrick Townsend & Stockton LLP

(57) ABSTRACT

Provided herein are compositions and methods for treating or preventing infection.

7 Claims, 6 Drawing Sheets

Related U.S. Application Data

(60) Provisional application No. 61/706,492, filed on Sep. 27, 2012.

(51) Int. Cl.
    *A61K 31/4545*     (2006.01)
    *C12Q 1/18*     (2006.01)
    *C12Q 1/48*     (2006.01)

(56) References Cited

U.S. PATENT DOCUMENTS

| | | | |
|---|---|---|---|
| 5,610,198 A | 3/1997 | Barry, III et al. | |
| 5,965,610 A | 10/1999 | Modak et al. | |
| 6,426,369 B1 | 7/2002 | Sato et al. | |
| 2002/0107238 A1 | 8/2002 | Bandyopadhyay et al. | |
| 2004/0241842 A1* | 12/2004 | Boyd | A61K 39/38 435/372 |
| 2008/0161324 A1 | 7/2008 | Johansen et al. | |
| 2009/0318403 A1 | 12/2009 | De Visser et al. | |
| 2010/0144626 A1 | 6/2010 | Young et al. | |
| 2011/0092488 A1 | 4/2011 | Dow et al. | |
| 2011/0104121 A1* | 5/2011 | Wira | A61K 31/138 424/93.2 |
| 2011/0257078 A1 | 10/2011 | Young et al. | |
| 2012/0040932 A1 | 2/2012 | Hirst et al. | |

FOREIGN PATENT DOCUMENTS

| | | |
|---|---|---|
| WO | 2011137376 | 11/2011 |
| WO | 2012032360 | 3/2012 |

OTHER PUBLICATIONS

Kristich et al. "Enterococcal infection-Treatment and antibiotic resistance," Enterococci: From Comments to leading cause of drug resistant infection. Ed. Gilmore et al. Boston: Massachusetts Eye and Ear infirmary, 2014, pp. 1-62.*
U.S. Appl. No. 14/431,031, Final Office Action dated Oct. 27, 2016, 9 pages.
U.S. Appl. No. 14/431,031, Non-Final Office Action dated Jun. 14, 2016, 8 pages.
U.S. Appl. No. 14/431,031, Restriction Requirement dated Mar. 7, 2016, 7 pages.
Amaral, et al., Why thioridazine in combination with antibiotics cures extensively drug-resistant Mycobacterium tuberculosis infections, International Journal of Antimicrobial Agents vol. 39, No. 5, May 2012, pp. 376-380.
An, et al., Cell-based assays for high-throughput screening, Molecular Biotechnology, vol. 45, No. 2, Jun. 2010, pp. 180-186.
Andrews, et al., Determination of minimum inhibitory concentrations, Journal of Antimicrobial Chemotherapy, vol. 48, No. 1, 2001, pp. 5-16.
Arhin, et al., Time-kill kinetics of oritavancin and comparator agents against streptococcus pyogenes, International Journal of Antimicrobial Agents, vol. 34, No. 6, Dec. 2009, pp. 550-554.
Beenken, et al., Mutation of sarA in *Staphylococcus aureus* Limits Biofilm Formation, Infection and Immunity vol. 71, No. 7, Jul. 2003, pp. 4206-4211.
Benoit, et al., New device for high-throughput viability screening of flow biofilms, Letters in Applied Microbiology vol. 76, No. 13, Jul. 2010, pp. 4136-4142.
Blasco, et al., Specific assays for bacteria using phage mediated release of adenylate kinase, Journal of Applied Microbiology, vol. 84, No. 4, Apr. 1998, pp. 661-666.
Boucher, et al., Bad bugs, no drugs: no eskape! An update from the infectious diseases society of america, Clinical Infectious Diseases vol. 48, No. 1, Jan. 1, 2009, pp. 1-12.
Cameron-Clarke, et al., The use of adenylate kinase measurement to determine causes of lysis in lager yeast, American Society of Brewing Chemists vol. 61, No. 3, 2003, pp. 152-156.

Carleton, et al., The slow bactericidal effect of tetracycline and minocycline on wall-defective staphylococcus, The Journal of Infectious Diseases, vol. 126, No. 4, Oct. 1972, pp. 457-459.
Cooksey, et al., A rapid method for screening antimicrobial agents for activities against a strain of mycobacterium tuberculosis expressing firefly luciferase, Antimicrob. Agents Chemotherapy, vol. 37, 1993, pp. 1348-1352.
Corbitt, et al., Adenylate kinase amplification of ATP bioluminescence for hygiene monitoring in the food and beverage industry, Letters in Applied Microbiology, vol. 30, No. 6, Jun. 2000, pp. 443-447.
Didone, et al., A high-throughput assay of yeast cell lysis for drug discovery and genetic analysis, Nature Protocols vol. 5, No. 6, Jun. 2010, pp. 1107-1114.
Doddanna, et al., Antimicrobial activity of plant extracts on candida albicans: an in vitro study, Indian J. Dent. Res., vol. 24, No. 4, 2013, pp. 401-405.
Dolan, et al., Antifungal activity of tamoxifen: in vitro and in vivo activities and mechanistic characterization, Antimicrobial Agents and Chemotherapy, vol. 53, No. 8, Aug. 2009, pp. 3337-3346.
Eiff, *Staphylococcus aureus* small colony variants: a challenge to microbiologists and clinicians, International Journal of Antimicrobial Agents, vol. 31, No. 6, Jun. 2008, pp. 507-510.
Gillaspy, et al., Role of the accessory gene regulator (agr) in pathogenesis of staphylococcal osteomyelitis, Infection and Immunity, vol. 63, No. 9, Sep. 1995, pp. 3373-3380.
Hayhoe, et al., Screening for antibacterial, antifungal and anti-quorum sensing activity, Methods Mol. Biol., vol. 1055, 2013, pp. 219-225.
Hindler, Antimicrobial susceptibility testing, In Clinical Microbiology Procedures Handbook, p. Section 5, American Society for Microbiology, 238 pages.
Hof, et al., Antibacterial effects of niridazole. II effects on aerobic and anaerobic bacteria, Zentralbl Bakteriol Mikrobiol. Hyg. A., vol. 253, No. 2, 1982, pp. 265-271.
Holloway, Genetic recombination in pseudomonas aeruginosa, Journal of General Microbiology, vol. 13, No. 3, Dec. 1955, pp. 572-581.
Jacobs, et al., Adenylate kinase release as a high-throughput-screening-compatible reporter of bacterial lysis for identification of antibacterial agents, Antimicrobial Agents and Chemotherapy, vol. 57, No. 1, 2013, pp. 26-36.
Jacobs, et al., Inactivation of phospholipase D diminishes acinetobacter baumannii pathogenesis, Infection and Immunity, vol. 78, No. 5, May 2010, pp. 1952-1962.
Karat, et al., Controlled clinical trial of clofazimine in untreated lepromatous leprosy, Brit. Med. J., vol. 4, No. 5786, 1971, pp. 514-516.
Kazakova, et al., A clone of methicillin-resistant *Staphylococcus aureus* among professional football players, The New England Journal of Medicine, vol. 352, No. 5, Feb. 3, 2005, pp. 468-475.
Krysan, et al., A high-throughput screening assay for small molecules that disrupt yeast cell integrity, Journal of Biomolecular Screening, vol. 13, No. 7, Aug. 2008, pp. 657-664.
Kunin, et al., Antimicrobial activities of mefloquine and a series of related compounds, Antimicrob. Agents Chemother., vol. 44, No. 4, 2000, pp. 848-852.
Landolt, et al., Use of real-time reverse transcriptase polymerase chain reaction assay and cell culture methods for detection of swine influenza A viruses, Am J. Vet Res., vol. 66, No. 1, 2005, pp. 119-124.
Lebreton, et al., Galleria mellonella as a model for studying enterococcus faecium host persistence, Journal of Molecular Microbiology and Biotechnology, vol. 21, No. 3-4, 2011, pp. 191-196.
Li, et al., Correlation between bactericidal activity and postantibiotic effect for five antibiotics with different mechanisms of action, Journal of Antimicrobial Chemotherapy, vol. 40, No. 1, Jul. 1997, pp. 39-45.
Lubbe, Secondary infections in patients with atopic dermatitis, Am. J. Clin. Dermatol, vol. 4, No. 9 2003, pp. 641-654.
Luxo, et al., Tamoxifen induces ultrastructural alterations in membranes of bacillus stearothermophilus, toxicology in vitro, vol. 17, No. 5-6, Oct.-Dec. 2003, pp. 623-628.

(56) References Cited

OTHER PUBLICATIONS

Mandal, et al., An investigation on in vitro and in vivo antimicrobial properties of the antidepressant: amitriptyline hydrochloride, Braz. J. Microbiol., vol. 41, No. 3, Oct. 2010, pp. 635-642.

Markaryan, et al., Adenylate kinase as a virulence factor of pseudomonas aeruginosa, Journal of Bacteriology, vol. 183, No. 11, Jun. 2001, pp. 3345-3352.

McKay, et al., Time-kill kinetics of oritavancin and comparator agents against *Staphylococcus aureus*, enterococcus faecalis and enterococcus faecium, Journal of Antimicrobial Chemotherapy, vol. 63, No. 6, Jun. 2009, pp. 1191-1199.

Morello, et al., Pharmacokinetics of selective estrogen receptor modulators, Clinical Pharmacokinetics, vol. 42, No. 4, 2003, pp. 361-372.

Müsken, et al., A 96-well-plate-based optical method for the quantitative and qualitative evaluation of pseudomonas aeruginosa biofilm formation and its application to susceptibility testing, Nature Protocols vol. 5, No. 8, Aug. 2010, pp. 1460-1469.

Nielsen, et al., Semimechanistic pharmacokinetic/pharmacodynamic model for assessment of activity of antibacterial agents from time-kill curve experiments, Antimicrobial Agents and Chemotherapy vol. 51, No. 1, Jan. 2007, pp. 128-136.

Oliva, et al., Anti-staphylococcal activity and mode of action of clofazimine, Journal of Antimicrobial Chemotherapy, vol. 53, No. 3, 2004, pp. 435-440.

Payne, et al., Drugs for bad bugs: confronting the challenges of antibacterial discovery, Nature Reviews Drug Discovery vol. 6, Jan. 2007, pp. 29-40.

Payungporn, et al., Single step multiplex real-time RT-PCR for H5N1 influenza virus detection, J. Virol Methods, vol. 131, Sep. 22, 2005, pp. 143-147.

International Application No. PCT/US2013/062309, International Preliminary Report on Patentability dated Apr. 9, 2015, 8 pages.

International Application No. PCT/US2013/062309, International Search Report and Written Opinion dated Mar. 20, 2014, 12 pages.

Peleg, et al., Reduced susceptibility to vancomycin influences pathogenicity in *Staphylococcus aureus* infection, The Journal of Infectious Diseases, vol. 199, No. 4, Feb. 15, 2009, pp. 532-536.

Peng, et al., Cloning, characterization, and sequencing of an accessory gene regulator (agr) in *Staphylococcus aureus*, Journal of Bacteriology, vol. 170, No. 9, Sep. 1988, pp. 4365-4372.

Perez, et al., A new microtitre plate screening method for evaluating the viability of aerobic respiring bacteria in high surface biofilms, Microbiology vol. 51, No. 3, Jul. 15, 2010, pp. 331-337.

Pomakova, et al., Clinical and phenotypic differences between classic and hypervirulent klebsiella pneumonia: an emerging and under-recognized pathogenic variant, European Journal of Clinical Microbiology & Infectious, vol. 31, No. 6, Jun. 2012, pp. 981-989.

Prasad, et al., Synthesis, characterization and antimicrobial activity of Cu(II), Co(II), Ni(II), Pd(II) and Ru(III) complexes with clomiphene citrate, Chemical Sciences Journal, vol. 2011: CSJ-28, 2011, 11 pages.

Reck, et al., Novel N-linked aminopiperidine inhibitors of bacterial topoisomerase type II: broad-spectrum antibacterial agents with reduced hERG activity, Journal of Medicinal Chemistry, vol. 54, No. 22, Nov. 2011, pp. 7834-7847.

Rice, Federal funding for the study of antimicrobial resistance in nosocomial pathogens: no eskape, The Journal of Infectious Diseases, vol. 197, No. 8, Apr. 15, 2008, pp. 1079-1081.

Rigoni, et al., Treatment of histamine-dependent allergic dermatoses with 120-mg terfenadine tablet once a day, Giornale italiano di dermatologia e venerologia vol. 124, No. 9, Sep. 1989, pp. XXXIX-XLI.

Robins, et al., Phase 2 trial of radiation plus high-dose tamoxifen for glioblastoma multiforme: RTOG protocol BR-002, Neuro Oncology, vol. 8, No. 1, Jan. 2006, pp. 47-52.

Rowlands, et al., Comparison between inhibition of protein kinase C and antagonism of calmodulin by tamoxifen analogues, Biochemical Pharmacology, vol. 50, No. 5, Aug. 25, 1995, pp. 723-726.

Silver, Challenges of antibacterial discovery, Clinical Microbiology Reviews vol. 24, No. 1, Jan. 1, 2011, pp. 71-109.

Singh, et al., Causal prophylactic activity of antihistaminic agents against plasmodium yoelii nigeriensis infection in swiss mice, Acta Tropica, vol. 69, No. 3, Jun. 1998, pp. 255-260.

Talbot, et al., Bad bugs need drugs: an update on the development pipeline from the antimicrobial availability task force of the infectious diseases society of america, Clinical Infectious Diseases vol. 42, No. 5, Mar. 1, 2006, pp. 657-668.

Tomaras, et al., Attachment to and biofilm formation on abiotic surfaces by acinetobacter baumannii: involvement of a novel chaperone-usher pili assembly system, Microbiology vol. 149, No. 12, Dec. 2003, pp. 3473-3484.

Von Eiff, *Staphylococcus aureus* small colony variants: a challenge to microbiologists and clinicians, International Journal of Antimicrobial Agents, vol. 31, No. 6, Jun. 2008, pp. 507-510.

Wang, et al., Nanostructured selenium for preventing biofilm formation on polycarbonate medical devices, Journal of Biomedical Materials Research Part A, vol. 100, No. 12, Dec. 2012, pp. 3205-3210.

Wermuth, Selective optimization of side activities: the SOSA approach, Drug Discovery Today, vol. 11, No. 3-4, Feb. 2006, pp. 160-164.

Wiseman, et al., Observation and significance of growth inhibition of saccharomyces cerevisiae (A224A) by the antioestrogen drug tamoxifen, Biochemical Society Transactions, vol. 17, No. 6, Dec. 1989, pp. 1038-1039.

Woosley, et al., Mechanism of the cardiotoxic actions of terfenadine, Jama, vol. 269, No. 12, Mar. 24-31, 1993, pp. 1532-1536.

Zhang, et al., A simple statistical parameter for use in evaluation and validation of high throughput screening assays, Journal of Biomolecular Screening, vol. 4, No. 2, Apr. 1999, pp. 67-73.

\* cited by examiner

METHODS AND COMPOSITIONS FOR TREATING INFECTION

CROSS REFERENCE TO RELATED APPLICATIONS

This application is a divisional of U.S. application Ser. No. 14/431,031, filed on Mar. 25, 2015, which is a U.S. national stage application under 35 U.S.C § 371 of PCT/US2013/062309, filed on Sep. 27, 2013, which claims the benefit of U.S. Provisional Application No. 61/706,492, filed on Sep. 27, 2012, all of which are incorporated by reference herein in their entirety.

STATEMENT REGARDING FEDERALLY FUNDED RESEARCH

This invention was made with government support under Grant Nos. 1R01AI1075033-03 and 5P50GM069663 awarded by the National Institutes of Health. The government has certain rights in this invention.

BACKGROUND

Infectious diseases affect the health of people and animals around the world, causing serious illness and death. Thus, an urgent need exists for treatments for infections.

SUMMARY

Provided herein is a method of treating or preventing an infection in a subject with or at risk of developing an infection, the method comprising administering to the subject a compound of Formula I

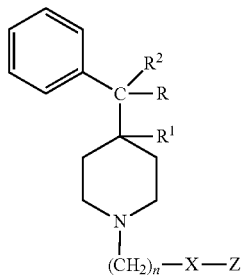

(I)

wherein R represents hydrogen or hydroxyl and $R^1$ represents hydrogen, or R and $R^1$ taken together form a second bond between the carbon atoms bearing R and $R^1$; $R^2$ represents hydrogen or phenyl; n is zero or a positive whole integer of from 1 to 4; X represents $CH_2$, CHOH, NH, C=O, $CHNR^3R^4$, where $R^3$ and $R^4$ independently are hydrogen or lower alkyl; and Z represents thienyl, pyridinyl, substituted pyridinyl, phenyl or substituted phenyl wherein the substituents on the substituted pyridinyl or substituted phenyl are selected from phenyl, pyridinyl, nitro, a halogen atom, such as chlorine, fluorine, bromine, or iodine, a straight or branched lower alkyl chain of from 1 to 4 carbon atoms, a lower alkoxy group of from 1 to 4 carbon atoms, amino, a mono or di(lower)alkylamino group, a saturated monocyclic heterocyclic group such as pyrrolidino, piperidino, morpholino, or N-(lower)alkylpiperazino, or a group having the structure $—COOR^5$, $—CR^6R^7COOR^5$, $—CF_3$, $CHF_2$, $CH_2F$, or

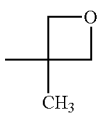

where $R^5$ is hydrogen or lower alkyl, and $R^6$ and $R^7$ independently are hydrogen or methyl or a pharmaceutically acceptable salt thereof.

Further provided is a method of treating or preventing an infection in a subject with or at risk of developing an infection, the method comprising administering to the subject a compound of Formula III

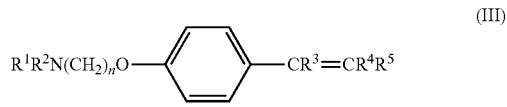

(III)

or a pharmaceutically acceptable salt thereof, wherein $R^1$ and $R^2$ are independently selected from ethyl or methyl, n 1 or 2, $R^3$ and $R^4$ are both phenyl or substituted phenyl, wherein the substituent can be halo (for example, fluoro-, chloro-, iodo- or bromo-), hydroxyl, a lower alkyl or a substituted lower alkyl wherein the substituent can be halo, hydroxy, or lower alkoxy, and $R^5$ is hydrogen, a halogen, a lower alkyl from about 1 to 4 carbon atoms or a substituted alkyl wherein the substituent can be halo, hydroxy, or lower alkoxy.

Also provided is a method of treating or preventing infection in a subject with or at risk of developing an infection, the method comprising administering to the subject a compound selected from the group consisting of:

a compound of Formula V

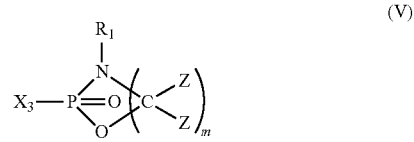

(V)

wherein $R_1$ is a lower alkyl group having from 1 to 4 carbon atoms being substituted with one or several halogen atoms, Z is hydrogen or a lower alkyl group having from 1 to 4 carbon atoms, m is 2 or 3 and $X_2$ is the ethylene imino group or the group having the formula:

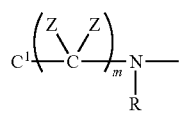

wherein R is hydrogen or a lower alkyl group having from 1 to 4 carbon atoms which can be substituted with a chlorine atom or a hydroxy group, and Z and m have the above-given meaning, a compound of Formula X

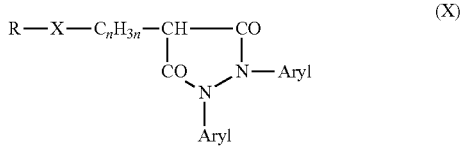

wherein R represents a lower alkyl or a lower alkenyl group, a phenyl group which can be substituted by halogen, methyl or lower alkoxy groups, or a benzyl group which can be nuclear substituted by halogen, methyl or lower alkoxy groups, X represents —O—, —S—, —SO—, or —$SO_2$—, n represents an integer from 1-4, and Aryl represents a phenyl group which can be substituted by lower alkoxy or lower alkylmercapto groups;

a compound of Formula XII

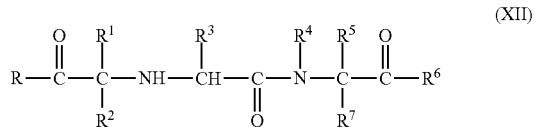

wherein R and $R^6$ are the same or different and are hydroxy, lower alkoxy, lower alkenoxy, dilower alkylamino lower alkoxy (dimethylaminoethoxy), acylamino lower alkoxy (acetylaminoethoxy), acyloxy lower alkoxy (pivaloyloxymethoxy), aryloxy, such as phenoxy, arloweralkoxy, such as benzyloxy, substituted aryloxy or substituted arloweralkoxy wherein the substitutent is methyl, halo or methoxy, amino, loweralkylamino, diloweralkylamino, hydroxyamino, arloweralkylamino such as benzylamino;

$R^1$ is hydrogen, alkyl of from 1 to 20 carbon atoms which include branched and cyclic and unsaturated (such as allyl) alkyl groups, substituted loweralkyl wherein the substituent can be halo, hydroxy, lower alkoxy, aryloxy such as phenoxy, amino, diloweralkylamino, acylamino, such as acetamido and benzamido, arylamino, guanidino, imidazolyl, indolyl, mercapto, loweralkylthio, arylthio such as phenylthio, carboxy or carboxamido, carboloweralkoxy, aryl such as phenyl or naphthyl, substituted aryl such as phenyl wherein the substituent is lower alkyl, lower alkoxy or halo, arloweralkyl, arloweralkenyl, heteroarlower alkyl or heteroarlower alkenyl such as benzyl, styryl or indolyl ethyl, substituted arloweralkyl, substituted arloweralkenyl, substituted heteroarlower alkyl, or substituted heteroarlower alkenyl, wherein the substituent(s) is halo, dihalo, lower alkyl, hydroxy, lower alkoxy, amino, aminomethyl, acylamino (acetyl amino or benzoylamino) diloweralkylamino, loweralkylamino, carboxyl, haloloweralkyl, cyano or sulfonamido; arloweralkyl or heteroarloweralkyl substituted on the alkyl portion by amino or acylamino (acetylamino or benzoylamino);

$R^2$ and $R^7$ are the same or different and are hydrogen or lower alkyl;

$R^3$ is hydrogen, lower alkyl, phenyl lower alkyl, aminomethyl phenyl lower alkyl, hydroxy phenyl lower alkyl, hydroxy lower alkyl, acylamino lower alkyl (such as benzoylamino lower alkyl, acetylamino lower alkyl), amino lower alkyl, dimethylamino lower alkyl, halo lower alkyl, guanidino lower alkyl, imidazolyl lower alkyl, indolyllower alkyl, mercapto lower alkyl, lower alkyl thio lower alkyl;

$R^4$ is hydrogen or lower alkyl;

$R^5$ is hydrogen, lower alkyl, phenyl, phenyl lower alkyl, hydroxy phenyl lower alkyl, hydroxy lower alkyl, amino lower alkyl, guanidino lower alkyl, imidazolyl lower alkyl, indolyl lower alkyl, mercapto lower alkyl or lower alkyl thio lower alkyl;

$R^4$ and $R^5$ can be connected together to form an alkylene bridge of from 2 to 4 carbon atoms, an alkylene bridge of from 2 to 3 carbon atoms and one sulfur atom, an alkylene bridge of from 3 to 4 carbon atoms containing a double bond or an alkylene bridge as above substituted with hydroxy, loweralkoxy, loweralkylor diloweralky;

a compound of Formula XIII

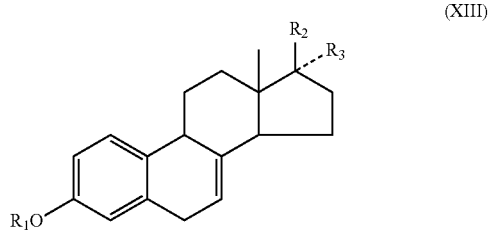

wherein $R_1$ is H, alkyl, acyl or silyl(alkyl)$_3$; $R^2$ is H and $R^3$ is OH, O-acyl, O-alkyl or O-silyl (alkyl)$_3$ or $R^3$ is H and $R^2$ is OH. O-acyl, O-alkyl or O-silyl (alkyl)$_3$; or $R^2$ and $R^3$ together represent O; or $R^2$ and $R^3$ together represent acetal or cyclic acetal. $R_1$ might also represent a substituted alkyl such as e.g. methoxy ethoxy methyl;

a compound of Formula XIV

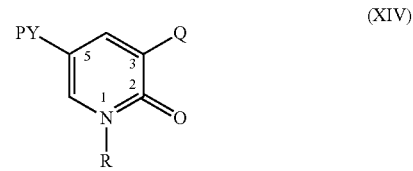

wherein PY is 4- or 3- or 2-pyridinyl or 4- or 3- or 2-pyridinyl having one or two lower-alkyl substituents, R is hydrogen, lower-alkyl or lower-hydroxyalkyl, and Q is nitro, carbamyl, halo, amino, lower-alkylamino, di(lower-alkyl) amino, or NHAc where Ac is lower-alkanoyl or lower-carbalkoxy;

a compound of Formula XV (XV)

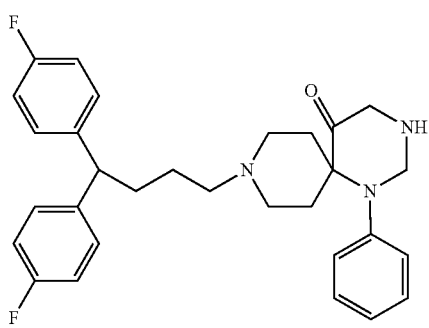

Fluspirilen (XVI)

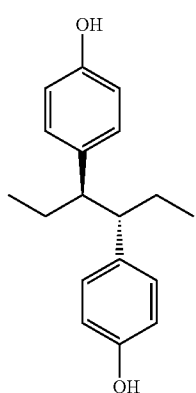

a compound of Formula XVI (XVII)

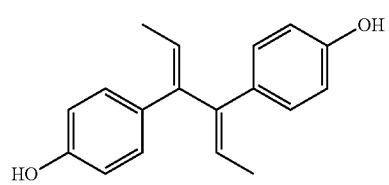

a compound of Formula XVIII (XVIII)

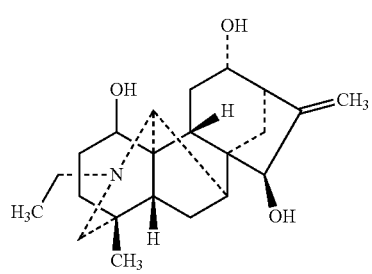

a compound of Formula XIX (XIX)

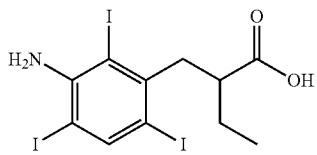

a compound of Formula (XX)

(XX)

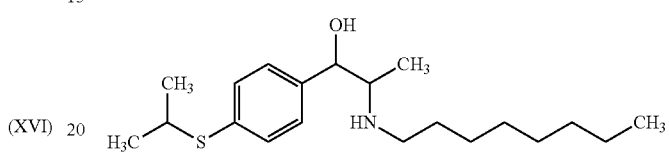

or a pharmaceutically acceptable salt thereof.

Further provided is a method of treating or preventing an infection in a subject with or at risk of developing an infection, the method comprising administering to the subject a compound selected from the group consisting of: Didanosine, Norcyclobenzaprine, Niridazole, Ifosfamide, Cefalonium, Tamoxifen citrate, Butoconazole, Suloctidil, Clomiphene, Sulconazole, Miconazole, Mefloquine, Sulfinpyrazone, Terfenadine, Lisinopril, Econzaole, Clofazimine, Equilin, Felodipine, Dacarbazine, Furazolidone, Perhexiline maleate, Oxethazaine, Pimozide, Trifluoperazine, Ellipticine, Fluspirilen, Hexestrol, Dienestrol, Zidovudine, Metoprolol, Napelline, Methimazole, Amrinone, Iopanoic acid, R-Propanolol, Rimexolone and Pyrvinium pamoate, wherein the infection is a bacterial infection.

Also provided is a method of removing or preventing biofilm formation on a surface, the method comprising administering to a biofilm containing surface or a surface susceptible to biofilm formation an effective amount of a compound selected from the group consisting of:

a compound of Formula I (I)

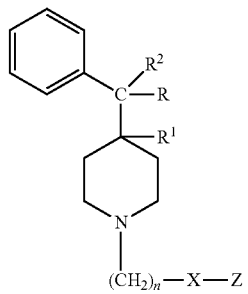

wherein R represents hydrogen or hydroxyl and $R^1$ represents hydrogen, or R and $R^1$ taken together form a second bond between the carbon atoms bearing R and $R^1$; $R^2$ represents hydrogen or phenyl; n is zero or a positive whole integer of from 1 to 4; X represents $CH_2$, CHOH, NH, C=O, $CHNR^3R^4$, where $R^3$ and $R^4$ independently are hydrogen or lower alkyl; and Z represents thienyl, pyridinyl, substituted pyridinyl, phenyl or substituted phenyl wherein the substituents on the substituted pyridinyl or substituted phenyl are selected from phenyl, pyridinyl, nitro, a halogen atom, such as chlorine, fluorine, bromine, or iodine, a straight or branched lower alkyl chain of from 1 to 4 carbon atoms, a lower alkoxy group of from 1 to 4 carbon atoms, amino, a mono or di(lower)alkylamino group, a saturated monocyclic heterocyclic group such as pyrrolidino, piperidino, morpholino, or N-(lower)alkylpiperazino, or a group having the structure —COOR$^5$, —CR$^6$R$^7$COOR$^5$, —CF$_3$, CHF$_2$, CH$_2$F, or

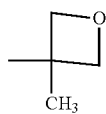

where R$^5$ is hydrogen or lower alkyl, and R$^6$ and R$^7$ independently are hydrogen or methyl or a pharmaceutically acceptable salt thereof.

DETAILED DESCRIPTION

Figure 1:
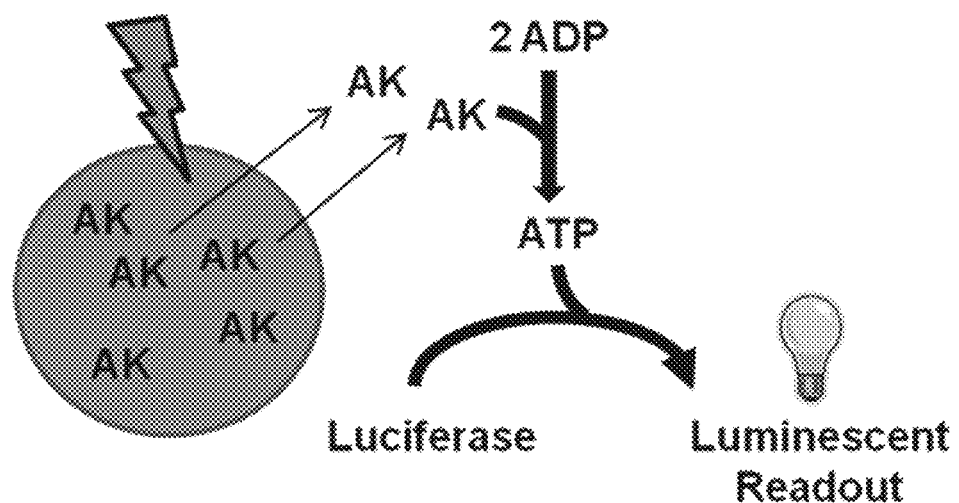
FIG. 1 depicts the adenylate kinase (AK) assay described in the Examples. Bactericidal agents compromise bacterial cell integrity, releasing cellular adenylate kinase. Extracellular AK is measured by the addition of a commercial ToxiLight AK cocktail containing ADP and luciferase, resulting in luminescence.

Provided herein is a method of treating or preventing an infection in a subject with or at risk of developing an infection, the method comprising administering to the subject a compound selected from the group consisting of:

a compound of Formula I

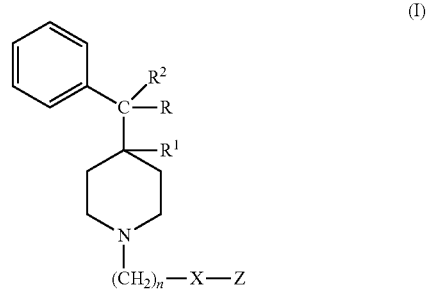

(I)

wherein R represents hydrogen or hydroxyl and R$^1$ represents hydrogen, or R and R$^1$ taken together form a second bond between the carbon atoms bearing R and R$^1$; R$^2$ represents hydrogen or phenyl; n is zero or a positive whole integer of from 1 to 4; X represents CH$_2$, CHOH, NH, C═O, CHNR$^3$R$^4$, where R$^3$ and R$^4$ independently are hydrogen or lower alkyl; and Z represents thienyl, pyridinyl, substituted pyridinyl, phenyl or substituted phenyl wherein the substituents on the substituted pyridinyl or substituted phenyl are selected from phenyl, pyridinyl, nitro, a halogen atom, such as chlorine, fluorine, bromine, or iodine, a straight or branched lower alkyl chain of from 1 to 4 carbon atoms, a lower alkoxy group of from 1 to 4 carbon atoms, amino, a mono or di(lower)alkylamino group, a saturated monocyclic heterocyclic group such as pyrrolidino, piperidino, morpholino, or N-(lower)alkylpiperazino, or a group having the structure —COOR$^5$, —CR$^6$R$^7$COOR$^5$, —CF$_3$, CHF$_2$, CH$_2$F, or

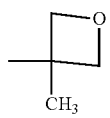

where R⁵ is hydrogen or lower alkyl, and R⁶ and R⁷ independently are hydrogen or methyl. The substituents on the substituted phenyl may be attached at the ortho, meta or para positions of the phenyl ring.

Compounds of Formula I include compounds of Formula II,

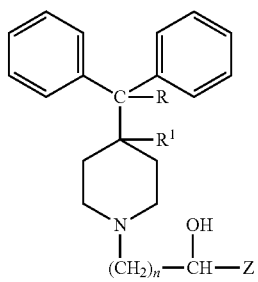

(II)

wherein R represents hydrogen or hydroxyl and $R^1$ represents hydrogen, or R and $R^1$ taken together form a second bond between the carbon atoms bearing R and $R^1$; n is zero or a positive whole integer of from 1 to 4; Z represents thienyl, pyridinyl, substituted pyridinyl, phenyl or substituted phenyl wherein the substituents on the substituted pyridinyl or substituted phenyl are selected from phenyl, pyridinyl, nitro, a halogen atom, such as chlorine, fluorine, bromine, or iodine, a straight or branched lower alkyl chain of from 1 to 4 carbon atoms, a lower alkoxy group of from 1 to 4 carbon atoms, amino, a mono or di(lower)alkylamino group, a saturated monocyclic heterocyclic group such as pyrrolidino, piperidino, morpholino, or N-(lower)alkylpiperazino, or a group having the structure —COOR⁵, —CR⁶R⁷COOR⁵, —CF₃, CHF₂, CH₂F, or

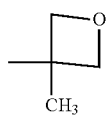

where R⁵ is hydrogen or lower alkyl, and R⁶ and R⁷ independently are hydrogen or methyl or a pharmaceutically acceptable salt thereof.

Compounds of Formula I also include terfenadine and derivatives thereof, including, but not limited to the following compounds. The compounds are identified by structure, name and registry number. The registry number for each compound is also set forth in Table 6 as an additional identifier for each compound.

Compound Lot#

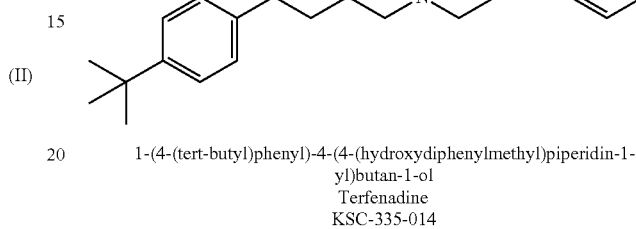

1-(4-(tert-butyl)phenyl)-4-(4-(hydroxydiphenylmethyl)piperidin-1-yl)butan-1-ol
Terfenadine
KSC-335-014

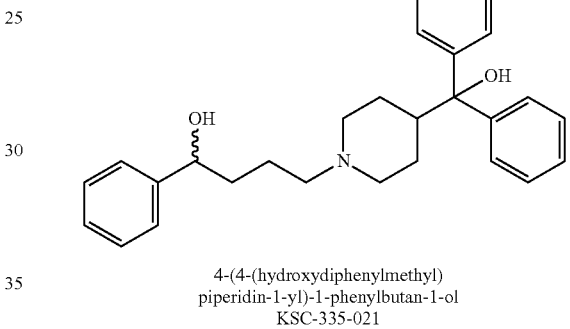

4-(4-(hydroxydiphenylmethyl)piperidin-1-yl)-1-phenylbutan-1-ol
KSC-335-021

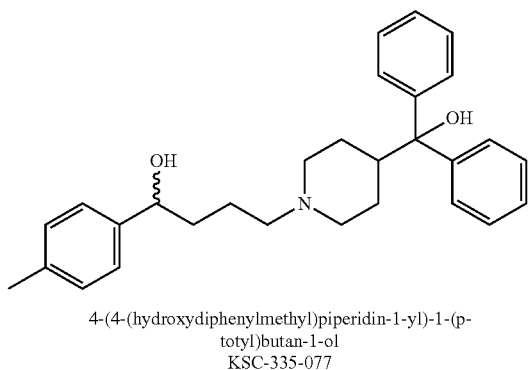

4-(4-(hydroxydiphenylmethyl)piperidin-1-yl)-1-(p-totyl)butan-1-ol
KSC-335-077

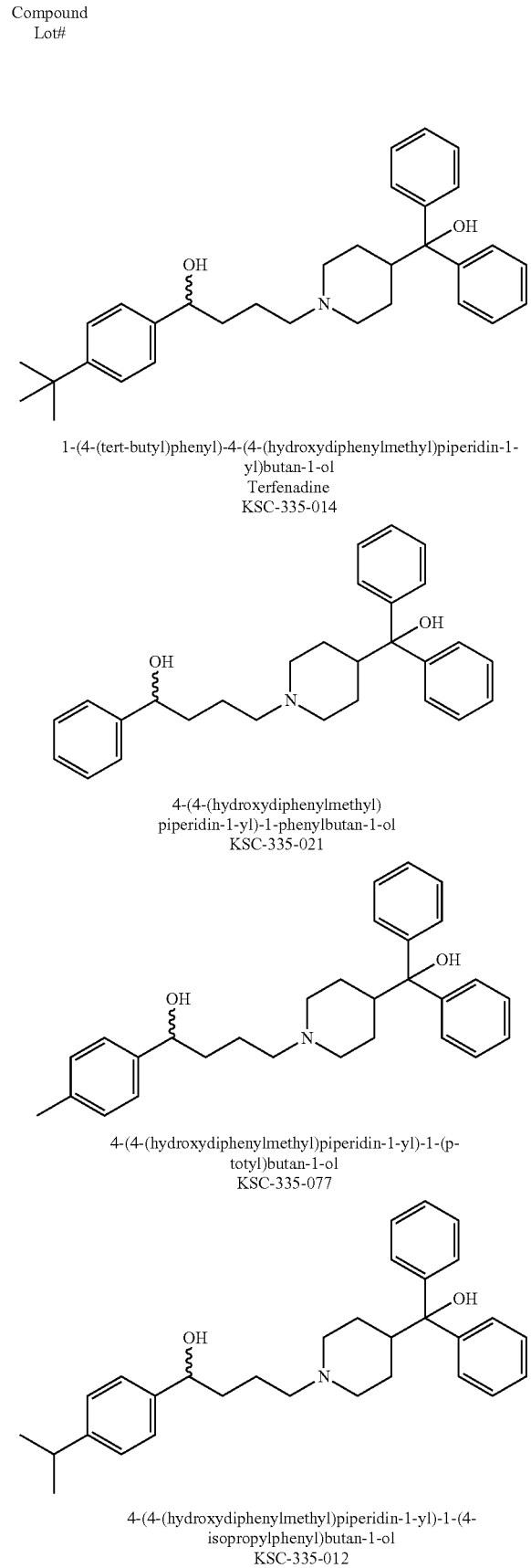

4-(4-(hydroxydiphenylmethyl)piperidin-1-yl)-1-(4-isopropylphenyl)butan-1-ol
KSC-335-012

-continued

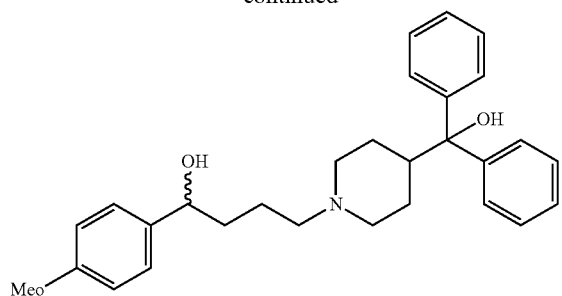

4-(4-(hydroxydiphenylmethyl)piperidin-1-yl)-1-(4-methoxyphenyl)butan-1-ol
KSC-335-030

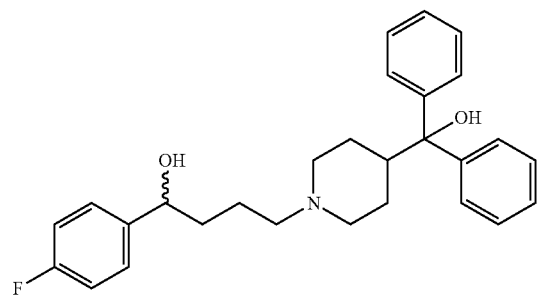

1-(4-fluorophenyl)-4-(4-(hydroxydiphenylmethyl)piperidin-1-yl)butan-1-ol
KSC-335-031

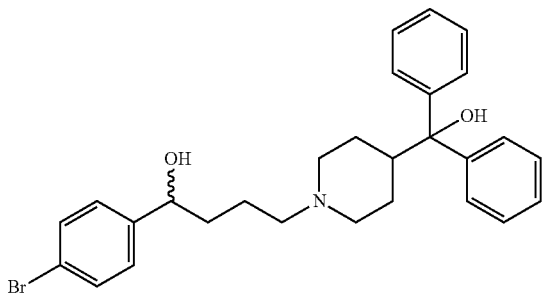

1-(4-bromophenyl)-4-(4-(hydroxydiphenylmethyl)piperidin-1-yl)butan-1-ol
KSC-335-032

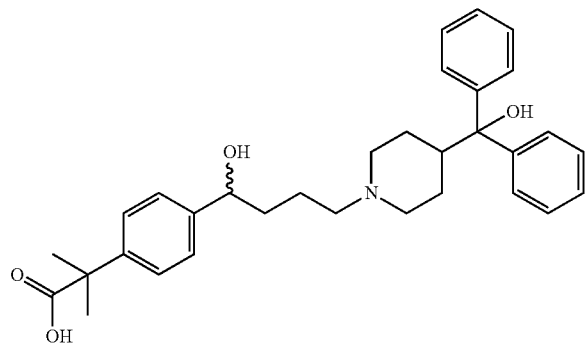

2-(4-(1-hydroxy-4-(4-(hydroxydiphenylmethyl)piperidin-1-yl)butyl)phenyl)-2-methylpropanoic acid
KSC-335-081

-continued

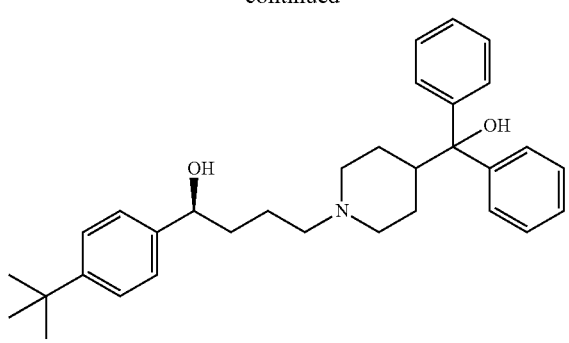

(S)-1-(4-(tert-butyl)phenyl)-4-(4-(hydroxydiphenylmethylmethyl)piperidin-1-yl)butan-1-ol
KSC-335-069

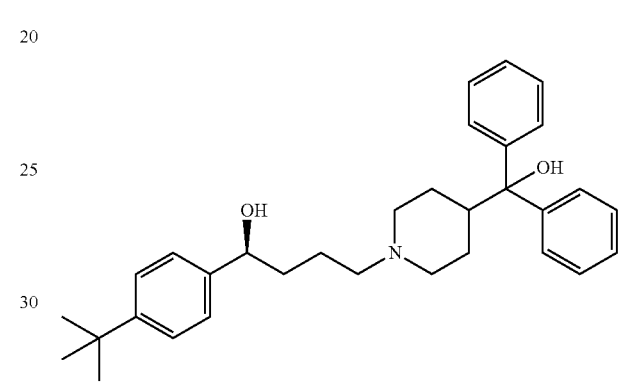

(R)-1-(4-(tert-butyl)phenyl)-4-(4-(hydroxydiphenylmethyl)piperidin-1-yl)butan-1-ol
KSC-335-070

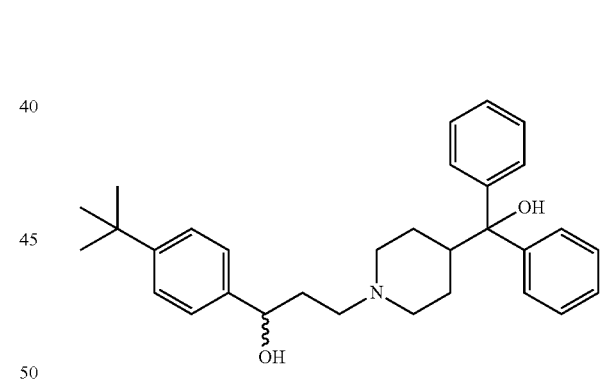

1-(4-(tert-butyl)phenyl)-3-(4-(hydroxydiphenylmethyl)piperidin-1-yl)propan-1-ol
KSC-335-016

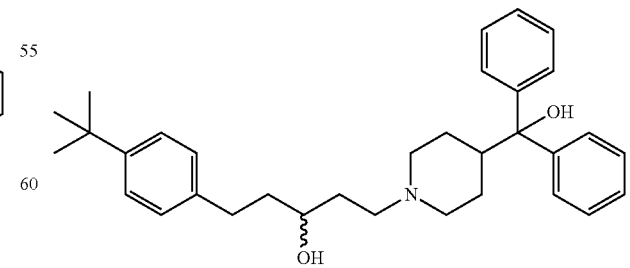

1-(4-(tert-butyl)phenyl)-3-(4-(hydroxydiphenylmethyl)piperidin-1-yl)pentan-1-ol
KSC-335-013

-continued

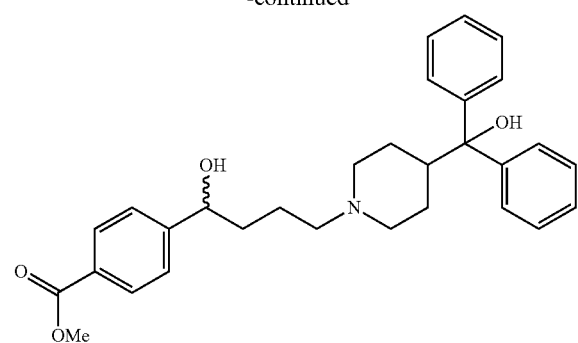

methyl 4-(1-hydroxy-4-(4-(hydroxydiphenylmethyl)
piperidin-1-yl)butyl)benzoate
KSC-342-017

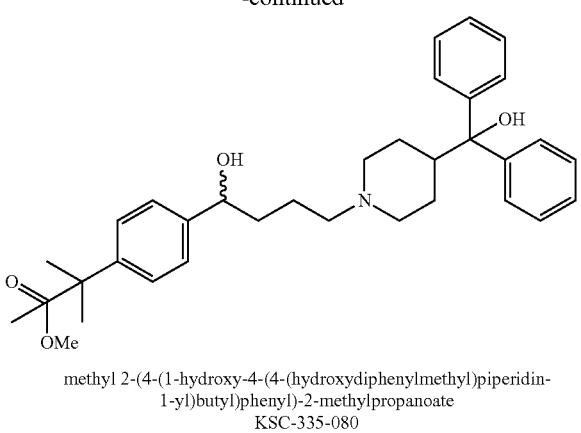

methyl 2-(4-(1-hydroxy-4-(4-(hydroxydiphenylmethyl)piperidin-
1-yl)butyl)phenyl)-2-methylpropanoate
KSC-335-080

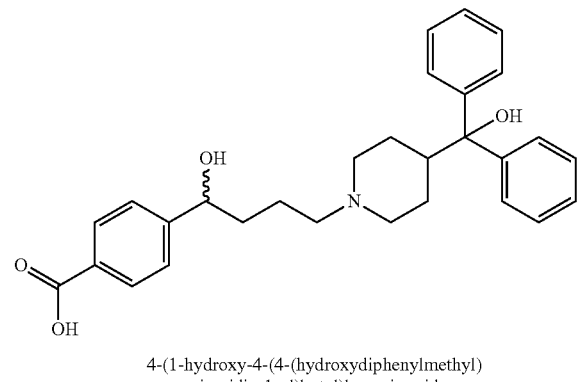

4-(1-hydroxy-4-(4-(hydroxydiphenylmethyl)
piperidin-1-yl)butyl)benzoic acid
KSC-342-021

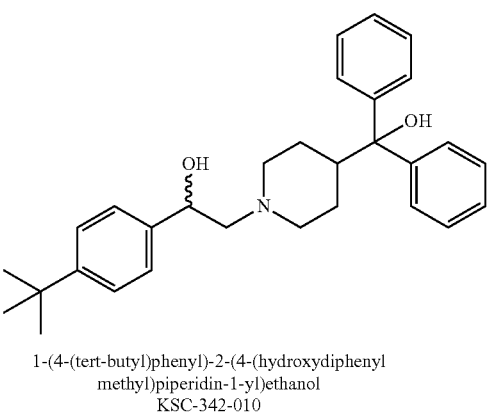

1-(4-(tert-butyl)phenyl)-2-(4-(hydroxydiphenyl
methyl)piperidin-1-yl)ethanol
KSC-342-010

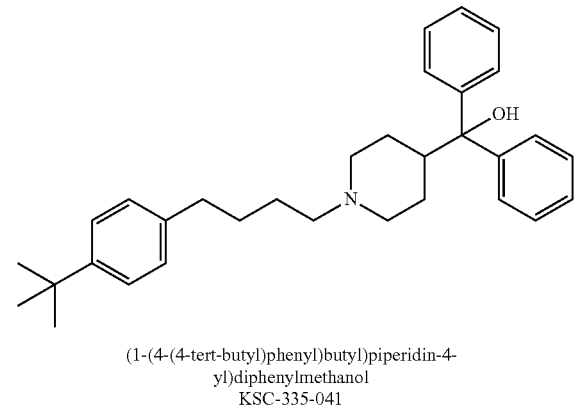

(1-(4-(4-tert-butyl)phenyl)butyl)piperidin-4-
yl)diphenylmethanol
KSC-335-041

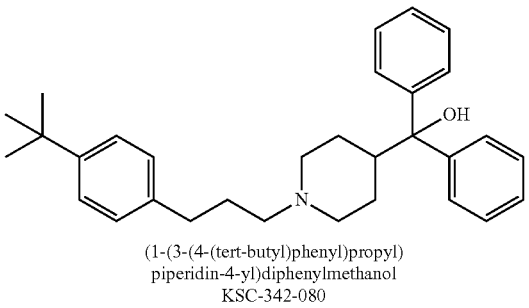

(1-(3-(4-(tert-butyl)phenyl)propyl)
piperidin-4-yl)diphenylmethanol
KSC-342-080

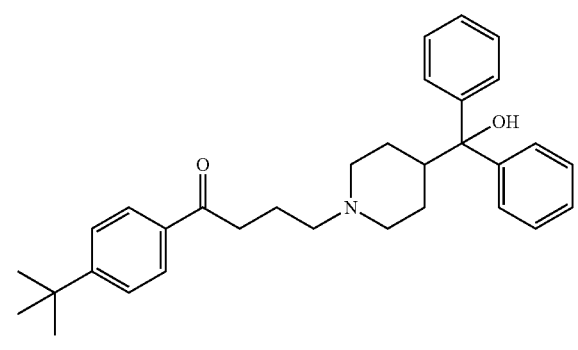

1-(4-(tert-butyl)pheny)-4-(hydroxydiphenylmethyl)
piperidin-1-yl)butan-1-one
KSC-335-007

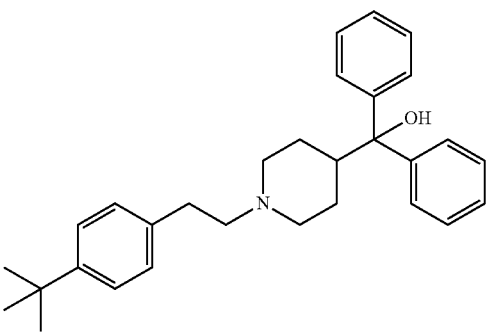

(1-(4-(tert-butyl)phenethyl)piperidin-4-yl)diphenylmethanol
KSC-342-081

-continued

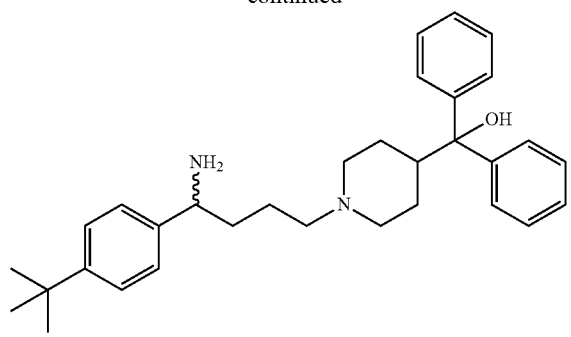

(1-(4-amino-4-(4-(tert-butyl)phenyl)butyl)
piperidin-4-yl)diphenylmethanol
KSC-342-088

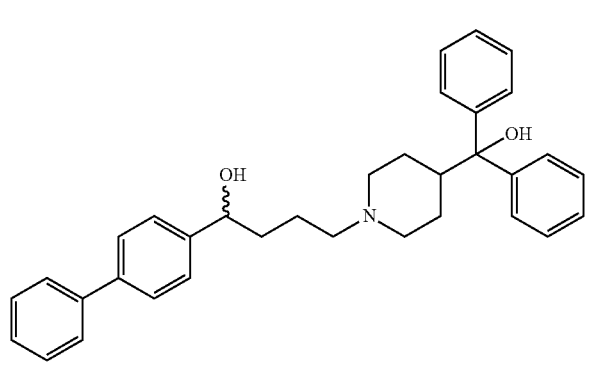

(1-([1,1-biphenyl]-4-yl)-4-(4-(hydroxydiphenylmethyl)
piperidin-1-yl)butan-1-ol
KSC-348-002

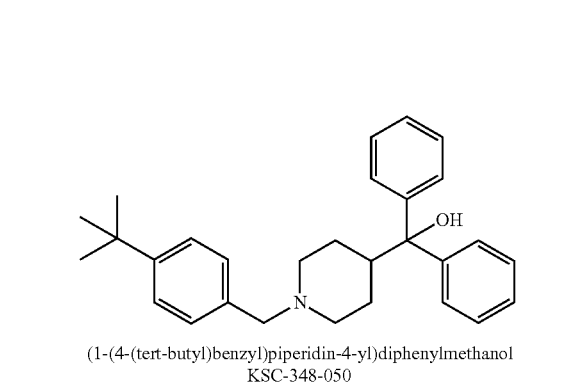

(1-(4-(tert-butyl)benzyl)piperidin-4-yl)diphenylmethanol
KSC-348-050

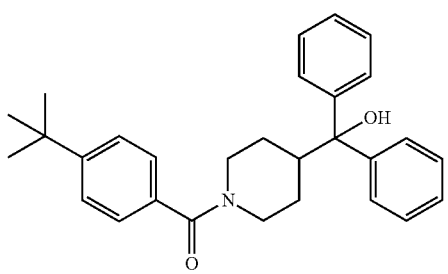

(4-(tert-butyl)phenyl)(4-(hydroxydiphenylmethyl)
piperidin-1-yl)methanone
KSC-346-049

-continued

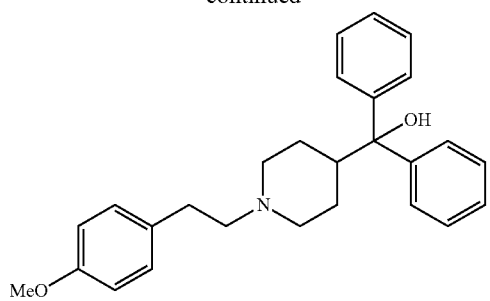

(1-(4-methoxyphenethyl)piperidin-4-yl)diphenylmethanol
KSC-348-058

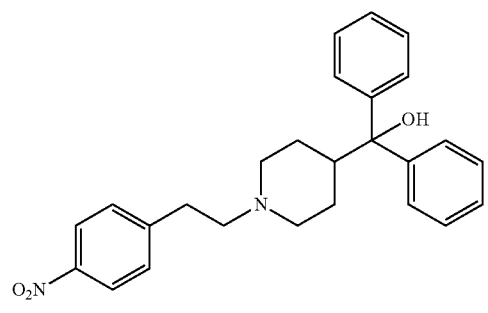

(1-(4-nitrophenethyl)piperidin-4-yl)diphenylmethanol
KSC-352-060

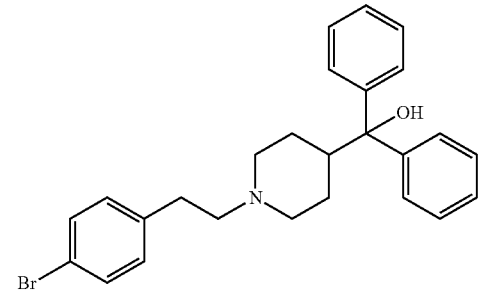

(1-(4-bromophenethyl)piperidin-4-yl)diphenylmethanol
KSC-352-061

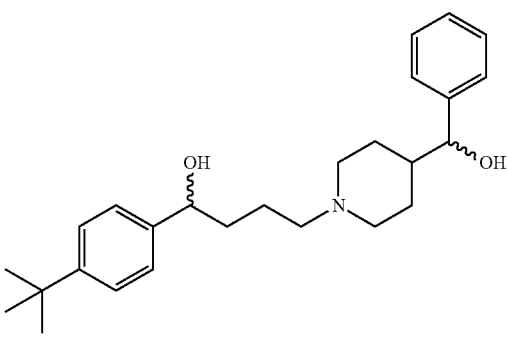

1-(4-(tert-butyl)phenyl)-4-(4-
hydroxy(phenyl)methyl)piperidin-
1-yl)butan-1-ol
KSC-352-066

-continued

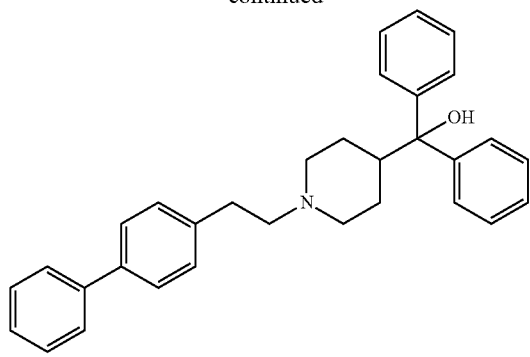

(1-(2-([1,1'-biphenyl]-4-yl)ethyl)piperidin-4-yl)diphenylmethanol
KSC-352-063

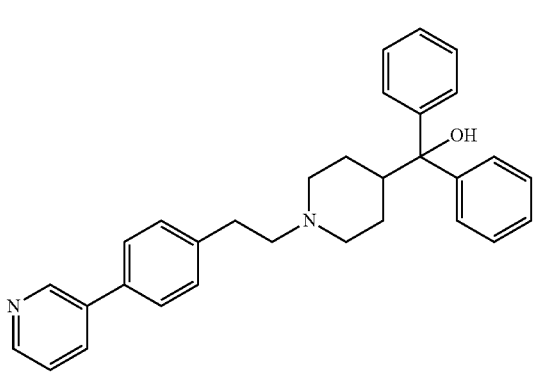

diphenyl(1-(4-(pyridin-3-yl)phenethyl)piperidin-4-yl)methanol
KSC-352-065

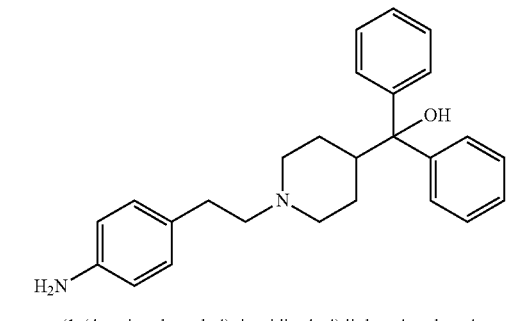

(1-(4-aminophenethyl)piperidin-4-yl)diphenylmethanol
KSC-352-069

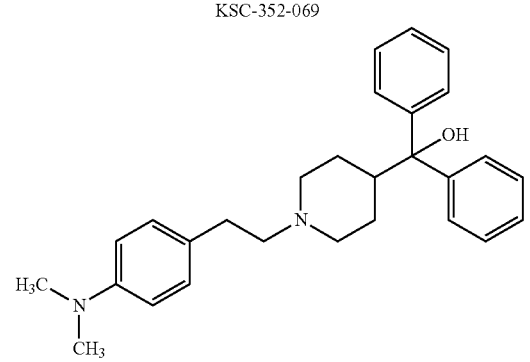

(1-(4-dimethylamino)phenethyl)piperidin-4-yl)diphenylmethanol
KSC-352-075

-continued

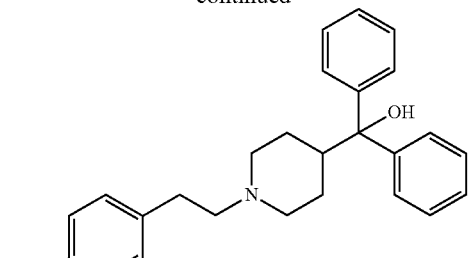

diphenyl(1-(4-(trifluoromethyl)phenethyl)piperidin-4-yl)methanol
KSC-352-082

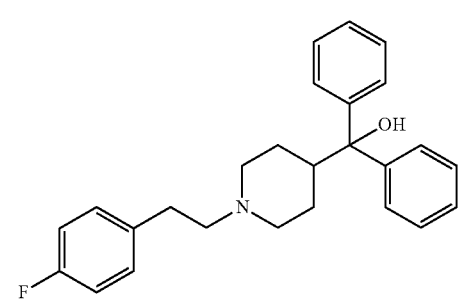

(1-(4-(fluorophenethyl)piperidin-4-yl)diphenylmethanol
KSC-352-088

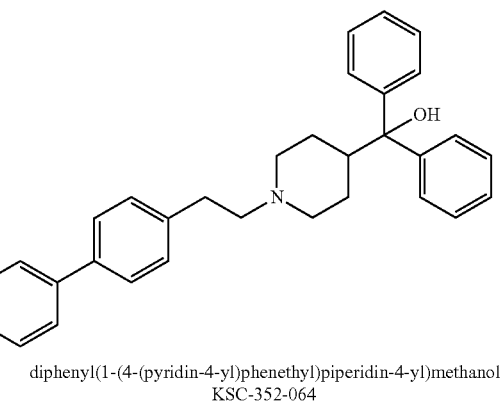

diphenyl(1-(4-(pyridin-4-yl)phenethyl)piperidin-4-yl)methanol
KSC-352-064

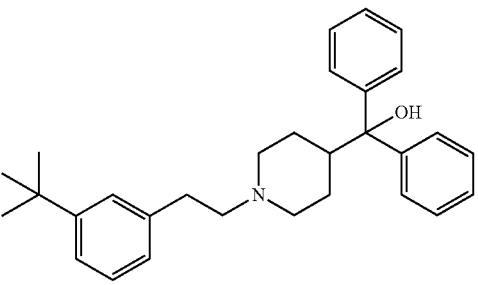

(1-(3-(tert-butyl)phenethyl)piperidin-4-yl)diphenylmethanol
KSC-352-097

-continued

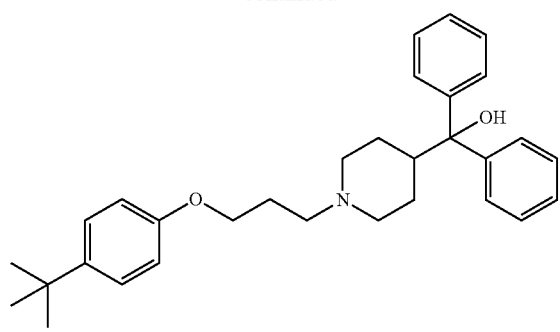

(1-(3-(4-(tert-butyl)phenoxy)propyl)
piperidin-4-yl)diphenylmethanol
KSC-367-044

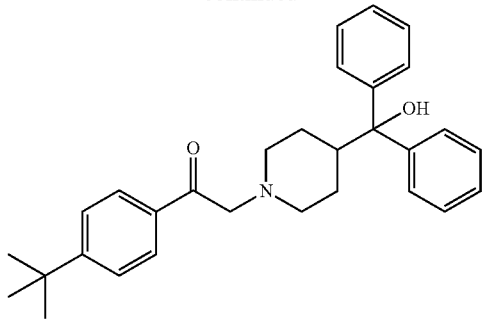

1-(4-(tert-butyl)phenyl)-2-(4-hydroxydiphenylmethyl)
piperidin-1-yl)ethanone
KSC-342-006

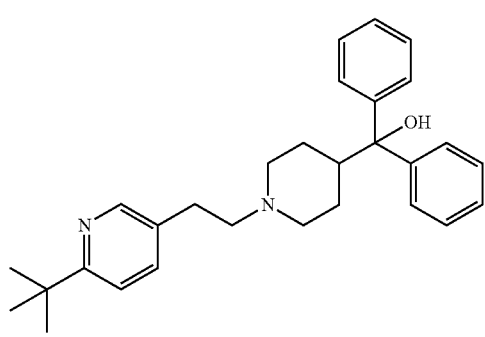

(1-(2-(6-(tert-butyl)pyridin-3-yl)ethyl)
piperidin-4-yl)diphenylmethanol
KSC-367-052

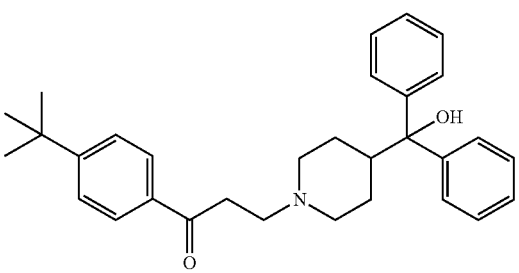

1-(4-(tert-butyl)phenyl)-3-(4-hydroxydiphenylmethyl)
piperidin-1-yl)propan-1-one
KSC-335-008

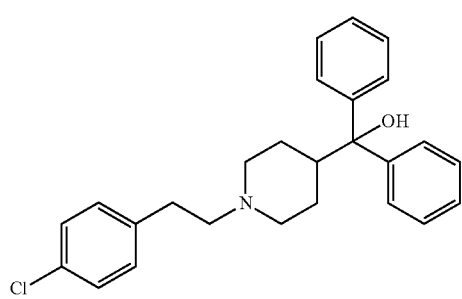

(1-(4-chlorophenethyl)piperidin-4-yl)diphenylmethanol
KSC-367-055

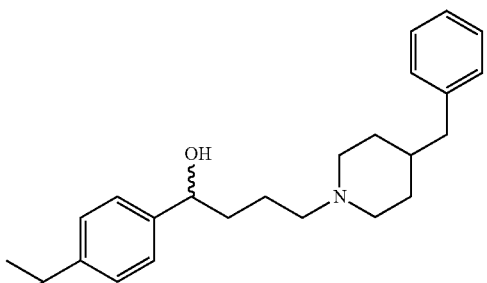

4-(4-benzylpiperidin-1-yl)-1-(4-(tert-butyl)phenyl)butan-1-ol
KSC-367-039

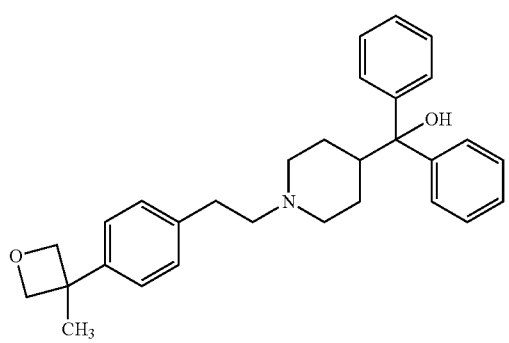

(1-(4-(3-methyloxetan-3-yl)phenethyl)piperidin-4-yl)
diphenylmethanol
KSC-367-072

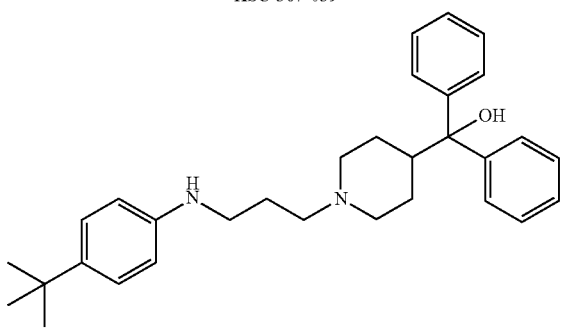

(1-(3-((4-(tert-butyl)phenyl)amino)propyl)piperidin-4-
yl)diphenylmethanol
KSC-367-043

-continued

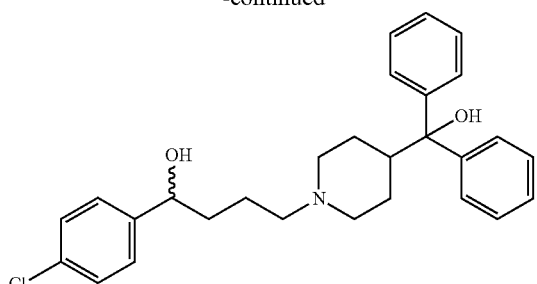

1-(4-chlorophenyl)-4-(4-(hydroxydiphenylmethyl)piperidin-1-yl)butan-1-ol
KSC-335-015

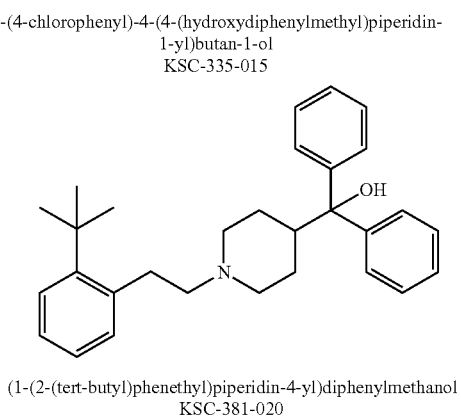

(1-(2-(tert-butyl)phenethyl)piperidin-4-yl)diphenylmethanol
KSC-381-020

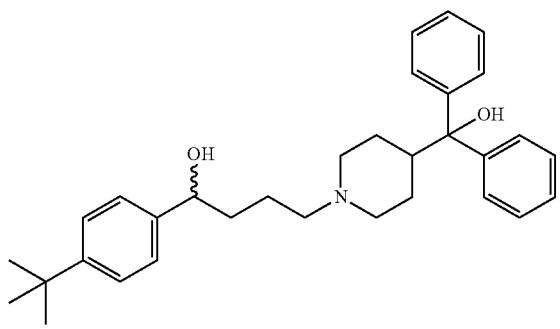

1-(4-(tert-butyl)phenethyl)-4-(4-(diphenylmethylene)piperidin-1-yl)butan-1-ol
KSC-367-058

Also provided is a method of treating or preventing an infection in a subject with or at risk of developing an infection, the method comprising administering to the subject a compound selected from the group consisting of:

a compound of Formula III

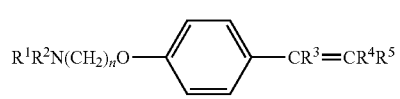

(III)

or a pharmaceutically acceptable salt thereof, wherein $R^1$ and $R^2$ are independently selected from ethyl or methyl, n 1 or 2, $R^3$ and $R^4$ are both phenyl or substituted phenyl, wherein the substituent can be halo (for example, fluoro-, chloro-, iodo- or bromo-), hydroxyl, a lower alkyl or a substituted lower alkyl wherein the substituent can be halo, hydroxy, or lower alkoxy, and $R^5$ is hydrogen, a halogen, a lower alkyl from about 1 to 4 carbon atoms or a substituted alkyl wherein the substituent can be halo, hydroxy, or lower alkoxy. Examples of the compounds of Formula III include, tamoxifen and derivatives

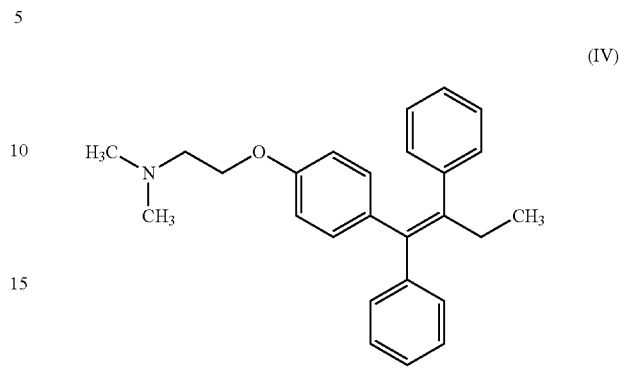

(IV)

thereof, including but not limited to tamoxifen (Formula IV), 4-hydroxy tamoxifen and clomiphene. In the methods provided herein, wherein a one or more compounds of Formula III are used to treat or prevent infection, the infection can be an infection, wherein the infection is not a fungal infection or a parasitic infection.

Further provided herein is a method of treating or preventing an infection in a subject with or at risk of developing an infection, the method comprising administering to the subject a compound selected from the group consisting of:

a compound of Formula V

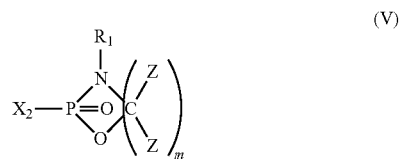

(V)

wherein $R_1$ is a lower alkyl group having from 1 to 4 carbon atoms being substituted with one or several halogen atoms, Z is hydrogen or a lower alkyl group having from 1 to 4 carbon atoms, m is 2 or 3 and $X_2$ is the ethylene imino group or the group having the formula:

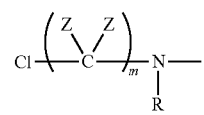

wherein R is hydrogen or a lower alkyl group having from 1 to 4 carbon atoms which may be substituted with a chlorine atom or a hydroxy group, and Z and m have the above-given meaning, or a pharmaceutically acceptable salt thereof.

As used throughout, the term "lower alkyl group containing from 1 to 4 carbon atoms" means methyl, ethyl, n-propyl, isopropyl, n-butyl, isobutyl, tertiary butyl, and I-methylpropyl. The term "halogen" means chlorine, bromine, fluorine, and iodine. Included herein are compounds of formula IV that correspond to formula VI:

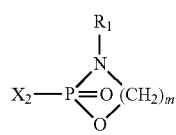

(VI)

wherein $R_1$, $X_2$ and m have the same meaning as in Formula IV. Additional compounds of formula IV, include the compounds of formula VII:

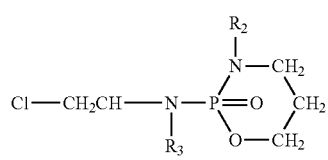

(VII)

wherein $R^2$ is a β-chloroethyl or a γ-chloropropyl group, and $R^3$ is hydrogen, a methyl group or an ethyl group, optionally substituted in the β-position with a chlorine atom or a hydroxy group. Among the compounds of formula VII, are the compounds of formula VIII and IX. The compound of formula VIII is 3-(2-chloroethyl)-2-[(2-chloroethyl)amino]tetrahydro-2H-1,3,2-oxazaphosphorine 2-oxide or ifosfamide. Ifosfamide is also known as IFEX.

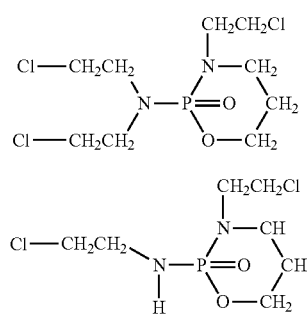

(VIII)

(IX)

Further provided herein is a method of treating or preventing an infection in a subject with or at risk of developing an infection, the method comprising administering to the subject a compound selected from the group consisting of:
a compound of Formula X

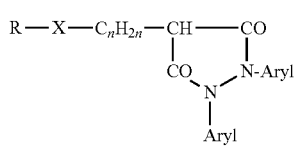

(X)

wherein R represents a lower alkyl or a lower alkenyl group, a phenyl group which can be substituted by halogen, methyl or lower alkoxy groups, or a benzyl group which can be nuclear substituted by halogen, methyl or lower alkoxy groups,
X represents —O—, —S—, —SO—, or —SO$_2$—,
n represents an integer from 1-4, and
Aryl represents a phenyl group which can be substituted by lower alkoxy or lower alkylmercapto groups;
or a pharmaceutically acceptable salt thereof.

With respect to Formula X, R represents a lower alkyl or a lower alkenyl group, a phenyl group which can be substituted by halogen, methyl or lower alkoxy groups, or a benzyl group which can be nuclear substituted by halogen, methyl or lower alkoxy groups, X represents —O—, —S—, —SO—, or —SO$_2$—, n represents an integer from 1-4, and aryl represents a phenyl group which can be substituted by lower alkoxy or lower alkylmercapto groups.

For example, —R—X—C$_n$H$_{2n}$— can represent the following groups: methoxy-, ethoxy-, propoxy-, isopropoxy-, butoxy-, isobutoxy-, allyloxy-, crotyloxy-, phenoxy-, o, -m- and p-methylphenoxy-, o,p-dimethylphenoxy-, m, p-dimethylphenoxy-, p-chlorophenoxy-, p-bromophenoxy-, -o, m and p-methoxyphenoxy-, p-ethoxyphenoxy-, benzyloxy-, o-, m-, and p-methylbenzyloxy-, p-chlorobenzyloxy-, p-bromobenzyloxy, o, m and p-methoxybenzyloxyand-, p-ethoxybenzyloxy-; methyl, -ethyl, -propyl, -isopropyl, and butyl radicals and analogous radicals with SO or SO$_2$ instead of O as divalent group X.

Besides the phenyl group, aryl can be, for example, the o- or p-methylmercaptophenyl group, the o- or p-ethyl mercaptophenyl group, the o-; m-, or p-methoxyphenyl group or the o-, m- or p-ethoxyphenyl group.

An example of the compound of formula X is set forth herein as formula XI. The compound of formula X is sulfinapyrazone. Sulfinapyrazone is also known as Anturane.

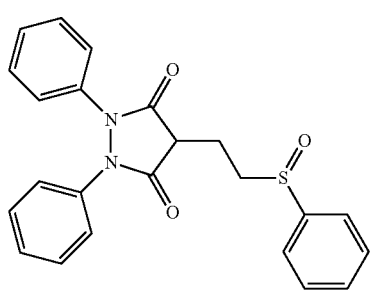

(XI)

Also provided herein is a method of treating or preventing an infection in a subject with or at risk of developing an infection, the method comprising administering to the subject a compound selected from the group consisting of:
a compound of Formula XII

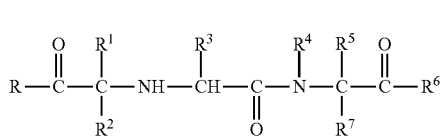

(XII)

wherein R and $R^6$ are the same or different and are hydroxy, lower alkoxy, lower alkenoxy, dilower alkylamino lower alkoxy (dimethylaminoethoxy), acylamino lower alkoxy (acetylaminoethoxy), acyloxy lower alkoxy (pivaloyloxymethoxy), aryloxy, such as phenoxy, arloweralkoxy, such as benzyloxy, substituted ayloxy or substituted arloweralkoxy wherein the substitutent is methyl, halo or methoxy, amino, loweralkylamino, diloweralkylamino, hydroxyamino, arloweralkylamino such as benzylamino;

$R^1$ is hydrogen, alkyl of from 1 to 20 carbon atoms which include branched and cyclic and unsaturated (such as allyl) alkyl groups, substituted loweralkyl wherein the substituent can be halo, hydroxy, lower alkoxy, aryloxy such as phenoxy, amino, diloweralkylamino, acylamino, such as acetamido and benzamido, arylamino, guanidino, imidazolyl, indolyl, mercapto, loweralkylthio, arylthio such as phenylthio, carboxy or carboxamido, carboloweralkoxy, aryl such as phenyl or naphthyl, substituted aryl such as phenyl wherein the substituent is lower alkyl, lower alkoxy or halo, arloweralkyl, arloweralkenyl, heteroarlower alkyl or heteroarlower alkenyl such as benzyl, styryl or indolyl ethyl, substituted arloweralkyl, substituted arloweralkenyl, substituted heteroarlower alkyl, or substituted heteroarlower alkenyl, wherein the substituent(s) is halo, dihalo, lower alkyl, hydroxy, lower alkoxy, amino, aminomethyl, acylamino (acetyl amino or benzoylamino) diloweralkylamino, loweralkylamino, carboxyl, haloloweralkyl, cyano or sulfonamido; arloweralkyl or heteroarloweralkyl substituted on the alkyl portion by amino or acylamino (acetylamino or benzoylamino);

$R^2$ and $R^7$ are the same or different and are hydrogen or lower alkyl;

$R^3$ is hydrogen, lower alkyl, phenyl lower alkyl, aminomethyl phenyl lower alkyl, hydroxy phenyl lower alkyl, hydroxy lower alkyl, acylamino lower alkyl (such as benzoylamino lower alkyl, acetylamino lower alkyl), amino lower alkyl, dimethylamino lower alkyl, halo lower alkyl, guanidino lower alkyl, imidazolyl lower alkyl, indolyllower alkyl, mercapto lower alkyl, lower alkyl thio lower alkyl;

$R^4$ is hydrogen or lower alkyl;

$R^5$ is hydrogen, lower alkyl, phenyl, phenyl lower alkyl, hydroxy phenyl lower alkyl, hydroxy lower alkyl, amino lower alkyl, guanidino lower alkyl, imidazolyl lower alkyl, indolyl lower alkyl, mercapto lower alkyl or lower alkyl thio lower alkyl;

$R^4$ and $R^5$ may be connected together to form an alkylene bridge of from 2 to 4 carbon atoms, an alkylene bridge of from 2 to 3 carbon atoms and one sulfur atom, an alkylene bridge of from 3 to 4 carbon atoms containing a double bond or an alkylene bridge as above substituted with hydroxy, loweralkoxy, loweralkylor diloweralky;

or a pharmaceutically acceptable salt thereof.

With respect to Formula XII, R and $R^6$ are the same or different and are hydroxy, lower alkoxy, lower alkenoxy, dilower alkylamino lower alkoxy (dimethylaminoethoxy), acylamino lower alkoxy (acetylaminoethoxy), acyloxy lower alkoxy (pivaloyloxymethoxy), aryloxy, such as phenoxy, arloweralkoxy, such as benzyloxy, substituted aryloxy or substituted arloweralkoxy wherein the substitutent is methyl, halo or methoxy, amino, loweralkylamino, diloweralkylamino, hydroxyamino, arloweralkylamino such as benzylamino;

$R^1$ is hydrogen, alkyl of from 1 to 20 carbon atoms which include branched and cyclic and unsaturated (such as allyl) alkyl groups, substituted loweralkyl wherein the substituent can be halo, hydroxy, lower alkoxy, aryloxy such as phenoxy, amino, diloweralkylamino, acylamino, such as acetamido and benzamido, arylamino, guanidino, imidazolyl, indolyl, mercapto, loweralkylthio, arylthio such as phenylthio, carboxy or carboxamido, carboloweralkoxy, aryl such as phenyl or naphthyl, substituted aryl such as phenyl wherein the substituent is lower alkyl, lower alkoxy or halo, arloweralkyl, arloweralkenyl, heteroarlower alkyl or heteroarlower alkenyl such as benzyl, styryl or indolyl ethyl, substituted arloweralkyl, substituted arloweralkenyl, substituted heteroarlower alkyl, or substituted heteroarlower alkenyl, wherein the substituent(s) is halo, dihalo, lower alkyl, hydroxy, lower alkoxy, amino, aminomethyl, acylamino (acetyl amino or benzoylamino) diloweralkylamino, loweralkylamino, carboxyl, haloloweralkyl, cyano or sulfonamido; arloweralkyl or heteroarloweralkyl substituted on the alkyl portion by amino or acylamino (acetylamino or benzoylamino);

$R^2$ and $R^7$ are the same or different and are hydrogen or lower alkyl;

$R^3$ is hydrogen, lower alkyl, phenyl lower alkyl, aminomethyl phenyl lower alkyl, hydroxy phenyl lower alkyl, hydroxy lower alkyl, acylamino lower alkyl (such as benzoylamino lower alkyl, acetylamino lower alkyl), amino lower alkyl, dimethylamino lower alkyl, halo lower alkyl, guanidino lower alkyl, imidazolyl lower alkyl, indolyllower alkyl, mercapto lower alkyl, lower alkyl thio lower alkyl;

$R^4$ is hydrogen or lower alkyl;

$R^5$ is hydrogen, lower alkyl, phenyl, phenyl lower alkyl, hydroxy phenyl lower alkyl, hydroxy lower alkyl, amino lower alkyl, guanidino lower alkyl, imidazolyl lower alkyl, indolyl lower alkyl, mercapto lower alkyl or lower alkyl thio lower alkyl;

$R^4$ and $R^5$ may be connected together to form an alkylene bridge of from 2 to 4 carbon atoms, an alkylene bridge of from 2 to 3 carbon atoms and one sulfur atom, an alkylene bridge of from 3 to 4 carbon atoms containing a double bond or an alkylene bridge as above substituted with hydroxy, loweralkoxy, loweralkylor diloweralky.

The loweralkyl or lower alkenyl groups except where noted otherwise represented by any of the variables include straight and branched chain hydrocarbon radicals from one to six carbon atoms, for example, methyl, ethyl, propyl, isopropyl, butyl, isobutyl, t-butyl, pentyl, isopentyl, hexyl or vinyl, allyl, butenyl and the like. The aralkyl groups represented by any of the above variables have from one to four carbon atoms in the alkyl portion thereof and include for example, benzyl, p-methoxy benzyl and the like. Halo means chloro, bromo, iodo or fluoro. Aryl where it appears in any of the radicals except where noted represents phenyl or naphthyl. Heteroaryl groups where they appear include for example pyridyl, thienyl, furyl, indolyl, benzthienyl, imidazoyl and thiazolyl. The $R^1$, $R^3$ and $R^5$ substituted lower alkyl moieties are exemplified by groups such as

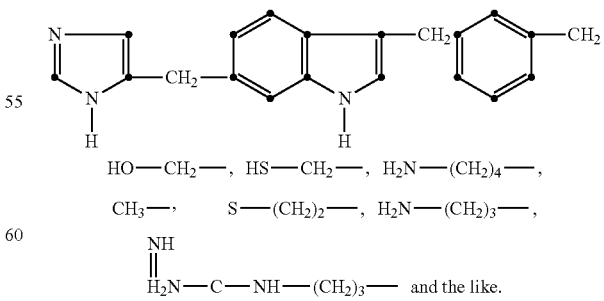

$R^4$ and $R^5$ when joined through the carbon and nitrogen atoms to which they are attached form a 4 to 6 membered ring which may contain one sulfur atom or a double bond.

Preferred rings have the formulae:

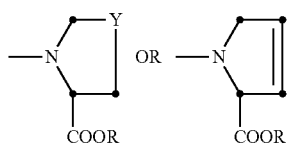

where Y is $CH_2$, S, or $CHOCH_3$.

Compounds of Formula XI include compounds wherein:
R and $R^6$ can each independently be hydroxy, lower alkoxy, lower alkenoxy, arloweralkyloxy, amino, dilower alkylamino lower alkoxy, acylamino lower alkoxy, acyloxy lower alkoxy wherein the substituent is methyl, halo or methoxy;

$R^2$ and $R^7$ are hydrogen; $R^3$ is lower alkyl, amino lower alkyl, imidazoyllower alkyl, halo lower alkyl;

$R^4$ and $R^5$ are joined to form the preferred rings as defined above where Y is $CH_2$, S, or CH—$OCH_3$;

$R^1$ is as defined previously.

Other compounds include compounds of Formula XI wherein further $R^1$ is alkyl having from 1 to 8 carbon atoms, substituted lower alkyl wherein the alkyl group has 1-5 carbon atoms and the substituent is amino, arylthio, aryloxy or arylamino, aralkyl or heteroaralkyl wherein the alkyl portion has 1 to 3 carbon atoms such as phenethyl or indolylethyl or substituted arloweralkyl 65 (phenyl lower alkyl or naphthyl lower alkyl) and substituted heteroarloweralkyl wherein the alkyl groups have 1-3 carbons and wherein the substituent(s) is halo, dihalo, amino, aminoalkyl, hydroxy, lower alkoxy or lower alkyl.

Other compounds of Formula XI include compounds wherein R and $R^6$ are hydroxy, lower alkoxy, aralkyloxy;

$R^2$ and $R^7$ are hydrogen;

$R^3$ is methyl or amino lower alkyl;

$R^4$ and $R^5$ are joined through the carbon and nitrogen atom to form proline, 4-thiaproline or 4-methoxy proline;

$R^1$ is alkyl having from 1 to 8 carbon atoms, substituted lower alkyl wherein the alkyl group has 1-5 carbon atoms and the substituent is amino, arylthio or aryloxy, aralkyl or heteroaralkyl wherein the alkyl portion has 1 to 3 carbon atoms such as phenethyl or indolylethyl or substituted aralkyl (phenyl lower alkyl or naphthyl lower alkyl) and substituted heteroaralkyl wherein the alkyl groups have 1-3 carbons and wherein the substituent(s) is halo, dihalo, amino, aminoalkyl, hydroxy, lower alkoxy or lower alkyl.

Further examples of compounds of Formula XII include, but are not limited to:
N-(1 (S)-carboxy-3-phenylpropyl)-L-alanyl-L-proline;
N-(1(S)-ethoxycarbonyl-3-phenylpropyl)-L-alanyl-L-proline and its maleate salt;
N-(1 (S)-ethoxycarbonyl-4-methylpentyl)-L-alanyl-L-proline;
N-(1-carboxy-5-aminopentyl)-L-alanyl-L-proline;
N-.alpha.-(1 (S)-carboxy-3-phenylpropyl)-L-lysyl-L-proline (lisinopril);
N-.alpha.(1(S)-ethoxycarbonyl-3-phenylpropyl)-L-lysyl-L-proline;
N-.alpha.[1 (S)-carboxy-3-(3-indolyl)propyl]-L-lysyl-L-proline;
N-.alpha.-[1 (S)-carboxy-3-(4-chlorophenyl)-propyl]-L-lysyl-L-proline;
N-.alpha.-[1(S)-carboxy-2-phenylthioethyl]-L-lysyl-L-proline;
N-.alpha.-[1(S)-carboxy-3-(4-chlorophenyl)-propyl]-L-lysyl-L-4.alpha.-methoxyproline;
N-.alpha.-[1 (S)-carboxy-5-aminopentyl]-L-lysyl-L-proline;
Ethyl N-(1 (S)-ethoxycarbonyl-3-phenylpropyl)-L-alanyl-L-prolinate hydrochloride;
and the like.

Also provided herein is a method of treating or preventing an infection in a subject with or at risk of developing an infection, the method comprising administering to the subject a compound selected from the group consisting of:
a compound of Formula XIII

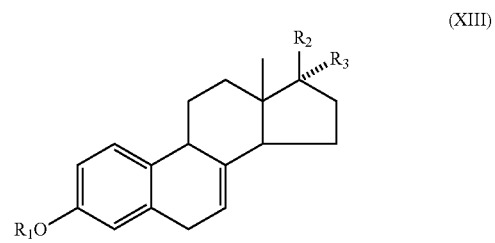

(XIII)

wherein $R_1$ is H, alkyl, acyl or silyl(alkyl)$_3$; $R^2$ is H and $R^3$ is OH, O-acyl, O-alkyl or O-silyl (alkyl)$_3$ or $R^3$ is H and $R^2$ is OH. O-acyl, O-alkyl or O-silyl (alkyl)$_3$; or $R^2$ and $R^3$ together represent O; or $R^2$ and $R^3$ together represent acetal or cyclic acetal. $R_1$ might also represent a substituted alkyl such as e.g. methoxy ethoxy methyl; or a pharmaceutically acceptable salt thereof.

Also provided herein is a method of treating or preventing an infection in a subject with or at risk of developing an infection, the method comprising administering to the subject a compound selected from the group consisting of:
a compound of Formula XIV

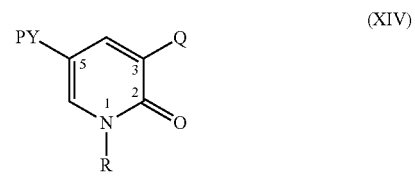

(XIV)

wherein PY is 4- or 3- or 2-pyridinyl or 4- or 3- or 2-pyridinyl having one or two lower-alkyl substituents, R is hydrogen, lower-alkyl or lower-hydroxyalkyl, and Q is nitro, carbamyl, halo, amino, lower-alkylamino, di(lower-alkyl) amino, or NHAc where Ac is lower-alkanoyl or lower-carbalkoxy;
or a pharmaceutically acceptable salt thereof.

With respect to Formula XIII, PY is 4- or 3- or 2-pyridinyl or 4- or 3- or 2-pyridinyl having one or two lower-alkyl substituents, R is hydrogen, lower-alkyl or lower-hydroxyalkyl, and Q is nitro, carbamyl, halo, amino, lower-alkylamino, di(lower-alkyl)amino, or NHAc where Ac is lower-alkanoyl or lower-carbalkoxy, or pharmaceutically-acceptable acid-addition salt thereof. Compounds of formula XIII where Q is amino, lower-alkylamino, di-(lower-alkyl) amino, or NHAc are provided herein. The compounds of formula XIII where Q is nitro or carbamyl are useful as intermediates for preparing the said compounds where Q is amino and those where Q is halo are useful as intermediates in the preparation of the compounds where Q is lower-alkylamino and di-(lower-alkyl)amino. Other compounds of Formula XIII include compounds where Q is amino, R is hydrogen and PY is 4-pyridinyl or 3-pyridinyl, for example, 3-amino-5-(4-pyridinyl)-2(1H)-pyridinone (amrinone).

Further provided herein is a method of treating or preventing an infection in a subject with or at risk of developing an infection, the method comprising administering to the subject a compound selected from the group consisting of:

a compound of Formula XV

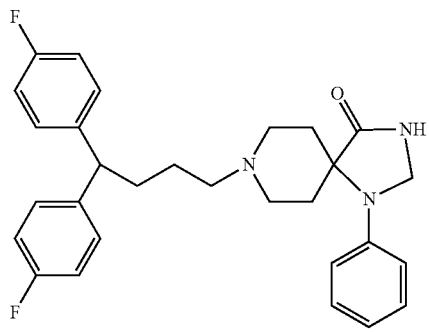

(XV)

Fluspirilen a compound of Formula XVI

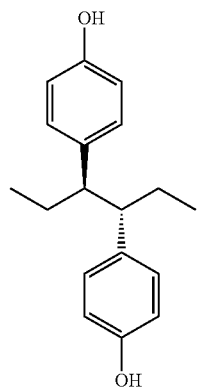

(XVI)

a compound of Formula XVII

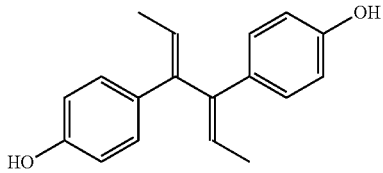

(XVII)

a compound of Formula XVIII

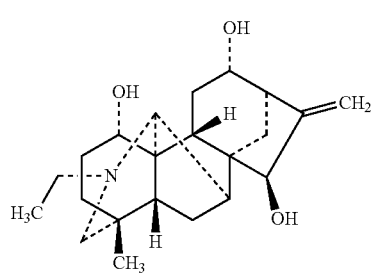

(XVIII)

a compound of Formula XIX

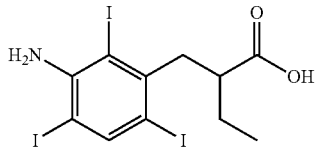

(XIX)

a compound of Formula (XX)

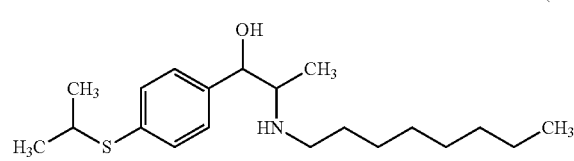

(XX)

or pharmaceutically acceptable salt thereof.

Formula XV is fluspirilen, Formula XVI is hexestrol, Formula XVII is dienestrol, Formula XVIII is napelline, Formula XIX is iopanoic acid and Formula XX is suloctodil.

Further provided is a method of treating or preventing an infection in a subject with or at risk of developing an infection, the method comprising administering to the subject a compound selected from the group consisting of: Didanosine, Norcyclobenzaprine, Niridazole, Ifosfamide, Cefalonium, Tamoxifen citrate, Butoconazole, Suloctidil, Clomiphene, Sulconazole, Miconazole, Mefloquine, Sulfinpyrazone, Terfenadine, Lisinopril, Econzaole, Clofazimine, Equilin, Felodipine, Dacarbazine, Furazolidone, Perhexiline maleate, Oxethazaine, Pimozide, Trifluoperazine, Ellipticine, Fluspirilen, Hexestrol, Dienestrol, Zidovudine, Metoprolol, Napelline, Methimazole, Amrinone, Iopanoic acid, R-Propanolol, Rimexolone and Pyrvinium pamoate, or a pharmaceutically acceptable salt thereof.

Further provided is a method of treating or preventing an infection in a subject with or at risk of developing an infection, the method comprising administering to the subject a compound selected from the group consisting of: Didanosine, Norcyclobenzaprine, Niridazole, Ifosfamide, Cefalonium, Tamoxifen citrate, Butoconazole, Suloctidil, Clomiphene, Sulconazole, Miconazole, Mefloquine, Sulfinpyrazone, Terfenadine, Lisinopril, Econzaole, Clofazimine, Equilin, Felodipine, Dacarbazine, Furazolidone, Perhexiline maleate, Oxethazaine, Pimozide, Trifluoperazine, Ellipticine, Fluspirilen, Hexestrol, Dienestrol, Zidovudine, Metoprolol, Napelline, Methimazole, Amrinone, Iopanoic acid, R-Propanolol, Rimexolone and Pyrvinium pamoate, or a pharmaceutically acceptable salt thereof, wherein the infection is a bacterial infection selected from the group consisting of *Enterobacterium faecium*, *Staphylococcus aureus*, *Klebsiella pneumonia*, *Acinebacter baumannii*, *Pseudomonas aeruginosa* and *Enterobacter* sp.

Further provided is a method of treating or preventing a bacterial infection in a subject with or at risk of developing a bacterial infection in a subject comprising administering to the subject a compound that inhibits bacterial DNA gyrase or topoisomerase IV. The compound can be, for example, a compound of Formula I. As set forth above, a compound of Formula I can be terfenadine or a derivative thereof. In the methods set forth herein an inhibitor of bacterial DNA gyrase or topoisomerase IV can be used to treat or prevent *Staphylococcus aureus* infection.

It is contemplated that one or more, for example, two, three, four, five, etc., of the compounds or derivatives of the compounds set forth herein can be administered to treat or prevent infection. Thus, combinations of the compounds set forth herein are also provided. Pharmaceutically acceptable salts of all of the compounds set forth herein are also provided. The term pharmaceutically acceptable salt as used herein refers to those salts of any of the compounds described herein or derivatives thereof that are, within the scope of sound medical judgment, suitable for use in contact with the tissues of subjects without undue toxicity, irritation, allergic response, and the like, commensurate with a reasonable benefit/risk ratio, and effective for their intended use, as well as the zwitterionic forms, where possible, of the compounds described herein. The term salts refers to the relatively non-toxic, inorganic and organic acid addition salts of the compounds described herein. These salts can be prepared in situ during the isolation and purification of the compounds or by separately reacting the purified compound in its free base form with a suitable organic or inorganic acid and isolating the salt thus formed. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate, methane sulphonate, and laurylsulphonate salts, and the like. These may include cations based on the alkali and alkaline earth metals, such as sodium, lithium, potassium, calcium, magnesium, and the like, as well as non-toxic ammonium, quaternary ammonium, and amine cations including, but not limited to ammonium, tetramethylammonium, tetraethylammonium, methylamine, dimethylamine, trimethylamine, triethylamine, ethylamine, and the like.

The infection can be a viral infection, bacterial infection, fungal infection or a parasitic infection, to name a few. All strains and types of pathogenic infection are contemplated herein. The infection can also be a respiratory infection, a gastrointestinal infection or a skin infection, to name a few.

In any of the methods of treating or preventing infection set forth herein, the infection can be any infection, wherein the infection is not a bacterial infection. In any of the methods of treating or preventing infection set forth herein, the infection can be any infection, wherein the infection is not a viral infection. In any of the methods of treating or preventing infection set forth herein, the infection can be any infection, wherein the infection is not a parasitic infection. In any of the methods of treating or preventing infection set forth herein, the infection can be any infection, wherein the infection is not a fungal infection. In any of the methods of treating or preventing infection set forth herein, the infection can be any infection, wherein the infection is not a protozoal infection.

Examples of bacterial infections include, but are not limited to infections caused by the Gram negative or Gram positive bacteria. For example, the infection can be caused by *Listeria* (sp.), *Franscicella tularensis*, *Enterobacter* sp. *Enterococcus faecium*, other *Enterococcus* species, *Klebsiella pneumonia*, *Acinetobacter baumannii*, *Mycobacterium tuberculosis*, *Rickettsia* (all types), *Ehrlichia* or *Chylamida*. Further examples of bacteria include *M. tuberculosis*, *Legionella pneumophila*, other *Legionella* species, *Salmonella typhi*, other *Salmonella* species, *Shigella* species, *Yersinia pestis*, *Pasteurella haemolytica*, *Pasteurella multocida*, other *Pasteurella* species, *Actinobacillus pleuropneumoniae*, *Listeria monocytogenes*, *Listeria ivanovii*, *Brucella abortus*, other *Brucella* species, *Chlamydia pneumoniae*, *Chlamydia trachomatis*, *Chlamydia psittaci*, *Coxiella burnetti*, other *Rickettsial* species, *Ehrlichia* species, *Staphylococcus aureus*, *Staphylococcus epidermidis*, *Streptococcus pyogenes*, *Streptococcus agalactiae*, *Bacillus anthracis*, *Escherichia coli*, *Vibrio cholerae*, *Kingella kingae*, *Campylobacter* species, *Neiserria meningitidis*, *Neiserria gonorrhea*, *Pseudomonas aeruginosa*, other *Pseudomonas* species, *Haemophilus influenzae*, *Haemophilus ducreyi*, other *Hemophilus* species, *Clostridium tetani*, other *Clostridium* species, *Yersinia enterolitica*, and other *Yersinia* species. In the methods provided herein, one or more compounds set forth herein can treat or prevent one or more bacterial infections selected from the group consisting of *Enterobacterium faecium*, *Staphylococcus aureus*, *Klebsiella pneumonia*, *Acinebacter baumannii*, *Pseudomonas aeruginosa* and *Enterobacter* sp. In the methods set forth herein, the bacteria can be a small colony variant strain, for example a small colony strain of *Staphylococcus aureus*. In any of the methods set forth herein, the infection can be a bacterial infection, wherein the bacterial infection is not tuberculosis, for example, *Mycobacterium tuberculosis*. For example, and not to be limiting any of the compounds set forth herein, including compounds of Formula I and II can be used to treat or prevent infection in a subject with or at risk of developing an infection, wherein the infection is not tuberculosis.

Examples of parasitic infections include, but are not limited to infections caused by the following parasites: *Cryptosporidium*, *Plasmodium* (all species), American trypanosomes (*T. cruzi*), African trypanosomes, *Acanthamoeba*, *Entaoeba histolytica*, *Angiostrongylus*, *Anisakis*, *Ascaris*, *Babesia*, *Balantidium*, *Baylisascaris*, lice, ticks, mites, fleas, *Capillaria*, *Clonorchis*, *Chilomastix mesnili*, *Cyclspora*, *Diphyllobothrium*, *Dipylidium caninum*, *Fasciola*, *Giardia*, *Gnathostoma*, *Hetetophyes*, *Hymenolepsis*, *Isospora*, *Loa loa*, *Microsporidia*, *Naegleria*, *Toxocara*, *Onchocerca*, *Opisthorchis*, *Paragonimus*, *Baylisascaris*, *Strongyloides*, *Taenia*, *Trichomonas* and *Trichuris*. In any of the methods set forth herein, the infection can be a parasitic infection, wherein the parasitic infection is not malaria, for example, malaria caused by any species of *Plasmodium* including *Plasmodium falciparum*. For example, and not to be limiting any of the compounds set forth herein, including compounds of Formula I and II can be used to treat or prevent infection in a subject with or at risk of developing an infection, wherein the infection is not malaria.

Furthermore, examples of protozoan and fungal species contemplated within the present methods include, but are not limited to, *Plasmodium falciparum*, other *Plasmodium* species, *Toxoplasma gondii*, *Pneumocystis carinii*, *Trypano*-

*soma cruzi*, other trypanosomal species, *Leishmania donovani*, other *Leishmania* species, *Theileria annulata*, other *Theileria* species, *Eimeria tenella*, other *Eimeria* species, *Histoplasma capsulatum, Cryptococcus neoformans, Blastomyces dermatitidis, Coccidioides immitis, Paracoccidioides brasiliensis, Penicillium marneffei*, and *Candida* species. In any of the methods set forth herein, the infection can be a protozoan infection, wherein the protozoan infection is not leishmaniasis, for example, leishmaniasis caused by a *Leishmania* species, for example, *Leishmania major*. For example, and not to be limiting any of the compounds set forth herein, including compounds of Formula I and III can be used to treat or prevent infection in a subject with or at risk of developing an infection, wherein the infection is not leishmaniasis.

Examples of viral infections include but are not limited to, infections caused by RNA viruses (including negative stranded RNA viruses, positive stranded RNA viruses, double stranded RNA viruses and retroviruses) and DNA viruses. All strains, types, subtypes of DNA and RNA viruses are contemplated herein.

Examples of RNA viruses include, but are not limited to picornaviruses, which include aphthoviruses (for example, foot and mouth disease virus O, A, C, Asia 1, SAT1, SAT2 and SAT3), cardioviruses (for example, encephalomyocarditis virus and Theiller's murine encephalomyelitis virus), enteroviruses (for example polioviruses 1, 2 and 3, human enteroviruses A-D, bovine enteroviruses 1 and 2, human coxsackieviruses A1-A22 and A24, human coxsackieviruses B1-B5, human echoviruses 1-7, 9, 11-12, 24, 27, 29-33, human enteroviruses 68-71, porcine enteroviruses 8-10 and simian enteroviruses 1-18), erboviruses (for example, equine rhinitis virus), hepatovirus (for example human hepatitis A virus and simian hepatitis A virus), kobuviruses (for example, bovine kobuvirus and Aichi virus), parechoviruses (for example, human parechovirus 1 and human parechovirus 2), rhinovirus (for example, human rhinovirus 1-100 and bovine rhinoviruses 1-3) and teschoviruses (for example, porcine teschovirus).

Additional examples of RNA viruses include caliciviruses, which include noroviruses (for example, Norwalk virus), sapoviruses (for example, Sapporo virus), lagoviruses (for example, rabbit hemorrhagic disease virus and European brown hare syndrome) and vesiviruses (for example vesicular exanthema of swine virus and feline calicivirus).

Other RNA viruses include astroviruses, which include mamastorviruses and avastroviruses. Togaviruses are also RNA viruses. Togaviruses include alphaviruses (for example, Chikungunya virus, Sindbis virus, Semliki Forest virus, Western equine encephalitis, Getah virus, Everglades virus, Venezuelan equine encephalitis virus and Aura virus) and rubella viruses. Additional examples of RNA viruses include the the flaviviruses (for example, tick-borne encephalitis virus, Tyuleniy virus, Aroa virus, Dengue virus (types 1 to 4), Kedougou virus, Japanese encephalitis virus (JEV), West Nile virus (WNV), Kokobera virus, Ntaya virus, Spondweni virus, Yellow fever virus, Entebbe bat virus, Modoc virus, Rio Bravo virus, Cell fusing agent virus, pestivirus, GB virus A, GBV-A like viruses, GB virus C, Hepatitis G virus, hepacivirus (hepatitis C virus (HCV)) all six genotypes), bovine viral diarrhea virus (BVDV) types 1 and 2, and GB virus B).

Other examples of RNA viruses are the coronaviruses, which include, human respiratory coronaviruses such as SARS—CoV, HCoV-229E, HCoV-NL63 and HCoV-OC43. Coronaviruses also include bat SARS-like CoV, turkey coronavirus, chicken coronavirus, feline coronavirus and canine coronavirus. Additional RNA viruses include arteriviruses (for example, equine arterivirus, porcine reproductive and respiratory syndrome virus, lactate dehyrogenase elevating virus of mice and simian hemorraghic fever virus). Other RNA viruses include the rhabdoviruses, which include lyssaviruses (for example, rabies, Lagos bat virus, Mokola virus, Duvenhage virus and European bat lyssavirus), vesiculoviruses (for example, VSV-Indiana, VSV-New Jersey, VSV-Alagoas, Piry virus, Cocal virus, Maraba virus, Isfahan virus and Chandipura virus), and ephemeroviruses (for example, bovine ephemeral fever virus, Adelaide River virus and Berrimah virus). Additional examples of RNA viruses include the filoviruses. These include the Marburg and Ebola viruses (for example, EBOV-Z, EBOV-S, EBOV-IC and EBOV-R.

The paramyxoviruses are also RNA viruses. Examples of these viruses are the rubulaviruses (for example, mumps, parainfluenza virus 5, human parainfluenza virus type 2, Mapuera virus and porcine rubulavirus), avulaviruses (for example, Newcastle disease virus), respoviruses (for example, Sendai virus, human parainfluenza virus type 1 and type 3, bovine parainfluenza virus type 3), henipaviruses (for example, Hendra virus and Nipah virus), morbilloviruses (for example, measles, Cetacean morvilliirus, Canine distemper virus, Peste-des-petits-ruminants virus, Phocine distemper virus and Rinderpest virus), pneumoviruses (for example, human respiratory syncytial virus A2, B1 and S2, bovine respiratory syncytial virus and pneumonia virus of mice), metapneumoviruses (for example, human metapneumovirus and avian metapneumovirus). Additional paramyxoviruses include Fer-de-Lance virus, Tupaia paramyxovirus, Menangle virus, Tioman virus, Beilong virus, J virus, Mossman virus, Salem virus and Nariva virus. Additional RNA viruses include the orthomyxoviruses.

These viruses include influenza viruses and strains (e.g., influenza A (H1N1 (including but not limited to A/WS/33 and A/California/04/2009 strains) H2N2, H3N2, H5N1, H7N7, H1N2, H9N2, H7N2, H7N3 and H10N7), B and C viruses, as well as avian influenza (for example, strains H5N1, H5N2, H7N1, H7N7 and H9N2) thogotoviruses and isaviruses. Orthobunyaviruses (for example, Akabane virus, California encephalitis, Cache Valley virus, Snowshoe hare virus,) nairoviruses (for example, Nairobi sheep virus, Crimean-Congo hemorrhagic fever virus Group and Hughes virus), phleboviruses (for example, Candiru, Punta Toro, Rift Valley Fever, Sandfly Fever, Naples, Toscana, Sicilian and Chagres), and hantaviruses (for example, Hantaan, Dobrava, Seoul, Puumala, Sin Nombre, Bayou, Black Creek Canal, Andes and Thottapalayam) are also RNA viruses. Arenaviruses such as lymphocytic choriomeningitis virus, Lujo virus, Lassa fever virus, Argentine hemorrhagic fever virus, Bolivian hemorrhagic fever virus, Venezuelan hemorrhagic fever virus, SABV and WWAV are also RNA viruses. Borna disease virus is also an RNA virus. Hepatitis D (Delta) virus and hepatitis E are also RNA viruses. Any of the compounds set forth herein, including, but not limited to the compounds of Formula I and II can be used to treat or prevent a viral infection, wherein the viral infection is not a Lassa fever virus infection.

Additional RNA viruses include reoviruses, rotaviruses, birnaviruses, chrysoviruses, cystoviruses, hypoviruses partitiviruses and totoviruses. Orbiviruses such as African horse sickness virus, Blue tongue virus, Changuinola virus, Chenuda virus, Chobar Gorge Corriparta virus, epizootic hemorraghic disease virus, equine encephalosis virus, Eubenangee virus, Ieri virus, Great Island virus, Lebombo virus, Orungo virus, Palyam virus, Peruvian Horse Sickness virus, St. Croix River virus, Umatilla virus, Wad Medani virus, Wallal virus, Warrego virus and Wongorr virus are also RNA viruses.

Retroviruses include alpharetroviruses (for example, Rous sarcoma virus and avian leukemia virus), betaretroviruses (for example, mouse mammary tumor virus, Mason-Pfizer monkey virus and Jaagsiekte sheep retrovirus), gammaretroviruses (for example, murine leukemia virus and feline leukemia virus, deltraretroviruses (for example, human T cell leukemia viruses (HTLV-1, HTLV-2), bovine leukemia virus, STLV-1 and STLV-2), epsilonretriviruses (for example, Walleye dermal sarcoma virus and Walleye epidermal hyperplasia virus 1), reticuloendotheliosis virus (for example, chicken syncytial virus, lentiviruses (for example, human immunodeficiency virus (HIV) type 1, human immunodeficiency virus (HIV) type 2, human immunodeficiency virus (HIV) type 3, simian immunodeficiency virus, equine infectious anemia virus, feline immunodeficiency virus, caprine arthritis encephalitis virus and Visna maedi virus) and spumaviruses (for example, human foamy virus and feline syncytia-forming virus).

Examples of DNA viruses include polyomaviruses (for example, simian virus 40, simian agent 12, BK virus, JC virus, Merkel Cell polyoma virus, bovine polyoma virus and lymphotrophic papovavirus), papillomaviruses (for example, human papillomavirus, bovine papillomavirus, adenoviruses (for example, adenoviruses A-F, canine adenovirus type I, canined adeovirus type 2), circoviruses (for example, porcine circovirus and beak and feather disease virus (BFDV)), parvoviruses (for example, canine parvovirus), erythroviruses (for example, adeno-associated virus types 1-8), betaparvoviruses, amdoviruses, densoviruses, iteraviruses, brevidensoviruses, pefudensoviruses, herpes viruses 1, 2, 3, 4, 5, 6, 7 and 8 (for example, herpes simplex virus 1, herpes simplex virus 2, varicella-zoster virus, Epstein-Barr virus, cytomegalovirus, Kaposi's sarcoma associated herpes virus, human herpes virus-6 variant A, human herpes virus-6 variant B and cercophithecine herpes virus 1 (B virus)), poxviruses (for example, smallpox (variola), cowpox, monkeypox, vaccinia, Uasin Gishu, camelpox, psuedocowpox, pigeonpox, horsepox, fowlpox, turkeypox and swinepox), and hepadnaviruses (for example, hepatitis B and hepatitis B-like viruses).

One or more of the compounds described herein can be contacted with a cell or populations of cells in vitro, ex vivo or in vivo. For example, the cell or population of cells can be in a subject, or in an in vitro culture. In another example, one or more compounds set forth herein can be used to inhibit bacterial growth, fungal growth, parasitic growth, protozoal growth or viral replication, in vitro, ex vivo or in vivo. Any of the compounds set forth herein can be used alone or in combination with other therapeutic agents such as antiviral compounds, antibacterial agents (for example, antibiotics), antifungal agents, antiparasitic agents, anti-inflammatory agents, anti-cancer agents, etc.

In the methods described herein, the level of infection, for example, in a cell, or a population of cells, or a cell culture, can be assessed by measuring an antigen or other product associated with a particular infection. The level of infection can also be measured in a tissue sample or a culture of cells from a subject, either before or after administration of one or more compounds disclosed herein. For example, the level of viral infection can be measured by real-time quantitative reverse transcription-polymerase chain reaction (RT-PCR) assay (See for example, Payungporn et al. "Single step multiplex real-time RT-PCR for H5N1 influenza A virus detection." *J Virol Methods*. Sep. 22, 2005; Landolt et la. "Use of real-time reverse transcriptase polymerase chain reaction assay and cell culture methods for detection of swine influenza A viruses" *Am J Vet Res*. 2005 January; 66(1): 119-24).

Methods of measuring bacterial growth and inhibition of bacterial growth are provided in the Examples. Further, one of skill in the art would know how to determine the concentration of a compound that inhibits bacterial infection (see, for example, Andrews, et al. "Determination of minimum inhibitory concentrations". *Journal of Antimicrobial Chemotherapy* 48 (suppl 1): 5-16 (2001)). Other methods for determining antifungal and antibacterial activity are known in the art. See, for example, Hayhoe et al. "Screening for Antibacterial, Antifungal and Anti quorum Sensing Activity," *Methods Mol. Biol.* 1055: 219-225 (2013)); Doddanna et al. "Antimicrobial activity of plant extracts on *Candida albicans*: An in vitro study *Indian J. Dent. Res.* 24(4): 401-405 (2013), both of which are incorporated by this reference in their entireties.

As used throughout, by subject is meant an individual. Preferably, the subject is a mammal such as a primate, and, more preferably, a human. Non-human primates are subjects as well. The term subject includes domesticated animals, such as cats, dogs, etc., livestock (for example, cattle, horses, pigs, sheep, goats, etc.) and laboratory animals (for example, ferret, chinchilla, mouse, rabbit, rat, gerbil, guinea pig, etc.). Thus, veterinary uses and medical formulations are contemplated herein.

As used herein, a biological sample is a sample derived from a subject such as a mammal or human and includes, but is not limited to, any biological fluid, including a bodily fluid. Examples of bodily fluids include, but are not limited to, whole blood, plasma, serum, urine, saliva, ocular fluid, ascites, a stool sample, spinal fluid, tissue infiltrate, pleural effusions, lung lavage fluid, and the like. The biological fluid includes a cell culture medium or supernatant of cultured cells from the subject.

The methods and compounds as described herein are useful for therapeutic treatment. Use of one or more of the compounds set forth herein for the treatment or prevention of infection is also contemplated herein. One or more of the compounds set forth herein for use in a method of treating or preventing infection is also provided herein. Therapeutic treatment involves administering to a subject a therapeutically effective amount of one or more of the agents described herein, optionally, after diagnosis of an infection or risk of infection in the subject. Therefore, all of the methods disclosed herein, can optionally comprise the step of diagnosing a subject with an infection or diagnosing a subject in need of prophylaxis or prevention of infection.

As used herein, the terms treatment, treat, or treating refers to a method of reducing the effects of a disease or condition or symptom of the disease or condition. Thus, in the disclosed methods, treatment can refer to a 10%, 20%, 30%, 40%, 50%, 60%, 70%, 80%, 90%, or 100% reduction in the severity of an established disease or condition or symptom of the disease or condition. For example, a method for treating a disease is considered to be a treatment if there is a 10% reduction in one or more symptoms of the disease in a subject as compared to a control. A control subject can be a subject that has not received a compound set forth herein. Thus, the reduction can be a 10%, 20%, 30%, 40%, 50%, 60%, 70%, 80%, 90%, 100%, or any percent reduction in between 10% and 100% as compared to native or control levels. It is understood that treatment does not necessarily refer to a cure or complete ablation of the disease, condition, or symptoms of the disease or condition.

As utilized herein, by preventing infection is meant a method of precluding, delaying, averting, obviating, forestalling, stopping, or hindering the onset, incidence, severity, or recurrence of infection. For example, the disclosed method is considered to be a prevention if there is about a 10% reduction in onset, incidence, severity, or recurrence of infection, or symptoms of infection (e.g., inflammation, fever, lesions, weight loss, etc.) in a subject exposed to an infection when compared to control subjects exposed to an infection that did not receive a composition for decreasing infection. Thus, the reduction in onset, incidence, severity, or recurrence of infection can be about a 10, 20, 30, 40, 50, 60, 70, 80, 90, 100%, or any amount of reduction in between as compared to a control subject. For example, and not to be limiting, if about 10% of the subjects in a population do not become infected as compared to subjects that did not receive preventive treatment, this is considered prevention.

The compounds set forth herein can also be used to decrease infection in a cell. A decrease or inhibition of infection can occur in a cell, in vitro, ex vivo or in vivo. As utilized throughout, the term "infection" encompasses all phases of pathogenic life cycles including, but not limited to, attachment to cellular receptors, entry, internalization, disassembly, replication, genomic integration of pathogenic sequences, transcription of pathogen RNA, translation of pathogen RNA, transcription of host cell mRNA, translation of host cell mRNA, proteolytic cleavage of pathogenic proteins or cellular proteins, assembly of particles, endocytosis, cell lysis, budding, and egress of the pathogen from the cells.

The compounds described herein can be provided in a pharmaceutical composition. Depending on the intended mode of administration, the pharmaceutical composition can be in the form of solid, semi-solid or liquid dosage forms, such as, for example, tablets, suppositories, pills, capsules, powders, liquids, or suspensions, preferably in unit dosage form suitable for single administration of a precise dosage. The compositions will include a therapeutically effective amount of the compound described herein or derivatives thereof in combination with a pharmaceutically acceptable carrier and, in addition, may include other medicinal agents, pharmaceutical agents, carriers, or diluents. By pharmaceutically acceptable is meant a material that is not biologically or otherwise undesirable, which can be administered to an individual along with the selected agent without causing unacceptable biological effects or interacting in a deleterious manner with the other components of the pharmaceutical composition in which it is contained.

As used herein, the term carrier encompasses any excipient, diluent, filler, salt, buffer, stabilizer, solubilizer, lipid, stabilizer, or other material well known in the art for use in pharmaceutical formulations. The choice of a carrier for use in a composition will depend upon the intended route of administration for the composition. The preparation of pharmaceutically acceptable carriers and formulations containing these materials is described in, e.g., Remington's Pharmaceutical Sciences, 21st Edition, ed. University of the Sciences in Philadelphia, Lippincott, Williams & Wilkins, Philadelphia Pa., 2005. Examples of physiologically acceptable carriers include buffers such as phosphate buffers, citrate buffer, and buffers with other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN® (ICI, Inc.; Bridgewater, N.J.), polyethylene glycol (PEG), and PLURONICS™ (BASF; Florham Park, N.J.).

Compositions containing the compound(s) described herein suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispensing agents. Prevention of the action of microorganisms can be promoted by various antibacterial and antifungal agents, for example, parabens, chlorobutanol, phenol, sorbic acid, and the like. Isotonic agents, for example, sugars, sodium chloride, and the like may also be included. Prolonged absorption of the injectable pharmaceutical form can be brought about by the use of agents delaying absorption, for example, aluminum monostearate and gelatin.

Solid dosage forms for oral administration of the compounds described herein or derivatives thereof include capsules, tablets, pills, powders, and granules. In such solid dosage forms, the compounds described herein or derivatives thereof is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, carboxymethylcellulose, alignates, gelatin, polyvinylpyrrolidone, sucrose, and acacia, (c) humectants, as for example, glycerol, (d) disintegrating agents, as for example, agar-agar, calcium carbonate, potato or tapioca starch, alginic acid, certain complex silicates, and sodium carbonate, (e) solution retarders, as for example, paraffin, (f) absorption accelerators, as for example, quaternary ammonium compounds, (g) wetting agents, as for example, cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar as well as high molecular weight polyethyleneglycol s, and the like.

Solid dosage forms such as tablets, dragees, capsules, pills, and granules can be prepared with coatings and shells, such as enteric coatings and others known in the art. They may contain opacifying agents and can also be of such composition that they release the active compound or compounds in a certain part of the intestinal tract in a delayed manner. Examples of embedding compositions that can be used are polymeric substances and waxes. The active compounds can also be in micro-encapsulated form, if appropriate, with one or more of the above-mentioned excipients.

Liquid dosage forms for oral administration of the compounds described herein or derivatives thereof include pharmaceutically acceptable emulsions, solutions, suspensions, syrups, and elixirs. In addition to the active compounds, the liquid dosage forms may contain inert diluents commonly used in the art, such as water or other solvents, solubilizing agents, and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil, sesame oil, glycerol, tetrahydrofurfuryl alcohol, polyethyleneglycols, and fatty acid esters of sorbitan, or mixtures of these substances, and the like.

Besides such inert diluents, the composition can also include additional agents, such as wetting, emulsifying, suspending, sweetening, flavoring, or perfuming agents.

Administration can be carried out using therapeutically effective amounts of the agents described herein for periods of time effective to treat or prevent infection in a subject. The effective amount may be determined by one of ordinary skill in the art and includes exemplary dosage amounts for a mammal of from about 0.5 to about 200 mg/kg of body weight of active compound per day, which may be administered in a single dose or in the form of individual divided doses, such as from 1 to 4 times per day. Alternatively, the dosage amount can be from about 0.5 to about 150 mg/kg of body weight of active compound per day, about 0.5 to 100 mg/kg of body weight of active compound per day, about 0.5 to about 75 mg/kg of body weight of active compound per day, about 0.5 to about 50 mg/kg of body weight of active compound per day, about 0.5 to about 25 mg/kg of body weight of active compound per day, about 1 to about 20 mg/kg of body weight of active compound per day, about 1 to about 10 mg/kg of body weight of active compound per day, about 20 mg/kg of body weight of active compound per day, about 10 mg/kg of body weight of active compound per day, or about 5 mg/kg of body weight of active compound per day.

According to the methods taught herein, the subject is administered an effective amount of the compound. The terms effective amount and effective dosage are used interchangeably. The term effective amount is defined as any amount necessary to produce a desired physiologic response. Effective amounts and schedules for administering the agent may be determined empirically, and making such determinations is within the skill in the art. The dosage ranges for administration are those large enough to produce the desired effect in which one or more symptoms of the disease or disorder are affected (e.g., reduced or delayed). The dosage should not be so large as to cause substantial adverse side effects, such as unwanted cross-reactions, anaphylactic reactions, and the like. Generally, the dosage will vary with the activity of the specific compound employed, the metabolic stability and length of action of that compound, the species, age, body weight, general health, sex and diet of the subject, the mode and time of administration, rate of excretion, drug combination, and severity of the particular condition and can be determined by one of skill in the art. The dosage can be adjusted by the individual physician in the event of any contraindications. Dosages can vary, and can be administered in one or more dose administrations daily, for one or several days. Guidance can be found in the literature for appropriate dosages for given classes of pharmaceutical products.

Any appropriate route of administration can be employed, depending on whether local or systemic treatment is desired, and on the area to be treated. The compositions are administered via any of several routes of administration, including topically, orally, parenterally, intravenously, intra-articularly, intraperitoneally, intramuscularly, subcutaneously, intracavity, transdermally, intrahepatically, intracranially, nebulization/inhalation, or by installation via bronchoscopy. Optionally, the composition is administered by oral inhalation, nasal inhalation, or intranasal mucosal administration. Administration of the compositions by inhalant can be through the nose or mouth via delivery by spraying or droplet mechanism, for example, in the form of an aerosol. Pharmaceutical compositions can be delivered locally to the area in need of treatment, for example by topical application or local injection. Multiple administrations and/or dosages can also be used. Effective doses can be extrapolated from dose-response curves derived from in vitro or animal model test systems.

The disclosure also provides a pharmaceutical pack or kit comprising one or more containers filled with one or more of the ingredients of the pharmaceutical compositions. Optionally associated with such container(s) can be a notice in the form prescribed by a governmental agency regulating the manufacture, use or sale of pharmaceuticals or biological products, which notice reflects approval by the agency of manufacture, use or sale for human administration. Instructions for use of the composition can also be included.

Also provided is a method of removing biofilm from a surface, comprising administering an effective amount of one or more of the compounds provided herein to a biofilm-containing surface, wherein the amount is effective to remove biofilm from the surface. Removal of the biofilm from this surface does not have to be complete as this can range from a reduction to complete removal of the biofilm. Thus, in the disclosed methods, removal can refer to a 10%, 20%, 30%, 40%, 50%, 60%, 70%, 80%, 90%, or 100% reduction in the amount of biofilm on a surface. For example, a method for removing biofilm from a surface is considered to be removal if there is a 10% reduction in the amount of biofilm on the surface as compared to a control. A control surface can be a biofilm containing surface that has not received a compound set forth herein. Thus, the reduction can be a 10%, 20%, 30%, 40%, 50%, 60%, 70%, 80%, 90%, 100%, or any percent reduction in between 10% and 100% as compared to control.

Further provided is a method of preventing biofilm formation on a surface comprising administering an effective amount of one or more of the compounds provided herein to the surface, wherein the amount is effective to prevent biofilm formation. The surface can be susceptible to biofilm formation. The biofilm can be produced by an organism selected from the group consisting of bacteria, algae, fungi and protozoa.

The compound can be, but is not limited to, a compound of Formula I

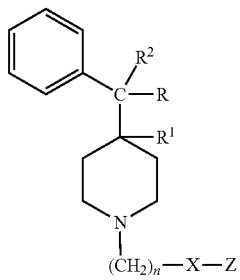

(I)

wherein R represents hydrogen or hydroxyl and $R^1$ represents hydrogen, or R and $R^1$ taken together form a second bond between the carbon atoms bearing R and R'; $R^2$ represents hydrogen or phenyl; n is zero or a positive whole integer of from 1 to 4; X represents $CH_2$, CHOH, NH, C=O, $CHNR^3R^4$, where $R^3$ and $R^4$ independently are hydrogen or lower alkyl; and Z represents thienyl, pyridinyl, substituted pyridinyl, phenyl or substituted phenyl wherein the substituents on the substituted pyridinyl or substituted phenyl are selected from phenyl, pyridinyl, nitro, a halogen atom, such as chlorine, fluorine, bromine, or iodine, a straight or branched lower alkyl chain of from 1 to 4 carbon atoms, a lower alkoxy group of from 1 to 4 carbon atoms, amino, a mono or di(lower)alkylamino group, a saturated monocyclic heterocyclic group such as pyrrolidino, piperidino, morpholino, or N-(lower)alkylpiperazino, or a group having the structure $-COOR^5$, $-CR^6R^7COOR^5$, $-CF_3$, $CHF_2$, $CH_2F$, or

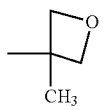

where $R^5$ is hydrogen or lower alkyl, and $R^6$ and $R^7$ independently are hydrogen or methyl
or a pharmaceutically acceptable salt thereof.

One or more of the compounds set forth herein can be combined with one or more biodegradable polymers to form a biodegradable antimicrobial composition. These compositions can be applied to a surface or used as a coating. The biodegradable polymers include but are not limited to polylactic acid, polyglycolic acid and copolymers and mixtures thereof such as poly(L-lactide) (PLLA), poly(D,L-lactide) (PLA), polyglycolic acid [polyglycolide (PGA)], poly(L-lactide-co-D,L-lactide) (PLLA/PLA), poly(L-lactide-co-glycolide) (PLLA/PGA), poly(D,L-lactide-co-glycolide) (PLA/PGA), poly(glycolide-co-trimethylene carbonate) (PGA/PTMC), poly(D,L-lactide-co-caprolactone) (PLA/PCL) and poly(glycolide-co-caprolactone) (PGA/PCL); polyethylene oxide (PEO), polydioxanone (PDS), polypropylene fumarate, poly(ethyl glutamate-co-glutamic acid), poly(tert-butyloxy-carbonylmethyl glutamate), polycaprolactone (PCL), polycaprolactone co-butylacrylate, polyhydroxybutyrate (PHBT) and copolymers of polyhydroxybutyrate, poly(phosphazene), polyphosphate ester), poly (amino acid), polydepsipeptides, maleic anhydride copolymers, polyiminocarbonates, poly [(97.5% dimethyltrimethylene carbonate)-co-(2.5% trimethylene carbonate)], poly(orthoesters), tyrosine-derived polyarylates, tyrosine-derived polycarbonates, tyrosine-derived polyiminocarbonates, tyrosine-derived polyphosphonates, polyethylene oxide, polyethylene glycol, polyalkylene oxides, hydroxypropylmethylcellulose, polysaccharides such as hyaluronic acid, chitosan and regenerate cellulose, and proteins such as gelatin and collagen, and mixtures and copolymers thereof, among others as well as PEG derivatives or blends of any of the foregoing.

In the methods of removing or preventing biofilm formation, the surface can be a hard (for example, glass, metal, wood, chrome, plastic, vinyl or formica) or a soft surface (for example, cloth or upholstery). The methods set forth herein can be used to remove or prevent biofilm formation in vitro, ex vivo or in vivo. The methods set forth herein can also be used to remove or prevent biofilm formation on a medical device or a part thereof. For example, the methods set forth herein can be used to remove or prevent biofilm formation on an implantable medical device such as a cardiac rhythm management device (for example, a pacemaker, a defibrillator, an implantable cardioverter defibrillator (ICD) and a cardiac resynchronization therapy defibrillator (CRT device), a neurostimulator, a pulse generator, a drug pump, an infusion device, a physiological monitoring device (for example, a glucose sensor), contact lenses, a stent, a catheter, tubing or a breast implant. Mesh, bandages, and implantable devices, for example, can be coated with a compositions comprising one or more of the compounds set forth herein. Further, organs can be treated with one or more of the compounds set forth herein prior to transplantation in a subject. One or more of the compounds set forth herein can be used to inhibit biofilm formation by one or more of *Staphylococcus aureus*, *Pseudomonas aeruginosa*, *Staphylococcus epidermidis*, *Escherichia coli* or *Acinetobacter baummanii*.

As utilized herein, by preventing biofilm formation is meant a method of precluding, delaying, averting, obviating, forestalling, stopping, or hindering the onset, incidence, severity, or recurrence of biofilm formation. For example, the disclosed method is considered to be prevention if there is about a 10% reduction in onset, incidence, severity, or recurrence of biofilm formation on a surface when compared to a control surface that did not receive a composition for preventing biofilm formation. Thus, the reduction in onset, incidence, severity, or recurrence of biofilm can be about a 10, 20, 30, 40, 50, 60, 70, 80, 90, 100%, or any amount of reduction in between as compared to a control surface.

A biofilm can also exist or form in a biological subject, for example, on the teeth or gums of a subject. Therefore, one or more of the compounds set forth herein can be in a toothpaste, mouth rinse, gel, foam, varnish, polish, floss, dental strip, or copolymer membrane in order to remove or prevent biofilm formation on a dental surface.

Further provided herein is a method of identifying an antimicrobial agent comprising contacting a bacterial culture with a test agent and measuring adenylate kinase release in the supernatant of the bacterial culture, wherein an increase in adenylate kinase release as compared to a control indicates that the test compound is an antimicrobial agent. The control can be a bacterial culture that was not contacted with the test compound. The bacterial culture can be a culture of any bacterial strain, for example, a culture of any of the bacteria disclosed herein. The bacterial culture can also be small colony variant bacterial culture or a biofilm associated bacterial culture. Examples of agents identified utilizing this method are provided in the Examples.

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutations of these compounds may not be explicitly disclosed, each is specifically contemplated and described herein. For example, if a method is disclosed and discussed and a number of modifications that can be made to a number of molecules including in the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

Publications cited herein and the material for which they are cited are hereby specifically incorporated by reference in their entireties.

The following examples are put forth so as to provide those of ordinary skill in the art with a complete disclosure and description of how the compounds and/or methods claimed herein are made and evaluated, and are intended to be purely exemplary of the invention and are not intended to limit the scope of what the inventors regard as their invention except as and to the extent that they are included in the accompanying claims.

Example I

Identification of Antimicrobial Compounds

Adenylate kinase (AK) is a ubiquitous intracellular enzyme that is released into the extracellular space upon cell lysis. As shown herein, AK release serves as a useful reporter of bactericidal agent activity and can be exploited for antimicrobial screening purposes. The AK assay exhibits improved sensitivity over that of growth-based assays and can detect agents that are active against bacteria in clinically relevant growth states that are difficult to screen using conventional approaches, such as small colony variants (SCV) and bacteria within established biofilms. The usefulness of the AK assay was validated by screening a library of off-patent drugs for agents that exhibit antimicrobial properties toward a variety of bacterial species, including *Escherichia coli* and all members of the "ESKAPE" pathogens (*Enterococcus faecium, Staphylococcus aureus, Klebsiella pneumoniae, Acinetobacter baumannii, Pseudomonas aeruginosa*, and *Enterobacter* species). The assay detected antibiotics within the library that were expected to be active against the organism screened. Moreover, 38 drugs elicited AK release. Examples include, the antihistamine, terfenadine, which was active against *S. aureus* planktonic, SCV population, and biofilm-associated cells, to name a few. Tamoxifen, an estrogen receptor antagonist, was active toward *E. faecium* in vitro and also reduced *E. faecium* pathogenesis in a *Galleria mellonella* infection model.

These data demonstrate that the AK assay provides an attractive screening approach for identifying new antimicrobial agents. Further, drugs identified using this screening approach, for example, terfenadine and tamoxifen, provide novel antimicrobial drug development scaffolds.

The ESKAPE pathogens frequently cause health care-associated bacterial infections and can escape the effects of most currently available antibiotics. The most successful and widely applied method to identify agents with antibacterial activity has been whole-cell, bacterial growth assays. In this approach, libraries of small molecules or natural products are screened for agents that limit bacterial growth. However, growth-based assays have limitations. For example, the growth or no-growth readout has a limited dynamic range. This is likely to be problematic because growth assays lack the sensitivity required to detect antimicrobial molecules that are present in low concentrations within complex natural product extract libraries or compounds with limited antimicrobial activity. While the latter would obviously not represent a molecule that could be directly translated to clinical use, these low-activity hits could provide structurally novel scaffolds suitable for medicinal chemistry-based optimization. In addition, traditional growth-based assays are not readily amenable to screening for agents that target bacteria within certain clinically relevant bacterial growth states, such as established biofilms and small-colony variants.

To address these limitations, provided herein is a high-throughput screen (HTS)-compatible whole-cell assay to detect agents that directly kill bacteria. The assay is based on the release of intracellular adenylate kinase (AK) into culture medium as a reporter of bacterial cell death. As shown herein, the AK assay exhibits improved sensitivity over that of conventional whole-cell growth assays and displays specificity for bactericidal agents. Further, the assay can be used to screen for agents that kill small-colony-variant bacteria and bacteria within established biofilms.

To validate the AK assay as an HTS-compatible screening platform, the Prestwick library of off-patent drugs was screened against *E. coli* and each of the ESKAPE pathogens. This library contains representative examples of nearly all classes of antibiotics, and the bactericidal agents within the library that were expected to be active against the organism screened were identified. Additionally, agents with no previously reported antibiotic activity were identified. Traditional MIC testing confirmed the antimicrobial properties of many of these molecules, showing that they could be repurposed as antimicrobials or serve as lead molecules for antibiotic development. Consistent with that prediction, it was shown that one of these compounds, tamoxifen, is active against *E. faecium* in a *Galleria mellonella* model of infection. Further, it was shown that terfenadine is active against planktonic, small-colony variant, and biofilm-associated *S. aureus*. Taken together, these data demonstrate that the AK assay provides a general approach to screening for new antimicrobial agents active against a variety of pathogens during planktonic and other disease-associated growth states.

Bacterial Growth Conditions—

The bacterial species and strains used in these experiments are listed in Table 1. *S. aureus* strain UAMS-1112 (generous gift from M. Smeltzer, University of Arkansas Medical Center) is a stable small-colony variant of the common laboratory *S. aureus* strain 8325-4, which harbors a hemB deletion. Unless otherwise noted, bacteria were grown for 16 h in Mueller-Hinton (MB) (Becton. Dickinson.

Franklin Lakes, N.J.) or brain heart infusion (BHI) (Becton, Dickinson) medium at 37° C. on a rotary shaker at 225 rotations per min (rpm) and then used to inoculate (1:100) fresh medium and processed, as described below.

TABLE 1

Bacterial Strains

| Species | Strain | Relevant resistance[a] | Source or reference[b] |
|---|---|---|---|
| Enterococcus faecium | 824-05 | Amp, Cf, Cp, Cl, Mp, Tmp, Sul, Erm, Kan | Clinical isolate |
| Staphylococcus aureus | USA300-0114 | Amp, Cf, Cl, Sul, Kan | 6 |
| | UAMS-1 | ND | 7 |
| | UAMS-1112 | Erm | Univ. of Arkansas |
| | RN4220 | Cl | 8 |
| Klebsiella pneumoniae | cKP1 | Amp, Cp, Sul, Erm, Van | 9 |
| Acinetobacter baumannii | 98-37-09 | Amp, Lz | 10 |
| Pseudomonas aeruginosa | PA01 | Amp, Kan, Lz, Sul, Van | 11 |
| Enterobacter cloacae | PMD1001 | Amp, Erm, Lz, Sul, Van | Clinical isolate |
| Escherichia coli | 8295 | Erm, Lz, Sul | Clinical isolate |

[a]Abbreviations: ampicillin, Amp; colistin, Cl; ceftriaxone, Cf; ciprofloxacin, Cp; erythromycin, Erm; kanamycin, Kan; linezolid, Lz; meropenem, Mp; minocycline, Min; Sulfamethoxazole, Sul; vancomycin, Van; not determined, ND; Univ., university.
[b]Clinical isolates were obtained from the University of Rochester School of Medicine and Dentistry.

Chemicals—

The Prestwick Chemical Library of molecules with known biological activities was acquired from Prestwick Chemical (Illkirch, France). ToxiLight BioAssay kits were obtained to from Lonza (Basel, Switzerland). Terfenadine, suloctidil, clomiphene citrate, ceftriaxone, sulfamethoxazole, erythromycin, kanamycin, ciprofloxacin, rifampin, ampicillin, minocycline, tamoxifen, and trimethoprim were purchased from Sigma-Aldrich (St. Louis, Mo.). Meropenem, linezolid, and vancomycin were purchased from Thermo Fisher (Waltham, Mass.). Colistin was purchased from APP Pharmaceuticals (Schaumburg, Ill.).

MIC Testing—

MIC testing was performed to determine the antibiotic susceptibility profile of selected bacterial strains according to Clinical and Laboratory Standards (CLSI) protocols (Hindler et al. Antimicrobial susceptibility testing, section 5. Clinical microbiology procedures handbook, Vol. 1 America Society of Microbiology. Washington, D.C. (2010). Briefly, colonies of each bacterial species were collected from MH agar plates and suspended in individual tubes of MH medium to an optical density (600 nm) of 0.8. The resulting cultures were incubated at 37° C. in a rotary shaker at 225 rpm to exponential phase ($\sim 1 \times 10^8$ CFU ml$^{-1}$) and then diluted in fresh MH medium to a cell density of $\sim 3 \times 10^7$ CFU ml$^{-1}$. Ten microliters of the diluted cultures was added to 88 µl of MH medium in individual wells of a 96-well, round-bottom plate (Corning, Inc.), and 2 µl of a stock solution of the indicated reference antibiotic or test compound (0 to 256 µg ml$^{-1}$) was added to each well. The carrier solvent was either water or dimethyl sulfoxide (DMSO); final DMSO concentrations were less than or equal to 2%. Plates were incubated at 37° C. for 24 h, and the MIC was defined as the lowest concentration of antibiotic in which there was no visible cell pellet in the wells.

Heat-Killed Bacterial AK Release Assays—

Overnight cultures of E. coli strain 8295 or S. aureus RN4220 were used to inoculate (1:100 dilution) 25 ml of fresh MH medium and grown at 37° C. on a rotary shaker at 225 rpm to exponential phase ($\sim 1 \times 10^8$ CFU ml$^{-1}$). Cells were pelleted by centrifugation (2,000×g) and resuspended in 2.5 ml of sterile water. One milliliter of the resulting suspension was boiled for 3 min and filter sterilized (0.45-µm filter) to remove cell debris. The filtrate was serially diluted in sterile water, and 100 µl of each dilution was added to individual wells of a white-walled, 96-well plate (Corning, Inc., Corning, N.Y.). To measure the AK activity in the supernatants at each dilution, 100 µl of ToxiLight AK reagent was added to each well, followed by incubation at room temperature for 30 min, and luminescence was measured using a SpectraMax M5 plate reader (Molecular Devices, Sunnyvale, Calif.). Cells were serially diluted and plated to enumerate CFU (CFU ml$^{-1}$) before and after boiling to correlate cell lysis with viability.

AK Assay 96-Well Format—

Overnight cultures of each bacterial species were used to inoculate (1:100 dilution) 25 ml of fresh MH medium and grown at 37° C. on a rotary shaker at 225 rpm to exponential phase ($\sim 1 \times 10^8$ CFU ml$^{-1}$) Ninety-eight microliters of MH medium, 2 µl of the indicated antibiotic, and $5 \times 10^6$ bacteria were added to individual wells of a white-walled, 96-well microtiter plate. Well components were mixed by pipetting and incubated at 37° C. for 3 h. The plate was equilibrated to room temperature for 30 min. Next, 100 µl of ToxiLight AK reagent was added to each well and incubated at room temperature for 30 min, and luminescence was measured using a SpectraMax M5 plate reader.

AK Assay 384-Well Format and High-Throughput Screening—

Overnight cultures of each bacterial species were used to inoculate (1:100 dilution) 25 ml of fresh medium and grown at 37° C. on a rotary shaker at 225 rpm to exponential phase ($\sim 1 \times 10^8$ CFU ml$^{-1}$). In a white-walled, 384-well plate, 24 µl of MH medium, 0.3 µl (50 µM) of antibiotic or compound, and $5 \times 10^6$ bacteria were added to individual wells and incubated at 37° C. for 3 h. The plates were equilibrated at room temperature for 1 h. Twenty-five microliters of ToxiLight AK reagent was then added to each well, followed by incubation at room temperature for 30 min, and luminescence was measured using a SpectraMax M5 plate reader.

AK Assay of Established Biofilms—

Biofilms were grown as previously described (Beenken et al. Infect. Immun. 71: 4206-4211 (2003); Musken et al. Nat. Protoc. 5: 1460-1459 (2010); Tomaras et al. Microbiology 149: 3473-3483 (2003)). Briefly, P. aeruginosa and A. baumannii were cultured overnight in Luria-Bertani medium and then used to seed 96-well, flat-bottom plates. Plates were incubated at 37° C. in a humidified incubator for 48 h to allow the formation of static biofilms. Nonadherent cells were removed by aspiration and washing with sterile phosphate-buffered saline (PBS). Fresh LB medium supplemented with 0, 1, 10×, or 100×MIC of antibiotic was added to each well and incubated overnight at 37° C. Following treatment, 100 µl of each biofilm supernatant was transferred to 96-well, white-walled plates, 100 µl of ToxiLight AK reagent was added to each well, mixtures were incubated for 30 min at room temperature, and luminescence was measured using a SpectraMax M5 plate reader. Biofilm-associated bacteria were enumerated by resuspending each biofilm in fresh PBS and plating. For S. aureus UAMS-1 biofilms, 96-well, flat-bottom plates were first coated with 100 µl of 20% human plasma in carbonate buffer overnight at 4° C.

Following coating, the plasma solution was removed and cells were inoculated in each well 1:200 in 100 µl of tryptic soy broth supplemented with 3% glucose and 0.5% NaCl. Biofilms were cultured for 48 h in a humidified incubator at 37° C. Established *S. aureus* biofilms were washed once with PBS and then treated with a 100 µl of ToxiLight lysis buffer for 3 h, after which the amount of AK released into supernatants was measured, as described above.

Small-Colony Variant AK Assays—

Thirty-six-hour cultures of *S. aureus* strain UAMS-1112 were used to inoculate (1:100 dilution) 100 ml of fresh MH medium and grown at 37° C. on a rotary shaker at 225 rpm to an optical density (600 nm) of 0.1 to 0.2, corresponding to $\sim 1 \times 10^6$ CFU ml$^{-1}$. Cells were pelleted by centrifugation and resuspended in 2 ml of fresh MH medium. Ninety-eight microliters of MH medium containing $5 \times 10^6$ bacteria and 2 µl of the indicated antibiotic were added to individual wells of a white-walled, 96-well microtiter plate. Well components were mixed by pipetting and incubated at 37° C. for 3 h. The plate was equilibrated to room temperature for 30 min. Next, 100 µl of ToxiLight AK reagent was added to each well, followed by incubation at room temperature for 30 min, and luminescence was measured using a SpectraMax M5 plate reader.

*Galleria mellonella* Model of *S. aureus* Infection—

A *Galleria mellonella* model of infection was used to measure the putative antimicrobial properties of tamoxifen against *E. faecium* and terfenadine against *S. aureus*. To do so, overnight cultures of *E. faecium* strain 824-05 or *S. aureus* strain USA300-0114 were used to inoculate (1:100 dilution) 25 ml of fresh MH medium and grown at 37° C. on a rotary shaker at 225 rpm to exponential phase ($\sim 1 \times 10^8$ CFU ml$^{-1}$). Cultures were pelleted by centrifugation (2,000×g), washed with sterile PBS, and resuspended at $\sim 1 \times 10^9$ CFU ml$^{-1}$ in fresh PBS. *Galleria mellonella* larvae (Vanderhorst Wholesale, Inc., St. Marys, Ohio) weighing 200 to 300 mg were inoculated with 5 µl of *E. faecium* or *S. aureus* ($5 \times 10^6$ CFU) into the last left proleg using a 10-µl Hamilton syringe. Worms were then mock treated with either DMSO (negative control), vancomycin (20 mg kg$^{-1}$ positive control) at 2 h and 24 h postinoculation. For *K. faecium* studies, groups were also treated with the test compound tamoxifen at 80, 160, or 320 mg kg$^{-1}$, whereas groups were treated with the test compound terfenadine (80, 160, or 320 mg kg$^{-1}$) for *S. aureus* studies. Treatments were administered in the same manner as infection, except that each injection was in the next left proleg moving toward the head of the worm. Larvae were housed in petri dishes in the dark at 37° C. and monitored for viability at the conclusion of the study (48 h postinoculation); worms were considered dead if they did not respond to physical stimuli. In addition to mock or compound treatment of infected larvae, studies included two additional noninfected negative-control groups: one group that did not receive injections and one group that was injected with PBS to control for the impact of physical trauma. All experimental groups contained 15 worms, and each experiment was repeated three times.

Rationale for Adenylate Kinase as a Reporter of Bacterial Cell Lysis—

Adenylate kinase (AK) is a ubiquitous intracellular enzyme that catalyzes the conversion of 2 ADP↔ATP+AMP and is released into the extracellular space upon cell lysis. The premise of the assay is that agents which disrupt cellular integrity, either directly through damage of the membrane/cell wall or indirectly following the death of the cell, will induce release of AK into the culture medium. Extracellular AK is subsequently detected by the addition of commercially available ToxiLight AK assay reporter cocktail (Lonza, Basel, Switzerland), which generates a luminescent signal by utilizing AK-generated ATP in the standard luciferase catalyzed reaction (see FIG. 1). As shown herein, an AK assay was developed as a high-throughput screening platform for antibacterial drug discovery.

The AK Assay Provides a Sensitive Measure of Bacterial Lysis—

As an initial test of AK release as a reporter of bacterial cell death for Gram-positive and Gram-negative organisms, the sensitivity with which the assay measures AK in the culture supernatants of heat-killed *E. coli* and *S. aureus* was determined. Each bacterial species was grown to exponential phase, harvested, and resuspended at $1 \times 10^9$ CFU per ml in Mueller-Hinton (MH) medium. Bacterial suspensions were heat killed, and a 10-fold dilution series of supernatants was prepared; an aliquot of each heat-killed sample was plated to ensure ≥99° % bacterial death. The AK activity of the dilution series was measured and compared to the AK activity of mock-treated (viable) bacteria by Student's t test. In comparison to untreated cells, a statistically significant increase in AK activity was detected at dilutions containing $1.7 \times 10^3$ or more heat-killed *E. coli* supernatants, compared to results for live bacteria (see FIG. 2A). AK activity increased ~433-fold and ~1,574-fold in cultures with $1 \times 10^7$ and $1 \times 10^8$ heat-killed *E. coli* supernatants, respectively, compared to results for mock-treated bacteria. A comparison of AK released from heat-killed *S. aureus* to that of mock-treated cells revealed a statistically significant difference in AK activity was detected at dilutions containing $1.8 \times 10^4$ or more heat-killed *S. aureus* supernatants, with a maximum 122-fold increase in AK activity observed for $1 \times 10$ lysed cells. Taken together, these results indicate that the AK assay reproducibly detects AK release following bacterial cell lysis and that the assay is extremely sensitive, allowing the identification of agents that cause lysis in 0.0001% or 0.001% of the starting inoculum of *E. coli* or *S. aureus* cells, respectively. Furthermore, the AK assay exhibited a dynamic range of nearly 3 orders of magnitude and an excellent signal-to-noise ratio.

The AK Assay Detects Bactericidal Molecules that are Active Against the ESKAPE Pathogens—

Figure 2:
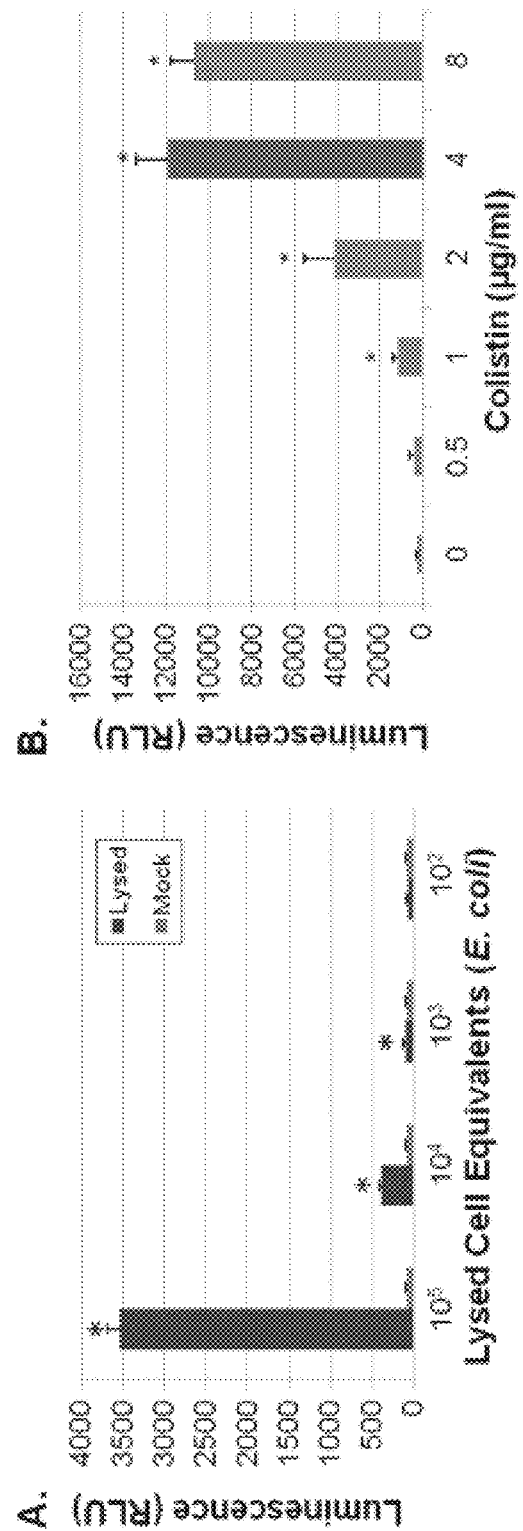
FIG. 2 shows AK assay development. (A) AK assay measures of *E. coli* lysed cell supernatants. *E. coli* DH5α cells (1×10$^9$) were heat inactivated by boiling and diluted, and the AK assay was used to measure adenylate kinase release. Background signal is also shown (mock-treated cells (right-hand column in FIG. 2A). "*" indicates a significant difference between results for boiled and mock treatment (Student's t test; P≤0.05). (B) AK assay results for colistin-treated *A. baumannii* strain 98-37-09. Cells were treated with the indicated concentration of colistin, and AK was measured; MIC (4 μg ml$^{-1}$ is indicated. "*" indicates a significant increase in signal compared to that for mock treatment (0 μg ml$^{-1}$; Student's t test, P≤0.05).

Next, ability of the AK assay to detect the activities of bactericidal antibiotics toward *E. coli* and each of the ESKAPE pathogens was examined. To do so, the MICs of six classes of bactericidal antibiotics (penicillin, cephalosporin, quinolone, glycopeptide, carbapenem, and polymyxin) were determined for each organism (see Table 2). An AK assay was then performed at 0, 0.125×, 0.25×, 0.5×, 1×, and 2×MIC of each antibiotic. As discussed below, AK release was detected at antibiotic concentrations below the MIC for most antibiotics tested, showing that the AK assay is more sensitive than growth-based assays for detecting bactericidal agents. As a representative example, FIG. 2B presents the AK assay measured polymyxin (colistin)-mediated killing of *A. baumannii* strain 98-37-09. The MIC of colistin for this strain is 4 µg ml$^{-1}$, whereas AK release was robustly detected at 0.25×, 0.5×, and 1×MIC value.

TABLE 2

MIC and AK measures of bacterial species and antibiotic combinations[a]

| | | Bactericidal | | | | | | Bacteriostatic | | | | |
|---|---|---|---|---|---|---|---|---|---|---|---|---|
| | Treatment | | | | | | | | | | | |
| Strain and parameter | (×MIC) | Ampicillin | Ceftriaxone | Ciprofloxacin | Vancomycin | Meropenem | Colistin | Sulfamethoxazole | Minocycline | Erythromycin | Kanamycin | Linezolid |
| *Enterococcus faecium* 824-05 | | | | | | | | | | | | |
| MIC | | >256 | >256 | 256 | 2 | >256 | >256 | >256 | 1 | >256 | >256 | 16 |
| Fold increase in AK signal | 0.5 | ND | ND | ND | 1 | ND | ND | ND | 3 | ND | ND | 2 |
| | 1.0 | ND | ND | ND | 2 | ND | ND | ND | 4 | ND | ND | 2 |
| *Staphylococcus aureus* USA300-0114 | | | | | | | | | | | | |
| MIC | | >256 | >256 | 2 | 1 | 4 | >256 | >256 | 1 | 64 | >256 | 2 |
| Fold increase in AK signal | 0.5 | ND | ND | 3 | 11 | 13 | ND | ND | 1 | 1 | ND | 1 |
| | 1.0 | ND | ND | 5 | 3 | 17 | ND | ND | 1 | 1 | ND | 1 |
| RN4220 | | | | | | | | | | | | |
| MIC | | 2 | 2 | 2 | 2 | 2 | >256 | 2 | 8 | 2 | 16 | 2 |
| Fold increase in AK signal | 0.5 | 4 | 10 | 8 | 3 | 11 | ND | 2 | 1 | 1 | 1 | 1 |
| | 1.0 | 3 | 12 | 10 | 6 | 11 | ND | 3 | 1 | 1 | 1 | 1 |
| *Klebsiella pneumoniae* cKP1 | | | | | | | | | | | | |
| MIC | | >256 | 2 | >256 | >256 | 2 | 8 | >256 | 64 | >256 | 2 | >256 |
| Fold increase in AK signal | 0.5 | ND | 50 | ND | ND | 128 | 34 | ND | 1 | ND | 1 | ND |
| | 1.0 | ND | 55 | ND | ND | 220 | 33 | ND | 1 | ND | 1 | ND |
| *Acinetobacter baumannii* 98-37-09 | | | | | | | | | | | | |
| MIC | | 256 | 8 | 0.0625 | 64 | 2 | 4 | 8 | 1 | 16 | 2 | 256 |
| Fold increase in AK signal | 0.5 | ND | 5 | 2 | 2 | 79 | 17 | 6 | 23 | 3 | 3 | ND |
| | 1.0 | ND | 21 | 2 | 4 | 134 | 49 | 5 | 14 | 12 | 14 | ND |

TABLE 2-continued

MIC and AK measures of bacterial species and antibiotic combinations[a]

| | | Bactericidal | | | | | | Bacteriostatic | | | | |
|---|---|---|---|---|---|---|---|---|---|---|---|---|
| Strain and parameter | Treatment (×MIC) | Ampicillin | Ceftriaxone | Ciprofloxacin | Vancomycin | Meropenem | Colistin | Sulfamethoxazole | Minocycline | Erythromycin | Kanamycin | Linezolid |
| *Pseudomonas aeruginosa* PA01 | | | | | | | | | | | | |
| MIC | | >256 | 4 | 2 | >256 | 2 | 4 | 256 | 32 | 32 | 256 | >256 |
| Fold increase in AK signal | 0.5 | ND | 2 | 27 | ND | 45 | 5 | ND | 1 | 3 | ND | ND |
| | 1.0 | ND | 14 | 182 | ND | 39 | 12 | ND | 6 | 1 | ND | ND |
| *Enterobacter cloacae* PMD1001 | | | | | | | | | | | | |
| MIC | | >256 | 2 | <1 | >256 | 2 | 2 | >256 | 4 | 256 | 2 | >256 |
| Fold increase in AK signal | 0.5 | ND | 20 | 6 | ND | 99 | 10 | ND | 4 | ND | 1 | ND |
| | 1.0 | ND | 17 | 7 | ND | 296 | 32 | ND | 9 | ND | 1 | ND |
| *Escherichia coli* 8295 | | | | | | | | | | | | |
| MIC | | 128 | 2 | 0.125 | 16 | 2 | 8 | >256 | 16 | 256 | 32 | >256 |
| Fold increase in AK signal | 0.5 | 50 | 51 | 17 | 1 | 60 | 15 | ND | 4 | ND | 55 | ND |
| | 1.0 | 74 | 76 | 39 | 2 | 85 | 22 | ND | 38 | ND | 70 | ND |
| % increase expected | 0.5 | 100 | 83.3 | 83.3 | 40 | 100 | 100 | 50 | 50 | 50 | 40 | 0 |
| | 1.0 | 100 | 100 | 83.3 | 60 | 100 | 100 | 100 | 62.5 | 25 | 40 | 0 |

[a]Shading indicates significant increase in AK signal (greater than or equal to threefold over vehicle-treated cells).

The MIC measures for each ESKAPE pathogen and each organism's corresponding fold increase in AK signal following treatment with 0.5× and 1.0×, the MIC are provided in Table 2 (bactericidal agents). For four of the six bactericidal antibiotics tested, the AK assay proved to be superior to growth-based assays with respect to detecting the killing properties of bactericidal agents at sub-MIC values. More specifically, 100% of the organisms that were determined to be susceptible to the cell wall-active antibiotics ampicillin, meropenem, and colistin exhibited a significant increase in AK signal (≥3-fold over that for vehicle-treated cells) at both 0.5× and 1.0× their MICs Eighty-three percent and 100% of ceftriaxone-susceptible species exhibited increased AK signal at 0.5× and 1× their MICs, respectively. Five of six (83%) ciprofloxacin-susceptible organisms exhibited AK signal at both 0.5× and 1.0×MIC. Interestingly, the cell wall-targeted glycopeptide, vancomycin, caused significant AK release at 0.5× and 1.0× their MICs in only 40% and 60% of susceptible species.

Figure 3:
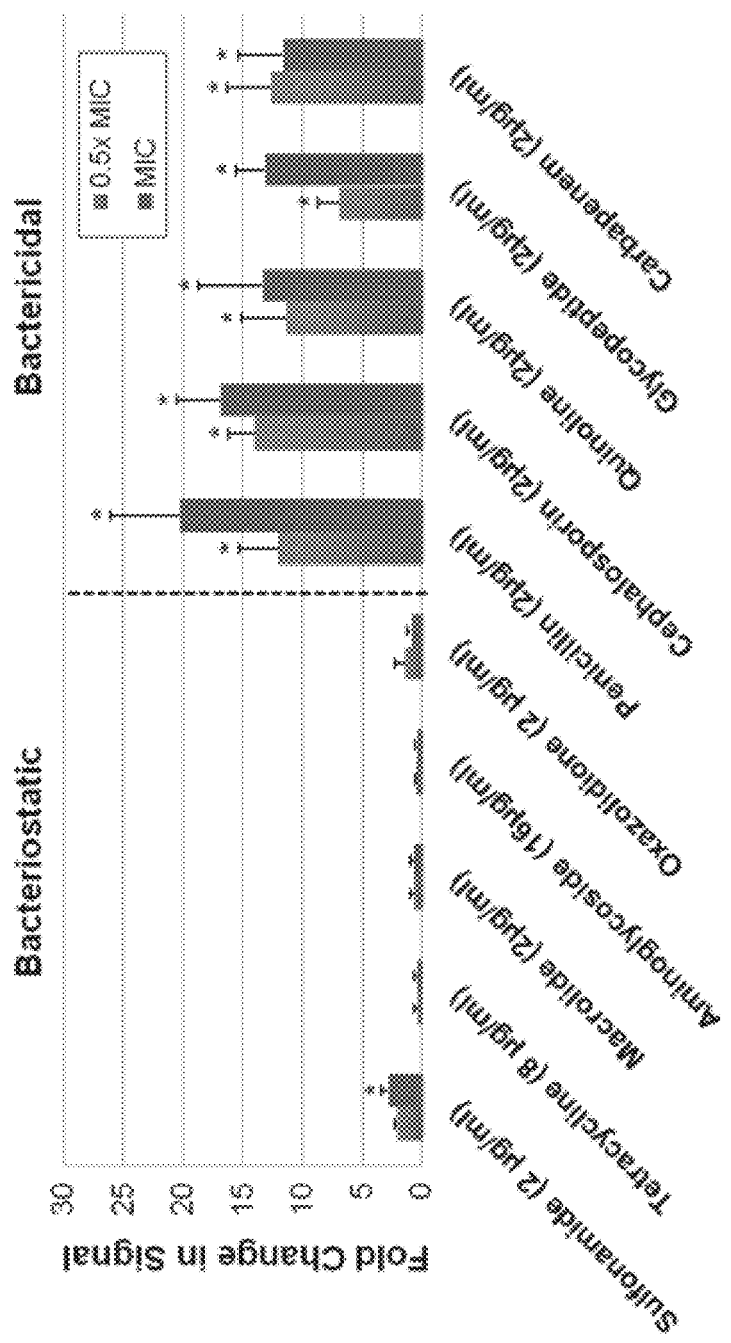
FIG. 3 shows AK assay measures of *S. aureus* strain RN4220 treatment with bacteriostatic and bactericidal antibiotics. Standard MIC testing determined the MIC of each antibiotic class (in parentheses). Graphed are the fold changes in AK signal of cells treated with 0.5× or 1.0× the MIC value (left hand column and right hand column, respectively) for each antibiotic, in comparison to untreated control cells; "*" indicates a significant change in signal as determined by Student's t test; P≤0.05 (compared to results for untreated cells).

To evaluate the specificity of the assay for detecting bactericidal agents, measured AK release by each of the ESKAPE pathogens following exposure to five classes of bacteriostatic agents (sulfonamide, tetracycline, macrolide, aminoglycoside, and oxazolidine) was also measured. To do this, the MIC value of each bacteriostatic antibiotic/organism pair was measured by a conventional growth-based approach. AK release by each bacterial species following treatment with 0.5× or 1.0×MIC of each bacteriostatic agent was subsequently measured. As shown in FIG. 3, S. aureus strain RN4220 was susceptible to all agents tested but bacteriostatic agents generated very low AK release, whereas bactericidal antibiotics generated robust AK detection. In most instances, a similar trend was observed for the other ESKAPE pathogens, indicating that the assay enriches for the identification of bactericidal agents, which are arguably the most valuable antibiotics because they can be used to treat patients with immunological defects or rapidly lethal infections (Table 2, bacteriostatic agents). Two exceptions were noted. Surprisingly, A. baumannii generated significant AK signal in response to all the bacteriostatic agents evaluated, showing that AK release may be a feature of a more general stress response in this organism. Additionally, the bacteriostatic agent minocycline generated signal by five of the eight (63%) organisms tested.

Taken together, these results show that the AK assay provides a viable screening approach for identifying bactericidal agents at sub-MICs that could otherwise be missed by growth-based assays. Further, because the AK assay relies on bacterial killing as opposed to growth changes to generate its readout, it was hypothesized that it would provide a format to develop screens that are not readily available by conventional, growth-based approaches.

Use of the AK Assay to Identify Agents with Antimicrobial Activities Against Established Biofilms and Small Colony Variants—

Established bacterial biofilms represent a particularly problematic disease state, in part because biofilm-associated bacteria are recalcitrant to conventional antibiotic therapy. Thus, they have been a focus of antibiotic development. As a result, a number of approaches to screening for molecules with activity toward bacterial biofilms have been developed recently (Benoit et al. Environ. Microb. 76: 4136-4142; Perez et al. Lett. App. Microb. 51:331-337 (2010)). Although each has its advantages, they also have a number of limitations, including reproducibility, reliance on specialized equipment, or low throughput. It was hypothesized that the AK assay would provide a solution to some of these problems because it is rapid, sensitive, and simple to perform and it detects bactericidal molecules, the type of antibiotics required to treat established biofilms.

Figure 4:
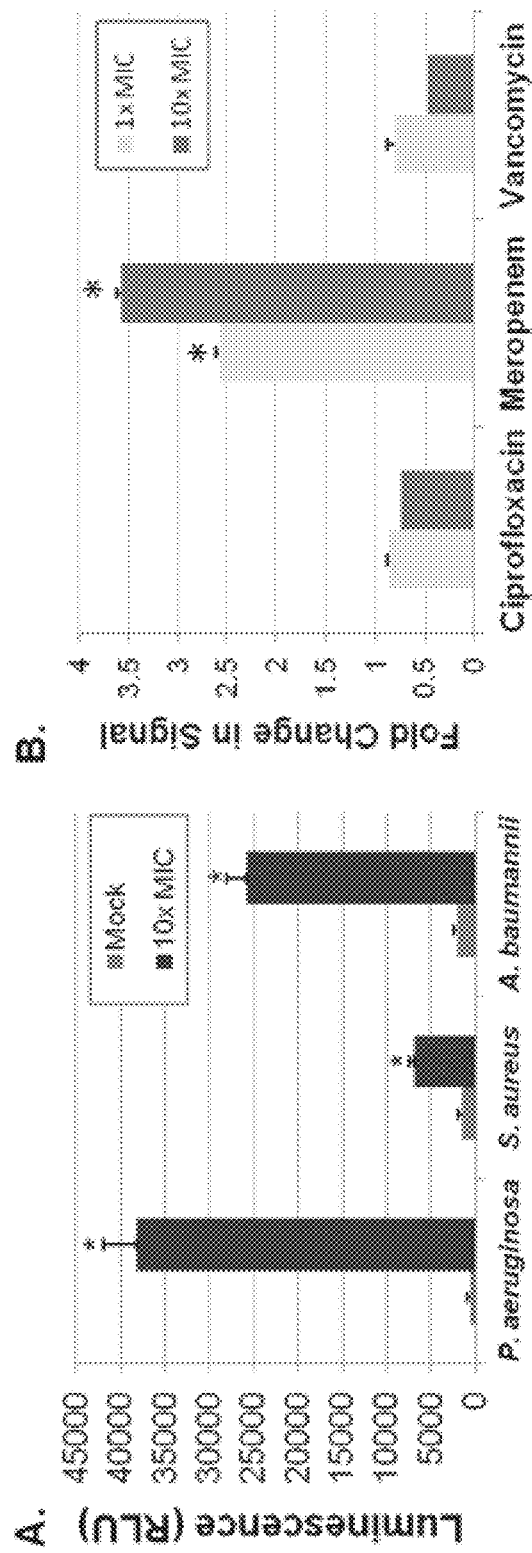
FIG. 4 shows AK assay measures of antibiotic-treated biofilms and small-colony variants. (A) Graphed are AK signals generated by static biofilm-associated cells following mock or antibiotic treatment: colistin (*P. aeruginosa*) or ciprofloxacin (*S. aureus* and *A. baumannii*). (B) Fold change of AK measures of *S. aureus* SCV UAMS-1112 cells following treatment with 1× and 10× ciprofloxacin, meropenem, and vancomycin, compared to results for mock treated cells. "*" indicates a significant change in signal in comparison to results for mock-treated cells (Student's t test, P≤0.05).

To determine whether the AK assay could detect agents with activity against established biofilms, S. aureus strain UAMS-1, A. baumannii strain 98-37-09, and P. aeruginosa strain PAO1 static biofilms were formed in 96-well flat-bottom plates Forty-eight hours postinoculation, one well corresponding to each organism was stained with crystal violet to verify that biofilm formation had occurred, whereas the remaining wells were treated with 10× the MIC value with either colistin (A. baumannii biofilms) or ciprofloxacin (P. aeruginosa, and S. aureus biofilms). Following overnight antibiotic treatment, biofilm-associated bacteria were enumerated by plating, and the corresponding supernatants were analyzed by the AK assay. Plating verified that 10×MIC antibiotic treatment resulted in a significant reduction in biofilm-associated P. aeruginosa (a 3.1-log decrease), S. aureus (a 0.7-log decrease), and A. baumannii (a 1.8-log decrease) compared to findings for untreated biofilms. As shown in FIG. 4A, corresponding AK measures indicated that the assay robustly detects the mild effects of these antibiotics on each bacterial species tested, showing that it represents a promising approach to identify agents that exhibit bactericidal activity toward established bacterial biofilms.

Another context in which the AK assay can be particularly valuable is in the identification of molecules that exhibit bactericidal activity toward bacterial small-colony variants (SCV). SCV are slow-growing populations of bacterial species that have been hypothesized to cause latent or recurrent infections and are tolerant of standard antibiotic treatment regimens. Based on the aberrant SCV growth characteristics, typical growth-based HTS assays would be difficult to employ. Accordingly, the ability of the AK assay to identify agents that kill S. aureus SCV strain UAMS-1112 was tested. To do so, $1 \times 10^6$ UAMS-1112 cells were treated with 1× or 10×MIC ciprofloxacin, meropenem, or vancomycin for 3 h. Following treatment, suspensions were plated to measure the antimicrobial properties of each antibiotic, and the AK assay was performed to measure adenylate kinase release. Plating revealed that ciprofloxacin and vancomycin had no effect on SCV viability at any concentration tested and exhibited no change in AK release in comparison to results for mock-treated cells (FIG. 4B), supporting the observation that S. aureus small-colony variants are recalcitrant to antibiotic treatment. Meropenem treatment resulted in a 0.5-log decrease in SCV viability, which corresponded to a 2.5-fold increase in AK signal compared to that for mock-treated cells (FIG. 4B). Taken together, these results show that the AK assay provides the sensitivity needed to detect the slight antimicrobial effects of antibiotics, such as meropenem, toward S. aureus SCV.

Validation of AK as an HTS-Compatible Assay of Antibacterial Activity—

Figure 5:
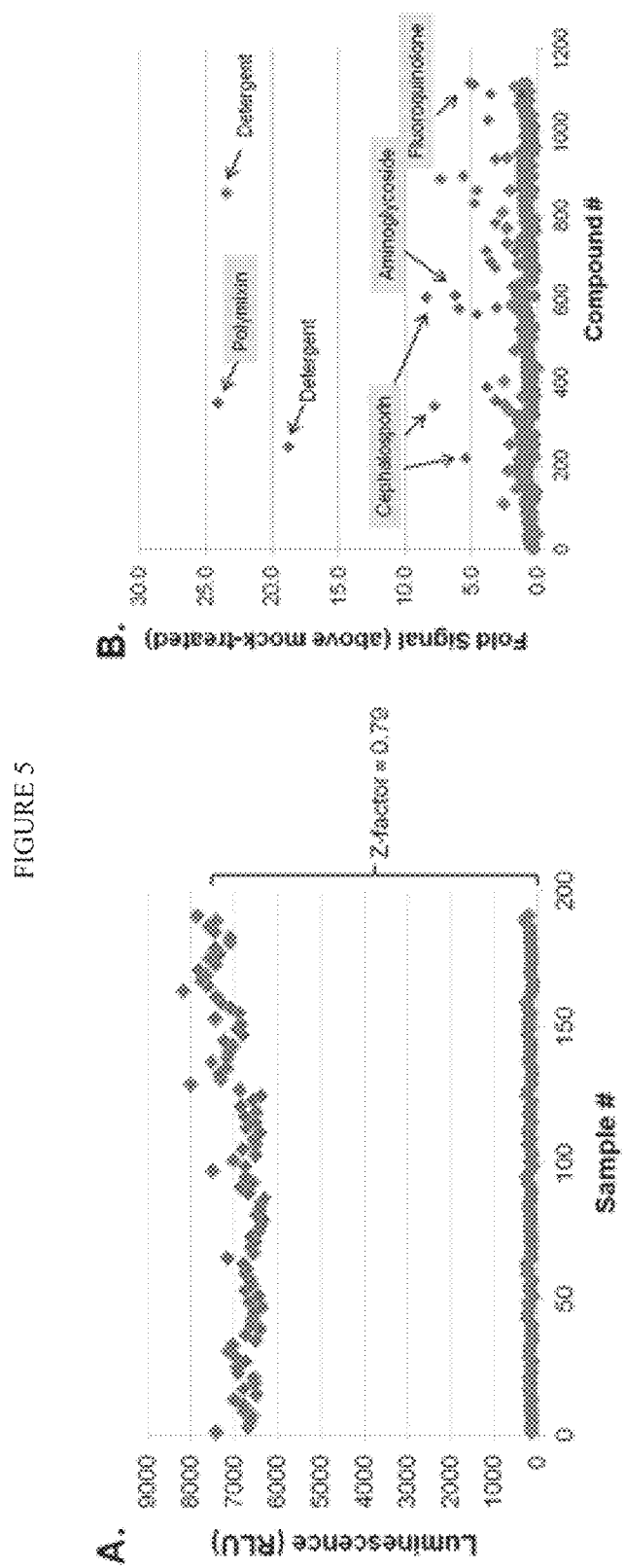
FIG. 5 shows AK-based HTS development and screening. (A) Z' factor assay results for *Klebsiella pneumoniae*. Three-hundred-eighty-four-well microtiter plates were seeded with *K. pneumoniae*, and alternating rows were mock treated (DMSO) or treated with 50 μM colistin. Following 3 h of incubation, AK release was measured and plotted. DMSO-treated well measures are shown at the bottom of FIG. 5A; colistin-treated wells are shown at the top of FIG. 5A. (B) Prestwick library *Klebsiella pneumoniae* screening results. In total, 26 compounds were determined to result in a 3-fold increase in AK signal, in comparison to results for DMSO-treated cells. Included among this list were polymyxin, cephalosporins, aminoglycosides, fluoroquinolones, and detergents; the complete Prestwick screening results for *K. pneumoniae* and all other organisms screened are provided in Table 4.

To test the viability of the AK assay as a general tool in HTS-based antibacterial small-molecule discovery, optimized assay parameters, including inoculum, drug incubation time, and AK reaction time, for screening planktonic ESKAPE species as well as E. coli in a 384-well format were determined. Based on these experiments, a standardized assay, as described above, was developed. As part of this optimization process, control assays in a 384-well format were performed to measure the signal to noise and reproducibility of the assay in an HTS manner. For this, plates were seeded with E. coli or an ESKAPE pathogen. Alternating columns of the plate were then mixed with either 2% DMSO (negative control) or a bactericidal antibiotic (positive control), and AK signal was detected, a representative result for DMSO- and colistin-treated K. pneumoniae is shown in FIG. 5A. Comparisons of the variance in signal between positive- and negative-control measures indicated that the AK assay provides Z'-factor scores between 0.59 and 0.82 (depending on the specific organism), indicating that the assay is sufficiently robust for HTS.

AK-Based Screening of Library of Off-Patent Drugs and Biologically Active Molecules—

To further validate the AK assay protocol, E. coli and each of the ESKAPE pathogens was screened against the Prestwick library of FDA-approved drugs and biologically active molecules (1,120 compounds, total; 50 μM final drug concentration). The Prestwick library contains representatives of nearly all classes of antibiotics currently in clinical use, making it an ideal library for testing the ability of the AK assay to detect bactericidal agents in a high-throughput screening format. Accordingly, the library was screened for antimicrobial agents that were active against planktonic E. coli and each of the ESKAPE pathogens using the AK assay; the cutoff for positive-scoring molecules was set at a 3-fold increase in extracellular AK activity, corresponding to the detection limit of statistically significant increases in AK activity for planktonic bacteria. The hit rates for the different organisms ranged from 1.4% to 4.8%; a representative example of raw screening data for *Klebsiella pneumoniae* is shown in FIG. 5B. Screening results for all ESKAPE pathogens are summarized in Table 3, whereas results for all compounds within the Prestwick library are provided in Table 4.

TABLE 3

Preswick library screening results

| Compound | No. of active agents for species | | | | | | |
|---|---|---|---|---|---|---|---|
| | E. coli | E. faecium | S. aureus[a] | K. pneumoniae | A. baumannii[a] | P. aeruginosa | E. cloacae |
| Bactericidal | 45 | 4 | 25 | 19 | 17 | 21 | 16 |
| Bacteriostatic | 2 | 1 | 14 | 0 | 7 | 0 | 1 |
| Detergent | 2 | 2 | 2 | 2 | 2 | 1 | 0 |
| Other | 5 | 9 | 10 | 4 | 18 | 1 | 12 |
| Total | 54 | 16 | 51 | 25 | 44 | 23 | 29 |

[a]Tetracyclines were identified.

TABLE 4

AK-based Prestwick Library Screening Results.

| E. coli | E. faecium | S. aureus | K. pneumoniae | A. baumannii | P. aeruginosa | E. cloacae | Chemical name | Mechanism | Therapeutic group |
|---|---|---|---|---|---|---|---|---|---|
| 0.4 | 0.8 | 0.6 | 0.3 | 0.3 | 0.3 | 0.3 | Azaguanine-8 | Purine antimetabolite | Antineoplastic |
| 0.4 | 0.8 | 0.4 | 0.4 | 0.4 | 0.3 | 0.3 | Metronidazole | Bacterial DNA damage | Antibacterial |
| 0.4 | 0.7 | 1.4 | 0.4 | 0.4 | 0.3 | 0.3 | Allantoin | Precipitate proteins | Vulnerary |
| 0.4 | 0.8 | 0.4 | 0.4 | 0.3 | 0.3 | 0.3 | Cotinine (−) | — | Antidepressant |
| 0.5 | 0.9 | 0.4 | 0.4 | 0.4 | 0.3 | 0.3 | Acetazolamide | Carbonic anhydrase inhibitor | Diuretic |
| 0.4 | 0.9 | 0.4 | 0.4 | 0.4 | 0.4 | 0.3 | Edrophonium chloride | Cholinergic | Myasthenia Gravis test |
| 0.5 | 0.8 | 0.4 | 0.4 | 0.4 | 0.4 | 0.3 | Metformin hydrochloride | — | Antidiabetic |
| 0.5 | 0.8 | 0.4 | 0.4 | 0.4 | 0.3 | 0.3 | Moroxidine hydrochloride | — | Antiviral |
| 0.5 | 0.8 | 0.5 | 0.5 | 0.4 | 0.3 | 0.3 | Atracurium besylate | Neuromuscular blocking agent | Curarizing agent |
| 0.5 | 0.8 | 0.4 | 0.6 | 0.4 | 0.4 | 0.3 | Baclofen (R,S) | GABAb agonist | Antispasmodic |
| 0.5 | 0.9 | 0.4 | 0.5 | 0.4 | 0.3 | 0.3 | Isoflupredone acetate | — | Anti-inflammatory |
| 0.5 | 0.9 | 0.5 | 0.5 | 0.4 | 0.4 | 0.4 | Acyclovir | ADN polymerase inhibitor | Antiviral |
| 0.5 | 0.8 | 0.4 | 0.4 | 0.4 | 0.4 | 0.3 | Amiloride hydrochloride dihydrate | Antialdosteron | Diuretic |
| 0.5 | 0.9 | 0.5 | 0.4 | 0.4 | 0.4 | 0.4 | Diazoxide | Activator of ATP-dependent K+ channels | Antihypertensor |
| 0.5 | 0.9 | 0.5 | 0.6 | 0.5 | 0.4 | 0.4 | Amprolium hydrochloride | Thiamine transport inhibitor | Coccidiostatic |
| 0.5 | 0.9 | 0.4 | 0.5 | 0.4 | 0.4 | 0.4 | Amidopyrine | ACTH secretor | Antipyretic |
| 0.5 | 1.1 | 0.5 | 0.6 | 0.5 | 0.5 | 0.4 | Hydrochlorothiazide | Na+ Cl− transport inhibitor | Diuretic |
| 0.4 | 2.8 | 0.1 | 0.4 | 0.5 | 0.4 | 0.5 | Ursolic acid | — | Diuretic |
| 0.5 | 1.0 | 0.5 | 0.6 | 0.5 | 0.4 | 0.4 | Sulfaguanidine | Inhibitor of folic acid synthesis | Antibacterial |
| 0.5 | 1.0 | 0.5 | 0.6 | 0.5 | 0.4 | 0.4 | Pindolol | Beta adrenergic antagonist | Antiarrhythmic |
| 0.5 | 1.0 | 0.7 | 0.6 | 0.6 | 0.6 | 0.6 | Isoniazid | — | Antibacterial |
| 0.6 | 0.9 | 0.7 | 0.6 | 0.5 | 0.7 | 0.7 | Mexiletine hydrochloride | Na+ channel blocker | Antiarrhythmic |
| 0.6 | 1.0 | 0.7 | 0.5 | 0.6 | 0.7 | 0.6 | Pentylenetetrazole | GABA antagonist | CNS stimulant |
| 0.5 | 0.9 | 0.6 | 0.6 | 0.5 | 0.6 | 0.6 | Flavoxate hydrochloride | Phosphodiesterase inhibitor | Antispasmodic |
| 0.6 | 0.9 | 0.5 | 0.5 | 0.6 | 0.6 | 0.6 | Chlorzoxazone | — | Muscle relaxant |
| 0.6 | 0.9 | 0.4 | 0.5 | 0.5 | 0.6 | 0.6 | Bufexamac | — | Antiinflammatory |
| 0.6 | 0.9 | 0.5 | 0.5 | 0.6 | 0.6 | 0.6 | Ornidazole | Bacterial DNA damage | Antibacterial |
| 0.6 | 0.9 | 0.5 | 0.5 | 0.6 | 0.6 | 0.5 | Glutethimide, para-amino | Aromatase inhibitor | Antineoplasic |
| 0.6 | 0.9 | 0.5 | 0.6 | 0.5 | 0.5 | 0.6 | Ethosuximide | Ca++ channel inhibitor voltage dependant | Anticonvulsant |
| 0.7 | 0.9 | 0.5 | 0.5 | 0.5 | 0.5 | 0.5 | Dropropizine (R,S) | — | Antitussive |
| 0.6 | 1.2 | 0.6 | 0.5 | 0.5 | 0.5 | 0.6 | Mafenide hydrochloride | Inhibitor of folic acid biosynthesis | Antibacterial |
| 0.5 | 0.9 | 0.5 | 0.5 | 0.5 | 0.6 | 0.6 | Pinacidil | K+ channel Ca++ dependant activator | Vasodilator |
| 0.2 | 0.3 | 0.2 | 0.2 | 0.2 | 0.2 | 0.5 | Riluzole hydrochloride | Glutamate antagonist | Neuroprotective |
| 0.3 | 0.5 | 0.2 | 0.3 | 0.3 | 0.3 | 0.4 | Albendazole | — | — |
| 0.4 | 1.0 | 0.4 | 0.8 | 0.5 | 0.4 | 0.6 | Nitrofurantoin | Bacterial DNA damage | Urinary antiseptic |
| 0.5 | 0.9 | 0.5 | 0.5 | 0.6 | 0.4 | 0.6 | Clonidine hydrochloride | Alpha2 agonist | Antihypertensor |
| 0.0 | 0.3 | 0.2 | 0.0 | 0.1 | 0.5 | 0.3 | Hydralazine hydrochloride | Adrenergic antagonist | Antihypertensor |
| 0.5 | 1.0 | 0.5 | 0.5 | 0.5 | 0.5 | 0.5 | Bupropion hydrochloride | — | Antidepressant |
| 0.5 | 0.8 | 0.5 | 0.6 | 0.5 | 0.5 | 0.5 | Phenelzine sulfate | MAO inhibitor | Antidepressant |
| 0.6 | 0.9 | 0.6 | 0.5 | 0.7 | 0.5 | 0.4 | Alprenolol hydrochloride | Beta1 antagonist | Antihypertensor |
| 0.6 | 0.9 | 0.8 | 0.6 | 0.8 | 0.6 | 0.7 | Meticrane | — | Antihypertensor |
| 0.6 | 0.9 | 0.7 | 0.6 | 0.7 | 0.6 | 0.7 | Khellin | Na+ channel blocker | Phototherapeutic agent |
| 0.7 | 0.8 | 0.7 | 0.6 | 0.7 | 0.7 | 0.7 | Benzonatate | — | Antitussive |

TABLE 4-continued

AK-based Prestwick Library Screening Results.

| E. coli | E. faecium | S. aureus | K. pneumoniae | A. baumannii | P. aeruginosa | E. cloacae | Chemical name | Mechanism | Therapeutic group |
|---|---|---|---|---|---|---|---|---|---|
| 0.7 | 0.9 | 0.8 | 0.5 | 0.7 | 0.6 | 0.8 | Zimelidine dihydrochloride monohydrate | 5-HT uptake inhibitor | Antidepressant |
| 0.7 | 0.9 | 0.5 | 0.5 | 0.7 | 0.5 | 0.7 | Hydroflumethiazide | Na+ Cl− transport inhibitor | Antihypertensor |
| 0.6 | 0.9 | 0.7 | 0.6 | 0.6 | 0.6 | 0.9 | Azacyclonol | H1 antagonist | Anxiolytic |
| 0.6 | 0.9 | 0.7 | 0.5 | 2.2 | 0.5 | 0.7 | Sulfacetamide sodic hydrate | — | Antipsoriasic |
| 0.6 | 0.8 | 0.7 | 0.5 | 0.7 | 0.5 | 0.8 | Azathioprine | Antimetabolite | Immunosuppressant |
| 0.8 | 0.9 | 0.5 | 0.5 | 0.6 | 0.5 | 0.7 | Heptaminol hydrochloride | — | Antihypotensive |
| 0.7 | 0.9 | 0.5 | 0.6 | 1.4 | 0.6 | 0.7 | Lynestrenol | Antioestrogen | Progestogen |
| 0.7 | 0.9 | 0.6 | 0.6 | 1.0 | 0.6 | 0.7 | Sulfathiazole | Inhibitor of folic acid synthesis | Antibacterial |
| 0.7 | 1.0 | 0.5 | 0.4 | 0.8 | 0.6 | 0.7 | Guanabenz acetate | Alpha agonist | Antihypertensor |
| 0.6 | 0.8 | 0.5 | 0.6 | 0.7 | 0.5 | 0.8 | Levodopa | Tyrosine aminotransferase inhibitor | Antiparkinsonian |
| 0.9 | 1.0 | 1.1 | 0.6 | 1.0 | 0.6 | 0.7 | Disulfiram | Dopamine beta-hydroxylase inhibitor | Alcohol deterrent |
| 0.7 | 1.0 | 0.7 | 0.6 | 0.7 | 0.6 | 0.8 | Idoxuridine | Nucleic acid synthesis inhibitors | Antiviral |
| 0.6 | 1.0 | 0.7 | 0.6 | 0.7 | 0.6 | 0.8 | Acetylsalicylsalicylic acid | Cyclooxygenase inhibitor | Antinflammatory |
| 0.7 | 1.0 | 0.7 | 0.6 | 0.8 | 0.6 | 0.8 | Captopril | Angiotensive converting enzyme inhibitor | Antihypertensor |
| 0.7 | 0.9 | 0.7 | 0.6 | 0.8 | 0.8 | 0.7 | Mianserine hydrochloride | 5-HT antagonist | Antidepressant |
| 0.6 | 1.0 | 0.7 | 0.6 | 0.8 | 0.6 | 0.8 | Minoxidil | K+ channel activator | Antihypertensor |
| 0.7 | 1.0 | 0.6 | 0.5 | 0.6 | 0.6 | 0.7 | Nocodazole | Microtubule poison | Antineoplastic |
| 0.8 | 1.1 | 0.7 | 0.7 | 0.8 | 0.9 | 0.9 | Tranexamic acid | Plasminogen inhibitor | Hemostatic |
| 0.9 | 1.0 | 0.8 | 0.7 | 0.9 | 0.8 | 0.9 | Chlorothiazide | Na+ Cl− transport inhibitor | Antihypertensor |
| 0.8 | 1.0 | 0.7 | 0.6 | 0.8 | 0.8 | 0.9 | Etofylline | Phosphodiesterase inhibitor | Cardiac analeptic |
| 0.8 | 1.0 | 0.7 | 0.7 | 0.7 | 0.8 | 0.8 | Diphenidol hydrochloride | — | Antivertigo |
| 0.8 | 1.0 | 0.8 | 0.6 | 0.9 | 0.8 | 0.9 | Tranylcypromine hydrochloride | MAO inhibitor | Antidepressant |
| 0.8 | 1.0 | 0.8 | 0.7 | 0.7 | 0.7 | 0.9 | Norethindrone | — | Progestogen |
| 0.9 | 0.9 | 0.7 | 0.7 | 0.9 | 0.8 | 0.9 | Alverine citrate salt | Anticholinergic | Spasmolytic |
| 0.9 | 0.9 | 1.0 | 0.7 | 0.9 | 0.8 | 0.9 | Nortriptyline hydrochloride | Norepinephrine uptake inhibitor | Antidepressant |
| 0.7 | 1.0 | 0.7 | 0.6 | 0.7 | 0.8 | 0.8 | Aceclofenac | Cyclooxygenase inhibitor | Antinflammatory |
| 0.6 | 0.9 | 0.7 | 0.6 | 0.7 | 0.7 | 0.8 | Niflumic acid | Prostaglandine synthesis inhibitor | Analgesic |
| 0.8 | 1.0 | 1.0 | 0.7 | 0.7 | 0.7 | 0.8 | Iproniazide phosphate | Monoamine oxydase inhibitor (non selective) | Antidepressant |
| 0.7 | 1.0 | 0.6 | 0.6 | 0.7 | 0.8 | 0.9 | Isotretinoin | — | Cystic acne |
| 0.7 | 1.0 | 0.7 | 0.6 | 1.3 | 0.7 | 0.7 | Sulfamethoxazole | — | — |
| 0.7 | 1.0 | 0.8 | 0.7 | 0.8 | 0.7 | 0.9 | Retinoic acid | — | Keratolytic |
| 0.7 | 1.0 | 0.8 | 0.7 | 0.8 | 0.6 | 0.9 | Mephenesin | — | Muscle relaxant |
| 0.7 | 1.0 | 0.8 | 0.6 | 0.8 | 0.6 | 0.8 | Antazoline hydrochloride | H1 antagonist | Antihistaminic |
| 0.8 | 1.0 | 0.7 | 0.6 | 0.8 | 0.7 | 0.8 | Phenformin hydrochloride | Neoglucogenese inhibitor | Antidiabetic |
| 0.7 | 1.3 | 1.4 | 0.6 | 0.8 | 0.7 | 0.8 | Ethacrynic acid | Na+ Cl− uptake inhibitor | Diuretic |
| 0.7 | 1.0 | 0.4 | 0.6 | 0.7 | 0.8 | 0.7 | Flutamide | Androgenic receptor antagonist | Anticancer |
| 0.9 | 1.0 | 0.8 | 0.6 | 0.7 | 0.6 | 0.7 | Praziquantel | Modulates cell membrane permeability | Anthelmintic |

TABLE 4-continued

AK-based Prestwick Library Screening Results.

| E. coli | E. faecium | S. aureus | K. pneumoniae | A. baumannii | P. aeruginosa | E. cloacae | Chemical name | Mechanism | Therapeutic group |
|---|---|---|---|---|---|---|---|---|---|
| 0.8 | 0.8 | 0.8 | 0.7 | 1.4 | 0.8 | 0.8 | Sulfaphenazole | Inhibitor of folic acid synthesis | Antibacterial |
| 0.8 | 0.8 | 0.9 | 0.8 | 0.8 | 0.6 | 0.9 | R(−)Apomorphine hydrochloride hemihydrate | D1 agonist | Emetic |
| 0.9 | 0.8 | 0.6 | 0.7 | 0.8 | 0.7 | 1.0 | Panthenol (D) | — | Vitamin |
| 1.0 | 0.9 | 0.7 | 0.8 | 0.8 | 0.9 | 0.9 | Amoxapine | Dopamine-reuptake inhibitor | Antidepressant |
| 1.0 | 0.8 | 0.7 | 0.7 | 1.2 | 0.8 | 0.9 | Sulfadiazine | Inhibitor of folic acid synthesis | Antibacterial |
| 0.9 | 0.9 | 0.6 | 0.6 | 0.9 | 0.9 | 0.9 | Cyproheptadine hydrochloride | 5-HT antagonist | Antipruritic |
| 0.9 | 0.9 | 0.7 | 0.7 | 0.7 | 0.8 | 1.0 | Norethynodrel | — | Progestogen |
| 0.9 | 0.8 | 0.5 | 0.8 | 0.8 | 0.8 | 0.9 | Famotidine | H2 histaminic antagonist | Antiulcerative |
| 0.9 | 0.9 | 8.7 | 0.4 | 0.9 | 0.8 | 1.4 | Thiamphenicol | Ribosomal protein synthesis inhibitor | Antibacterial |
| 0.7 | 0.9 | 0.6 | 0.6 | 0.9 | 0.8 | 0.9 | Danazol | Estrogen antagonist | Antigonadotropin |
| 0.9 | 0.9 | 0.8 | 0.7 | 0.8 | 0.8 | 1.0 | Cimetidine | H2 antagonist | Antiulcer |
| 0.9 | 0.9 | 0.6 | 0.8 | 0.8 | 0.7 | 0.9 | Nicorandil | — | Antihypertensor |
| 0.8 | 0.9 | 0.7 | 0.6 | 0.8 | 0.8 | 1.0 | Doxylamine succinate | H1 antagonist | Antihistaminic |
| 0.8 | 1.0 | 0.8 | 0.7 | 1.0 | 0.8 | 1.1 | Tomatine | — | Antifungal |
| 0.9 | 0.9 | 0.6 | 0.7 | 0.8 | 0.7 | 1.1 | Ethambutol dihydrochloride | Chelating agent | Antibacterial |
| 0.9 | 0.9 | 0.7 | 0.7 | 0.8 | 0.8 | 1.0 | Nomifensine maleate | Dopamine uptake inhibitor | Antidepressant |
| 0.9 | 1.0 | 0.7 | 0.7 | 1.0 | 0.8 | 1.0 | Antipyrine | — | Analgesic |
| 0.9 | 0.9 | 0.7 | 0.7 | 0.8 | 0.9 | 1.0 | Dizocilpine maleate | Probe for NMDA receptors | — |
| 0.9 | 1.0 | 0.7 | 0.7 | 0.8 | 0.8 | 1.0 | Antipyrine, 4-hydroxy | — | Antipyrine metabolite |
| 0.9 | 0.9 | 0.8 | 0.7 | 0.8 | 0.9 | 0.9 | Acenocoumarol | Vitamin K antagonist | Anticoagulant |
| 0.9 | 0.9 | 0.8 | 0.7 | 0.9 | 1.0 | 1.0 | Ampyrone | — | Analgesic |
| 0.9 | 0.9 | 0.8 | 0.8 | 0.9 | 1.0 | 1.1 | Ethisterone | — | Progestogen |
| 1.0 | 1.0 | 0.9 | 0.7 | 1.1 | 1.0 | 1.0 | Levamisole hydrochloride | Alkaline phosphatase inhibitor | Immunomodulator |
| 1.0 | 1.0 | 0.6 | 0.7 | 0.9 | 1.0 | 1.0 | Triprolidine hydrochloride | H1 antagonist | Antihistaminic |
| 1.0 | 0.9 | 0.8 | 0.8 | 0.9 | 1.0 | 0.9 | Pargyline hydrochloride | Monoamine oxidase inhibitor | Antihypertensor |
| 1.1 | 1.0 | 0.9 | 0.8 | 0.9 | 1.1 | 1.0 | Doxepin hydrochloride | Adrenaline uptake inhibitor | Anticonvulsant |
| 0.9 | 0.9 | 0.8 | 0.6 | 0.9 | 0.9 | 1.0 | Methocarbamol | — | Muscle relaxant |
| 1.0 | 0.9 | 0.9 | 0.7 | 0.9 | 1.0 | 1.1 | Dyclonine hydrochloride | Na+ channel blocker | Local anesthesic |
| 15.9 | 1.0 | 0.6 | 2.6 | 5.4 | 9.1 | 18.4 | Aztreonam | Bacterial transpeptidase inhibitor | Antibacterial |
| 1.0 | 0.8 | 0.8 | 0.7 | 0.8 | 1.0 | 1.2 | Dimenhydrinate | H1 antogonist | Antihistaminic |
| 1.0 | 1.0 | 5.3 | 0.7 | 1.3 | 1.0 | 1.0 | Cloxacillin sodium salt | Bacterial transpeptidase inhibitor | Antibacterial |
| 0.9 | 0.9 | 0.9 | 0.6 | 0.9 | 0.9 | 1.0 | Disopyramide | Na+ channel blocker | Antiarrhythmic |
| 1.0 | 1.0 | 0.8 | 0.8 | 0.8 | 0.7 | 1.0 | Catharanthine | — | Antihypertensor |
| 1.0 | 1.3 | 2.0 | 1.0 | 3.3 | 1.0 | 1.0 | Clotrimazole | Specific inhibitor of Ca2+ activated K+ channels | Antibacterial |
| 0.8 | 0.9 | 0.7 | 0.7 | 1.0 | 1.0 | 1.1 | Pentolinium bitartrate | Ganglionic blocking agent | Antihypertensor |
| 0.9 | 1.0 | 0.8 | 0.8 | 0.9 | 1.0 | 1.0 | Vinpocetine | Phosphodiesterase inhibitor | Nootropic drug |
| 0.9 | 0.9 | 0.7 | 0.8 | 0.8 | 0.9 | 1.1 | Aminopurine, 6-benzyl | Inhibitor of respiratory kinase in plants | |

TABLE 4-continued

AK-based Prestwick Library Screening Results.

| E. coli | E. faecium | S. aureus | K. pneumoniae | A. baumannii | P. aeruginosa | E. cloacae | Chemical name | Mechanism | Therapeutic group |
|---|---|---|---|---|---|---|---|---|---|
| 1.1 | 1.1 | 0.8 | 0.7 | 1.0 | 0.9 | 1.0 | Clomipramine hydrochloride | Noradrenaline reuptake inhibitor | Antidepressant |
| 0.8 | 1.0 | 0.7 | 0.8 | 0.9 | 0.9 | 1.0 | Tolbutamide | K+ channel ATP dependant inhibitor | Hypoglycemic |
| 1.0 | 1.1 | 0.8 | 0.8 | 1.5 | 1.1 | 0.9 | Fendilline hydrochloride | Ca++ channel activator | Antianginal |
| 0.7 | 0.8 | 9.7 | 0.2 | 1.0 | 0.8 | 1.5 | Chloramphenicol | Ribosomal peptidyltransferase inhibitor | Antibacterial |
| 0.9 | 0.8 | 0.7 | 0.6 | 0.8 | 0.8 | 1.1 | Naloxone hydrochloride | Opiate antagonist | Opiate antidote |
| 1.0 | 0.8 | 2.2 | 0.6 | 0.9 | 0.8 | 1.2 | Epirizole | — | Antiinflammatory |
| 0.8 | 0.8 | 0.7 | 0.6 | 0.8 | 0.7 | 1.0 | Metolazone | — | Diuretic |
| 1.0 | 0.9 | 0.7 | 0.6 | 0.8 | 0.7 | 1.1 | Diprophylline | Phosphodiesterase inhibitor | Cardiac analeptic |
| 33.6 | 1.2 | 1.5 | 0.8 | 2.2 | 29.7 | 4.7 | Ciprofloxacin hydrochloride | — | Anti-bacterial |
| 0.6 | 0.7 | 0.6 | 0.5 | 1.1 | 0.6 | 1.2 | Triamterene | Non competitive aldosterone antagonist | Diuretic |
| 12.2 | 1.1 | 0.5 | 0.6 | 1.6 | 0.7 | 3.5 | Ampicillin trihydrate | — | Antibacterial |
| 0.8 | 0.9 | 0.6 | 0.7 | 1.3 | 0.8 | 1.1 | Dapsone | Folic acid antagonist | Antiinflammatory |
| 0.9 | 0.9 | 0.8 | 0.6 | 1.0 | 0.9 | 1.1 | Haloperidol | Dopamine antagonist | Antipsychotic |
| 0.9 | 1.0 | 6.5 | 0.6 | 0.8 | 0.7 | 1.1 | Troleandomycin | Ribosomal protein synthesis inhibitor | Antibacterial |
| 0.9 | 1.0 | 0.7 | 0.6 | 0.9 | 0.8 | 1.3 | Naltrexone hydrochloride dihydrate | Opioid antagonist | Analgesic |
| 1.4 | 0.9 | 0.7 | 0.7 | 2.5 | 0.9 | 1.1 | Pyrimethamine | H1 antagonist | Antimalarial |
| 1.0 | 0.8 | 0.8 | 0.6 | 0.9 | 0.8 | 1.1 | Chlorpheniramine maleate | Ganglion blocking agent | Antihistaminic |
| 0.9 | 0.9 | 0.7 | 0.8 | 0.9 | 0.8 | 1.2 | Hexamethonium dibromide dihydrate | — | Antihypertensor |
| 0.9 | 0.9 | 0.7 | 0.7 | 0.9 | 0.8 | 1.2 | Nalbuphine hydrochloride | Opioid ligand | Analgesic |
| 0.7 | 0.9 | 0.6 | 0.6 | 0.7 | 0.6 | 1.2 | Diflunisal | Cyclooxygenase inhibitor | Antiinflammatory |
| 0.9 | 0.9 | 0.7 | 0.8 | 0.9 | 0.8 | 1.2 | Picotamide monohydrate | Eicosenoid receptor antagonist | Antithrombotic |
| 0.1 | 0.1 | 0.4 | 0.1 | 0.2 | 0.1 | 0.5 | Niclosamide | Helmintic DNA damage | Anthelmintic |
| 1.0 | 1.0 | 0.8 | 0.7 | 0.9 | 0.7 | 1.2 | Triamcinolone | — | Antiinflammatory |
| 1.0 | 1.0 | 0.9 | 0.7 | 0.9 | 0.9 | 1.0 | Midodrine hydrochloride | Alpha adrenergic | Hypotensor |
| 0.9 | 1.0 | 0.7 | 0.7 | 0.9 | 1.0 | 1.2 | Vincamine | — | Cerebral antianoxic |
| 1.0 | 1.0 | 1.0 | 0.8 | 0.9 | 0.9 | 1.1 | Thalidomide | — | Immunosuppressant |
| 0.9 | 0.9 | 0.6 | 0.8 | 1.0 | 0.9 | 1.1 | Indomethacin | Cyclooxygenase inhibitor | Antiinflammatory |
| 13.1 | 1.1 | 1.0 | 1.6 | 2.3 | 1.0 | 4.3 | Oxolinic acid | Topoisomerase II inhibitor | Antibacterial |
| 0.9 | 0.9 | 0.8 | 0.8 | 1.0 | 0.9 | 1.2 | Cortisone | — | Antiinflammatory |
| 0.9 | 0.8 | 0.7 | 0.7 | 0.9 | 0.9 | 1.4 | Nimesulide | Cyclooxygenase 2 inhibitor | Antiinflammatory |
| 1.0 | 1.0 | 0.8 | 0.8 | 1.0 | 0.9 | 1.3 | Prednisolone | — | Glucocorticoid |
| 1.0 | 0.9 | 0.7 | 0.7 | 0.9 | 0.9 | 1.2 | Hydrastinine hydrochloride | Dopamine receptor blocker | Cardiotonic |
| 1.0 | 0.8 | 0.8 | 0.8 | 0.9 | 0.8 | 1.2 | Fenofibrate | Lipoprotein lipase activator | Hypolipidemiant |
| 0.8 | 0.8 | 0.8 | 0.6 | 0.7 | 0.8 | 1.1 | Pentoxifylline | Phosphodiesterase inhibitor | Vasodilator |
| 0.9 | 0.9 | 0.7 | 0.7 | 0.9 | 0.8 | 1.3 | Bumetanide | Vascular cyclooxygenase activator | Diuretic |
| 1.0 | 1.0 | 0.7 | 0.8 | 0.9 | 0.8 | 1.3 | Metaraminol bitartrate | Adrenergic agonist | Vasoconstrictor |
| 0.9 | 0.9 | 0.8 | 0.7 | 0.9 | 0.9 | 1.3 | Labetalol hydrochloride | Beta adrenergic agonist | — |
| 1.0 | 1.0 | 1.0 | 0.8 | 0.9 | 0.8 | 1.4 | Salbutamol | — | Bronchodilatator |
| 0.9 | 1.0 | 0.8 | 0.8 | 2.3 | 0.9 | 1.2 | Cinnarizine | H1 antagonist | Antihistaminic |
| 0.9 | 0.9 | 0.8 | 0.7 | 0.9 | 0.9 | 1.3 | Prilocaine hydrochloride | Na+ channel blocker | Local anesthesic |

TABLE 4-continued

AK-based Prestwick Library Screening Results.

| E. coli | E. faecium | S. aureus | K. pneumoniae | A. baumannii | P. aeruginosa | E. cloacae | Chemical name | Mechanism | Therapeutic group |
|---|---|---|---|---|---|---|---|---|---|
| 0.8 | 1.0 | 0.8 | 0.7 | 0.9 | 0.9 | 1.3 | Methylprednisolone, 6-alpha | — | Glucocorticoid |
| 0.9 | 0.9 | 0.7 | 0.8 | 0.8 | 0.8 | 1.1 | Camptothecine (S,+) | Topoisomerase I inhibitor | Antitumor agent |
| 1.0 | 1.0 | 0.9 | 0.8 | 0.9 | 0.9 | 1.1 | Quinidine hydrochloride monohydrate | Heme polymerase inhibitor | Antiarrhythmic |
| 1.2 | 0.9 | 1.2 | 1.0 | 1.1 | 1.0 | 1.4 | Procaine hydrochloride | Na+ channel blocker | Local anesthesic |
| 1.3 | 0.9 | 0.6 | 1.1 | 1.4 | 1.1 | 1.7 | Bromocryptine mesylate | Prolactin inhibitor | Antiparkinsonian |
| 1.2 | 0.9 | 1.1 | 1.0 | 1.1 | 1.1 | 1.6 | Moxisylyte hydrochloride | Alpha antagonist | Vasodilator |
| 1.3 | 1.0 | 1.2 | 1.0 | 1.1 | 1.1 | 1.3 | Metanephrine hydrochloride DL | Isoprenaline uptake inhibitor extraneuronal | — |
| 1.3 | 1.0 | 1.2 | 0.9 | 1.2 | 1.0 | 1.4 | Betazole hydrochloride | Histamine analog | Gastric secretion stimulant |
| 1.3 | 1.0 | 1.0 | 0.8 | 1.0 | 1.1 | 1.3 | Dehydrocholic acid | — | Choleretic |
| 1.2 | 1.0 | 1.0 | 1.0 | 1.0 | 1.1 | 1.4 | Isoxicam | Cyclooxygenase inhibitor | Antiinflammatory |
| 1.1 | 0.9 | 0.5 | 0.9 | 1.1 | 0.9 | 1.3 | Hesperetin | P450 inhibitor | — |
| 1.2 | 1.0 | 0.8 | 0.9 | 1.1 | 1.1 | 1.4 | Naproxen | Cyclooxygenase inhibitor | Antiinflammatory |
| 1.5 | 1.2 | 0.9 | 1.3 | 1.6 | 1.1 | 1.4 | Perphenazine | Dopamine antagonist | Antipsychotic |
| 1.3 | 1.1 | 1.0 | 0.8 | 1.1 | 1.0 | 1.5 | Naphazoline hydrochloride | Adrenergic ligand | Vasoconstrictor |
| 1.3 | 1.0 | 3.2 | 1.3 | 2.6 | 1.1 | 1.2 | Mefloquine hydrochloride | Heme polymerase inhibitor | Antimalarial |
| 1.3 | 1.0 | 0.8 | 1.0 | 1.1 | 1.1 | 2.0 | Ticlopidine hydrochloride | ADP antagonist | Platelet antiaggregant |
| 1.8 | 1.8 | 5.2 | 1.4 | 5.6 | 1.3 | 1.7 | Isoconazole | Sterol 14-demethylase inhibitor | Antibacterial |
| 1.2 | 1.1 | 1.0 | 0.9 | 1.3 | 1.2 | 1.5 | Dicyclomine hydrochloride | Anticholinergic | Antispasmodic |
| 1.4 | 1.0 | 1.2 | 1.1 | 1.1 | 1.3 | 1.3 | Spironolactone | Aldosterone antagonist | Diuretic |
| 1.4 | 1.1 | 1.1 | 0.8 | 1.1 | 0.9 | 1.2 | Amyleine hydrochloride | Na+ channel blocker | Local Anesthesic |
| 1.4 | 1.1 | 1.1 | 1.0 | 1.1 | 1.0 | 1.1 | Prenzepine dihydrochloride | M1 antagonist | Antiulcerative |
| 1.3 | 1.2 | 1.0 | 1.1 | 1.1 | 1.1 | 1.3 | Lidocaine hydrochloride | Na+ channel blocker | Local anesthesic |
| 1.4 | 1.2 | 1.2 | 1.1 | 1.1 | 1.0 | 1.2 | Dexamethasone acetate | — | Antiinflammatory |
| 1.4 | 1.1 | 1.1 | 0.9 | 1.1 | 1.1 | 1.1 | Ranitidine hydrochloride | H2 antagonist | Antiulcerative |
| 1.1 | 1.1 | 1.0 | 1.0 | 1.1 | 1.2 | 1.4 | Fludrocortisone acetate | — | Mineralocorticoid |
| 1.1 | 1.3 | 0.4 | 1.0 | 1.2 | 1.2 | 1.5 | Tiratricol, 3,3',5-triiodothyroacetic acid | — | Hypocholesterolemic drug |
| 1.3 | 1.1 | 1.0 | 0.9 | 1.3 | 1.1 | 1.4 | Fenoterol hydrobromide | Beta adrenergic agonist | Bronchodilator |
| 1.0 | 1.1 | 0.5 | 1.0 | 1.3 | 1.1 | 1.8 | Flufenamic acid | Cyclooxygenase inhibitor | Analgesic |
| 1.5 | 1.2 | 1.0 | 1.1 | 1.2 | 1.2 | 1.8 | Homochlorcyclizine dihydrochloride | H1 antagonist | Antihistaminic |
| 13.6 | 1.5 | 2.2 | 2.2 | 2.9 | 1.4 | 24.4 | Flumequine | Topoisomerase II inhibitor | Antibacterial |
| 1.3 | 1.2 | 1.1 | 0.9 | 1.1 | 1.1 | 1.7 | Diethylcarbamazine citrate | Lipoxygenase inhibitor | Antihelmintic |
| 1.1 | 1.1 | 0.5 | 0.8 | 1.4 | 1.2 | 1.6 | Tolfenamic acid | Cyclooxygenase inhibitor | Antiinflammatory |
| 1.0 | 1.0 | 1.7 | 0.8 | 1.0 | 1.2 | 1.5 | Chenodiol | Detergent | Anticholelithogenic |
| 1.1 | 1.2 | 0.6 | 1.0 | 1.2 | 1.1 | 1.4 | Meclofenamic acid sodium salt monohydrate | Cyclooxygenase inhibitor | Antiinflammatory |
| 1.8 | 1.2 | 0.8 | 1.6 | 3.4 | 1.4 | 1.5 | Perhexiline maleate | Ca2+ blocking agent | Vasodilator |
| 1.1 | 1.1 | 1.0 | 1.0 | 1.2 | 1.0 | 1.4 | Kawain | Ca++ channel blocker | Antiaggregant |
| 1.1 | 1.1 | 1.2 | 0.9 | 1.1 | 1.1 | 1.6 | Oxybutynin chloride | Anticholinergic | Spasmolytic |
| 1.4 | 1.1 | 1.0 | 0.8 | 3.1 | 1.1 | 7.2 | Trimethoprim | Folic acid antagonist | Antibacterial |
| 1.3 | 1.2 | 1.0 | 0.9 | 1.2 | 1.2 | 1.3 | Spiperone | D2 antagonist | Antipsychotic |
| 1.3 | 1.2 | 0.9 | 0.9 | 1.2 | 1.1 | 1.6 | Metoclopramide monohydrochloride | 5-HT3 antagonist | Antiemetic |

TABLE 4-continued

AK-based Prestwick Library Screening Results.

| E. coli | E. faecium | S. aureus | K. pneumoniae | A. baumannii | P. aeruginosa | E. cloacae | Chemical name | Mechanism | Therapeutic group |
|---|---|---|---|---|---|---|---|---|---|
| 1.4 | 1.2 | 1.4 | 1.0 | 1.1 | 1.1 | 1.4 | Pyrilamine maleate | H1 antagonist | Antihistaminic |
| 0.9 | 0.9 | 0.6 | 0.7 | 0.9 | 0.9 | 1.3 | Fenbendazole | Microtubule formation inhibitor | Antihelmintic |
| 1.3 | 1.1 | 3.5 | 1.0 | 1.2 | 1.0 | 1.2 | Sulfinpyrazone | — | Uricosuric |
| 1.2 | 0.8 | 1.1 | 1.1 | 0.9 | 1.0 | 1.5 | Trichlorfon | Cholinesterase inhibitor | Antihelminthic |
| 1.2 | 0.9 | 1.2 | 0.8 | 1.0 | 1.0 | 1.3 | Glipizide | — | — |
| 1.0 | 0.8 | 1.0 | 0.9 | 0.9 | 1.0 | 1.5 | Carbamazepine | Cholinergic antagonist | Anticonvulsivant |
| 1.0 | 0.9 | 1.1 | 1.0 | 1.0 | 0.9 | 1.5 | Loxapine succinate | Dopamine antagonist | Anxiolytic |
| 1.1 | 0.9 | 1.1 | 1.0 | 1.5 | 1.0 | 1.6 | Triflupromazine hydrochloride | Dopaminergic antagonist ? | Antipsychotic |
| 1.0 | 0.9 | 0.9 | 0.8 | 1.0 | 1.0 | 1.6 | Hydroxyzine dihydrochloride | H1 antogonist | Antihistaminic |
| 0.9 | 0.9 | 0.7 | 1.0 | 1.2 | 0.9 | 1.6 | Mefenamic acid | Cyclooxygenase inhibitor | Antiinflammatory |
| 1.0 | 0.9 | 0.8 | 1.0 | 1.0 | 0.9 | 1.5 | Diltiazem hydrochloride | Ca2+ channel inhibitor (L-Type) | Antianginal |
| 1.2 | 0.9 | 1.1 | 0.8 | 1.1 | 1.2 | 1.7 | Acetohexamide | Blocking of ATP-sensitive K+ channel | Antidiabetic (type II, noninsulin-dependent) |
| 1.1 | 0.8 | 0.9 | 0.8 | 1.0 | 1.0 | 1.3 | Methotrexate | D2 antagonist | Antipsychotic |
| 1.0 | 1.0 | 1.1 | 1.0 | 1.0 | 1.1 | 1.6 | Sulpiride | H1 antagonist | Antihistaminic |
| 1.3 | 1.0 | 2.2 | 1.0 | 1.6 | 1.0 | 1.6 | Astemizole | Na+ channel blocker | Local anesthesic |
| 1.3 | 0.9 | 1.0 | 1.0 | 1.1 | 0.9 | 1.1 | Benoxinate hydrochloride | Ribosomal protein synthesis inhibitor | Antibacterial |
| 0.8 | 1.2 | 8.4 | 0.5 | 1.0 | 1.1 | 1.7 | Clindamycin hydrochloride | | |
| 1.0 | 1.0 | 1.0 | 1.5 | 4.2 | 1.5 | 1.5 | Oxethazaine | Na+ channel blocker | Local anesthesic |
| 1.7 | 1.5 | ### | 1.1 | 3.1 | 1.0 | 1.2 | Terfenadine | H1 antagonist | Antihistaminic |
| 1.4 | 1.0 | 1.0 | 1.0 | 1.0 | 1.0 | 1.7 | Pheniramine maleate | H1 antagonist | Antihistaminic |
| 21.9 | 1.0 | 2.9 | 5.5 | 2.2 | 10.0 | 22.0 | Cefotaxime sodium salt | Bacterial transpeptidase inhibitor | Antibacterial |
| 1.4 | 1.0 | 1.2 | 1.0 | 1.3 | 1.1 | 1.5 | Tolazoline hydrochloride | Alpha antagonist | Vasodilatator |
| 0.8 | 1.0 | 9.2 | 0.2 | 4.4 | 0.5 | 1.0 | Tetracycline hydrochloride | Ribosomal protein synthesis inhibitor | Antibacterial |
| 1.2 | 1.1 | 1.4 | 1.0 | 1.0 | 1.2 | 1.4 | Piroxicam | Cyclooxygenase inhibitor | Antiinflammatory |
| 1.2 | 1.0 | 1.1 | 0.9 | 1.1 | 1.1 | 1.5 | Dantrolene sodium salt | Blocker of Ca2+ release | Skeletal muscle relaxant |
| 1.3 | 1.1 | 1.2 | 0.9 | 1.1 | 1.2 | 1.4 | Pyrantel tartrate | Neuromuscular depolarizing agent | Anthelmintic |
| 0.9 | 1.0 | 0.9 | 1.0 | 1.0 | 1.2 | 1.3 | Trazodone hydrochloride | 5-HT uptake inhibitor | Antidepressant |
| 1.3 | 1.1 | 1.1 | 1.0 | 1.2 | 1.1 | 1.6 | Fenspiride hydrochloride | Bradykinin antagonist | Antiinflammatory |
| 1.3 | 1.0 | 1.1 | 1.0 | 1.1 | 1.2 | 1.5 | Glafenine hydrochloride | — | Analgesic |
| 1.3 | 1.1 | 0.9 | 0.9 | 1.3 | 1.1 | 1.5 | Gemfibrozil | — | Antihyperlipoproteinemic |
| 1.4 | 1.1 | 0.9 | 1.2 | 1.1 | 1.1 | 1.4 | Pimethixene maleate | Anticholinergic | Antihistaminic |
| 1.2 | 1.0 | 0.9 | 0.9 | 1.1 | 1.1 | 1.3 | Mefexamide hydrochloride | | Psychoanaleptic |
| 1.1 | 1.0 | 1.0 | 0.8 | 1.3 | 1.0 | 1.4 | Pergolide mesylate | Dopaminergic agonist | Antiparkinsonian |
| 1.2 | 1.1 | 1.0 | 0.9 | 1.1 | 1.2 | 1.3 | Tiapride hydrochloride | Dopamine antagonist | Antidyskinetic |
| 0.8 | 0.9 | 1.1 | 0.9 | 1.1 | 1.1 | 1.3 | Acemetacin | Cyclooxygenase inhibitor | Antiinflammatory |
| 1.3 | 1.1 | 1.1 | 0.8 | 0.7 | 0.8 | 1.2 | Mebendazole | | |
| 1.3 | 0.8 | 0.7 | 1.0 | 1.0 | 1.2 | 1.2 | Benzydamine hydrochloride | 5-HT receptor antagonist | Analgesic |
| 0.8 | 1.1 | 0.9 | 0.8 | 1.0 | 0.8 | 1.6 | Fenbufen | Cyclooxygenase inhibitor | Antiinflammatory |
| 1.3 | 0.9 | 1.0 | 1.1 | 1.0 | 1.0 | 1.3 | Fipexide hydrochloride | Glutamatergic | Nootropic |
| 1.1 | 0.9 | 1.0 | 1.1 | 1.0 | 1.0 | 1.5 | Ketoprofen | Cyclooxygenase inhibitor | Antiinflammatory |
| 1.3 | 1.1 | 0.7 | 0.9 | 1.1 | 1.0 | 1.4 | Mifepristone | Progesterone receptor antagonist | Abortifacient |

TABLE 4-continued

AK-based Prestwick Library Screening Results.

| E. coli | E. faecium | S. aureus | K. pneumoniae | A. baumannii | P. aeruginosa | E. cloacae | Chemical name | Mechanism | Therapeutic group |
|---|---|---|---|---|---|---|---|---|---|
| 1.1 | 1.1 | 1.0 | 1.1 | 1.0 | 1.1 | 1.7 | Indapamide | — | Diuretic |
| 1.4 | 1.1 | 1.2 | 0.9 | 1.1 | 1.1 | 1.4 | Diperodon hydrochloride | Fumarate reductase inhibitor | Local anesthesic |
| 1.4 | 0.8 | 1.2 | 0.9 | 1.1 | 1.2 | 1.3 | Morantel tartrate | | Anthelmintic |
| 1.3 | 0.9 | 1.2 | 0.9 | 1.5 | 1.2 | 1.2 | Verapamyl hydrochloride | Alpha1 antagonist | Antyhypertensive |
| 1.4 | 0.8 | 1.1 | 0.9 | 1.3 | 1.1 | 1.4 | Homatropine hydrobromide (R,S) | Muscarinic antagonist | Antispasmodic |
| 1.3 | 0.9 | 0.8 | 0.9 | 1.2 | 1.1 | 1.4 | Dipyridamole | | |
| 1.4 | 0.9 | 0.5 | 0.9 | 1.5 | 1.0 | 1.4 | Nifedipine | L-type Ca2+ channels blocker | Antihypertensor |
| 50.1 | 4.0 | ### | 18.8 | 12.3 | 23.8 | 1.8 | Chlorhexidine | Detergent | Bacteriostatic |
| 1.4 | 1.0 | 1.4 | 1.1 | 1.5 | 1.1 | 1.4 | Chlorpromazine hydrochloride | Dopamine antagonist | Antiemetic |
| 1.4 | 0.9 | 1.0 | 0.9 | 1.5 | 1.2 | 1.5 | Loperamide hydrochloride | Ca2+ channel antagonist | Antidiarrhoeic |
| 1.3 | 0.9 | 1.1 | 1.0 | 1.3 | 1.0 | 1.4 | Diphenhydramine hydrochloride | H1 receptor antagonist | Antihistaminic |
| 0.8 | 0.9 | 6.8 | 0.2 | 3.9 | 0.7 | 1.0 | Chlortetracycline hydrochloride | Ribosomal protein synthesis inhibitor | Antibacterial |
| 1.3 | 0.8 | 1.0 | 0.9 | 1.3 | 1.1 | 1.3 | Minaprine dihydrochloride | Dopamine agonist | Antidepressant |
| 1.9 | 4.0 | 2.1 | 2.1 | 6.6 | 1.4 | 1.3 | Tamoxifen citrate | Oestrogen receptor antagonist | |
| 1.4 | 2.5 | 2.2 | 1.4 | 4.7 | 1.2 | 1.6 | Miconazole | Sterol 14-demethylase inhibitor | Antifungal |
| 1.3 | 1.0 | 1.4 | 1.0 | 1.4 | 1.2 | 1.2 | Nicergoline | Alpha agonist | Vasodilatator |
| 1.1 | 1.0 | 1.1 | 1.0 | 1.5 | 1.1 | 1.5 | Isoxsuprine hydrochloride | beta adrenergic agonist | Vasodilatator |
| 1.4 | 1.1 | 1.1 | 0.9 | 1.5 | 1.3 | 1.2 | Canrenoic acid potassium salt | Detergent | Antihypercholesterolemic |
| 1.3 | 1.0 | 1.1 | 1.1 | 1.3 | 1.1 | 1.2 | Acebutolol hydrochloride | Beta1 antagonist | Antianginal |
| 1.5 | 1.0 | 1.0 | 0.9 | 1.7 | 1.1 | 1.3 | Thioproperazine dimesylate | Dopamine antagonist | Antipsychotic |
| 1.1 | 1.0 | 1.3 | 1.1 | 1.5 | 1.0 | 1.2 | Tolnaftate | | Antifungal |
| 1.3 | 1.0 | 1.0 | 0.9 | 1.5 | 1.2 | 1.3 | Dihydroergotamine tartrate | Serotonine antagonist | Antimigraine |
| 33.1 | 1.5 | 1.8 | 0.8 | 3.1 | 31.3 | 3.1 | Norfloxacin | Topoisomerase II inhibitor | Antibacterial |
| 1.2 | 1.0 | 4.3 | 1.0 | 1.3 | 1.2 | 1.5 | Lisinopril | Converting enzyme inhibitor | Antihypertensor |
| 1.3 | 1.1 | 1.0 | 1.0 | 1.4 | 1.1 | 1.3 | Antimycin A | Inhibitor of mitochondrial electron transport | Antifungal |
| 0.9 | 1.3 | 7.9 | 0.9 | 1.2 | 1.2 | 1.3 | Lincomycin hydrochloride | Ribosomal protein synthesis inhibitor | Antibacterial |
| 1.2 | 1.0 | 1.2 | 0.9 | 1.3 | 1.2 | 1.4 | Xylometazoline hydrochloride | | Vasoconstrictor |
| 1.5 | 1.1 | 1.3 | 1.0 | 1.6 | 1.2 | 1.2 | Telenzepine dihydrochloride | M1 muscarinic antagonist | Antiulcerative |
| 1.1 | 1.0 | 1.1 | 1.1 | 1.4 | 1.3 | 1.2 | Oxymetazoline hydrochloride | Partial alpha2A agonist | Vasoconstrictor |
| 1.3 | 1.5 | 3.7 | 1.3 | 6.7 | 1.1 | 1.3 | Econazole nitrate | Ergosterol synthesis inhibition | Antifungal |
| 1.2 | 1.0 | 1.3 | 1.0 | 1.6 | 1.2 | 1.2 | Nifenazone | Cyclooxygenase inhibitor | Analgesic |
| 1.2 | 1.1 | 1.1 | 1.0 | 1.4 | 1.2 | 1.5 | Bupivacaine hydrochloride | Na+ channel blocker | Local anesthesic |
| 1.3 | 1.1 | 1.4 | 0.9 | 1.4 | 1.3 | 1.3 | Griseofulvin | Enzymatic inductor | Antifungal |
| 1.4 | 1.1 | 1.2 | 1.1 | 1.5 | 1.2 | 1.2 | Clemastine fumarate | H1 antagonist | Antihistaminic |
| 1.2 | 1.2 | 1.6 | 1.0 | 1.6 | 1.2 | 1.1 | Clemizole hydrochloride dihydrate | H1 antagonist | Antihistaminic |
| 1.0 | 0.9 | 3.4 | 0.2 | 5.3 | 0.5 | 1.1 | Oxytetracycline dihydrate | Ribosomal protein synthesis inhibitor | Antibacterial |
| 1.2 | 1.0 | 1.1 | 1.1 | 1.5 | 1.2 | 1.4 | Tropicamide | Muscarinic antagonist | Mydriatic |
| 1.7 | 1.3 | 2.3 | 1.3 | 8.7 | 1.3 | 1.2 | Pinozide | Dopamine antagonist ? | Antipsychotic |
| 1.2 | 1.0 | 1.1 | 0.9 | 1.4 | 1.2 | 1.4 | Nefopam hydrochloride | | Analgesic |
| 1.2 | 1.1 | 1.3 | 0.9 | 1.5 | 1.2 | 1.4 | Amodiaquin dihydrochloride dihydrate | Heme polymerase inhibitor | Antimalarial |

TABLE 4-continued

AK-based Prestwick Library Screening Results.

| E. coli | E. faecium | S. aureus | K. pneumoniae | A. baumannii | P. aeruginosa | E. cloacae | Chemical name | Mechanism | Therapeutic group |
|---|---|---|---|---|---|---|---|---|---|
| 1.4 | 1.0 | 1.1 | 1.1 | 1.4 | 1.2 | 1.2 | Phentolamine hydrochloride | Alpha adrenergic antagonist | Antihypertensor |
| 1.3 | 1.0 | 1.1 | 1.0 | 1.4 | 1.1 | 1.3 | Mebeverine hydrochloride | Antispasmodic | |
| 1.3 | 0.8 | 1.3 | 1.0 | 1.1 | 1.1 | 1.7 | Todralazine hydrochloride | — | Antihypertensor |
| 1.0 | 1.0 | 8.2 | 1.0 | 1.5 | 0.7 | 1.6 | Erythromycin | Ribosomal protein synthesis inhibitor | Antibacterial |
| 1.2 | 0.9 | 1.2 | 1.0 | 1.3 | 1.1 | 1.7 | Imipramine hydrochloride | 5-HT transport inhibitor | Antidepressant |
| 1.1 | 1.0 | 3.6 | 1.0 | 1.1 | 1.0 | 1.6 | Oleandomycin phosphate | Ribosomal protein synthesis inhibitor | Antibacterial |
| 1.1 | 0.9 | 0.8 | 1.0 | 1.1 | 0.8 | 1.5 | Sulindac | Cyclooxygenase inhibitor | Antiinflammatory |
| 4.7 | 0.9 | 1.2 | 0.9 | 1.5 | 1.0 | 4.2 | Didanosine | Transcriptase inverse inhibitor | Antiviral |
| 1.2 | 1.0 | 1.4 | 1.1 | 1.3 | 1.0 | 1.8 | Amitryptiline hydrochloride | Alpha 1 antogonist | Antidiabetic |
| 1.3 | 1.0 | 8.4 | 1.0 | 1.1 | 0.9 | 1.4 | Josamycin | Ribosomal protein synthesis inhibitor | Antibacterial |
| 1.2 | 1.0 | 1.3 | 1.0 | 1.3 | 0.9 | 1.5 | Adiphenine hydrochloride | Anticholinergic | Local anesthesic |
| 1.1 | 1.0 | 1.0 | 1.0 | 1.3 | 1.0 | 1.6 | Paclitaxel | Tubuline inhibitor | Antineoplastic |
| 1.1 | 0.9 | 1.3 | 1.1 | 1.3 | 1.1 | 1.7 | Dibucaine | Na+ channel blocker | Local anesthesic |
| 1.3 | 1.2 | 2.1 | 1.0 | 1.5 | 1.0 | 1.6 | Ivermectin | GABA ligand | Anthelmintic |
| 1.2 | 0.9 | 1.1 | 0.9 | 1.2 | 0.9 | 1.4 | Prednisone | — | Glucocorticoid |
| 1.3 | 1.0 | 1.1 | 1.1 | 1.1 | 1.0 | 1.5 | Gallamine triethiodide | M2 antagonist allosteric | Muscle relaxant |
| 1.6 | 1.0 | 1.3 | 1.3 | 2.9 | 1.1 | 1.5 | Thioridazine hydrochloride | Ca2+ channel antagonist | Neuroleptic |
| 1.2 | 1.0 | 1.1 | 1.0 | 1.4 | 0.9 | 1.3 | Neomycin sulfate | Ribosomal protein synthesis inhibitor | Antibacterial |
| 1.2 | 1.1 | 1.5 | 1.1 | 1.3 | 1.0 | 1.6 | Diphemanil methylsulfate | Anticholinergic | Bronchodilatator |
| 1.2 | 1.0 | 1.2 | 0.7 | 1.2 | 0.9 | 1.3 | Dihydrostreptomycin sulfate | Ribosomal protein synthesis inhibitor | Antibacterial |
| 1.2 | 1.1 | 1.2 | 1.1 | 1.2 | 1.0 | 1.3 | Trimethobenzamide hydrochloride | D2 antagonist | Antiemetic |
| 1.3 | 1.0 | 1.1 | 1.0 | 1.5 | 0.9 | 1.4 | Gentamicine sulfate | Ribosomal protein synthesis inhibitor | Antibacterial |
| 1.2 | 1.1 | 1.0 | 1.3 | 1.4 | 1.5 | 1.2 | Etodolac | Cyclooxygenase inhibitor | Antiinflammatory |
| 1.2 | 1.1 | 1.1 | 1.3 | 1.4 | 1.2 | 1.5 | Ifenprodil tartrate | Adrenergic antagonist | Vasodilatator |
| 1.2 | 1.1 | 1.4 | 1.2 | 1.4 | 1.3 | 1.5 | Scopolamin-N-oxide hydrobromide | Anticholinergic | Antiparkinsonian |
| 1.7 | 1.3 | 1.1 | 1.4 | 2.6 | 1.3 | 1.6 | Flunarizine dihydrochloride | Na+ channel blocker | Vasodilator |
| 1.3 | 1.0 | 1.2 | 1.2 | 1.4 | 1.2 | 1.5 | Hyoscyamine (L) | Cholinergic | Antispasmodic |
| 1.7 | 1.1 | 1.2 | 1.5 | 3.4 | 1.4 | 1.3 | Trifluoperazine dihydrochloride | Dopamine antagonist | Psycholeptic |
| 1.2 | 0.9 | 1.0 | 1.1 | 1.3 | 1.1 | 1.4 | Chlorphensin carbamate | — | Muscle relaxant |
| 1.2 | 1.1 | 1.3 | 1.2 | 1.3 | 1.2 | 1.3 | Enalapril maleate | Converting enzyme inhibitor | Antihypertensor |
| 16.8 | 1.6 | 1.3 | 1.0 | 1.1 | 1.3 | 4.3 | Metampicillin sodium salt | Bacterial transpeptidase inhibitor | Antibacterial |
| 2.3 | 1.1 | 6.9 | 0.6 | 3.9 | 0.7 | 0.9 | Minocycline hydrochloride | Ribosomal protein synthesis inhibitor | Antibacterial |
| 1.5 | 1.1 | 1.2 | 1.4 | 1.4 | 1.3 | 1.1 | Dilazep dihydrochloride | Adenosine uptake inhibitor | Vasodilator |
| 1.2 | 1.0 | 0.9 | 1.1 | 1.3 | 1.2 | 1.4 | Glibenclamide | ATP-dependent K+ channel inhibitor | Antidiabetic |
| 15.7 | 1.4 | 2.8 | 1.0 | 3.7 | 20.0 | 4.1 | Ofloxacin | Topoisomerase II inhibitor | Antibacterial |
| 1.4 | 1.1 | 1.1 | 1.1 | 1.3 | 1.4 | 1.4 | Guanethidine sulfate | Catecholamine depletor | Antihypertensor |
| 26.8 | 1.5 | 3.4 | 1.0 | 3.8 | 30.2 | 3.5 | Lomefloxacin hydrochloride | Topoisomerase II inhibitor | Antibacterial |

TABLE 4-continued

AK-based Prestwick Library Screening Results.

| E. coli | E. faecium | S. aureus | K. pneumoniae | A. baumannii | P. aeruginosa | E. cloacae | Chemical name | Mechanism | Therapeutic group |
|---|---|---|---|---|---|---|---|---|---|
| 1.2 | 1.0 | 1.2 | 1.0 | 1.3 | 0.9 | 1.4 | Quinacrine dihydrochloride dihydrate | Monoamine oxydase inhibitor | Antimalarial |
| 1.3 | 1.0 | 1.0 | 1.2 | 1.3 | 1.1 | 1.2 | Orphenadrine hydrochloride | H1 antogonist | Antihistaminic |
| 1.5 | 1.4 | 1.2 | 1.5 | 1.6 | 1.3 | 1.2 | Clofilium tosylate | K+ channel blocker | Antiarrhythmic |
| 1.3 | 1.0 | 1.1 | 1.2 | 1.3 | 1.1 | 1.5 | Proglumide | Gastrin inhibitor | Antiulcerative |
| 1.3 | 1.1 | 1.0 | 1.5 | 1.6 | 1.1 | 1.6 | Fluphenazine dihydrochloride | Dopamine antagonist | Antipsychotic |
| 0.5 | 0.9 | 0.4 | 0.3 | 0.4 | 0.4 | 0.3 | Streptomycin sulfate | Ribosomal protein synthesis inhibitor | Antibacterial |
| 0.5 | 0.9 | 0.3 | 0.4 | 0.5 | 0.4 | 0.3 | Testosterone propionate | — | Androgen |
| 0.5 | 0.9 | 0.3 | 0.4 | 0.4 | 0.4 | 0.4 | Alfuzosin hydrochloride | Alpha 1-adrenergic antagonist | Antihypertensor |
| 0.4 | 0.9 | 0.4 | 0.4 | 0.4 | 0.4 | 0.3 | Arecoline hydrobromide | Cholinergic | Anthelmintic |
| 0.4 | 0.9 | 0.4 | 0.4 | 0.3 | 0.3 | 0.3 | Chlorpropamide | Glucagon secretogen, somatostatin secretogen | Antidiabetic |
| 0.5 | 1.0 | 0.2 | 0.4 | 0.4 | 0.4 | 0.3 | Thyroxine (L) | Thyroid hormone | Hypocholesterolemic drug |
| 0.5 | 0.8 | 0.3 | 0.5 | 0.4 | 0.4 | 0.4 | Phenylpropanolamine hydrochloride | Alpha adrenergic agonist | Decongestant |
| 0.6 | 0.9 | 0.4 | 0.4 | 0.4 | 0.4 | 0.4 | Tocopherol (R,S) | — | Anti-oxidant |
| 0.5 | 0.9 | 0.4 | 0.5 | 0.4 | 0.3 | 0.4 | Ascorbic acid | — | Vitamin |
| 0.5 | 0.8 | 0.4 | 0.5 | 0.4 | 0.4 | 0.4 | Pepstatin A | Aspartic proteases irreversible inhibitor | Antiviral |
| 0.6 | 0.9 | 0.4 | 0.6 | 0.5 | 0.4 | 0.5 | Methyldopa (L,-) | L-aromatic aminoacid decarboxylase inhibitor | Antihypertensor |
| 0.5 | 0.8 | 0.4 | 0.5 | 0.5 | 0.4 | 0.4 | SR-95639A | M1 agonist receptor | |
| 16.5 | 0.9 | 0.7 | 2.1 | 0.7 | 5.2 | 12.0 | Cefoperazone dihydrate | Bacterial transpeptidase inhibitor | Antibacterial |
| 0.5 | 0.9 | 0.4 | 0.5 | 0.5 | 0.4 | 0.4 | Adamantamine fumarate | Inhibition of viral uncoating and viral assembly, alteration of dopamine release and reuptake | Antiviral |
| 0.7 | 0.8 | 0.4 | 0.6 | 0.4 | 0.4 | 0.4 | Zoxazolamine | Uric acid uptake inhibitor | Muscle relaxant |
| 0.7 | 3.3 | 0.6 | 0.7 | 2.0 | 0.5 | 0.5 | Butoconazole nitrate | Ergosterol inhibitor | Antifungal |
| 0.5 | 0.9 | 0.5 | 0.4 | 0.5 | 0.5 | 0.4 | Tacrine hydrochloride hydrate | Cholinesterase inhibitor | Cognition enhancer |
| 0.7 | 1.7 | 0.7 | 0.6 | 2.2 | 0.5 | 0.5 | Amiodarone hydrochloride | Na+ channel blocker, K+ channel blocker, non-competitive beta-adrenergic blocker | Antiarrhythmic |
| 0.5 | 0.9 | 0.6 | 0.5 | 0.5 | 0.5 | 0.6 | Bisoprolol fumarate | Beta1 antagonist | Antihypertensor |
| 0.5 | 0.9 | 0.5 | 0.7 | 0.5 | 0.4 | 0.5 | Amphotericin B | Ergosterol ligand | Antibacterial |
| 0.8 | 0.9 | 0.6 | 0.6 | 0.6 | 0.6 | 0.6 | Serotonin hydrochloride | 5-HT agonist | Neurotransmitter |
| 0.7 | 0.9 | 0.5 | 0.6 | 0.7 | 0.5 | 0.6 | Tubocurarine chloride pentahydrate (+) | Curarising | Muscle relaxant |
| 23.9 | 0.9 | 2.3 | 7.8 | 0.9 | 0.6 | 15.6 | Cefotiam hydrochloride | — | Antibacterial |
| 0.7 | 0.9 | 0.5 | 0.6 | 0.7 | 0.6 | 0.6 | Dihydroergocristine mesylate | 5-HT antagonist, partial adrenergic agonist, partial dopaminergic agonist | Vasodilator |
| 0.6 | 0.9 | 0.4 | 0.5 | 0.5 | 0.6 | 0.6 | Azathymine, 6 | Antimetabolite | Anticancer |

TABLE 4-continued

AK-based Prestwick Library Screening Results.

| E. coli | E. faecium | S. aureus | K. pneumoniae | A. baumannii | P. aeruginosa | E. cloacae | Chemical name | Mechanism | Therapeutic group |
|---|---|---|---|---|---|---|---|---|---|
| 0.6 | 0.9 | 0.5 | 0.5 | 0.6 | 0.5 | 0.6 | Noscapine | Inhibitor of carbachol-stimulated phosphoinositide turnover | Antitussive |
| 0.6 | 1.0 | 0.5 | 0.5 | 0.5 | 0.6 | 0.6 | Benperidol | Dopamine antagonist, 5-HT antagonist | Antipsychotic |
| 0.6 | 0.9 | 0.3 | 0.5 | 0.6 | 0.5 | 0.6 | Syrosingopine | Catecholamine depletor | — |
| 10.7 | 0.9 | 0.5 | 2.5 | 1.5 | 0.5 | 0.7 | Cefaclor | Bacterial transpeptidase inhibitor | Antibacterial |
| 0.6 | 0.8 | 0.5 | 0.5 | 0.5 | 0.5 | 0.5 | Atropine sulfate monohydrate | Muscarinic antagonist | Anticholinergic |
| 42.2 | 1.0 | 0.6 | 24.1 | 10.0 | 23.6 | 0.7 | Colistin sulfate | Performs membrane ionophores | Antibacterial |
| 0.7 | 0.9 | 0.4 | 0.5 | 0.5 | 0.6 | 0.7 | Eserine sulfate, physostigmine sulfate | Cholinesterase inhibitor | Ophtalmic agent |
| 0.9 | 2.3 | 2.1 | 0.5 | 0.6 | 0.5 | 0.6 | Daunorubicin hydrochloride | DNA intercaling | Antineoplastic |
| 0.6 | 0.9 | 0.5 | 0.5 | 0.6 | 0.5 | 0.6 | Aconitine | Open TTX-Na+ channel | Analgesic |
| 0.6 | 0.9 | 0.5 | 0.5 | 0.5 | 0.5 | 0.5 | Dosulepin hydrochloride | — | Antidepressant |
| 0.7 | 1.0 | 0.3 | 0.6 | 1.1 | 0.4 | 0.6 | Rescinnamin | Catecholamine depletor | Antihypertensor |
| 11.5 | 0.9 | 0.4 | 3.2 | 0.5 | 7.8 | 12.9 | Ceftazidime pentahydrate | Bacterial transpeptidase | Antibacterial |
| 0.6 | 0.8 | 0.4 | 0.5 | 0.5 | 0.4 | 0.6 | Dihydroergotoxine mesylate | High affinity GABA A receptor Cl− channel, prolactin inhibitor | Anticonvulsant |
| 0.5 | 0.9 | 0.5 | 0.5 | 0.5 | 0.4 | 0.5 | Iobenguane sulfate | — | Antineoplastic if radiolabeled |
| 0.5 | 0.9 | 0.5 | 0.6 | 0.5 | 0.5 | 0.5 | Emetine dihydrochloride | Protein synthesis inhibitor, 5-HT ligand | Antiamebic |
| 0.7 | 1.0 | 0.5 | 0.6 | 0.7 | 0.6 | 0.7 | Trenorine dihydrochloride | Cholinergic | Convulsant |
| 0.6 | 1.0 | 0.5 | 0.5 | 0.7 | 0.6 | 0.7 | Androsterone | Beta antagonist | Antihypertensor |
| 0.7 | 0.9 | 0.6 | 0.5 | 0.7 | 0.6 | 0.8 | Practolol | Acetylcholine esterase inhibitor | Antihypertensor |
| 0.7 | 1.0 | 0.7 | 0.5 | 0.7 | 0.7 | 0.7 | Anisomycin | — | Antiprotozoal |
| 2.1 | 0.9 | 0.6 | 1.2 | 1.8 | 0.6 | 4.2 | Zidovudine, AZT | Transcriptase reverse inhibitor | Antiviral |
| 0.6 | 1.0 | 0.6 | 0.5 | 0.6 | 0.6 | 0.7 | Carbarsone | — | Antiamebic |
| 0.7 | 0.9 | 0.5 | 0.5 | 1.0 | 0.6 | 0.7 | Sulfisoxazole | Inhibitor of folic acid biosynthesis, Eta endothelin receptor antagonist | Antibacterial |
| 0.2 | 0.3 | 0.0 | 0.2 | 0.2 | 0.2 | 0.5 | Apigenin | MAP kinase inhibitor | Antiproliferative |
| 0.7 | 1.0 | 0.6 | 0.5 | 0.6 | 0.7 | 0.8 | Zaprinast | cGMP phosphodiesterase inhibitor, phosphodiesterase 5 inhibitor | Erectogen |
| 0.6 | 0.9 | 0.5 | 0.5 | 0.6 | 0.6 | 0.7 | Aspartic acid, N-acetyl (R,S) | — | — |
| 0.7 | 1.0 | 0.7 | 0.6 | 0.7 | 0.6 | 0.7 | Chlormezanone | — | Skeletal muscle relaxant |
| 11.9 | 1.1 | 0.5 | 0.6 | 1.3 | 0.6 | 0.6 | Bacampicillin hydrochloride | Bacterial transpeptidase inhibitor | Antibacterial |
| 0.6 | 1.0 | 0.6 | 0.6 | 0.7 | 0.6 | 0.9 | Procainamide hydrochloride | Alpha antagonist, antinuclear antibodies, anticholinergic | Antiarrhythmic |
| 0.6 | 0.9 | 0.1 | 0.5 | 0.6 | 0.6 | 0.7 | Betulinic acid | Apoptosis inducer, PLA2 inhibitor | Antimalarial |
| 0.6 | 0.9 | 0.5 | 0.5 | 0.6 | 0.6 | 0.7 | N6-methyladenosine | Antimetabolite | Anticancer |

TABLE 4-continued

AK-based Prestwick Library Screening Results.

| E. coli | E. faecium | S. aureus | K. pneumoniae | A. baumannii | P. aeruginosa | E. cloacae | Chemical name | Mechanism | Therapeutic group |
|---|---|---|---|---|---|---|---|---|---|
| 0.6 | 0.9 | 1.4 | 0.6 | 0.8 | 0.7 | 0.8 | Biotin | — | Vitamin H |
| 0.8 | 1.1 | 0.6 | 0.5 | 0.7 | 0.7 | 0.9 | Guanfacine hydrochloride | Alpha 2A agonist | Antihypertensor |
| 0.6 | 1.0 | 0.5 | 0.6 | 0.8 | 0.6 | 0.9 | Bisacodyl | Na+ uptake inhibitor | Cathartic |
| 0.6 | 0.9 | 0.8 | 0.6 | 0.7 | 0.6 | 0.8 | Domperidone | Dopamine Antagonists | Antiemetic |
| 0.8 | 0.9 | 0.5 | 0.7 | 0.7 | 0.7 | 0.7 | Calciferol | Stimulator of calcium and phosphate absorption | Vitamin D |
| 0.9 | 1.0 | 0.7 | 0.8 | 1.0 | 0.8 | 0.9 | Metixene hydrochloride | Anticholinergic | Antiparkinsonian |
| 0.9 | 0.9 | 0.6 | 0.6 | 0.8 | 0.8 | 0.9 | Tetracaine hydrochloride | — | Local anesthesic |
| 0.7 | 1.0 | 0.5 | 0.2 | 1.0 | 0.8 | 0.8 | Nitrofural | Bacterial DNA damage | Antibacterial |
| 0.9 | 1.0 | 0.4 | 0.7 | 0.9 | 0.6 | 0.9 | Mometasone furoate | — | Antiinflammatory |
| 0.7 | 0.8 | 0.2 | 0.6 | 0.8 | 0.8 | 0.8 | Omeprazole | Non competitive ATPase H+ pump inhibitor | Antiulcerative |
| 0.7 | 1.2 | 0.5 | 0.6 | 0.7 | 0.7 | 1.0 | Tomatidine | Cholinesterase activity | Antifungal |
| 0.7 | 1.0 | 0.7 | 0.6 | 0.8 | 0.9 | 1.1 | Propylthiouracil | Antimetabolite | Antihyperthyroid |
| 2.0 | 1.1 | 0.7 | 3.8 | 1.6 | 0.9 | 0.8 | Dacarbazine | Alkylating agent | Antineoplastic |
| 0.9 | 1.0 | 0.6 | 0.7 | 0.8 | 0.8 | 0.9 | Terconazole | Sterol 14-demethylase inhibitor | Antifungal |
| 0.6 | 0.9 | 0.7 | 0.6 | 0.6 | 0.8 | 0.8 | Ipratropium bromide | Antimuscarinic agent | Bronchodilator |
| 0.6 | 0.8 | 0.5 | 0.5 | 0.7 | 0.6 | 0.6 | Tiaprofenic acid | Cyclooxygenase inhibitor | Antiinflammatory |
| 0.8 | 1.0 | 0.8 | 0.6 | 0.8 | 0.8 | 0.8 | Acetopromazine maleate salt | Dopaminergic antagonist ? | Tranquilizer |
| 1.2 | 1.5 | ### | 0.8 | 1.1 | 0.9 | 0.9 | Vancomycin hydrochloride | Bacterial mucopeptide biosynthesis inhibitor | Antibacterial |
| 0.7 | 1.0 | 0.7 | 0.6 | 0.8 | 0.6 | 0.8 | Rauwolscine hydrochloride | Alpha2 antagonist | Antidepressant |
| 0.5 | 0.9 | 0.5 | 0.6 | 0.7 | 0.6 | 0.7 | Artemisinin | Oxidant | Antimalarial |
| 0.7 | 1.0 | 0.7 | 0.6 | 0.6 | 0.7 | 0.8 | Corynanthine hydrochloride | Alpha1-adrenoreceptor antagonist | Anti-leishmania drug |
| 1.0 | 1.0 | 0.7 | 0.6 | 0.7 | 0.7 | 0.8 | Propafenone hydrochloride | Beta adrenergic antagonist | Antiarrhytmic |
| 0.7 | 1.0 | 0.8 | 0.5 | 0.7 | 0.7 | 0.9 | Palmatine chloride | Anticholinestrase activity | Uterine contractant |
| 0.6 | 1.0 | 0.6 | 0.6 | 0.9 | 0.6 | 0.9 | Ethamivan | — | Respiratory analeptic |
| 0.8 | 1.2 | 0.6 | 0.7 | 1.0 | 0.9 | 0.8 | Trimethylcolchicinic acid | Tubuline inhibitor ? | Anticancer agent |
| 1.0 | 0.9 | 0.7 | 0.7 | 0.8 | 0.7 | 0.8 | Furosemide | Na+ Cl− uptake inhibitor, carbonic anhydrase inhibitor | Diuretic |
| 1.9 | 5.4 | 2.0 | 2.5 | 4.1 | 6.8 | 0.9 | Sulocitdil | — | Vasodilatator |
| 0.9 | 1.0 | 0.5 | 0.6 | 0.9 | 0.9 | 0.9 | Methapyrilene hydrochloride | Histamine H1 antagonist | Antihistaminic |
| 0.8 | 0.9 | 0.7 | 0.6 | 0.8 | 0.8 | 0.8 | Carcinine | Adrenergic transport inhibitor, 5-HT transport inhibitor | Anti-oxidant |
| 0.8 | 0.8 | 0.7 | 0.7 | 0.7 | 0.9 | 0.7 | Desipramine hydrochloride | — | Antidepressant |
| 0.9 | 0.9 | 0.7 | 0.6 | 0.8 | 0.9 | 0.8 | Carisoprodol | — | Muscle relaxant |
| 0.7 | 0.7 | 0.5 | 0.5 | 0.6 | 0.7 | 0.7 | Clorgyline hydrochloride | Monoamine oxidase A inhibitor | Antidepressant |
| 0.9 | 0.9 | 0.6 | 0.7 | 0.8 | 0.8 | 0.8 | Cephalosporanic acid, 7-amino | Bacterial transpeptidase inhibitor | Antibacterial |
| 0.8 | 0.9 | 0.7 | 0.7 | 0.8 | 0.8 | 0.9 | Clenbuterol hydrochloride | Beta adrenergic agonist | Bronchodilator |
| 0.5 | 0.5 | 0.0 | 0.3 | 0.4 | 0.4 | 0.9 | Chicago sky blue 6B | Competitive glutamate uptake inhibitor | — |
| 0.8 | 0.8 | 1.1 | 0.6 | 0.8 | 0.9 | 0.9 | Maprotiline hydrochloride | Noradrenaline uptake inhibitor, 5-HT uptake inhibitor | Antidepressant |

TABLE 4-continued

AK-based Prestwick Library Screening Results.

| E. coli | E. faecium | S. aureus | K. pneumoniae | A. baumannii | P. aeruginosa | E. cloacae | Chemical name | Mechanism | Therapeutic group |
|---|---|---|---|---|---|---|---|---|---|
| 0.8 | 0.8 | 0.6 | 0.6 | 0.7 | 0.8 | 0.9 | Buflomedil hydrochloride | — | Vasodilator |
| 0.8 | 0.9 | 0.5 | 0.7 | 0.9 | 0.8 | 0.9 | Thioguanosine | Antimetabolite | Anticancer |
| 0.8 | 0.9 | 0.5 | 0.7 | 0.8 | 0.7 | 0.8 | Chlorogenic acid | Glucose-6-phosphate translocase inhibitor | Antiinflammatory |
| 1.0 | 1.0 | 0.6 | 0.8 | 1.2 | 0.9 | 1.0 | Chloprothixene hydrochloride | D2 dopamine receptor antagonist, GABAA receptors antagonist | Neuroleptic |
| 0.8 | 1.0 | 0.6 | 0.7 | 0.8 | 0.7 | 0.9 | Roxatidine Acetate HCl | — | Antiulcerative |
| 0.8 | 0.9 | 0.5 | 0.7 | 0.8 | 0.9 | 0.9 | Ritodrine hydrochloride | Beta2 agonist | Tocolytic |
| 1.0 | 0.9 | 0.7 | 0.7 | 0.8 | 0.9 | 1.0 | Cholecalciferol | — | Vitamin |
| 0.9 | 0.9 | 0.7 | 0.8 | 0.9 | 1.0 | 1.0 | Clozapine | 5-HT antagonist, dopamine antagonist, GABA ligand | Antipsychotic |
| 0.9 | 0.9 | 0.6 | 0.7 | 1.1 | 0.9 | 0.9 | Cisapride | 5-HT antagonist | Peristaltic stimulant |
| 1.0 | 0.9 | 0.7 | 0.8 | 1.1 | 0.9 | 0.8 | Vigabatrin | GABA transaminase inhibitor | Anticonvulsant |
| 0.9 | 1.0 | 0.6 | 0.8 | 1.0 | 0.9 | 0.9 | Hydrastine hydrochloride | GABAa antagonist | Hypotensor |
| 0.9 | 0.9 | 0.6 | 0.8 | 0.8 | 0.8 | 0.9 | Biperiden hydrochloride | Anticholinergic | Antiparkinsonian |
| 1.0 | 0.9 | 0.6 | 0.8 | 1.0 | 1.0 | 1.0 | Lobelanidine hydrochloride | Nicotinic ligand | — |
| 0.9 | 0.9 | 0.6 | 0.7 | 1.1 | 0.9 | 0.9 | Cetirizine dihydrochloride | H1 antagonist | Antihistaminic |
| 0.9 | 1.0 | 0.6 | 0.8 | 0.8 | 1.0 | 0.9 | Papaverine hydrochloride | Phosphodiesterase inhibitor | Vasodilator |
| 1.1 | 0.9 | 0.5 | 0.8 | 0.9 | 0.9 | 1.0 | Etifenin | Chelating agent | Diagnostic agent |
| 0.8 | 0.9 | 0.6 | 0.8 | 0.8 | 0.8 | 1.0 | Yohimbine hydrochloride | Alpha antagonist | Mydriatic |
| 1.0 | 0.9 | 0.6 | 0.7 | 0.9 | 0.9 | 1.0 | Metaproterenol sulfate, orciprenaline sulfate | Beta-adrenergic agonist | Bronchodilatator |
| 1.0 | 0.9 | 0.8 | 0.7 | 0.8 | 0.9 | 1.0 | Lobeline alpha (−) hydrochloride | Nicotinic receptor ligand | Respiratory stimulant |
| 0.8 | 0.9 | 0.6 | 0.6 | 0.9 | 0.9 | 1.0 | Sisomicin sulfate | Ribosomal protein synthesis inhibitor | Antibacterial |
| 1.0 | 1.0 | 0.7 | 0.7 | 0.9 | 0.9 | 1.1 | Berberine chloride | Anti-HIV reverse transcriptase, cholinesterase inhibitor | Antibacterial |
| 0.7 | 0.8 | 0.1 | 0.6 | 0.4 | 0.6 | 0.9 | Quercetine dihydrate | Lipoxygenase inhibitor | Antimalarial |
| 0.9 | 0.9 | 0.8 | 0.7 | 0.9 | 0.9 | 0.9 | Cilostazol | — | Antithrombotic |
| 0.0 | 0.0 | 0.0 | 0.0 | 0.0 | 0.0 | 0.1 | Resveratrol | — | Antiinflammatory |
| 0.9 | 0.9 | 0.8 | 0.8 | 0.8 | 0.8 | 1.0 | Galanthamine hydrobromide | Cholinesterase inhibitor, nicotinic receptor agonist | Alzheimer treatment |
| 0.8 | 0.9 | 0.7 | 0.7 | 1.0 | 1.1 | 1.1 | Bromperidol | Dopamine antagonist | Antipsychotic |
| 0.9 | 0.9 | 0.6 | 0.8 | 0.8 | 0.9 | 0.9 | Bicuculline (+) | GABAa receptor antagonist | Convulsant |
| 1.0 | 1.0 | 0.9 | 0.8 | 1.0 | 1.0 | 0.9 | Cyclizine hydrochloride | H1 antagonist | Antiemetic |
| 0.9 | 0.9 | 0.7 | 0.7 | 0.8 | 0.9 | 0.9 | Yohimbinic acid monohydrate | — | — |
| 0.9 | 0.9 | 0.7 | 0.6 | 0.8 | 0.8 | 1.0 | Chlorthalidone | Na+ uptake inhibitor, carbonic anhydrase inhibitor | Diuretic |
| 0.9 | 0.9 | 0.4 | 0.6 | 0.8 | 0.8 | 1.1 | Coralyne chloride hydrate | Topoisomerase I inhibitor | Anti-leukemic |
| 0.8 | 0.8 | 0.1 | 0.8 | 0.7 | 0.6 | 1.1 | Dobutamine hydrochloride | Beta1, Beta2 agonist | Bronchodilator |
| 0.9 | 0.9 | 0.6 | 0.7 | 0.9 | 0.8 | 1.2 | Corticosterone | — | Glucocorticoid |
| 0.9 | 0.9 | 0.6 | 0.6 | 0.7 | 0.8 | 1.2 | Moclobemide | Mono amine oxidase inhibitor (Type A) | Antidepressant |
| 0.8 | 0.8 | 0.5 | 0.6 | 0.8 | 0.7 | 1.2 | Cyanocobalamin | — | Vitamin |
| 0.8 | 0.9 | 0.7 | 0.7 | 0.8 | 0.8 | 1.0 | Clopamide | Gonad stimuling agent | Antihypertensor |
| 0.9 | 0.8 | 0.5 | 0.8 | 0.9 | 0.8 | 1.2 | Cefadroxil | Bacterial transpeptidase inhibitor | Antibacterial |

TABLE 4-continued

AK-based Prestwick Library Screening Results.

| E. coli | E. faecium | S. aureus | K. pneumoniae | A. baumannii | P. aeruginosa | E. cloacae | Chemical name | Mechanism | Therapeutic group |
|---|---|---|---|---|---|---|---|---|---|
| 0.9 | 1.2 | 0.8 | 0.7 | 0.8 | 0.8 | 1.1 | Hycanthone | DNA intercaling agent | Anthelmintic |
| 0.9 | 0.9 | 0.6 | 0.7 | 0.9 | 0.8 | 1.4 | Cyclosporin A | IL 2 synthesis inhibitor, calcineurine phosphatase inhibitor | Immunosuppressant |
| 0.8 | 0.8 | 0.6 | 0.6 | 0.7 | 0.8 | 1.2 | Adenosine 5′-monophosphate monohydrate | Ca++ channel block, adenosine receptor activation, activation of outward K+ current | Nutrient |
| 0.9 | 0.9 | 0.6 | 0.7 | 0.8 | 0.8 | 1.2 | Digitoxigenin | Na+ K+ ATPase inhibitor | Cardiotonic |
| 10.6 | 1.4 | 0.4 | 0.7 | 1.7 | 0.7 | 1.0 | Amoxicillin | Bacterial transpeptidase inhibitor | Antibacterial |
| 0.8 | 0.9 | 0.8 | 0.7 | 0.9 | 0.8 | 1.2 | Digoxin | Na+ K+ ATPase inhibitor | Cardiotonic |
| 0.8 | 0.9 | 0.7 | 0.7 | 0.9 | 0.8 | 1.4 | Cephalexin monohydrate | Bacterial transpeptidase inhibitor | Antibacterial |
| 1.0 | 1.7 | 0.9 | 0.7 | 1.0 | 0.6 | 1.2 | Doxorubicin hydrochloride | DNA intercalant | Antibacterial |
| 0.8 | 0.9 | 0.7 | 0.7 | 0.8 | 0.8 | 1.1 | Dextromethorphan hydrobromide monohydrate | Opioid ligand | Antitussive |
| 0.8 | 0.9 | 0.6 | 0.7 | 0.8 | 0.7 | 1.2 | Carbimazole | Iodine oxidazing inhibitor | Antityroidic hormone |
| 0.9 | 1.0 | 0.9 | 0.7 | 1.0 | 0.7 | 1.2 | Droperidol | Alpha adrenergic antagonist, 5-HT antagonist, dopamine antagonist | Antipsychotic |
| 1.0 | 1.0 | 0.6 | 0.7 | 0.8 | 0.8 | 1.1 | Epiandrosterone | — | Anabolic steroid |
| 1.0 | 0.9 | 1.1 | 0.8 | 1.0 | 0.9 | 1.1 | Fluoxetine hydrochloride | 5-HT uptake inhibitor | Antidepressant |
| 1.0 | 0.9 | 0.7 | 0.7 | 0.9 | 0.9 | 1.3 | Laudanosine (R,S) | — | Convulsant |
| 1.0 | 0.9 | 0.7 | 0.7 | 0.9 | 0.8 | 1.1 | Iohexol | — | Diagnostic aid |
| 0.9 | 0.9 | 0.5 | 0.7 | 0.9 | 0.9 | 1.2 | Ajmalicine hydrochloride | Alpha antagonist | Antihypertensor |
| 6.3 | 0.8 | 0.6 | 0.9 | 1.1 | 1.0 | 1.3 | Norcyclobenzaprine | — | Antiulcerative |
| 0.9 | 0.9 | 0.8 | 0.7 | 0.9 | 0.8 | 1.2 | Trigonelline | Antihyperglycaemic agent | — |
| 0.9 | 0.8 | 0.7 | 0.8 | 0.9 | 0.9 | 1.2 | Pyrazinamide | — | Antibacterial |
| 0.9 | 0.9 | 0.8 | 0.7 | 0.8 | 0.9 | 1.2 | Diclofenac sodium | Cyclooxygenase inhibitor | Antinflammatory |
| 1.0 | 0.9 | 0.7 | 0.7 | 0.9 | 0.8 | 1.4 | Trimethadione | Ca++ channel blocker voltage dependant ? | Anticonvulsant |
| 0.9 | 0.8 | 0.6 | 0.7 | 0.8 | 0.8 | 1.2 | Calycanthine | Calcium channel blocker | — |
| 1.0 | 1.0 | 0.3 | 0.8 | 1.0 | 0.8 | 1.2 | Lovastatin | HMG CoA reductase inhibitor | Antihypercholesterolemic |
| 1.1 | 0.9 | 0.6 | 0.7 | 1.0 | 0.8 | 1.3 | Convolamine hydrochloride | Cholinergic ligand | Vasodilator |
| 1.0 | 0.8 | 0.7 | 0.8 | 0.9 | 0.8 | 1.4 | Nystatine | Performs membrane ionophores | Antifungal |
| 0.9 | 0.9 | 0.7 | 0.7 | 0.9 | 0.8 | 1.3 | Isocorydine (+) | Ganglioblocker | Hypotensor |
| 0.9 | 0.9 | 0.6 | 0.7 | 0.9 | 0.9 | 1.4 | Budesonide | — | Antiinflammatory |
| 0.8 | 0.9 | 0.8 | 0.7 | 0.9 | 0.9 | 1.4 | Xylazine | Alpha-2 adrenergic agonist | Antinociceptive |
| 12.1 | 0.9 | 2.5 | 1.7 | 1.2 | 1.0 | 2.4 | Imipenem | Bacterial transpeptidase inhibitor | Antibacterial |
| 0.9 | 0.9 | 0.8 | 0.7 | 0.8 | 0.8 | 1.2 | Seneciphylline | — | Antitumor activity |
| 0.8 | 0.9 | 0.8 | 0.7 | 1.1 | 0.8 | 1.1 | Sulfasalazine | 15-hydroxydehydrogenase inhibitor | Treatment of ulcerative colitis |
| 0.9 | 0.9 | 0.8 | 0.7 | 0.8 | 0.9 | 1.2 | Boldine | Smooth muscle relaxant | Choleretic |
| 1.3 | 1.1 | 1.2 | 0.9 | 1.0 | 1.2 | 1.2 | Bambuterol hydrochloride | Beta2 adrenergic receptor agonist | Bronchodilator |

TABLE 4-continued

AK-based Prestwick Library Screening Results.

| E. coli | E. faecium | S. aureus | K. pneumoniae | A. baumannii | P. aeruginosa | E. cloacae | Chemical name | Mechanism | Therapeutic group |
|---|---|---|---|---|---|---|---|---|---|
| 1.1 | 0.9 | 0.8 | 0.8 | 0.8 | 1.0 | 1.3 | Estradiol-17 beta | — | Estrogen |
| 1.1 | 1.1 | 1.1 | 0.9 | 0.9 | 1.1 | 1.3 | Betamethasone | — | Glucocorticoid |
| 0.8 | 1.1 | 0.9 | 0.9 | 0.9 | 1.1 | 1.2 | Fusaric acid | Dopamine beta hydroxylase inhibitor | Antibacterial |
| 1.2 | 1.0 | 1.0 | 0.9 | 1.0 | 1.0 | 1.1 | Colchicine | Tubulin polymerisation inhibitor | Antiinflammatory |
| 1.0 | 1.1 | 1.1 | 0.8 | 1.1 | 1.0 | 1.3 | Gabazine | Antagonist GABA | — |
| 1.2 | 1.0 | 1.1 | 1.0 | 1.3 | 1.1 | 1.3 | Metergoline | 5-HT1 antagonist, D2 agonist, 5-HT2 antagonist | Antiprolactin |
| 1.3 | 1.0 | 1.1 | 1.0 | 1.0 | 1.1 | 1.2 | Ginkgolide A | Cholinergic antagonist | Alzheimer treatment |
| 1.1 | 1.4 | 1.0 | 0.9 | 1.1 | 1.1 | 1.5 | Brinzolamide | Carbonic anhydrase inhibitor | Antiglaucoma drug |
| 1.3 | 1.0 | 1.0 | 0.9 | 1.2 | 1.1 | 1.2 | Cyclobenzaprine hydrochloride | — | Muscle relaxant |
| 1.0 | 1.0 | 1.0 | 1.0 | 1.2 | 1.2 | 1.5 | Ambroxol hydrochloride | — | Expectorant |
| 1.2 | 1.0 | 1.1 | 0.8 | 1.0 | 1.1 | 1.1 | Carteolol hydrochloride | — | Antihypertensor |
| 1.4 | 0.9 | 1.2 | 1.1 | 1.0 | 1.1 | 1.4 | Benfluorex hydrochloride | Increase of glucose penetration and use by cells, decrease of triglyceride intestinal absorption | Hypolipedimic |
| 1.1 | 1.0 | 1.3 | 0.9 | 1.3 | 1.1 | 1.4 | Hydrocortisone base | — | Glucocorticoid |
| 1.3 | 1.1 | 1.6 | 1.0 | 1.5 | 1.2 | 1.4 | Bepridil hydrochloride | Ca++ channel blocker | Antianginal |
| 1.3 | 1.0 | 3.0 | 1.0 | 1.0 | 1.0 | 1.3 | Hydroxytacrine maleate (R,S) | Acetylcholine esterase inhibitor | — |
| 1.0 | 0.9 | 2.0 | 0.8 | 0.9 | 0.9 | 1.2 | Meloxicam | Cyclooxygenase inhibitor | Anti-inflammatory |
| 1.0 | 1.1 | 1.3 | 0.9 | 1.0 | 1.0 | 1.5 | Pilocarpine nitrate | Cholinergic | Antiglaucoma drug |
| 1.1 | 1.2 | 0.4 | 0.9 | 1.4 | 1.5 | 1.4 | Benzbromarone | Uric acid transport inhibitor | Coronarodilatator |
| 1.2 | 1.0 | 7.1 | 0.9 | 1.5 | 1.4 | 1.2 | Dicloxacillin sodium salt | Bacterial transpeptidase inhibitor | Antibacterial |
| 1.1 | 1.1 | 1.2 | 1.0 | 1.1 | 1.1 | 1.4 | Glycocholic acid | Detergent | Anticholelithogenic |
| 1.2 | 1.0 | 1.0 | 1.0 | 1.3 | 1.1 | 1.6 | Scoulerine | Dopamine antagonist, alpha1 antagonist | Antiemetic |
| 1.3 | 1.0 | 0.4 | 1.0 | 1.1 | 0.9 | 1.4 | Thiostrepton | — | Antibacterial |
| 1.2 | 1.1 | 1.0 | 0.9 | 1.1 | 1.1 | 1.6 | Ajmaline | Inhibitor of glucose uptake by heart tissue | Antihypertensor |
| 1.3 | 1.0 | 1.1 | 0.9 | 1.0 | 1.2 | 1.5 | Methionine sulfoximine (L) | Glutamine synthetase inhibitor | — |
| 1.3 | 1.1 | 1.0 | 1.0 | 1.2 | 1.2 | 1.3 | Monocrotaline | — | For inducing pulmonary diseases in rats |
| 0.6 | 0.5 | 0.6 | 0.4 | 0.5 | 0.6 | 1.3 | Tiabendazole | Microtubule inhibitor | Anthelmintic |
| 1.2 | 1.0 | 1.0 | 1.0 | 1.0 | 1.1 | 1.6 | Piperlongumine | — | Antifungal |
| 1.3 | 0.8 | 0.8 | 0.7 | 3.0 | 0.6 | 1.4 | Rifampicin | RNA polymerase inhibitor | Antibacterial |
| 1.2 | 1.0 | 1.0 | 0.9 | 1.3 | 1.2 | 1.4 | Hydrocotamine hydrobromide | — | Hemostatic |
| 1.1 | 1.0 | 1.3 | 1.0 | 1.2 | 1.1 | 1.4 | Ethionamide | — | Antibacterial |
| 1.3 | 1.0 | 0.9 | 0.8 | 1.1 | 1.1 | 1.6 | (−)-Cinchonidine | — | Antimalarial |
| 1.3 | 1.0 | 1.2 | 0.9 | 1.0 | 1.0 | 1.6 | Tenoxicam | Cyclooxygenase inhibitor | Antiinflammatory |
| 1.2 | 1.1 | 1.0 | 1.0 | 1.0 | 1.3 | 1.4 | Eburnamonine (−) | — | Cerebral vasodilator |
| 1.2 | 1.0 | 1.4 | 0.9 | 1.0 | 1.2 | 1.3 | Triflusal | Cyclooxygenase inhibitor | Antithrombotic |
| 1.2 | 1.1 | 1.6 | 1.0 | 1.1 | 1.2 | 1.5 | Cinchonine | Heme polymerase inhibitor | Antimalarial |
| 1.1 | 1.1 | 1.3 | 1.0 | 1.0 | 1.2 | 1.3 | Mesoridazine besylate | D antagonist | Antipsychotic |

TABLE 4-continued

AK-based Prestwick Library Screening Results.

| E. coli | E. faecium | S. aureus | K. pneumoniae | A. baumannii | P. aeruginosa | E. cloacae | Chemical name | Mechanism | Therapeutic group |
|---|---|---|---|---|---|---|---|---|---|
| 1.2 | 1.1 | 1.6 | 0.9 | 1.1 | 1.1 | 1.4 | Canavanine sulfate monohydrate (L,+) | Nitric oxide inductible synthetase inhibitor | Anticancer agent |
| 1.1 | 1.1 | 1.6 | 1.1 | 1.1 | 1.1 | 1.6 | Trolox | — | Vitamin E analog |
| 1.1 | 1.0 | 1.4 | 0.9 | 1.0 | 1.0 | 1.3 | Harmaline hydrochloride dihydrate | Monoamine oxydase inhibitor | Antihelminthic |
| 1.3 | 1.0 | 1.1 | 0.9 | 1.1 | 1.1 | 1.7 | Ketotifen fumarate | H1 antagonist | Antihistaminic |
| 1.0 | 1.0 | 1.0 | 0.9 | 1.1 | 1.1 | 1.4 | Alizapride HCl | — | Antiemetic |
| 1.2 | 1.0 | 0.9 | 0.8 | 0.9 | 1.0 | 1.7 | Debrisoquin sulfate | Catecholamine depletor | Antihypertensor |
| 1.0 | 1.0 | 0.8 | 0.9 | 1.1 | 1.0 | 1.2 | Lactobionic acid | — | Antithrombonic |
| 1.1 | 0.9 | 1.0 | 0.8 | 0.9 | 1.1 | 1.3 | Amethopterin (R,S) | Dehydrofolate reductase inhibitor | Antineoplastic |
| 1.1 | 1.0 | 0.9 | 1.0 | 1.2 | 1.1 | 1.4 | Lumicolchicine gamma | Microtubule depolymerizing agent | — |
| 1.0 | 0.9 | 0.8 | 1.0 | 0.9 | 0.9 | 1.6 | Methylergometrine maleate | 5-HT antagonist, alpha adrenergic agonist | Oxytocic |
| 1.1 | 0.9 | 0.9 | 0.8 | 1.0 | 1.1 | 1.6 | Lysergol | 5-HT antagonist | — |
| 1.4 | 1.0 | 1.3 | 1.3 | 1.5 | 1.1 | 1.8 | Methiothepin maleate | 5-HT autoreceptor antagonist, 5-HT1c antagonist, 5-HT release inhibitor electrical or K+ induced | Antipsychotic |
| 1.1 | 1.0 | 0.9 | 0.8 | 0.9 | 1.1 | 1.5 | Mebhydroline 1,5-naphtalenedisulfonate | H1 antagonist | Antihistaminic |
| 1.2 | 1.0 | 4.6 | 1.1 | 5.0 | 1.0 | 1.8 | Clofazimine | — | Antileprosy |
| 0.8 | 1.0 | 4.3 | 0.3 | 3.2 | 0.5 | 2.1 | Meclocycline sulfosalicylate | Ribosomal protein synthesis inhibitor | Antibacterial |
| 1.0 | 1.0 | 0.9 | 1.0 | 1.0 | 1.1 | 1.4 | Nafronyl oxalate | Phosphodiesterase inhibitor ?, 5-HT antagonist, bradykinine antagonist | Vasodilator |
| 1.2 | 1.2 | 2.1 | 0.9 | 1.9 | 1.2 | 1.4 | Meclozine dihydrochloride | Histamine antagonist | Antiemetic |
| 0.9 | 0.8 | 1.1 | 0.7 | 0.8 | 1.0 | 1.6 | Bezafibrate | Lipoprotein lipase activator | Antihyperlipoproteinemic |
| 0.9 | 1.0 | 1.3 | 0.8 | 1.2 | 1.1 | 1.4 | Melatonin | Melatonin receptor ligand | Immunostimulant |
| 1.0 | 1.0 | 1.4 | 0.9 | 0.9 | 1.1 | 1.5 | Mimosine | Cell cycle blocker, apoptosis inducer | Anticancer agent |
| 1.0 | 1.1 | 1.4 | 1.0 | 1.0 | 1.2 | 1.5 | Menadione | — | Vitamin K3 |
| 1.1 | 1.1 | 1.2 | 1.0 | 1.0 | 0.9 | 1.6 | Clebopride maleate | — | Spasmolytic |
| 1.0 | 1.1 | 1.4 | 1.0 | 1.2 | 1.0 | 1.1 | Dinoprost trometamol | Protaglandin agonist | Smooth muscle activator |
| 1.1 | 1.1 | 1.1 | 1.0 | 1.2 | 1.2 | 1.5 | Prenperone | 5-HT2 antagonist | — |
| 1.2 | 0.8 | 0.8 | 0.8 | 1.1 | 1.2 | 1.6 | Harmalol hydrochloride dihydrate | — | Vasorelaxant |
| 1.3 | 0.9 | 1.0 | 1.0 | 1.0 | 1.2 | 1.5 | Isoquinoline, 6,7-dimethoxy-1-methyl-1,2,3,4-tetrahydro, hydrochloride | — | — |
| 1.4 | 1.0 | 0.9 | 0.9 | 1.1 | 1.1 | 1.6 | Harmol hydrochloride monohydrate | Liver conjugation probe | Anxiolytic |
| 1.2 | 0.9 | 0.8 | 0.9 | 1.1 | 0.9 | 1.4 | Phenacetin | Cyclooxygenase inhibitor | Analgesic |
| 1.1 | 1.1 | 0.9 | 0.7 | 1.0 | 1.2 | 1.5 | Harmine hydrochloride | Topoisomerase II inhibitor | Antibacterial |
| 1.0 | 1.0 | 1.2 | 0.8 | 1.2 | 1.4 | 1.4 | Atovaquone | — | Antipneumocystic |
| 1.3 | 1.3 | 0.8 | 1.0 | 4.1 | 1.2 | 1.8 | Ellipticine | Intercaling agent | Anticancer |
| 1.1 | 1.0 | 0.9 | 1.0 | 1.0 | 1.2 | 1.4 | Methoxamine hydrochloride | Alpha adrenergic agonist | Antihypotensive |

TABLE 4-continued

AK-based Prestwick Library Screening Results.

| E. coli | E. faecium | S. aureus | K. pneumoniae | A. baumannii | P. aeruginosa | E. cloacae | Chemical name | Mechanism | Therapeutic group |
|---|---|---|---|---|---|---|---|---|---|
| 1.1 | 0.9 | 0.1 | 0.8 | 0.8 | 1.0 | 1.4 | Chrysene-1,4-quinone | — | — |
| 1.2 | 1.0 | 1.2 | 0.9 | 1.1 | 1.1 | 1.7 | (S)-(−)-Atenolol | Blokage of the action of adrenergic mediators on beta receptors | Antihypertensor |
| 1.4 | 1.0 | 0.8 | 1.0 | 1.1 | 1.3 | 2.0 | Demecarium bromide | — | Cholinergic (ophtalmic) |
| 1.1 | 0.9 | 1.0 | 1.0 | 0.9 | 1.1 | 1.4 | Piracetam | — | Nootropic drug |
| 1.1 | 1.0 | 1.0 | 0.8 | 1.0 | 1.2 | 1.3 | Quipazine dimaleate salt | 5-HT agonist, 5-HT3 ligand | — |
| 1.2 | 0.9 | 1.1 | 1.1 | 1.1 | 0.9 | 1.3 | Phenindione | Antivitamin K | Anticoagulant |
| 1.3 | 1.0 | 1.1 | 1.0 | 1.0 | 1.0 | 1.7 | Sparteine (−) | Ganglioplegic | Antiarrhythmic |
| 1.0 | 1.1 | 1.2 | 0.8 | 0.9 | 1.0 | 1.7 | Thiocolchicoside | GABA agonist ? | Muscle relaxant |
| 1.1 | 1.1 | 1.1 | 1.0 | 0.9 | 1.0 | 1.4 | Diflorasone Diacetate | — | Anti-inflammatory (topical) |
| 1.0 | 1.4 | 1.5 | 1.0 | 1.0 | 1.0 | 1.7 | Clorsulon | — | Anthelmintic |
| 1.1 | 1.0 | 1.3 | 0.6 | 1.0 | 0.9 | 1.4 | Harmane hydrochloride | Imidazoline receptors ligand | Vasorelaxant |
| 1.1 | 1.1 | 1.4 | 1.1 | 2.9 | 1.3 | 1.4 | Lidoflazine | Ca++ channel activator | Coronary vasodilatator |
| 1.1 | 1.0 | 0.9 | 0.8 | 1.3 | 1.1 | 1.3 | Tropisetron HCl | 5 HT3 antagonist | Antiemetic |
| 1.2 | 0.9 | 0.9 | 1.0 | 1.4 | 1.1 | 1.6 | Betaxolol hydrochloride | Beta adrenergic antagonist | Antihypertensor |
| 18.6 | 1.1 | 1.2 | 4.6 | 1.8 | 11.7 | 21.9 | Cefixime | Constituent of bacterial peptidoglycan | Antibacterial |
| 1.2 | 1.1 | 0.6 | 1.0 | 1.3 | 1.1 | 1.4 | Nicardipine hydrochloride | Ca2+ channel antagonist | Antihypertensor |
| 1.1 | 1.0 | 1.2 | 1.0 | 1.3 | 1.1 | 1.3 | Metrizamide | — | Contrasting product |
| 1.1 | 0.9 | 0.6 | 0.9 | 1.4 | 1.1 | 1.3 | Probucol | — | Antihyperlipoproteinemic |
| 1.1 | 1.0 | 1.0 | 1.0 | 1.5 | 1.1 | 1.4 | Muramic acid, N-acetyl | Constituent of bacterial peptidoglycan | — |
| 1.5 | 0.8 | 0.7 | 1.0 | 1.5 | 0.9 | 1.2 | Mitoxantrone dihydrochloride | DNA topoisomerase II inhibitor | Antineoplastic |
| 0.9 | 0.8 | 0.5 | 0.9 | 0.8 | 0.9 | 1.2 | Myricetin | Neutral endopeptidase inhibitor | — |
| 1.4 | 1.3 | 1.5 | 1.0 | 2.2 | 1.2 | 1.5 | GBR 12909 dihydrochloride | Dopamine reuptake inhibitor | Antidepressant |
| 1.1 | 0.9 | 0.5 | 0.9 | 1.2 | 1.0 | 1.5 | Naringenine | — | Antiestrogenic |
| 1.4 | 1.0 | 1.1 | 1.0 | 1.4 | 1.1 | 1.4 | Carbetapentane citrate | Signal receptor ligand | Antitussive |
| 1.3 | 1.0 | 1.2 | 0.9 | 1.2 | 1.3 | 1.2 | Naringin hydrate | — | Anti-oxidant |
| 3.0 | 1.1 | 1.2 | 1.6 | 3.2 | 2.3 | 1.8 | Dequalinium dichloride | Blocker of the apamin-sensitive small conductance Ca2+ activated K+ channel, detergent | Antibacterial |
| 1.3 | 1.0 | 1.2 | 1.0 | 1.3 | 1.1 | 1.2 | Neostigmine bromide | Cholinesterase inhibitor | Spinal analgesic |
| 1.3 | 0.9 | 1.2 | 1.2 | 1.5 | 1.1 | 1.5 | Ketoconazole | Cytochrome P450c17 inhibitor, sterol 14-demethylase inhibitor | Antifungal |
| 1.0 | 1.0 | 1.8 | 6.0 | 1.4 | 1.2 | 6.1 | Niridazole | Helminthic DNA damage | Anthelmintic |
| 1.1 | 1.1 | 4.2 | 1.1 | 1.3 | 1.1 | 1.4 | Fusidic acid sodium salt | Protein synthesis inhibitor | Antibacterial |
| 12.2 | 1.0 | 1.8 | 3.1 | 1.8 | 1.2 | 1.9 | Ceforanide | GTPase coupled | Antibacterial |
| 1.1 | 1.6 | 0.7 | 0.9 | 1.2 | 1.0 | 1.2 | Ciclopirox ethanolamine | Cell membrane proteins synthesis inhibitor | Antifungal |
| 1.4 | 1.0 | 0.8 | 1.0 | 1.3 | 1.2 | 1.4 | Methoxy-6-harmalan | Benzodiazepine receptor ligand | Psoriasis treatment |
| 1.4 | 1.0 | 1.0 | 1.1 | 1.3 | 1.2 | 1.4 | Probenecid | Uric acid uptake inhibitor | Uricosuric |
| 1.4 | 1.0 | 1.0 | 1.1 | 1.4 | 1.2 | 1.5 | Stachydrine hydrochloride | Potent inhibitor of tyrosinase | — |

TABLE 4-continued

AK-based Prestwick Library Screening Results.

| E. coli | E. faecium | S. aureus | K. pneumoniae | A. baumannii | P. aeruginosa | E. cloacae | Chemical name | Mechanism | Therapeutic group |
|---|---|---|---|---|---|---|---|---|---|
| 1.4 | 0.9 | 0.9 | 1.1 | 1.2 | 1.1 | 1.3 | Betahistine mesylate | H1 agonist, H3 antagonist | Vasodilatator |
| 1.4 | 1.0 | 1.3 | 1.1 | 1.4 | 1.2 | 1.7 | Pyridoxine hydrochloride | — | Vitamin |
| 7.5 | 0.9 | 1.1 | 2.0 | 5.7 | 17.1 | 1.5 | Tobramycin | Ribosomal protein synthesis inhibitor | Antibacterial |
| 1.3 | 1.0 | 1.0 | 1.2 | 1.4 | 1.2 | 1.5 | Cytisine (−) | Partial nicotinic receptor agonist | Antiinflammatory |
| 1.3 | 1.0 | 1.1 | 1.1 | 1.4 | 1.2 | 1.4 | Tetramisole hydrochloride | Alkaline phosphatase inhibitor | Antihelminthic |
| 1.4 | 0.9 | 1.0 | 1.2 | 1.2 | 1.1 | 1.5 | Pseudopelletierine hydrochloride | — | — |
| 1.2 | 1.1 | 1.1 | 1.1 | 1.3 | 1.1 | 1.5 | Pregnenolone | — | Estrogen |
| 1.2 | 1.0 | 1.9 | 1.1 | 1.3 | 1.1 | 1.5 | Racecadotril | Enkephalinase inhibitor | Antidiarrhoeic |
| 1.4 | 0.9 | 0.9 | 1.0 | 1.2 | 1.1 | 1.5 | Molsidomine | NO° production ? | Vasodilatator |
| 1.3 | 1.1 | 1.0 | 1.0 | 1.3 | 1.1 | 1.3 | Folic acid | — | Vitamin Bc or M |
| 1.2 | 0.9 | 1.1 | 1.1 | 1.3 | 1.1 | 1.6 | Chloroquine diphosphate | Heme polymerase inhibitor | Antipaludic |
| 1.2 | 1.0 | 1.1 | 1.1 | 1.2 | 1.1 | 1.5 | Salsolinol hydrobromide | Dopamine analog | — |
| 1.4 | 1.0 | 1.2 | 1.1 | 1.3 | 1.1 | 1.7 | Trimetazidine dihydrochloride | — | Antianoxic |
| 1.2 | 1.0 | 1.3 | 1.0 | 1.3 | 1.1 | 1.5 | Gramine | Cholinesterase inhibitor | Antibacterial |
| 1.5 | 1.0 | 1.3 | 1.1 | 1.3 | 1.2 | 1.4 | Parthenolide | MAP kinase inhibitor | Antiinflammatory |
| 1.3 | 1.0 | 1.3 | 1.2 | 1.5 | 1.2 | 1.5 | Dimethisoquin hydrochloride | — | Local anesthesic |
| 1.2 | 1.0 | 1.1 | 1.3 | 1.1 | 1.1 | 1.4 | Terbutaline hemisulfate | Beta-2 adrenergic agonist | Bronchodilatator |
| 1.2 | 1.0 | 1.1 | 0.9 | 1.2 | 1.1 | 1.7 | Strophantine octahydrate | Na+ K+ ion dependant ATPase inhibitor | Cardiotonic |
| 1.3 | 1.0 | 1.0 | 1.0 | 1.2 | 1.0 | 1.4 | Ketanserin tartrate hydrate | 5-HT1, 5-HT2, 5-HT2A antagonist | Antihypertensor |
| 1.1 | 1.1 | 1.1 | 1.0 | 1.1 | 1.0 | 1.4 | Pantothenic acid calcium salt monohydrate | — | Nutritional factor |
| 1.1 | 0.9 | 1.0 | 1.0 | 1.2 | 0.9 | 2.0 | Hemicholinium bromide | Acetylcholine stores depleter, acetylcholine uptake inhibitor | — |
| 22.1 | 1.2 | 2.5 | 8.4 | 2.0 | 1.2 | 25.3 | Cefotetan | — | Antibacterial |
| 1.2 | 0.9 | 2.5 | 1.0 | 1.1 | 1.0 | 1.9 | Kanamycin A sulfate | Ribosomal protein synthesis inhibitor | Antibacterial |
| 0.4 | 0.3 | 0.2 | 0.3 | 0.4 | 0.4 | 1.6 | Piperine | Enzyme inhibitor | Antidiarrhoeic |
| 22.1 | 1.0 | 1.3 | 6.2 | 7.6 | 14.2 | 4.9 | Amikacin hydrate | Ribosomal protein synthesis inhibitor | Antibacterial |
| 1.4 | 1.0 | 1.1 | 1.1 | 1.2 | 1.1 | 2.0 | Brompheniramine maleate | H1 Antagonist, anticholinergic | Antihistaminic |
| 1.2 | 1.1 | 1.4 | 1.0 | 1.2 | 1.0 | 1.4 | Etoposide | Topoisomerase II inhibitor, kinase inhibitor | Antineoplastic |
| 1.2 | 0.9 | 2.1 | 1.0 | 1.1 | 1.0 | 1.4 | Primaquine diphosphate | Heme polymerase inhibitor | Antimalarial |
| 1.8 | 4.4 | 2.0 | 1.6 | 5.4 | 1.4 | 1.9 | Clomiphene citrate (Z,E) | Antioestrogen, gonad-stimulating agent | Ovulation inductor |
| 1.0 | 1.1 | 1.1 | 1.1 | 1.1 | 1.0 | 1.7 | Progesterone | — | Progestogen |
| 1.1 | 1.0 | 1.3 | 1.0 | 1.1 | 1.1 | 1.8 | Oxantel pamoate | Fumarate reductase inhibitor, neuromuscular depolarizing agent | Anthelmintic |
| 1.2 | 1.3 | 2.5 | 1.0 | 3.0 | 1.0 | 1.7 | Felodipine | L-type Ca2+ channels blocker | Antihypertensor |
| 1.2 | 1.1 | 1.1 | 1.2 | 1.6 | 1.2 | 2.0 | Prochlorperazine dimaleate | Dopamine antagonist | Antiemetic |
| 1.1 | 1.1 | 1.0 | 0.9 | 1.0 | 1.0 | 1.5 | Methoxy-8-psoralen | Apoptosis inducer with UV | Psoriasis treatment |

TABLE 4-continued

AK-based Prestwick Library Screening Results.

| E. coli | E. faecium | S. aureus | K. pneumoniae | A. baumannii | P. aeruginosa | E. cloacae | Chemical name | Mechanism | Therapeutic group |
|---|---|---|---|---|---|---|---|---|---|
| 1.1 | 1.1 | 1.3 | 1.0 | 1.2 | 1.0 | 1.4 | Hesperidin | — | Anticancer |
| 1.1 | 1.1 | 1.1 | 1.1 | 1.6 | 1.0 | 1.6 | Puromycin dihydrochloride | Antimetabolite | Antiprotozoal |
| 1.5 | 1.1 | 1.2 | 1.4 | 3.0 | 1.1 | 1.6 | Hexetidine | Detergent | Antifungal |
| 1.4 | 1.0 | 1.1 | 1.4 | 1.3 | 1.3 | 1.3 | Thiamine hydrochloride | — | Vitamin |
| 1.3 | 1.0 | 1.1 | 1.2 | 1.1 | 1.2 | 1.6 | Selegiline hydrochloride | Monoamine B oxydase inhibitor | Antiparkinsonian |
| 1.4 | 1.0 | 1.2 | 1.3 | 1.4 | 1.3 | 1.6 | Dipivefrin hydrochloride | — | Antiglaucoma drug |
| 1.4 | 1.4 | 1.9 | 1.2 | 1.2 | 1.2 | 1.4 | Pentamidine isethionate | — | Antiparasitic |
| 1.2 | 1.0 | 1.3 | 1.3 | 1.2 | 1.2 | 1.5 | Thiorphan | Neutral endopeptidase inhibitor | Antinociceptive |
| 1.5 | 1.0 | 1.0 | 1.4 | 1.2 | 1.4 | 1.6 | Tolazamide | ATP-sensitive K+ ion channels blocker | Antidiabetic |
| 1.1 | 1.0 | 0.9 | 1.6 | 1.2 | 1.2 | 1.5 | Riboflavine | — | Vitamin |
| 1.2 | 1.0 | 0.7 | 1.8 | 1.1 | 1.2 | 1.6 | Nifuroxazide | Bacterial DNA damage | Antibacterial |
| 1.2 | 1.1 | 1.0 | 1.3 | 1.2 | 1.2 | 1.6 | Hydroquinine hydrobromide hydrate | — | Preventor of muscular cramp |
| 1.2 | 1.1 | 1.1 | 1.5 | 1.2 | 1.2 | 1.3 | Mycophenolic acid | Inosine monophosphate dehydrogenase inhibitor | Antineoplastic |
| 1.3 | 1.0 | 1.0 | 1.2 | 1.2 | 1.2 | 1.6 | Epivincamine | Ribosomal protein synthesis inhibitor | Antiaggregant |
| 1.1 | 1.2 | 2.1 | 1.2 | 1.8 | 0.9 | 1.5 | Dirithromycin | | Antibacterial |
| 1.3 | 1.0 | 1.2 | 1.2 | 1.2 | 1.2 | 1.5 | Retrorsine | K+ channel voltage dependant inhibitor | Antineoplastic |
| 1.2 | 1.0 | 1.0 | 1.2 | 1.3 | 1.2 | 1.8 | Gliclazide | — | Antidiabetic |
| 1.5 | 1.1 | 1.2 | 1.2 | 1.4 | 1.2 | 1.6 | Conessine | D3 antagonist | Antiamebic |
| 1.4 | 1.0 | 1.1 | 1.3 | 1.2 | 1.3 | 1.7 | DO 897/99 | Acetylcholinesterase release stimulant | — |
| 1.1 | 1.0 | 1.2 | 1.2 | 1.2 | 1.1 | 1.3 | Protoveratrine A | Ca++ channel activator | Antihypertensor |
| 1.6 | 1.2 | 1.6 | 1.3 | 1.9 | 1.3 | 1.6 | Prenylamine lactate | Butyrylcholinesterase inhibitor | Vasodilatator |
| 1.2 | 1.0 | 1.2 | 1.2 | 1.3 | 1.2 | 1.7 | Solanine alpha | — | Antifungal |
| 0.3 | 0.9 | 0.4 | 0.5 | 0.3 | 0.3 | 0.3 | Sulmazole | Phosphodiesterase III inhibitor | Cardiotonic |
| 0.4 | 1.0 | 0.4 | 0.4 | 0.4 | 0.4 | 0.3 | Althiazide | Na+ Cl− transport inhibitor | Diuretic |
| 0.4 | 0.9 | 0.3 | 0.4 | 0.3 | 0.3 | 0.3 | Epicatechin-(−) | — | Antidiarrhoeic |
| 0.4 | 0.8 | 0.4 | 0.4 | 0.3 | 0.4 | 0.3 | Isopryn hydrochloride | Cyclooxygenase inhibitor | Antipyretic |
| 0.5 | 0.9 | 0.4 | 0.5 | 0.4 | 0.3 | 0.3 | Flunisolide | — | Glucocorticoid |
| 0.5 | 1.0 | 0.6 | 0.5 | 0.8 | 0.4 | 0.3 | Phenethicillin potassium salt | Bacterial transpeptidase inhibitor | Antibacterial |
| 0.5 | 0.8 | 0.4 | 0.4 | 0.4 | 0.3 | 0.7 | N-Acetyl-DL-homocysteine Thiolactone | Disulfure bridge breaker | Expectorant |
| 0.5 | 0.9 | 0.4 | 0.5 | 0.7 | 0.3 | 0.3 | Sulfamethoxypyridazine | Inhibitor of folic acid synthesis | Antibacterial |
| 0.5 | 0.8 | 0.4 | 0.5 | 0.5 | 0.4 | 0.3 | Flurandrenolide | — | Glucocorticoid |
| 0.4 | 0.9 | 0.4 | 0.5 | 0.4 | 0.4 | 0.4 | Deferoxamine mesylate | Iron chelating agent | — |
| 0.5 | 0.9 | 0.4 | 0.5 | 0.4 | 0.4 | 0.4 | Helveticoside | Inhibitor of membrane ATP | Cardiotonic |
| 0.5 | 0.8 | 0.4 | 0.5 | 0.4 | 0.4 | 0.3 | Mephentermine hemisulfate | Alpha-adrenergic receptor agonist | Antihypotensive |
| 0.5 | 0.9 | 0.4 | 0.5 | 0.5 | 0.4 | 0.4 | Myosmine | Cholinergic | — |

TABLE 4-continued

AK-based Prestwick Library Screening Results.

| E. coli | E. faecium | S. aureus | K. pneumoniae | A. baumannii | P. aeruginosa | E. cloacae | Chemical name | Mechanism | Therapeutic group |
|---|---|---|---|---|---|---|---|---|---|
| 0.4 | 0.7 | 0.2 | 0.5 | 0.5 | 0.4 | 0.4 | Ergocryptine-alpha | — | Vasoconstrictor |
| 0.4 | 0.9 | 0.4 | 0.6 | 0.4 | 0.4 | 0.4 | Betonicine | — | — |
| 0.6 | 0.9 | 0.5 | 0.5 | 0.9 | 0.4 | 0.4 | Sulfadimethoxine | Inhibitor of folic acid biosynthesis | Antibacterial |
| 0.5 | 0.8 | 0.4 | 0.5 | 0.5 | 0.4 | 0.4 | Etanidazole | DNA damage | Antineoplastic adjunct (radiosensitizer) |
| 0.5 | 0.9 | 0.4 | 0.6 | 1.5 | 0.5 | 0.4 | Sulfanilamide | Inhibitor of folic acid biosynthesis | Antibacterial |
| 0.5 | 0.8 | 0.5 | 0.5 | 0.5 | 0.5 | 0.4 | Butirosin disulfate salt | Ribosomal protein synthesis inhibitor | Antibacterial |
| 0.5 | 0.9 | 0.4 | 0.7 | 0.5 | 0.5 | 0.4 | Balsalazide Sodium | — | Anti-inflammatory |
| 0.7 | 0.8 | 0.6 | 0.6 | 0.7 | 0.6 | 0.7 | Carbinoxamine maleate salt | Histamine antagonist | Antihistaminic |
| 0.7 | 0.9 | 0.6 | 0.5 | 0.6 | 0.6 | 0.7 | Niacin | — | Antihyperlipoproteine-mic |
| 0.5 | 1.5 | 0.6 | 0.5 | 0.5 | 0.6 | 0.7 | Methazolamide | Anhydrase carbonic inhibitor | Diuretic |
| 0.6 | 0.9 | 0.7 | 0.6 | 0.7 | 0.6 | 0.6 | Bemegride | — | Respiratory stimulant |
| 0.7 | 0.8 | 0.6 | 0.6 | 0.5 | 0.6 | 0.7 | Pyrithyldione | — | Sedative |
| 0.7 | 0.8 | 0.6 | 0.6 | 0.6 | 0.5 | 0.7 | Digoxigenin | Mainly used as a non-isotopic label for DNA | Diagnosis |
| 0.6 | 1.0 | 0.6 | 0.2 | 0.5 | 0.5 | 0.6 | Spectinomycin dihydrochloride | Ribosomal protein synthesis inhibitor | Antibacterial |
| 0.5 | 0.8 | 0.5 | 0.7 | 0.5 | 0.5 | 0.6 | Meglumine | — | Expectorant |
| 0.6 | 0.9 | 0.7 | 0.6 | 0.5 | 0.5 | 0.6 | Piromidic acid | Topoisomerase II inhibitor | Antibacterial |
| 0.6 | 0.8 | 0.5 | 0.6 | 0.5 | 0.6 | 0.6 | Cantharidin | — | Aphrodisiac |
| 0.8 | 0.9 | 0.5 | 0.6 | 0.6 | 0.6 | 0.6 | Trimipramine maleate salt | noradrednaline and 5-HT uptake inhibitor, alpha antagonist, anticholinergic, Dopamine and Histamine antagonist | |
| 0.5 | 0.9 | 0.2 | 0.6 | 1.1 | 0.4 | 0.5 | Clioquinol | — | Anti-infective |
| 0.7 | 0.9 | 0.5 | 0.6 | 0.6 | 0.5 | 0.6 | Chloropyramine hydrochloride | H1 antagonist | Antihistaminic |
| 0.5 | 0.7 | 0.4 | 0.4 | 0.4 | 0.6 | 0.6 | Oxybenzone | — | Ultraviolet screen |
| 0.8 | 0.9 | 0.8 | 3.2 | 0.4 | 0.6 | 0.6 | Furazolidone | Monoamine oxidase inhibitor and protozoal DNA damage | Antinfective |
| 0.6 | 0.8 | 0.5 | 0.5 | 0.6 | 0.6 | 0.5 | Promethazine hydrochloride | — | Antihistaminic |
| 0.6 | 1.1 | 0.5 | 0.5 | 0.5 | 0.5 | 0.5 | Dichlorphenamide | Carbonic anhydrase inhibitor | — |
| 0.2 | 0.3 | 0.2 | 0.2 | 0.2 | 0.1 | 0.6 | Chrysin | 5-lipoxygenase inhibitor | — |
| 0.8 | 3.5 | 0.7 | 0.9 | 2.6 | 0.5 | 0.6 | Sulconazole nitrate | Ergosterol synthesis inhibition | Antifungal |
| 0.5 | 0.9 | 0.5 | 0.5 | 0.6 | 0.5 | 0.5 | Proxyphylline | — | Antifungal |
| 0.5 | 1.4 | 0.5 | 0.7 | 0.7 | 0.7 | 0.9 | Glimepiride | — | Vasodilator |
| 0.6 | 0.9 | 0.7 | 0.6 | 1.0 | 0.6 | 0.8 | Sulfaquinoxaline sodium salt | Inhibitor of folic acid synthesis | Antibacterial |
| 0.6 | 1.0 | 0.6 | 0.6 | 0.7 | 0.6 | 0.7 | Picrotoxinin | GABA channel blocker | Analeptic |
| 0.7 | 2.6 | 1.2 | 1.4 | 0.7 | 0.7 | 0.7 | Streptozotocin | — | Antineoplastic |
| 0.6 | 1.0 | 0.6 | 0.6 | 0.7 | 0.6 | 0.7 | Mepenzolate bromide | Anticholinergic and muscarinic antagonist | — |
| 0.6 | 0.9 | 0.6 | 0.5 | 0.7 | 0.7 | 7.0 | Metoprolol-(+,−) (+)-tartrate salt | Beta adrenergic antagonist | — |
| 0.7 | 0.9 | 0.5 | 0.6 | 0.7 | 0.6 | 0.8 | Benfotiamine | — | Vitamin |

TABLE 4-continued

AK-based Prestwick Library Screening Results.

| E. coli | E. faecium | S. aureus | K. pneumoniae | A. baumannii | P. aeruginosa | E. cloacae | Chemical name | Mechanism | Therapeutic group |
|---|---|---|---|---|---|---|---|---|---|
| 0.6 | 0.9 | 0.6 | 0.6 | 0.7 | 0.7 | 0.8 | Flumethasone | | Antiinflammatory |
| 0.6 | 0.9 | 0.6 | 0.5 | 0.7 | 0.7 | 0.8 | Halcinonide | | Antiinflammatory |
| 0.6 | 0.9 | 0.7 | 0.6 | 0.8 | 0.6 | 0.7 | Flecainide acetate | | Antiarrhythmic |
| 0.6 | 0.9 | 0.7 | 0.6 | 0.8 | 0.6 | 1.0 | Lanatoside C | Na+ K+ ATPase inhibitor | Cardiotonic |
| 16.5 | 0.9 | 3.1 | 3.6 | 0.5 | 0.7 | 0.9 | Cefazolin sodium salt | Bacterial transpeptidase inhibitor | Antibacterial |
| 0.6 | 1.1 | 0.7 | 0.6 | 0.6 | 0.6 | 0.7 | Benzamil hydrochloride | Na+ channel blocker and blocker of Na+/Ca++ exchanger | |
| 0.7 | 0.9 | 0.7 | 0.6 | 0.8 | 0.6 | 0.8 | Atractyloside potassium salt | Nucleotide transport inhibitor | Anticancer |
| 0.6 | 0.9 | 0.6 | 0.6 | 0.8 | 0.6 | 0.8 | Suxibuzone | | Antiinflammatory |
| 0.7 | 1.0 | 0.7 | 0.6 | 0.7 | 0.6 | 0.7 | Folinic acid calcium salt | | Antianemic |
| 0.7 | 0.9 | 0.6 | 0.5 | 0.7 | 0.6 | 0.9 | 6-Furfurylaminopurine | | Plant growth accelerator |
| 0.7 | 1.0 | 0.6 | 0.8 | 0.8 | 0.6 | 0.7 | Levonordefrin | Adrenergic receptor agonist | Vasoconstrictor |
| 0.8 | 1.2 | 1.7 | 0.6 | 0.8 | 0.7 | 0.9 | Avermectin B1 | Ligand GABA receptors | Antihelmetic |
| 0.6 | 0.9 | 0.5 | 0.6 | 0.7 | 0.6 | 0.7 | Ebselen | Cyclooxygenase inhibitor | Antiinflammatory |
| 0.7 | 0.9 | 0.9 | 0.8 | 0.9 | 0.8 | 1.1 | Bergenin monohydrate | | Antiarrhythmic |
| 0.7 | 0.9 | 0.6 | 0.6 | 0.8 | 0.7 | 1.1 | 3-Acetylcoumarin | | |
| 0.7 | 0.9 | 0.7 | 0.7 | 0.9 | 0.8 | 1.0 | Cromolyn disodium salt | | Antiasthmatic |
| 0.7 | 0.9 | 0.7 | 0.6 | 0.8 | 0.8 | 0.9 | Esculin Hydrate | | Skin protectant |
| 0.7 | 0.9 | 0.7 | 0.6 | 0.8 | 0.8 | 0.8 | Bucladesine sodium salt | Adenylate cyclase modulator | Cardiotonic |
| 0.7 | 0.9 | 0.6 | 0.6 | 0.8 | 0.7 | 1.0 | Felbinac | | Analgesic |
| 0.9 | 0.9 | 1.0 | 0.7 | 1.1 | 8.6 | 0.9 | Cefsulodin sodium salt | Bacterial transpeptidase inhibitor | Antibacterial |
| 0.5 | 0.5 | 0.7 | 0.4 | 0.6 | 0.6 | 1.0 | Butylparaben | | Antifungal |
| 0.7 | 0.9 | 0.7 | 0.6 | 0.8 | 0.7 | 0.8 | Fosfosal | Cyclooxygenase inhibitor | Analgesic |
| 0.7 | 0.9 | 0.6 | 0.6 | 0.7 | 0.7 | 0.8 | Aminohippuric acid | | Diagnostic aid (renal function) |
| 0.7 | 0.9 | 0.6 | 0.7 | 0.8 | 0.7 | 0.9 | Suprofen | Cyclooxygenase inhibitor | Analgesic |
| 0.7 | 0.9 | 0.6 | 0.6 | 0.7 | 0.7 | 0.9 | N-Acetyl-L-leucine | | Vertigo |
| 0.7 | 0.9 | 0.7 | 0.6 | 0.7 | 0.6 | 1.0 | Catechin-(+,-) hydrate | | Antidiarrhoeic |
| 14.7 | 0.9 | 0.7 | 1.7 | 0.9 | 0.9 | 1.0 | Pipemidic acid | | Antibacterial |
| 0.8 | 1.1 | 0.7 | 0.6 | 0.7 | 0.8 | 0.8 | Nadolol | Adrenergic beta antagonist | Antihypertensor |
| 0.8 | 0.9 | 0.5 | 0.7 | 0.6 | 0.7 | 1.0 | Dioxybenzone | | Ultraviolet screen |
| 18.1 | 1.3 | 4.4 | 3.9 | 0.6 | 0.6 | 0.8 | Moxalactam disodium salt | Bacterial transpeptidase inhibitor | Antibacterial |
| 0.7 | 0.9 | 0.6 | 0.6 | 0.8 | 0.6 | 1.2 | Adrenosterone | | Androgenic activity |
| 0.6 | 0.9 | 0.6 | 0.6 | 0.7 | 0.8 | 0.8 | Aminophylline | Mastocytes degranulation inhibitor and benzodiazepines antagonist | Vasodilatator |
| 0.7 | 1.0 | 0.6 | 0.6 | 0.7 | 0.7 | 0.8 | Methylatropine nitrate | | Mydriatic |
| 0.8 | 1.0 | 0.7 | 0.8 | 0.7 | 0.8 | 0.8 | Vitexin | | Antiviral |
| 0.9 | 0.9 | 0.6 | 0.7 | 0.8 | 0.9 | 0.9 | Nadide | Coenzyme nicotinamide adenine dinucleotide | — |
| 0.9 | 0.9 | 0.7 | 0.7 | 0.7 | 0.9 | 0.9 | Gelsemine | | Tumour inhibitor |
| 1.0 | 0.9 | 0.7 | 0.7 | 1.4 | 0.8 | 0.9 | Sulfamethizole | Inhibitor of folic acid synthesis | Antibacterial |
| 1.0 | 0.9 | 0.6 | 0.7 | 0.7 | 1.0 | 0.9 | Solasodine | | Cytotoxic |
| 0.7 | 1.0 | 0.6 | 0.7 | 0.7 | 0.8 | 1.0 | Medrysone | — | Glucocorticoid |

TABLE 4-continued

AK-based Prestwick Library Screening Results.

| E. coli | E. faecium | S. aureus | K. pneumoniae | A. baumannii | P. aeruginosa | E. cloacae | Chemical name | Mechanism | Therapeutic group |
|---|---|---|---|---|---|---|---|---|---|
| 0.8 | 0.9 | 0.7 | 0.7 | 0.9 | 0.9 | 1.2 | Delcorine | Nicotinic ligand | Antiarrhythmic |
| 0.6 | 0.6 | 0.5 | 0.5 | 0.5 | 0.6 | 1.0 | Flunixin meglumine | Glycine receptor antagonist | Analgesic |
| 0.7 | 0.8 | 0.6 | 0.7 | 0.7 | 0.8 | 1.1 | Evoxine | | Sedative |
| 0.9 | 1.0 | 6.6 | 0.8 | 0.9 | 0.7 | 1.2 | Spiramycin | Ribosomal protein synthesis inhibitor | Antibacterial |
| 0.9 | 0.9 | 0.4 | 0.7 | 1.4 | 0.8 | 1.0 | Nisoldipine | | Antihypertensive |
| 0.9 | 0.9 | 0.7 | 0.8 | 0.8 | 0.9 | 1.1 | Glycopyrrolate | | Antispasmodic |
| 0.9 | 0.9 | 0.7 | 0.8 | 0.8 | 0.8 | 1.0 | Foliosidine | | Anticonvulsant |
| 10.5 | 0.9 | 1.3 | 2.3 | 0.6 | 0.7 | 0.9 | Cefamandole sodium salt | Bacterial transpeptidase inhibitor | Antibacterial |
| 0.6 | 0.6 | 0.6 | 0.5 | 0.5 | 0.6 | 1.1 | Skimmianine | 5-HT ligand | Sedative |
| 0.9 | 1.1 | 0.7 | 0.6 | 0.7 | 0.9 | 1.1 | Monensin sodium salt | Performs membrane ionophores | Antibacterial |
| 1.0 | 0.9 | 0.6 | 0.8 | 0.8 | 0.9 | 1.0 | Anabasine | | Insecticide |
| 0.9 | 0.9 | 0.6 | 1.4 | 0.8 | 0.6 | 0.9 | Isoetharine mesylate salt | Beta adrenergic agonist | Bronchodilator |
| 0.9 | 1.0 | 0.9 | 0.9 | 0.9 | 0.9 | 1.1 | Tetrandrine | | Analgesic |
| 1.0 | 1.0 | 0.9 | 0.8 | 0.9 | 0.8 | 0.9 | Mevalonic-D, L acid lactone | HMG CoA substrate | — |
| 12.3 | 0.9 | 0.4 | 0.7 | 2.1 | 9.7 | 1.0 | Azlocillin sodium salt | Bacterial transpeptidase inhibitor | Antibacterial |
| 0.9 | 1.0 | 1.0 | 0.7 | 0.8 | 1.0 | 1.1 | Hymecromone | | Antispasmodic |
| 1.0 | 0.9 | 0.9 | 0.8 | 1.1 | 1.1 | 1.3 | Clidinium bromide | Anticholinergic | Spasmolytic |
| 1.0 | 0.9 | 0.8 | 0.8 | 0.8 | 0.9 | 1.0 | Caffeic acid | | Antineoplastic |
| 0.9 | 0.9 | 0.7 | 0.8 | 1.6 | 1.1 | 1.1 | Sulfamonomethoxine | Inhibitor of folic acid synthesis | Antiseptic |
| 1.0 | 0.8 | 0.7 | 0.7 | 0.9 | 1.0 | 1.2 | Diloxanide furoate | | Antiamebic |
| 0.9 | 1.4 | 0.8 | 0.8 | 0.9 | 0.9 | 1.1 | Benzthiazide | Na+ Cl− transport inhibitor | Diuretic |
| 0.9 | 0.8 | 0.8 | 0.7 | 1.0 | 0.8 | 1.2 | Metyrapone | | Diagnostic aid (pituitary function) |
| 0.8 | 1.4 | 1.3 | 0.8 | 1.0 | 0.8 | 1.2 | Trichlormethiazide | Na+ Cl− transport inhibitor | Diuretic |
| 1.0 | 0.9 | 0.9 | 0.7 | 1.0 | 1.0 | 1.1 | Urapidil hydrochloride | | Antihypertensor |
| 0.9 | 0.8 | 0.8 | 0.7 | 0.8 | 0.9 | 1.2 | Oxalamine citrate salt | | Antiinflammatory |
| 1.3 | 1.3 | 1.4 | 1.1 | 6.6 | 0.8 | 1.0 | Fluspirilen | | Antipsychotic |
| 0.9 | 0.8 | 0.8 | 0.8 | 1.0 | 0.9 | 1.3 | Propantheline bromide | Muscarinic antagonist | Antiulcerative |
| 0.9 | 0.9 | 0.8 | 0.7 | 0.8 | 0.9 | 1.3 | S-(+)-ibuprofen | | Analgesic |
| 1.0 | 0.9 | 3.7 | 0.7 | 2.6 | 0.7 | 1.0 | Lasalocid sodium salt | Membrane ionophores producer | Antibacterial |
| 0.8 | 0.9 | 0.5 | 0.9 | 0.9 | 0.9 | 1.1 | Ethynodiol diacetate | | Progestogen |
| 0.9 | 0.9 | 0.7 | 0.8 | 0.8 | 0.8 | 1.0 | Dimethadione | | Anticonvulsant |
| 0.5 | 0.4 | 0.4 | 0.5 | 0.4 | 0.6 | 1.0 | Nabumetone | | Analgesic |
| 0.9 | 1.0 | 0.5 | 0.7 | 0.9 | 0.9 | 1.0 | Ethaverine hydrochloride | | Antispasmodic |
| 0.9 | 1.0 | 0.7 | 0.8 | 0.8 | 0.9 | 0.9 | Nisoxetine hydrochloride | Inhibitor of noradrenaline | Antipsychotic |
| 0.9 | 1.0 | 0.7 | 0.8 | 0.8 | 0.9 | 1.2 | Dydrogesterone | | Progestogen |
| 0.8 | 0.8 | 0.8 | 0.7 | 0.7 | 0.6 | 1.2 | Terazosin hydrochloride | Alpha adrenergic antagonist | Treatment of benign prostatic hyperplasia |
| 0.8 | 0.9 | 0.7 | 0.7 | 0.9 | 0.8 | 1.3 | (d,l)-Tetrahydroberberine | | Sedative |
| 0.1 | 0.1 | 0.3 | 0.1 | 0.1 | 0.1 | 1.4 | Phenazopyridine hydrochloride | | Analgesic |
| 0.9 | 0.9 | 0.8 | 0.7 | 0.8 | 0.8 | 1.1 | Deltaline | Nicotinic receptor ligand | Antiarrhythmic |
| 0.5 | 0.9 | 7.1 | 0.2 | 3.4 | 0.4 | 1.3 | Demeclocycline hydrochloride | Ribosomal protein synthesis inhibitor | Antibacterial |

TABLE 4-continued

AK-based Prestwick Library Screening Results.

| E. coli | E. faecium | S. aureus | K. pneumoniae | A. baumannii | P. aeruginosa | E. cloacae | Chemical name | Mechanism | Therapeutic group |
|---|---|---|---|---|---|---|---|---|---|
| 0.8 | 0.8 | 0.7 | 0.6 | 0.8 | 0.8 | 1.2 | Graveoline | topoisomerase II inhibitor? and CNS stimulant | Antihypotensive |
| 0.8 | 0.9 | 0.8 | 0.7 | 0.8 | 0.8 | 1.4 | Fenoprofen calcium salt dihydrate | Cyclooxygenase inhibitor | Antiinflammatory |
| 0.9 | 0.9 | 0.7 | 0.6 | 0.8 | 0.9 | 1.4 | Hippeastrine hydrobromide | — | Hypotensor |
| 12.6 | 0.9 | 0.4 | 2.3 | 3.3 | 8.7 | 1.3 | Piperacillin sodium salt | Bacterial transpeptidase inhibitor | Antibacterial |
| 0.9 | 0.9 | 0.8 | 0.7 | 0.8 | 0.7 | 1.4 | Beta-Escin | — | Peripheral vascular disorders |
| 0.9 | 1.1 | 0.6 | 0.7 | 1.8 | 0.8 | 1.4 | Diethylstilbestrol | — | Estrogen |
| 0.6 | 1.3 | 0.2 | 0.3 | 0.4 | 0.5 | 1.5 | Gossypol | Ca2+ uptake inhibitor | Local contraceptive |
| 0.9 | 1.0 | 0.8 | 0.8 | 0.8 | 0.8 | 1.4 | Chlorotrianisene | Nuclear receptor ligand | Non-steroidal estrogen |
| 0.8 | 0.9 | 0.9 | 0.8 | 0.8 | 0.7 | 1.3 | Ricinine | — | — |
| 0.9 | 0.9 | 0.8 | 0.7 | 0.8 | 0.8 | 1.2 | Ribostamycin sulfate salt | Ribosomal protein synthesis inhibitor | Antibacterial |
| 0.9 | 0.9 | 0.8 | 0.7 | 0.9 | 0.8 | 1.3 | Delsoline | Nicotinic receptor antagonist and Ganglioblocker | — |
| 0.9 | 0.9 | 0.7 | 0.7 | 0.8 | 0.9 | 1.3 | Methacholine chloride | Cholinergic agonist | Muscle relaxant |
| 0.9 | 0.9 | 0.8 | 0.7 | 0.9 | 0.8 | 1.4 | Fluorocurarine chloride | — | Spasmolytic |
| 0.9 | 0.9 | 0.8 | 0.7 | 0.7 | 0.8 | 0.9 | Pipenzolate bromide | Nicotinic receptor antagonist | Local anesthesic |
| 0.9 | 0.9 | 0.8 | 0.8 | 0.9 | 1.0 | 1.4 | Butacaine | Na+ channel blocker | Sympathomimetic (VET) |
| 0.9 | 0.9 | 0.8 | 1.0 | 0.8 | 0.8 | 1.4 | (+)-Isoproterenol (+)-bitartrate salt | — | — |
| 20.1 | 1.0 | 3.4 | 3.2 | 1.3 | — | 1.2 | Cefoxitin sodium salt | Bacterial transpeptidase inhibitor | Antibacterial |
| 0.7 | 0.6 | 0.6 | 0.5 | 0.5 | 0.7 | 1.4 | Monobenzone | — | Depigmentor |
| 9.0 | 0.8 | 0.8 | 0.7 | 0.8 | 0.9 | 1.4 | Ifosfamide | — | Antineoplastic |
| 1.1 | 0.9 | 0.8 | 0.7 | 0.9 | 0.9 | 1.4 | 2-Aminobenzenesulfonamide | Ligand and potent inhibitor of carbonic anhydrase B | — |
| 3.2 | 1.5 | 4.5 | 0.7 | 1.1 | 1.0 | 1.6 | Novobiocin sodium salt | DNA topoisomerase IV inhibitor | Antibacterial |
| 0.8 | 0.8 | 0.7 | 0.7 | 0.8 | 0.8 | 1.4 | Estrone | — | Estrogen |
| 0.9 | 0.9 | 0.8 | 0.8 | 1.1 | 0.9 | 1.3 | Tetrahydroxy-1,4-quinone monohydrate | — | Keratolytic |
| 0.9 | 1.0 | 0.3 | 0.7 | 0.8 | 0.9 | 1.3 | Lorglumide sodium salt | CCKa ligand | Analgesic |
| 0.2 | 0.1 | 0.2 | 0.1 | 0.2 | 0.2 | 1.5 | Indoprofen | Cyclooxygenase inhibitor | Antihypertensor |
| 0.9 | 0.9 | 0.4 | 0.8 | 0.9 | 0.8 | 1.2 | Nitrendipine | — | Antiulcerative |
| 0.8 | 0.9 | 1.6 | 0.7 | 1.1 | 0.9 | 1.6 | Carbenoxolone disodium salt | Mucus stimulating synthesis | Anti-inflammatory |
| 0.8 | 0.9 | 0.6 | 0.7 | 0.9 | 0.8 | 1.6 | Flurbiprofen | — | Diagnostic aid (radiopaque medium) |
| 0.9 | 0.9 | 0.8 | 0.8 | 0.8 | 0.9 | 1.4 | Iocetamic acid | — | |
| 0.9 | 1.0 | 0.7 | 0.7 | 1.0 | 0.9 | 1.4 | Nimodipine | — | Vasodilator |
| 0.9 | 0.8 | 0.9 | 0.8 | 0.8 | 0.9 | 1.4 | Ganciclovir | Antimetabolite | Antiviral |
| 1.0 | 1.3 | 0.4 | 0.8 | 1.1 | 0.9 | 1.2 | Bacitracin | — | Antibacterial |
| 0.9 | 0.9 | 0.7 | 0.8 | 1.0 | 1.0 | 1.3 | Ethopropazine hydrochloride | Anticholinergic | Antiparkinsonian |
| 0.8 | 0.9 | 0.8 | 0.7 | 0.8 | 0.8 | 1.2 | L(−)-vesamicol hydrochloride | Potent inhibitor of vesicular acetylcholine storage | — |
| 1.2 | 1.1 | 1.2 | 1.0 | 1.0 | 1.1 | 1.3 | Austricine hydrate | — | Antiatherosclerotic |
| 0.8 | 0.8 | 1.1 | 0.6 | 0.7 | 0.9 | 1.7 | Butamben | Na+ channel blocker | Anesthetic |
| 1.2 | 1.0 | 1.3 | 0.9 | 1.0 | 1.2 | 1.3 | beta-Belladonnine dichloroethylate | Muscarinic receptor and nicotinic receptor lignad | — |

TABLE 4-continued

AK-based Prestwick Library Screening Results.

| E. coli | E. faecium | S. aureus | K. pneumoniae | A. baumannii | P. aeruginosa | E. cloacae | Chemical name | Mechanism | Therapeutic group |
|---|---|---|---|---|---|---|---|---|---|
| 1.2 | 1.0 | 1.4 | 0.9 | 2.2 | 1.1 | 1.6 | Sulfapyridine | Nicotinic acetylcholine receptor antagonist | Antibacterial |
| 1.1 | 1.0 | 1.1 | 1.0 | 1.1 | 1.1 | 1.5 | Pempidine tartrate | | Antihypertensor |
| 1.2 | 1.0 | 1.2 | 1.0 | 1.0 | 1.1 | 1.4 | Meclofenoxate hydrochloride | Acetylcholine precursor | Cerebral stimulant |
| 1.2 | 1.0 | 1.4 | 1.0 | 1.0 | 1.0 | 1.7 | Heliotrine | Model for hepatitis and cirrhosis in liver | |
| 0.9 | 1.1 | 0.7 | 2.6 | 1.0 | 1.1 | 1.7 | Furaltadone hydrochloride | Bacterial DNA damage | Antibacterial |
| 1.2 | 1.0 | 1.3 | 1.1 | 1.0 | 1.1 | 1.4 | Nitrarine dihydrochloride | — | Hypotensor |
| 1.1 | 0.9 | 1.1 | 0.9 | 0.9 | 1.1 | 1.4 | Ethoxyquin | — | Antifungal |
| 1.0 | 1.0 | 1.4 | 0.8 | 1.0 | 1.1 | 1.5 | Lycorine hydrochloride | Inhibitor of protein translation | Antitumoral |
| 1.2 | 0.9 | 1.2 | 0.8 | 1.0 | 1.1 | 1.5 | Tinidazole | Protozoal and bacterial DNA damage | Antiprotozoal |
| 1.0 | 1.0 | 1.2 | 0.9 | 1.0 | 1.1 | 1.3 | Karakoline | Inhibitor of ACE | Hypotensor |
| 1.3 | 1.0 | 1.2 | 0.7 | 1.0 | 1.1 | 1.4 | Guanadrel sulfate | | Antihypertensor |
| 1.3 | 1.0 | 1.1 | 1.0 | 1.0 | 1.1 | 1.3 | Estropipate | | Menopause |
| 1.1 | 1.1 | 1.5 | 0.7 | 1.0 | 1.0 | 1.8 | Vidarabine | Adenosine antimetabolite | Antiviral |
| 1.3 | 1.0 | 1.2 | 1.0 | 1.1 | 1.1 | 1.4 | Ungerine nitrate | Enhancer of analgesics | Sedative |
| 1.3 | 1.0 | 1.2 | 1.0 | 2.3 | 1.1 | 1.2 | Sulfameter | Inhibitor of folic acid synthesis | Antibacterial |
| 1.3 | 1.0 | 1.4 | 1.0 | 1.0 | 1.1 | 3.6 | Napelline | Anticholinergic agent | Antiarrhythmic |
| 1.1 | 1.1 | 1.2 | 1.1 | 1.0 | 1.2 | 1.5 | Isopropamide iodide | Anticholinergic | CNS stimulant |
| 1.2 | 1.0 | 1.1 | 0.8 | 1.1 | 1.2 | 1.6 | Securinine | | Antiulcerative |
| 1.3 | 1.0 | 1.2 | 0.9 | 1.0 | 1.2 | 1.7 | Nizatidine | H2 antagonist | Antipruritic |
| 1.2 | 1.0 | 1.1 | 0.9 | 1.1 | 1.2 | 1.5 | Trimeprazine tartrate | Histamine antagonist | Antiemetic |
| 1.2 | 1.0 | 1.1 | 1.0 | 1.0 | 1.3 | 1.6 | Thioperamide maleate | H3 antagonist | Antibacterial |
| 1.2 | 1.0 | 6.5 | 1.0 | 1.5 | 1.3 | 1.4 | Nafcillin sodium salt monohydrate | Bacterial transpeptidase inhibitor | |
| 1.3 | 1.0 | 1.1 | 0.8 | 1.0 | 1.2 | 1.8 | Xamoterol hemifumarate | beta1-Adrenoceptor selective partial agonist | Cardiotonic |
| 1.4 | 1.1 | 1.2 | 0.9 | 1.1 | 1.2 | 1.8 | Procyclidine hydrochloride | Muscarinic antagonist | Antiparkinsonian |
| 1.1 | 1.0 | 1.3 | 1.0 | 1.2 | 1.2 | 1.7 | Rolipram | | Nootropic drug |
| 1.3 | 1.1 | 1.3 | 0.9 | 1.2 | 1.2 | 1.5 | Amipilose hydrochloride | | Immunomodulator |
| 3.2 | 7.5 | ### | 4.7 | 5.6 | 1.5 | 1.8 | Thonzonium bromide | Detergent | |
| 1.2 | 0.9 | 0.8 | 0.8 | 1.1 | 1.2 | 1.5 | Ethynylestradiol 3-methyl ether | | Estrogen |
| 1.1 | 1.0 | 1.1 | 1.0 | 1.1 | 1.2 | 1.5 | Idazoxan hydrochloride | Alpha2 agonist | Antiparkinsonian |
| 1.3 | 1.0 | 1.0 | 1.0 | 1.0 | 1.2 | 1.9 | (−)-Levobunolol hydrochloride | Adrenergic beta antagonist | Antiglaucoma drug |
| 1.2 | 1.1 | 1.2 | 1.0 | 1.2 | 1.2 | 1.6 | Quinapril HCl | | Angiotensin |
| 1.3 | 1.1 | 1.3 | 1.0 | 1.0 | 1.2 | 1.5 | Iodixanol | | Diagnostic aid (radiopaque medium) |
| 1.2 | 1.0 | 1.3 | 1.0 | 1.2 | 1.2 | 1.4 | Nilutamide | | Antineoplastic |
| 1.1 | 1.0 | 1.1 | 1.0 | 1.2 | 1.1 | 1.7 | Rolitetracycline | Ribosomal protein synthesis inhibitor | Antibacterial |
| 1.3 | 1.0 | 1.1 | 1.0 | 1.0 | 1.0 | 1.4 | Ketorolac tromethamine | | Analgesic |
| 1.3 | 1.0 | 3.9 | 0.9 | 1.0 | 1.1 | 1.4 | Equilin | | Estrogen |
| 1.2 | 1.0 | 2.8 | 1.1 | 1.1 | 1.2 | 1.4 | Protriptyline hydrochloride | | Antidepressant |
| 1.2 | 1.0 | 1.0 | 0.8 | 0.9 | 1.0 | 1.8 | Fillalbin | | — |
| 1.1 | 1.0 | 1.1 | 1.1 | 0.9 | 1.1 | 1.2 | Alclometasone dipropionate | Corticoide | — |
| 1.0 | 1.0 | 1.0 | 0.9 | 0.9 | 1.2 | 1.5 | Citalopram Hydrobromide | 5HT uptake inhibitor | Anti-inflammatory |

TABLE 4-continued

AK-based Prestwick Library Screening Results.

| E. coli | E. faecium | S. aureus | K. pneumoniae | A. baumannii | P. aeruginosa | E. cloacae | Chemical name | Mechanism | Therapeutic group |
|---|---|---|---|---|---|---|---|---|---|
| 0.8 | 0.7 | 0.6 | 0.6 | 0.8 | 0.8 | 1.5 | Leflunomide | Inhibitor of T and B cell proliferation | Immunosuppressive |
| 1.2 | 1.0 | 1.4 | 0.8 | 0.9 | 1.1 | 1.7 | Promazine hydrochloride | Dopamine receptor antagonist | Antipsychotic |
| 1.0 | 1.0 | 1.1 | 1.1 | 1.1 | 1.1 | 1.7 | Norgestrel-(−)-D | Progestogen | Oral contraceptive |
| 1.1 | 1.0 | 0.9 | 1.0 | 2.1 | 1.0 | 1.9 | Sulfamerazine | Inhibitor of folic acid synthesis | Antibacterial |
| 1.0 | 1.0 | 1.1 | 0.9 | 0.9 | 1.2 | 1.7 | Fluocinonide | Inhibitor of glutathione reductase and of topoisomerase I | Antiinflammatory |
| 0.7 | 0.5 | 0.7 | 0.6 | 0.3 | 0.6 | 1.6 | Acacetin | | Antitumor agent |
| 1.0 | 1.0 | 1.4 | 1.0 | 1.6 | 1.1 | 1.4 | Sulfamethazine sodium salt | Inhibitor of folic acid synthesis | Antibacterial |
| 1.2 | 1.0 | 1.2 | 1.0 | 1.1 | 0.9 | 1.6 | Ethotoin | | Anticonvulsant |
| 1.1 | 1.0 | 1.2 | 0.8 | 1.0 | 1.1 | 1.6 | Guaifenesin | | Expectorant |
| 1.2 | 1.0 | 1.0 | 0.9 | 0.9 | 1.1 | 1.9 | 3-alpha-Hydroxy-5-beta-androstan-17-one | | |
| 43.3 | 7.4 | ### | 23.4 | 12.3 | 19.2 | 1.5 | Alexidine dihydrochloride | Detergent | Antibacterial |
| 1.4 | 1.0 | 1.1 | 0.9 | 1.0 | 1.0 | 1.4 | Tetrahydrozoline hydrochloride | Adrenergic | Vasoconstrictor |
| 1.2 | 1.1 | 0.8 | 0.8 | 1.1 | 1.1 | 1.7 | Proadifen hydrochloride | Cytochrome P450 mono-oxygenases inhibitor, Na+ channel blocker | Local anesthesic |
| 1.4 | 1.2 | 0.7 | 0.7 | 3.0 | 1.1 | 1.6 | Hexestrol | Nuclear receptor ligand | Estrogen antineoplastic |
| 1.1 | 1.1 | 0.9 | 1.0 | 1.1 | 0.9 | 1.6 | Zomepirac sodium salt | Cyclooxygenase inhibitor | |
| 20.0 | 1.4 | 5.0 | 4.6 | 1.4 | 1.0 | 1.6 | Cefmetazole sodium salt | Bacterial transpeptidase inhibitor | Antibacterial |
| 10.3 | 1.1 | 1.3 | 2.1 | 1.3 | 1.2 | 1.4 | Cinoxacin | Topoisomerase II inhibitor | Antibacterial |
| 1.4 | 0.9 | 1.4 | 1.2 | 1.3 | 1.3 | 1.6 | Paroxetine Hydrochloride | 5-HT uptake inhibitor | |
| 1.3 | 1.0 | 1.2 | 1.1 | 1.0 | 1.2 | 1.7 | Propofol | | Anesthetic (intravenous) |
| 2.0 | 1.1 | 9.4 | 0.3 | 3.4 | 0.7 | 1.5 | Doxycycline hyclate | Ribosomal protein synthesis inhibitor | Antibacterial |
| 0.9 | 1.0 | 1.6 | 1.1 | 1.0 | 1.3 | 1.8 | S(−)Eticlopride hydrochloride | | |
| 1.2 | 1.1 | 1.0 | 0.9 | 1.1 | 1.1 | 1.6 | Liothyronine | Thyroid hormone | Thyroidic drug |
| 1.0 | 0.9 | 1.3 | 0.9 | 1.2 | 1.2 | 1.8 | Primidone | | Anticonvulsant |
| 0.9 | 1.4 | 2.8 | 1.1 | 1.0 | 0.9 | 1.5 | Roxithromycin | Ribosomal protein synthesis inhibitor | Antibacterial |
| 1.1 | 0.9 | 1.1 | 0.8 | 1.2 | 1.1 | 1.8 | Flucytosine | | Antifungal |
| 1.1 | 1.0 | 0.5 | 0.9 | 1.0 | 1.0 | 1.5 | Beclomethasone dipropionate | | Antiinflammatory |
| 1.2 | 0.9 | 1.1 | 1.0 | 1.1 | 1.3 | 1.9 | (−)-MK 801 hydrogen maleate | NMDA antagonist | Anticonvulsant |
| 0.9 | 0.8 | 0.9 | 0.6 | 0.8 | 1.0 | 2.0 | Tolmetin sodium salt dihydrate | Cyclooxygenase inhibitor | Antiinflammatory |
| 1.2 | 1.0 | 1.2 | 1.0 | 0.9 | 1.0 | 2.0 | Bephenium hydroxynaphthoate | | Antihelmintic |
| 1.2 | 0.9 | 1.3 | 0.9 | 0.9 | 1.2 | 1.5 | (+)Levobunolol hydrochloride | Beta adrenergic antagonist | Antiglaucoma drug |
| 1.0 | 1.1 | 0.8 | 0.9 | 1.1 | 1.1 | 1.7 | Dehydroisoandosterone 3-acetate | | Menopausal syndrome |
| 1.4 | 1.1 | 1.2 | 0.9 | 1.3 | 1.1 | 1.5 | Doxazosin mesylate | Alpha 1 adrenergic antagonist | Antihypertensor |
| 1.3 | 0.9 | 1.4 | 1.2 | 1.0 | 1.1 | 1.8 | Benserazide hydrochloride | Inhibitor of L-aromatic amino acid decarboxylase | In combination with levodopa as antiparkinsonian |
| 1.3 | 1.0 | 1.0 | 0.9 | 0.9 | 1.0 | 1.7 | Fluvastatin sodium salt | HMG CoA reductase inhibitor | Anti-hyperlipoproteinemic |

TABLE 4-continued

AK-based Prestwick Library Screening Results.

| E. coli | E. faecium | S. aureus | K. pneumoniae | A. baumannii | P. aeruginosa | E. cloacae | Chemical name | Mechanism | Therapeutic group |
|---|---|---|---|---|---|---|---|---|---|
| 1.2 | 1.0 | 1.0 | 1.0 | 1.2 | 1.1 | 1.6 | Iodipamide | — | Diagnostic aid (radiopaque medium-cholecystographic) |
| 1.4 | 1.1 | 1.3 | 1.0 | 1.0 | 1.1 | 2.0 | Methylhydantoin-5-(L) | — | Antifungal |
| 1.4 | 1.0 | 1.1 | 1.2 | 1.1 | 0.9 | 1.4 | Esculetin | — | — |
| 1.2 | 1.1 | 1.4 | 1.1 | 1.4 | 1.3 | 1.5 | Trihexyphenidyl-D,L Hydrochloride | Anticholinergic | Antiparkinsonian |
| 1.2 | 1.0 | 0.9 | 1.0 | 1.3 | 1.1 | 1.3 | Clobetasol propionate | — | Glucocorticoid |
| 1.4 | 1.0 | 1.3 | 1.1 | 1.3 | 1.1 | 1.4 | Succinylsulfathiazole | Inhibitor of folic acid synthesis | Antibacterial |
| 1.2 | 0.9 | 1.0 | 1.2 | 1.2 | 1.1 | 1.3 | Podophyllotoxin | — | Antiviral |
| 1.2 | 1.0 | 0.8 | 1.1 | 1.1 | 1.2 | 1.5 | Famprofazone | — | Antipyretic |
| 1.2 | 1.1 | 1.4 | 1.1 | 1.3 | 1.2 | 1.5 | Clofibric acid | Lipoproteine lipase activator ? | Antihyperlipoproteinemic |
| 1.3 | 0.9 | 1.3 | 1.0 | 1.3 | 1.1 | 1.3 | Bromopride | Dopamine antagonist | Antiemetic |
| 1.3 | 1.2 | 1.3 | 1.1 | 1.3 | 1.1 | 1.5 | Bendroflumethiazide | Na+ Cl− transport inhibitor | Diuretic |
| 5.1 | 7.4 | ## | 7.4 | 5.8 | 8.9 | 1.3 | Methyl benzethonium chloride | Detergent | Antibacterial |
| 1.1 | 1.3 | 1.3 | 1.1 | 1.3 | 1.2 | 1.5 | Dicumarol | Vitamin K antagonist | Anticoagulant |
| 1.3 | 1.0 | 1.2 | 1.1 | 1.3 | 1.1 | 1.6 | Chlorcyclizine hydrochloride | Histamine antagonist | Antihistaminic |
| 1.3 | 0.9 | 1.0 | 1.0 | 1.5 | 1.0 | 27.1 | Methimazole | Iodine oxidazing inhibitor | Antihyperthyroid |
| 1.3 | 1.1 | 1.2 | 1.0 | 1.3 | 1.1 | 1.4 | Diphenylpyraline hydrochloride | H1 antagonist | Antihistaminic |
| 0.5 | 0.6 | 0.2 | 0.4 | 0.7 | 0.4 | 1.4 | Merbromin | — | Antibacterial |
| 2.9 | 6.2 | ## | 5.7 | 5.4 | 5.8 | 1.3 | Benzethonium chloride | Detergent | Antibacterial |
| 1.2 | 1.0 | 1.3 | 1.0 | 1.3 | 1.1 | 1.4 | Hexylcaine hydrochloride | — | Local anesthesic |
| 1.2 | 0.9 | 0.9 | 1.0 | 1.2 | 1.0 | 1.3 | Trioxsalen | — | Pigmentation agent (photosensitizer) |
| 1.5 | 1.0 | 1.5 | 1.2 | 1.3 | 1.2 | 1.5 | Drofenine hydrochloride | — | Spasmolytic |
| 1.4 | 1.0 | 1.3 | 1.0 | 1.3 | 1.1 | 1.3 | Strophanthidin | ATPase inhibitor | Cardiotonic |
| 1.3 | 1.0 | 1.1 | 1.0 | 1.2 | 1.1 | 0.9 | Cycloheximide | — | Antibacterial |
| 1.4 | 1.0 | 1.5 | 1.1 | 1.4 | 1.3 | 1.6 | Gabapentin | GABA receptor ligand | Anticonvulsant |
| 1.3 | 0.9 | 1.4 | 1.1 | 1.3 | 1.2 | 1.5 | Pentetic acid | Chelating agent (iron) | — |
| 1.5 | 0.9 | 1.2 | 1.1 | 1.5 | 1.1 | 1.3 | Raloxifene hydrochloride | — | — |
| 1.3 | 1.0 | 1.3 | 1.1 | 1.3 | 1.1 | 1.6 | Bretylium tosylate | — | Antiadrenergic |
| 1.3 | 1.0 | 1.2 | 1.0 | 1.2 | 1.1 | 1.4 | Etidronic acid, disodium salt | — | Calcium regulator |
| 1.3 | 1.0 | 1.3 | 1.0 | 1.4 | 1.1 | 1.4 | Pralidoxime chloride | — | — |
| 1.2 | 1.0 | 1.2 | 1.1 | 1.3 | 1.2 | 1.5 | Methylhydantoin-5-(D) | — | — |
| 1.4 | 0.9 | 1.1 | 1.2 | 1.3 | 1.1 | 1.4 | Phenoxybenzamine hydrochloride | Nonselective alpha-adrenergic blockade | Antihypertensor |
| 1.6 | 1.0 | 0.4 | 1.2 | 2.5 | 1.1 | 1.5 | Simvastatin | HMG-CoA reductase inhibitor | Antihyperlipidemic |
| 1.4 | 1.0 | 1.9 | 1.1 | 1.5 | 1.2 | 1.5 | Salmeterol | beta 2 adrenergic agonist | Bronchodilator |
| 2.2 | 1.0 | 1.2 | 0.9 | 1.4 | 1.2 | 1.5 | Azacytidine-5 | Antimetabolite | Antineoplastic |
| 1.3 | 1.0 | 1.1 | 1.0 | 1.3 | 1.2 | 1.4 | Altretamine | — | — |
| 1.4 | 0.9 | 1.3 | 1.0 | 1.5 | 1.0 | 1.4 | Paromomycin sulfate | Ribosomal protein synthesis inhibitor | Antiamebic |
| 1.2 | 1.1 | 1.4 | 0.9 | 1.4 | 1.1 | 1.5 | Prazosin hydrochloride | — | Antihypertensor |
| 1.4 | 1.0 | 1.6 | 1.2 | 1.5 | 1.1 | 1.6 | Acetaminophen | Cyclooxygenase inhibitor | Antipyretic |
| 1.3 | 1.0 | 1.3 | 1.1 | 1.5 | 1.1 | 1.4 | Timolol maleate salt | — | Antiglaucoma drug |
| 1.4 | 1.0 | 1.4 | 1.0 | 1.4 | 1.0 | 1.2 | Phthalylsulfathiazole | Inhibitor of folic acid synthesis | Antibacterial |

TABLE 4-continued

AK-based Prestwick Library Screening Results.

| E. coli | E. faecium | S. aureus | K. pneumoniae | A. baumannii | P. aeruginosa | E. cloacae | Chemical name | Mechanism | Therapeutic group |
|---|---|---|---|---|---|---|---|---|---|
| 1.3 | 1.0 | 1.3 | 1.1 | 1.3 | 1.0 | 1.4 | (+,-)-Octopamine hydrochloride | beta-3 Adrenergic receptor agonist | Adrenergic |
| 0.4 | 0.5 | 0.2 | 0.5 | 0.3 | 0.5 | 1.6 | Luteolin | — | Expectorant |
| 1.4 | 1.0 | 1.3 | 1.2 | 1.3 | 1.0 | 1.3 | (±)-Nipecotic acid | Activates GABA-like ion channels | |
| 1.1 | 1.1 | 1.2 | 1.1 | 2.8 | 1.1 | 1.6 | Sulfabenzamide | Inhibitor of folic acid synthesis | Antibacterial |
| 1.1 | 1.0 | 1.0 | 1.0 | 1.1 | 1.0 | 1.7 | (R)-Naproxen sodium salt | Cyclooxygenase inhibitor | Antiinflammatory |
| 1.1 | 1.0 | 1.2 | 0.9 | 1.2 | 1.1 | 1.6 | Benzocaine | Na+ channel blocker | Anesthetic |
| 1.3 | 0.8 | 1.4 | 0.8 | 1.1 | 1.0 | 1.6 | Propidium iodide | Detergent | Antibacterial |
| 1.1 | 1.0 | 1.4 | 1.1 | 1.1 | 1.1 | 1.4 | Dipyrone | Cyclooxygenase inhibitor | Antipyretic |
| 1.2 | 1.1 | 1.3 | 1.2 | 1.4 | 1.2 | 2.0 | Cloperastine hydrochloride | Histamine antagonist | Antitussive |
| 1.1 | 1.0 | 1.2 | 1.0 | 1.1 | 1.0 | 1.8 | Isosorbide dinitrate | Nitric oxide (NO) donor | Antianginal |
| 1.2 | 1.1 | 1.3 | 0.9 | 1.1 | 1.0 | 1.6 | Eucatropine hydrochloride | Anticholinergic | |
| 1.0 | 1.0 | 1.1 | 1.1 | 2.1 | 1.0 | 1.5 | Sulfachloropyridazine | Inhibitor of folic acid synthesis | Antibacterial |
| 1.1 | 1.0 | 1.5 | 1.1 | 1.1 | 1.1 | 1.5 | Isocarboxazid | | Antidepressant |
| 1.1 | 1.0 | 1.3 | 1.1 | 1.1 | 1.2 | 1.5 | Pramoxine hydrochloride | | Local anesthesic |
| 0.8 | 1.2 | 1.1 | 0.8 | 1.0 | 1.0 | 1.7 | Lithocholic acid | Anticholelithogenic, gastrointestinal agent | Cholagogue |
| 1.1 | 1.1 | 1.0 | 0.9 | 1.2 | 1.1 | 1.8 | Finasteride | | Antialopecia agent |
| 1.3 | 1.0 | 1.2 | 1.0 | 1.1 | 1.1 | 1.8 | Methotrimeprazine maleat salt | | Analgesic |
| 1.1 | 1.0 | 1.2 | 1.0 | 1.3 | 1.1 | 1.7 | Fluorometholone | — | Glucocorticoid |
| 1.1 | 1.3 | 0.4 | 0.9 | 3.2 | 1.1 | 21.9 | Dienestrol | Nuclear receptor ligand | Non-steroidal estrogen |
| 11.8 | 1.0 | 5.3 | 3.2 | 1.1 | 1.1 | 2.0 | Cephalothin sodium salt | Bacterial transpeptidase inhibitor | Antibacterial |
| 1.1 | 1.1 | 1.2 | 0.9 | 1.1 | 1.1 | 1.6 | Pridinol methanesulfonate salt | Anticholinergic | Antiparkinsonian |
| 12.1 | 1.0 | 3.4 | 2.4 | 1.4 | 1.6 | 1.6 | Cefuroxime sodium salt | Bacterial transpeptidase inhibitor | Antibacterial |
| 1.3 | 1.0 | 1.1 | 1.1 | 1.2 | 1.0 | 44.0 | Amrinone | TNF production inhibitor | Diagnostic aid (radiopaque medium) |
| 1.2 | 1.0 | 1.3 | 1.2 | 1.2 | 1.2 | 1.4 | Iopamidol | | Scabicide |
| 1.5 | 1.1 | 1.3 | 1.1 | 1.3 | 1.3 | 1.3 | Crotamiton | Contrast molecule | |
| 1.2 | 1.0 | 1.3 | 1.1 | 1.1 | 1.2 | 1.4 | Iopromide | Beta blocking agent | Antiarrhythmic |
| 1.2 | 1.1 | 1.4 | 1.1 | 1.2 | 1.4 | 1.2 | Propranolol hydrochloride | Mastocyte degranulation inhibitor in vitro | Bronchodilatator |
| 1.2 | 1.0 | 1.3 | 1.1 | 1.2 | 1.1 | 1.3 | Theophylline monohydrate | | |
| 1.3 | 1.0 | 1.2 | 1.2 | 1.3 | 1.2 | 1.3 | (R)-(+)-Atenolol | Adenosine receptor antagonist | Cardiotonic |
| 1.2 | 1.1 | 1.3 | 1.2 | 1.1 | 1.2 | 1.4 | Theobromine | | |
| 1.4 | 1.0 | 1.4 | 1.5 | 1.3 | 1.2 | 1.2 | Tyloxapol | | Mucolytic |
| 1.3 | 1.1 | 1.3 | 1.2 | 1.5 | 1.4 | 1.5 | Reserpine | | |
| 1.2 | 1.0 | ### | 0.3 | 1.2 | 1.4 | 1.4 | Florfenicol | | Antibacterial |
| 0.7 | 0.6 | 0.9 | 0.7 | 0.8 | 0.8 | 1.2 | Arcaine sulfate | Lowers blood sugar | |
| 1.1 | 1.2 | 0.9 | 1.0 | 1.2 | 1.2 | 1.6 | Megestrol acetate | | Progestogen |
| 1.2 | 1.0 | 1.2 | 1.1 | 1.2 | 1.1 | 1.5 | Scopolamine hydrochloride | Non-selective muscarinic antagonist | Antiemetic |

TABLE 4-continued

AK-based Prestwick Library Screening Results.

| E. coli | E. faecium | S. aureus | K. pneumoniae | A. baumannii | P. aeruginosa | E. cloacae | Chemical name | Mechanism | Therapeutic group |
|---|---|---|---|---|---|---|---|---|---|
| 1.2 | 1.2 | 1.6 | 1.2 | 1.3 | 1.3 | 1.3 | Deoxycorticosterone | Corticoide | Antiinflammatory |
| 1.2 | 1.0 | 1.2 | 1.2 | 1.3 | 1.2 | 1.4 | Ioversol | | Diagnostic aid (radiopaque medium) |
| 1.2 | 1.0 | 1.2 | 1.0 | 1.3 | 1.2 | 1.4 | Urosiol | | Anticholelithogenic |
| 1.3 | 1.1 | 1.2 | 1.0 | 1.2 | 1.1 | 1.5 | Capsaicin | Vanilloid receptor ligand | Topical analgesic |
| 1.3 | 1.0 | 1.2 | 1.1 | 1.4 | 1.1 | 1.2 | Proparacaine hydrochloride | | Local anesthesic (VET) |
| 1.2 | 1.1 | 1.4 | 1.2 | 1.3 | 1.2 | 1.2 | Carbachol | Cholinergic agonist, Cholinesterase inhibitor ? | Myotic |
| 1.2 | 1.1 | 1.2 | 1.2 | 1.3 | 1.1 | 1.6 | Aminocaproic acid | | Antiallergic |
| 0.5 | 0.9 | 0.4 | 0.4 | 0.3 | 0.4 | 0.4 | Denatonium benzoate | Bittering agent to prevent poisoning | |
| 0.5 | 0.9 | 0.3 | 0.4 | 0.3 | 0.4 | 0.3 | Etomidate | | Hypnotic |
| 0.4 | 0.9 | 0.3 | 0.4 | 0.4 | 0.4 | 0.3 | Scopoletin | | Antispasmodic |
| 0.4 | 0.8 | 0.4 | 0.4 | 0.4 | 0.4 | 0.3 | Tridihexethyl chloride | | Antispasmodic |
| 0.5 | 1.1 | 0.4 | 0.5 | 0.4 | 0.4 | 0.4 | Enilconazole | | Antifungal |
| 0.5 | 0.8 | 0.4 | 0.5 | 0.4 | 0.5 | 0.4 | Penbutolol sulfate | | Antiarrhythmic |
| 3.2 | 0.9 | 1.9 | 0.2 | 4.2 | 0.2 | 0.4 | Methacycline hydrochloride | | Antibacterial |
| 0.4 | 0.9 | 0.4 | 0.5 | 0.4 | 0.4 | 0.3 | Prednicarbate | | Glucocorticoid (topical) |
| 0.5 | 0.8 | 0.4 | 0.5 | 0.4 | 0.4 | 0.4 | Gibberellic acid | | Plant growth regulator |
| 0.7 | 2.8 | 0.7 | 0.7 | 2.4 | 0.5 | 0.4 | Sertaconazole nitrate | | Antibacterial |
| 0.4 | 0.8 | 0.4 | 0.5 | 0.5 | 0.4 | 0.4 | Sotalol hydrochloride | Beta-blocker | |
| 0.4 | 0.9 | 0.3 | 0.4 | 0.4 | 0.4 | 0.4 | Repaglinide | | Antidiabetic |
| 0.5 | 0.9 | 0.4 | 0.5 | 0.5 | 0.4 | 0.4 | 6-Hydroxytropinone | | |
| 0.5 | 0.8 | 0.4 | 0.4 | 0.4 | 0.4 | 0.4 | Piretanide | | Antihypertensor |
| 0.5 | 0.9 | 0.4 | 0.5 | 0.5 | 0.5 | 0.5 | Decamethonium bromide | | Muscle relaxant (skeletal) |
| 0.5 | 0.9 | 0.5 | 0.5 | 0.6 | 0.4 | 0.4 | Piperacetazine | | Antipsychotic |
| 0.5 | 0.8 | 0.4 | 0.4 | 0.4 | 0.4 | 0.4 | 3-Acetamidocoumarin | | Anti-inflammatory |
| 0.5 | 0.9 | 0.4 | 0.5 | 0.5 | 0.5 | 0.5 | Oxyphenbutazone | Inhibition of cyclo-oxygenase | |
| 0.4 | 0.8 | 0.6 | 0.4 | 0.5 | 0.5 | 0.5 | Roxarsone | | Control of enteric infections. To improve growth and feed efficiency (VET) |
| 0.6 | 0.9 | 0.4 | 0.6 | 0.5 | 0.5 | 0.4 | Quinethazone | | Diuretic |
| 0.7 | 0.9 | 0.6 | 0.6 | 0.7 | 0.7 | 0.8 | Remoxipride Hydrochloride | Dopaminergic antagonist | Antipsychotic |
| 0.6 | 1.0 | 0.6 | 0.6 | 0.6 | 0.6 | 0.7 | Moricizine hydrochloride | | Antiarrhythmic |
| 0.6 | 1.0 | 0.6 | 0.6 | 0.6 | 0.6 | 0.8 | THIP Hydrochloride | GABAergic Agonist | |
| 0.6 | 0.9 | 0.4 | 0.6 | 0.6 | 0.6 | 9.6 | Iopanoic acid | Contrast molecule | |
| 0.7 | 0.9 | 0.6 | 0.6 | 0.7 | 0.7 | 0.7 | Pirlindole mesylate | Highly selective reversible inhibitor of monoamine oxidase type A | Anti depressant Seizures |
| 7.7 | 0.9 | 0.6 | 0.5 | 1.1 | 0.6 | 0.8 | Pivmecillinam hydrochloride | | Antibacterial |
| 0.7 | 0.9 | 0.6 | 0.6 | 0.6 | 0.6 | 0.9 | Pronethalol hydrochloride | | Antihypertensor |
| 0.6 | 1.0 | 0.6 | 0.6 | 0.7 | 0.7 | 0.7 | Levopropoxyphene napsylate | | Antitussive |
| 0.9 | 0.8 | 0.5 | 0.6 | 0.7 | 0.7 | 0.9 | Naftopidil dihydrochloride | Alpha1 agonist | Antihypertensor |
| 0.7 | 1.0 | 0.6 | 0.6 | 0.6 | 0.6 | 0.9 | Piperidolate hydrochloride | | Antispasmodic |
| 0.5 | 1.1 | 0.5 | 0.6 | 0.8 | 0.6 | 0.7 | Tracazolate hydrochloride | GABA receptor ligand | |
| 0.9 | 0.9 | 0.7 | 1.1 | 1.1 | 0.6 | 0.7 | Trifluridine | | Antiviral (ophthalmic) |
| 0.6 | 1.0 | 0.6 | 0.7 | 0.7 | 0.7 | 0.9 | Zardaverine | Phosphodiesterase III & IV inhibitor | |

TABLE 4-continued

AK-based Prestwick Library Screening Results.

| E. coli | E. faecium | S. aureus | K. pneumoniae | A. baumannii | P. aeruginosa | E. cloacae | Chemical name | Mechanism | Therapeutic group |
|---|---|---|---|---|---|---|---|---|---|
| 0.7 | 0.9 | 0.6 | 0.6 | 0.6 | 0.6 | 0.9 | Oxprenolol hydrochloride | Blocking beta-adrenergic receptors | Antiarrhythmic |
| 0.6 | 0.9 | 0.6 | 0.5 | 0.7 | 0.6 | 0.7 | Memantine Hydrochloride | NMDA receptor antagonist | Altzheimer disease |
| 0.7 | 1.1 | 0.6 | 0.6 | 0.7 | 0.7 | 0.8 | Ondansetron Hydrochloride | Antagonist of 5-hydroxytryptamine (serotonin) subtype 3 (5-HT 3) receptors | Antiemetic |
| 0.6 | 0.9 | 0.5 | 0.5 | 0.7 | 0.6 | 0.9 | Ozagrel hydrochloride | Thromboxane synthase inhibitor | Antianginal |
| 0.6 | 1.0 | 0.7 | 0.6 | 0.8 | 0.7 | 0.8 | Propoxycaine hydrochloride | | Local anesthesic |
| 0.6 | 0.9 | 0.6 | 0.5 | 0.7 | 0.6 | 1.0 | Piribedil hydrochloride | Dopaminergic agonist | Vasodilator (peripheral) |
| 0.6 | 1.1 | 0.5 | 0.6 | 0.7 | 0.7 | 0.9 | Oxaprozin | | Analgesic |
| 0.9 | 0.9 | 0.6 | 0.7 | 0.7 | 0.8 | 1.2 | Nitrocaramiphen hydrochloride | | Muscarinic antagonist |
| 1.0 | 1.0 | 0.7 | 0.8 | 0.8 | 0.7 | 1.1 | Phensuximide | | Anticonvulsant |
| 0.9 | 0.9 | 0.7 | 0.7 | 0.8 | 0.9 | 1.0 | Nandrolone | | Anabolic |
| 0.9 | 0.9 | 0.6 | 0.8 | 0.8 | 0.8 | 1.1 | Ioxaglic acid | Low-osmolar, ionic contrast medium | Diagnostic aid (radiopaque medium) |
| 0.8 | 0.9 | 0.7 | 0.7 | 0.8 | 0.8 | 1.0 | Dimaprit dihydrochloride | Histamine H2 receptor agonist | |
| 1.0 | 1.0 | 0.8 | 0.7 | 1.1 | 0.8 | 1.0 | Naftifine hydrochloride | | Antifungal |
| 0.9 | 0.9 | 0.6 | 0.7 | 0.8 | 0.9 | 1.0 | Reserpinic acid hydrochloride | | |
| 0.9 | 0.9 | 0.6 | 0.7 | 0.8 | 0.8 | 0.8 | Meprylcaine hydrochloride | | Local anesthesic |
| 0.8 | 0.9 | 0.7 | 0.8 | 0.8 | 0.9 | 1.1 | Beta-sistosterol | | Anticholesteremic |
| 0.8 | 0.9 | 0.7 | 0.7 | 0.8 | 0.9 | 0.9 | Milrinone | | Cardiotonic |
| 0.9 | 0.8 | 0.6 | 0.7 | 0.8 | 0.9 | 0.9 | Proscillaridin A | Potent cytotoxic | Glucoside cardiotonic |
| 0.9 | 0.9 | 0.7 | 0.8 | 0.8 | 0.9 | 1.1 | Methantheline bromide | | Antispasmodic |
| 0.6 | 0.9 | 0.1 | 0.2 | 0.7 | 0.3 | 0.9 | Sanguinarine | | Antimicrobial drug |
| 12.8 | 0.3 | 0.7 | 0.7 | 2.6 | 0.8 | 1.4 | Ticarcillin sodium | | Antibacterial |
| 0.8 | 1.2 | 0.7 | 0.7 | 0.9 | 0.8 | 0.9 | Harpagoside | | Antiinflammatory |
| 1.1 | 0.9 | 0.8 | 1.0 | 2.1 | 0.8 | 1.0 | Thiethylperazine malate | adrenergic antagonist | Antiemetic |
| 0.8 | 1.0 | 0.8 | 0.7 | 0.8 | 0.9 | 1.0 | Asiaticoside | | Antibiotic |
| 0.9 | 0.9 | 0.7 | 0.7 | 0.9 | 0.9 | 1.0 | Mesalamine | | Anti-inflammatory (gastrointestinal) |
| 0.8 | 0.9 | 0.3 | 0.7 | 0.8 | 0.7 | 1.3 | Betulin | | Antineoplastic |
| 0.9 | 1.0 | 0.9 | 0.7 | 0.8 | 0.8 | 0.9 | alpha-Santonin | | Anthelmintic |
| 0.9 | 0.9 | 0.5 | 0.8 | 0.7 | 0.8 | 1.1 | Gliquidone | | Antidiabetic |
| 0.9 | 0.9 | 0.7 | 0.7 | 0.8 | 0.8 | 1.2 | Imidurea | | |
| 1.0 | 1.0 | 0.7 | 0.7 | 0.8 | 0.8 | 1.3 | Pizotifen malate | | Antihistaminic |
| 0.6 | 0.6 | 0.2 | 0.5 | 0.6 | 0.7 | 1.0 | Lansoprazole | | Antiulcerative |
| 0.8 | 0.9 | 0.7 | 0.7 | 0.8 | 1.1 | 1.2 | Ribavirin | | Antiviral |
| 1.0 | 0.9 | 0.7 | 0.7 | 0.9 | 0.7 | 0.9 | Bethanechol chloride | | Cholinergic |
| 0.8 | 0.9 | 0.7 | 0.8 | 0.8 | 0.8 | 1.2 | Cyclopenthiazide | | Diuretic |
| 0.8 | 1.0 | 0.6 | 0.7 | 0.8 | 0.8 | 1.4 | Cyproterone acetate | | Antiandrogen |
| 0.9 | 0.8 | 0.7 | 0.7 | 0.9 | 0.8 | 1.1 | Fluvoxamine maleate | | Antidepressant |
| 0.8 | 0.9 | 0.8 | 0.7 | 0.9 | 0.8 | 17.3 | (R)-Propranolol hydrochloride | Beta-adrenergic receptor blocking agent | Antihypertensor |
| 16.6 | 0.9 | 1.6 | 3.8 | 1.5 | 0.8 | 1.4 | Cefalonium | | Prophylactic use in mastitis and dry udder therapy |
| 0.8 | 0.9 | 0.7 | 0.8 | 0.8 | 0.7 | 1.2 | Ciprofibrate | | Antihyperlipoproteine-mic |

TABLE 4-continued

AK-based Prestwick Library Screening Results.

| E. coli | E. faecium | S. aureus | K. pneumoniae | A. baumannii | P. aeruginosa | E. cloacae | Chemical name | Mechanism | Therapeutic group |
|---|---|---|---|---|---|---|---|---|---|
| 0.8 | 0.9 | 0.7 | 0.7 | 0.8 | 0.8 | 1.5 | Fluticasone propionate | | Anti-inflammatory |
| 0.9 | 0.9 | 0.7 | 0.8 | 0.8 | 0.8 | 1.2 | Tropine | Blocking of D1 and D2 dopaminergic receptors | Schizophrenia |
| 1.2 | 1.0 | 0.7 | 1.0 | 1.9 | 0.9 | 1.3 | Zuclopenthixol hydrochloride | | Antibacterial |
| 11.3 | 1.7 | 0.8 | 0.6 | 2.9 | 0.7 | 1.2 | Benzylpenicillin sodium | | |
| 0.9 | 0.8 | 0.9 | 0.7 | 0.9 | 0.8 | 1.1 | Proguanil hydrochloride | Inhibition of dihydrofolate reductase | |
| 0.9 | 0.9 | 0.8 | 0.7 | 0.9 | 0.8 | 1.2 | Chlorambucil | | Antineoplastic |
| 0.8 | 1.0 | 0.7 | 0.7 | 0.8 | 0.7 | 1.2 | Lymecycline | | Antibiotic |
| 0.4 | 0.5 | 1.3 | 0.4 | 0.5 | 0.5 | 1.3 | Methiazole | | In combination with alfaxalone as anesthesic (intravenous) |
| 1.2 | 1.1 | 1.0 | 0.9 | 1.0 | 1.0 | 1.4 | Alfadolone acetate | | |
| 1.2 | 1.1 | 1.0 | 1.0 | 1.0 | 1.1 | 1.6 | (S)-propranolol hydrochloride | Beta-adrenergic blocking agent | Antihypertensor |
| 1.2 | 1.1 | 1.2 | 1.0 | 1.0 | 1.2 | 1.7 | Alfaxalone | | In combination with alfadolone acetate as anesthetic (intravenous) |
| 1.0 | 1.1 | 0.9 | 0.9 | 0.9 | 0.8 | 1.4 | (−)-Eseroline fumarate salt | Anti-acetylcholinesterase activity & opiate agonist activity | Potent analgesic |
| 1.1 | 1.0 | 0.8 | 0.9 | 0.9 | 1.0 | 1.5 | Azapropazone | Cyclooxygenase inhibitor | Analgesic |
| 1.0 | 1.1 | 1.1 | 1.0 | 1.1 | 1.0 | 1.2 | Condelphine | | |
| 1.1 | 1.1 | 0.9 | 0.9 | 1.1 | 1.1 | 1.4 | Meptazinol hydrochloride | | Analgesic (narcotic) |
| 1.3 | 1.1 | 0.9 | 1.0 | 1.0 | 1.1 | 1.6 | Leucomisine | | |
| 1.2 | 1.0 | 0.9 | 0.8 | 1.0 | 1.1 | 1.4 | Apramycin | | Antibacterial |
| 1.4 | 1.0 | 2.4 | 0.9 | 1.1 | 1.0 | 1.3 | Dubinidine | | |
| 1.2 | 1.0 | 0.9 | 0.9 | 1.1 | 1.1 | 1.3 | Epitiostanol | | Antineoplastic |
| 1.4 | 1.2 | 1.4 | 1.1 | 1.0 | 1.2 | 1.2 | D-cycloserine | Competitive inhibition of alanin racenase and D-alanin synthase (bacterial cell wall) | |
| 1.4 | 1.1 | 1.0 | 1.0 | 1.3 | 1.1 | 1.2 | Fursultiamine Hydrochloride | | Alzheimer's disease |
| 1.0 | 1.1 | 1.1 | 0.9 | 1.2 | 1.0 | 1.4 | 2-Chloropyrazine | | Cardiotonic |
| 1.1 | 1.1 | 1.3 | 0.9 | 1.1 | 1.1 | 1.4 | Gabexate mesilate | | Anticoagulant |
| 1.3 | 1.1 | 1.0 | 1.0 | 1.1 | 1.1 | 1.3 | (+,−)-Synephrine | | Hypertensive |
| 1.5 | 1.1 | 0.4 | 1.0 | 1.8 | 0.9 | 1.2 | Pivampicillin | | Antibacterial |
| 1.3 | 1.1 | 1.1 | 1.0 | 1.1 | 1.1 | 1.6 | (S)(−)-Cycloserine | | Tuberculosis |
| 15.2 | 1.4 | 1.2 | 0.8 | 0.8 | 1.1 | 1.5 | Talampicillin hydrochloride | | Antibacterial |
| 1.3 | 1.1 | 1.2 | 1.1 | 1.8 | 1.1 | 1.6 | Homosalate | Tool for uv screen | |
| 1.4 | 1.0 | 6.1 | 1.1 | 1.5 | 1.2 | 1.3 | Flucloxacillin sodium | | Antibacterial |
| 1.4 | 1.1 | 1.0 | 0.9 | 0.9 | 1.1 | 1.6 | Spaglumic acid | NMDA receptor ligands | |
| 1.3 | 1.1 | 0.9 | 1.0 | 1.0 | 1.0 | 1.5 | Trapidil | | Vasodilator (coronary) |
| 1.2 | 0.9 | 1.0 | 0.9 | 1.2 | 1.0 | 1.4 | Ranolazine | | Antianginal |
| 1.5 | 1.1 | 1.1 | 0.9 | 1.3 | 1.0 | 1.6 | Deptropine citrate | | Chronic bronchitis |
| 1.1 | 1.0 | 1.2 | 1.0 | 1.0 | 0.9 | 1.7 | (−)-Quinpirole hydrochloride | D2-dopamine receptor agonist, some selectivity for D3 sites | |
| 1.6 | 1.1 | 1.6 | 1.4 | 2.9 | 1.2 | 1.5 | Sertraline | 5-HT uptake inhibitor | |
| 1.0 | 1.0 | 0.9 | 1.0 | 2.9 | 1.0 | 1.3 | Sulfadoxine | Inhibition of dihydropteroate synthase | Antibacterial |

TABLE 4-continued

AK-based Prestwick Library Screening Results.

| E. coli | E. faecium | S. aureus | K. pneumoniae | A. baumannii | P. aeruginosa | E. cloacae | Chemical name | Mechanism | Therapeutic group |
|---|---|---|---|---|---|---|---|---|---|
| 1.2 | 0.9 | 1.0 | 1.1 | 1.2 | 1.0 | 0.8 | Ethamsylate | | Retinopathy |
| 1.1 | 1.0 | 1.1 | 1.0 | 1.0 | 1.1 | 1.3 | Cyclopentolate hydrochloride | | Mydriatic |
| 1.1 | 0.9 | 1.0 | 1.1 | 1.1 | 1.1 | 1.8 | Moxonidine | Imidazoline receptor ligand | Antihypertensor |
| 1.1 | 1.1 | 1.2 | 0.8 | 1.2 | 1.0 | 1.4 | Estriol | | Estrogen |
| 1.0 | 1.0 | 1.1 | 0.8 | 1.4 | 1.1 | 1.5 | Etilefrine hydrochloride | Adrenergic agonist | Antihypotensive |
| 1.2 | 0.9 | 0.9 | 1.2 | 0.9 | 1.1 | 2.3 | (−)-Isoproterenol hydrochloride | Beta Adrenergic Agonist | Cardiovascular drug (Sick Sinus Syndrome) |
| 1.3 | 1.0 | 1.1 | 1.1 | 1.0 | 1.1 | 1.4 | Alprostadil | | Vasodilator |
| 0.5 | 1.0 | 0.2 | 0.6 | 0.5 | 0.6 | 1.6 | Kaempferol | Topoisomerase I inhibitor, tyrosin kinase, xanthin oxidase | Anti-inflammatory |
| 0.9 | 1.1 | 0.6 | 0.9 | 1.7 | 1.1 | 1.5 | Tribenoside | | Antihaemorrhoidic drug |
| 1.2 | 1.1 | 1.2 | 0.9 | 1.0 | 1.2 | 1.4 | Nialamide | | Antidepressant |
| 0.9 | 0.9 | 1.1 | 0.8 | 0.9 | 1.0 | 4.9 | Rimexolone | Corticoid | Anti-inflammatory (local) |
| 0.9 | 1.0 | 1.8 | 0.8 | 1.1 | 1.1 | 1.6 | Vitamin K2 | | Dietary factor for controlling blood pressure |
| 1.1 | 1.1 | 0.7 | 1.1 | 1.2 | 1.1 | 1.4 | Isradipine | | Antianginal |
| 1.1 | 1.0 | 1.1 | 1.1 | 1.4 | 1.2 | 1.4 | Perindopril | | Antihypertensive |
| 1.1 | 1.0 | 1.1 | 1.1 | 1.6 | 1.1 | 1.4 | Tiletamine hydrochloride | | Anesthetic |
| 1.1 | 1.0 | 1.1 | 1.1 | 1.3 | 1.0 | 1.3 | Fexofenadine HCl | | Antihistaminic |
| 1.2 | 1.0 | 1.2 | 1.3 | 1.5 | 1.1 | 1.2 | Isometheptene mutate | Adrenergic | Sympathomimetic (VET) |
| 1.2 | 0.9 | 0.8 | 1.2 | 1.4 | 1.1 | 1.3 | Quinic acid | | |
| 1.1 | 1.0 | 1.2 | 1.1 | 1.5 | 1.1 | 1.3 | Nifurtimox | | Antiprotozoal (Trypanosoma) |
| 1.0 | 0.9 | 1.2 | 1.1 | 1.4 | 1.0 | 1.5 | Clonixin Lysinate | | Analgesic |
| 1.2 | 1.0 | 1.2 | 1.1 | 1.3 | 1.0 | 1.4 | Letrozole | | Antineoplastic |
| 0.7 | 1.2 | 0.5 | 0.8 | 0.9 | 0.8 | 1.6 | Verteporfin | | Treatment of age-related macular degeneration |
| 1.2 | 0.9 | 1.1 | 1.2 | 1.5 | 1.1 | 1.4 | Arbutin | Tyrosinase inhibitor and Melanin biosynthesis inhibitor | Antibacterial |
| 13.4 | 1.0 | 3.9 | 3.6 | 1.5 | 14.8 | 1.2 | Meropenem | | Antibacterial |
| 1.2 | 1.0 | 1.1 | 1.1 | 1.6 | 1.1 | 1.4 | Tocainide hydrochloride | | Antiarrhythmic |
| 1.1 | 1.0 | 1.2 | 1.0 | 1.3 | 1.2 | 1.1 | Ramipril | Converting enzyme inhibitor | Antihypertensor |
| 15.6 | 1.6 | 1.0 | 1.0 | 5.9 | 1.1 | 1.6 | Benzathine benzylpenicillin | | Antibacterial |
| 1.1 | 1.0 | 1.1 | 1.0 | 1.3 | 1.0 | 1.2 | Mephenytoin | | Anticonvulsant |
| 1.1 | 1.3 | 1.3 | 1.1 | 1.5 | 1.1 | 1.3 | Risperidone | 5-HT2 antagonist | Antipsychotic |
| 1.3 | 1.2 | 0.7 | 1.3 | 3.3 | 0.6 | 1.6 | Rifabutin | Inhibition of RNA-polymerase DNA-dependent | Antibacterial |
| 1.1 | 1.0 | 1.5 | 1.3 | 1.6 | 1.1 | 1.4 | Torsemide | | Diuretic |
| 0.7 | 0.6 | 0.7 | 0.7 | 0.8 | 0.7 | 1.2 | Parbendazole | | Anthelmintic (VET) |
| 1.0 | 1.0 | 1.2 | 1.1 | 1.3 | 1.1 | 1.3 | Halofantrine hydrochloride | | Antimalarial |
| 1.4 | 1.1 | 1.4 | 1.0 | 1.2 | 1.1 | 1.6 | Mecamylamine hydrochloride | DNA depolymerization | Antihypertensor |
| 1.1 | 1.2 | 1.1 | 1.1 | 1.2 | 1.0 | 1.6 | Articaine hydrochloride | | Local Anesthesic |
| 1.1 | 1.0 | 1.1 | 1.0 | 1.1 | 0.9 | 1.7 | Nomegestrol acetate | | Progestin |
| 1.0 | 1.2 | 1.3 | 0.9 | 1.1 | 1.1 | 1.5 | Vionycin sulfate | | Antibacterial |
| 1.1 | 1.0 | 1.1 | 1.0 | 1.1 | 0.9 | 1.6 | Pancuronium bromide | Competitive antagonist of autonomic cholinergic receptors | Neuromuscular blocking agent |

TABLE 4-continued

AK-based Prestwick Library Screening Results.

| E. coli | E. faecium | S. aureus | K. pneumoniae | A. baumannii | P. aeruginosa | E. cloacae | Chemical name | Mechanism | Therapeutic group |
|---|---|---|---|---|---|---|---|---|---|
| 1.3 | 1.2 | 0.9 | 1.1 | 1.5 | 1.0 | 1.8 | Saquinavir mesylate | Protease inhibitor | Antipsychotic |
| 1.1 | 1.0 | 1.1 | 1.0 | 1.1 | 0.9 | 1.7 | Molindone hydrochloride | | Antimicrobial |
| 1.1 | 1.1 | 1.3 | 1.7 | 1.6 | 1.0 | 1.6 | Ronidazole | | Neuromuscular blocking agent |
| 1.4 | 1.0 | 1.2 | 1.0 | 1.4 | 1.0 | 2.2 | Alcuronium chloride | | Antiglaucoma drug |
| 1.1 | 2.3 | 1.0 | 1.1 | 1.2 | 0.9 | 1.3 | Dorzolamide hydrochloride | | Antiviral (HIV) |
| 1.3 | 1.1 | 1.1 | 1.1 | 1.2 | 1.0 | 1.8 | Zalcitabine | Reverse transcriptase inhibitor | |
| 1.1 | 1.0 | 1.2 | 1.0 | 1.2 | 1.0 | 1.9 | Azaperone | | Tranquilizer |
| 1.2 | 1.1 | 1.2 | 1.2 | 1.4 | 1.1 | 1.8 | Methyldopate hydrochloride | | Antihypertensor |
| 19.3 | 1.0 | 3.1 | 4.9 | 3.4 | 15.6 | 1.9 | Cefepime hydrochloride | | Antibacterial |
| 1.1 | 1.0 | 1.1 | 1.1 | 1.2 | 1.0 | 1.6 | Levocabastine hydrochloride | | Antihistaminic |
| 1.0 | 1.1 | 1.1 | 1.0 | 1.2 | 1.0 | 1.6 | Clocortolone pivalate | | Glucocorticoid |
| 0.8 | 1.5 | 1.4 | 0.8 | 0.9 | 0.7 | 13.2 | Pyrvinium pamoate | | Anthelmintic (Nematodes, enterobiasis) |
| 13.4 | 2.8 | 4.3 | 5.2 | 2.9 | 17.7 | 1.7 | Nadifloxacin | | Antibacterial |

Consistent with expectations, a detailed assessment of the hits revealed that AK screening enriches for the identification of bactericidal compounds (Table 3). More specifically, 100% of the antibiotics that were identified to be active against *P. aeruginosa* or *K. pneumoniae* represented bactericidal agents. Similarly, 96%, 94%, and 80% of the antibiotics that were active against *E. coli*, *E. cloacae*, and *E. faecium*, respectively, were bactericidal antibiotics. The assay identified 71% and 64% bactericidal antibiotics for *A. baumannii* and *S. aureus*.

Among the bactericidal antibiotics detected, 3-lactam, cephalosporin, polymyxin, and fluoroquinolone antibiotics were active against Gram-negative pathogens (*E. coli* and the ESKAPE pathogens *A. baumannii*, *P. aeruginosa*, and *K. pneumoniae*), and penicillins, cephalosporins, quinolines, glycopeptides, and carbapenems were active toward *S. aureus* (see Table 4). It was also determined that clofazimine, which was initially developed as an antimycobacterial agent and was recently shown to exhibit bactericidal activity toward *S. aureus*, was indeed active against *S. aureus*. Bacteriostatic compounds, such as clindamycin, and macrolides, such as erythromycin, were not identified as being active toward any of the species tested. Interestingly, many tetracyclines were identified as killing *S. aureus* strain USA300-0114 and *A. baumannii* strain 98-37-09. In addition, the library contains membrane-active antiseptics, such as chlorhexidine, and with the exception of *E. cloacae*, these were also strong hits against all organisms tested. Screening results also revealed that the *E. faecium* strain tested proved to be resistant to most classes of antibiotics within the Prestwick library by MIC testing (Table 2), and this was also observed in the AK assay, indicating that the assay exhibits a low false-positive rate. Interestingly, the assay also detected 38 drugs with no known antimicrobial properties (denoted as "other" in Table 3) that were active against each organism; see Table 4 for a complete list of these compounds.

Antimicrobial Activities of Nonantibiotic Drugs that Induce AK Release—

Recently, the exploration of the so-called "off-target" activities of previously developed drugs has emerged as an approach to identify chemical scaffolds that could be exploited for new therapeutic indications. In that regard, Prestwick library screening results revealed that 4% to 56% (depending on the organism) of the members that generated significant AK signal were compounds with no previously reported antimicrobial activity (see Table 4).

To determine whether the 38 nonantibiotics identified in the screen have potential for repurposing as anti-infectives, 4 nonantibiotic drugs that were commercially available were further evaluated by two secondary assays. First, dose-response assays were performed to validate that they induced AK activity, and all were reconfirmed. Second, the in vitro antimicrobial activity for each drug was measured by standard MIC testing. With the exception of one drug/organism pair, all drugs exhibited in vitro activity toward each organism. More specifically, tamoxifen, suloctidil, and clomiphene exhibited MICs of 8 µg ml$^{-1}$ against *E. faecium*. *S. aureus* and *A. baumannii* were susceptible to terfenadine (16-µg ml$^{-1}$ MIC and 64-Lag ml$^{-1}$ MIC, respectively). Suloctidil was also detected to be active against *P. aeruginosa* by both primary and confirmatory AK screens, but the drug did not elicit an antimicrobial response by MIC measures. Some strains of *P. aeruginosa* secrete AK at high cell density, and it is possible that suloctidil may trigger a similar response.

Terfenadine and tamoxifen, which exhibited antimicrobial properties toward planktonic *S. aureus* and *E. faecium* cells, respectively, were characterized further. Terfenadine was evaluated for activity against *S. aureus* biofilms and small-colony variants using the AK assays described above. Treatment of 48-h *S. aureus* strain UAMS-1 biofilms with 10×-MIC terfenadine elicited a modest 2.7-fold increase in AK release (see FIG. 6A); plating-based viability assays determined that this correlated with a 1.1-log reduction in biofilm cell viability, which was comparable to the activity of ciprofloxacin under the same assay conditions (see FIG. 4A). Similarly, treatment of *S. aureus* small-colony-variant UAMS-1112 cells with 10×MIC terfenadine elicited a 3.3-fold increase in AK signal in comparison to that for mock-treated cells (see FIG. 6A). Conventional MIC testing subsequently verified that terfenadine is active against UAMS-1112 at 2 µg ml$^{-1}$.

Figure 6:
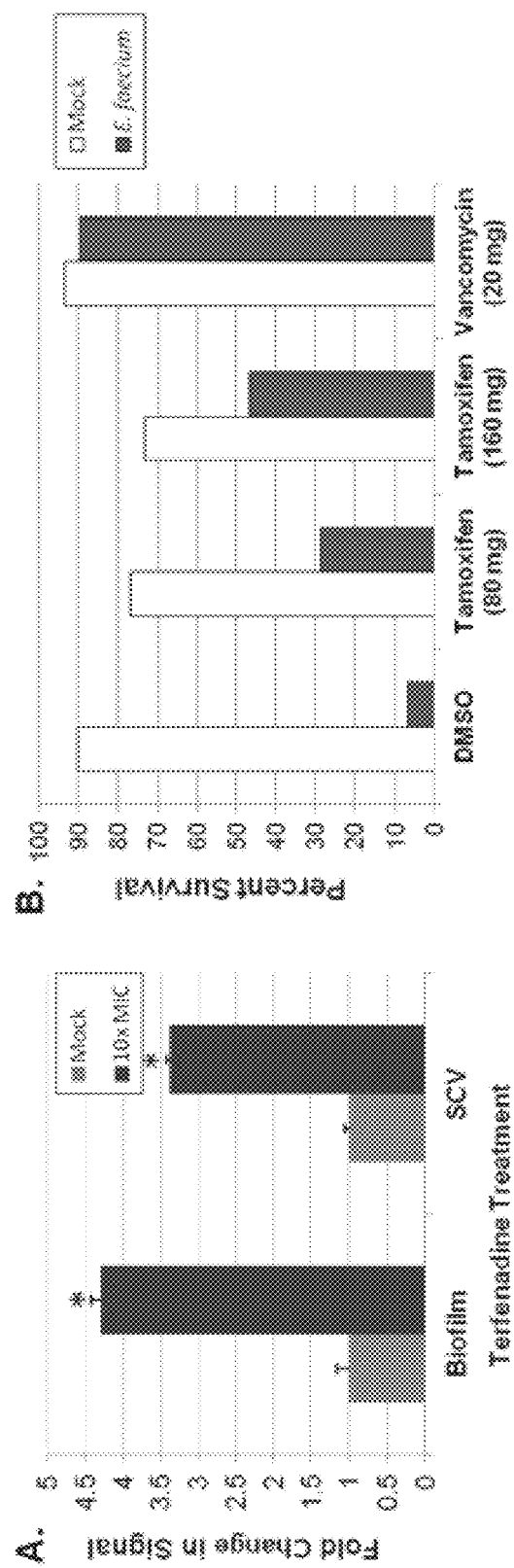
FIG. 6 shows antimicrobial properties of terfenadine and tamoxifen. (A) Fold changes in AK signal of terfenadine-treated (10×MIC) *S. aureus* strain UAMS-1 static biofilms and the SCV strain UAMS-1112, compared to those for mock (DMSO)-treated populations, are plotted. "*" indicates a significant increase in signal over that with mock-treated cells (Student's t test, P≤0.05). (B) Plotted are the percent survival of *G. mellonella* larvae at 48 h post-*E. faecium* inoculation. Groups of larvae (n=45) were treated at 2 h and 24 h with either PBS (mock), DMSO, 80 mg kg$^{-1}$ tamoxifen, 160 mg kg$^{-1}$ tamoxifen, or 20 mg kg$^{-1}$ vancomycin.

Next, the in vivo antimicrobial properties of terfenadine and tamoxifen were evaluated using a *Galleria mellonella* model of *S. aureus* and *E. faecium* infection, respectively. For terfenadine, groups of larvae (n=45) were infected with 1.0×10$^6$ *S. aureus* USA300-1114 cells. Worms were then treated at 2 h and 24 h with a range of terfenadine concentrations (20 to 160 mg kg$^{-1}$), vehicle (DMSO; negative control), or 20 mg kg$^{-1}$ vancomycin (positive control), and larval survival was assessed 48 h postinoculation. For tamoxifen studies, experiments were performed exactly as described above except that larvae were inoculated with 1.4×10$^6$ *E. faecium* strain 824-05 cells and larvae were treated with either 80 or 160 mg kg$^{-1}$ tamoxifen. Terfenadine-treated larvae did not reproducibly exhibit increased survival relative to vehicle-treated larvae. However, tamoxifen treatment of *E. faecium*-infected larvae resulted in a dose-dependent increase in survival. As shown in FIG. 6B, treatment with 80 or 160 mg kg-1 resulted in a 4.2-fold- or 7-fold-higher survival, respectively, than was found with vehicle-treated controls. Taken together, these results indicate that terfenadine exhibits in vitro activity toward *S. aureus* planktonic, SCV, and biofilm populations and that tamoxifen is active toward planktonic *E. faecium* and against the organism in a simple animal model of infection. As discussed below, these data show that tamoxifen and terfenadine represent attractive new chemical scaffolds for antibacterial optimization.

As set forth herein, Prestwick library screening revealed that each bacterial species studied was susceptible to members of the library with no previously reported antimicrobial activity. The antimicrobial properties of two of these drugs was studied in more detail: terfenadine and tamoxifen. Terfenadine is a nonsedating antihistamine based on a 4-substituted piperidine scaffold. Based on further studies, it was determined that terfenadine acts as a topoisomerase inhibitor and is structurally similar to certain topoisomerase inhibitors, including for example novel bacterial topoisomerase II inhibitor (NBTI). Based on the structural similarity between terfenadine and these molecules, it is likely that terfenadine is acting as a DNA gyrase and topoisomerase inhibitor. More specifically, terfenadine and derivatives thereof act as topoisomerase 4 inhibitors. Furthermore, it was found that terfenadine has activity against *S. aureus* small-colony variants and biofilms, properties not previously reported for this scaffold.

A screen of *E. faecium* identified two structurally related nonsteroid estrogen receptor antagonists, tamoxifen and clomiphene. Tamoxifen is used to treat some forms of estrogen-receptor-positive breast cancer, while clomiphene is used in fertility treatment regimens. These two compounds are members of the triarylethylene class of estrogen receptors.

Since the number of agents with activity toward *enterococcus* is quite limited, tamoxifen's in vivo activity was investigated using a Galleria model of *enterococcus* infection. Although it was not as active as vancomycin, tamoxifen did impart a survival benefit, indicating that it has in vivo antimicrobial activity. High-dose tamoxifen therapy has been used in experimental treatment of refractory human cancers, and dosing results in micromolar serum concentrations of tamoxifen corresponding to the levels of drug associated with antienterococcal activity observed in the studies provided herein.

In addition to providing a powerful new HTS approach to identify antimicrobial agents active against planktonic bacteria, an AK assay that is easily amenable to screening bacteria in disease states that cannot be readily screened via conventional approaches is provided herein. In that regard, the AK assay is capable of measuring the killing properties of bactericidal agents administered to biofilms formed by both Gram-negative and Gram-positive representatives of the ESKAPE pathogens. Similarly, the AK assay can detect the bactericidal properties of antibiotics toward a phenotypically stable *S. aureus* small-colony variant. These features can be exploited to develop corresponding high-throughput screening assays for the identification of agents that kill established biofilms and small-colony variants or provide powerful secondary assays aimed at characterizing the potential antimicrobial properties of molecules of interest.

Example II

Antimicrobial Properties of Terfenadine and Terfenadine Derivatives

Terfenadine derivatives were synthesized as described below.

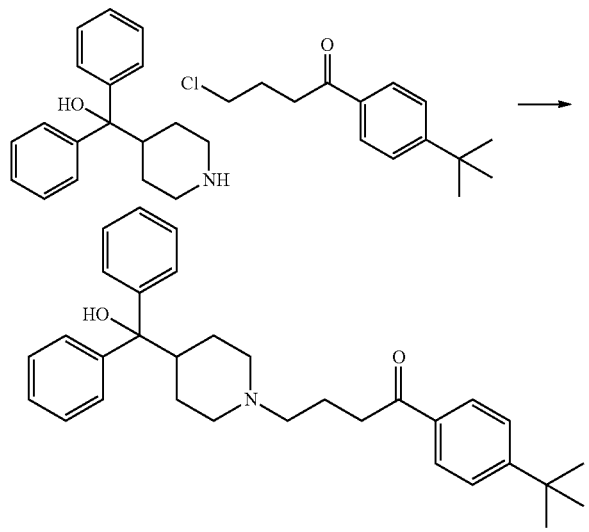

General Method A
KSC-335-007

1-(4-(tert-butyl)phenyl)-4-(4-(hydroxydiphenylmethyl)piperidin-1-yl)butan-1-one

To a vial was added the diphenyl(piperidin-4-yl)methanol (1.190 g, 4.45 mmol), 1-(4-(tert-butyl)phenyl)-4-chlorobutan-1-one (1.012 g, 4.24 mmol), sodium bicarbonate (0.427 g, 5.09 mmol) with water:2-butanone (18 mL, 1:5). The reaction stirred at 85° C. for 16 h and was then cooled to rt and water (50 mL) was added. The reaction was extracted with EtOAc (3×50 mL). The EtOAc layer was dried with MgSO$_4$, filtered, concentrated and purified by MPLC (20 min, 0-10% MeOH:DCM) to produce pure 1-(4-(tert-butyl)phenyl)-4-(4-(hydroxydiphenylmethyl) piperidin-1-yl)butan-1-one (1.37 g, 2.92 mmol, 69% yield) as a colorless oil. $^1$H NMR (500 MHz, CDCl$_3$): δ 7.90 (d, J=8.4 Hz, 2H), 7.49-7.45 (m, 6H), 7.31-7.25 (m, 4H), 7.20-7.14 (m, 2H), 2.97-2.92 (m, 4H), 2.45-2.36 (m, 3H), 2.09 (br s, 1H), 2.00-1.87 (m, 4H), 1.49-1.32 (m, 4H), 1.34 (s, 9H). $^{13}$C NMR (125 MHz, CDCl$_3$): δ 199.7, 156.5, 146.0, 134.5, 128.1, 128.0, 126.4, 125.7, 125.4, 79.4, 57.9, 43.9, 43.4, 44.1, 36.2, 35.0, 31.0, 26.2, 21.9. LCMS Retention time: 4.207 min. LCMS purity 99.5%. HRMS (ESI): m/z calcd for C$_{32}$H$_{39}$NO$_2$ [M+H]$^+$ 470.2981, found 470.3054.

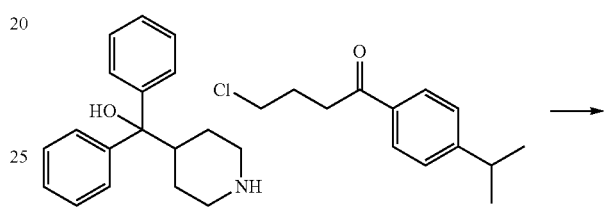

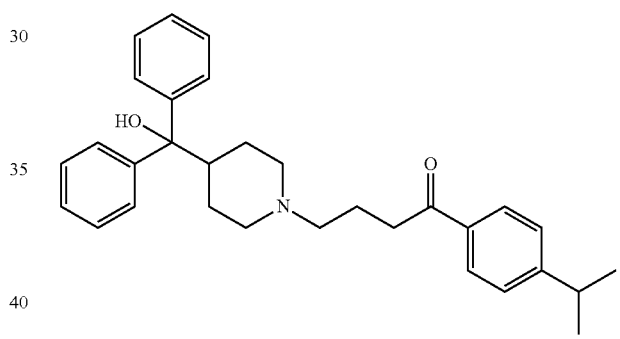

KSC-335-005

4-(4-(Hydroxydiphenylmethyl)piperidin-1-yl)-1-(4-isopropylphenyl)butan-1-one

Method

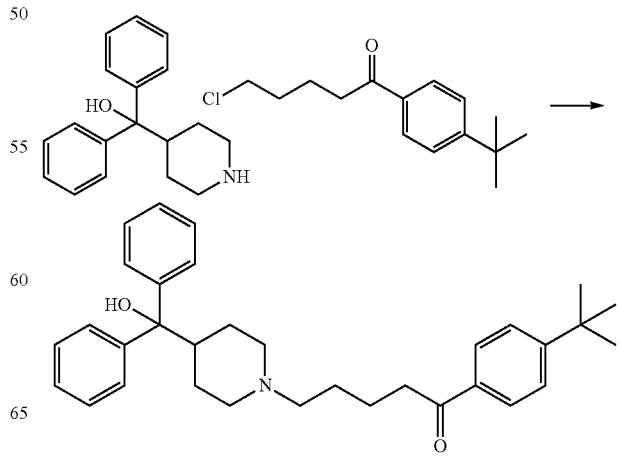

A: diphenyl(piperidin-4-yl)methanol (0.620 g, 2.317 mmol), 4-chloro-1-(4-isopropylphenyl)butan-1-one (0.496 g, 2.207 mmol), sodium bicarbonate (0.222 g, 2.65 mmol) with water (3 mL) and 2-butanone (15 mL, Ratio: 5). to produce pure 4-(4-(hydroxydiphenylmethyl)piperidin-1-yl)-1-(4-isopropylphenyl)butan-1-one (0.481 g, 1.056 mmol, 48% yield) as a colorless oil. $^1$H NMR (500 MHz, CDCl$_3$): δ 7.89 (d, J=8.4 Hz, 2H), 7.49-7.45 (m, 4H), 7.31-7.26 (m, 6H), 7.20-7.14 (m, 2H), 2.98-2.91 (m, 4H), 2.45-2.35 (m, 1H), 2.38 (t, J=6.8 Hz, 2H), 2.08 (br s, 1H), 1.99-1.89 (m, 4H), 1.61 (br s, 1H), 1.48-1.33 (m, 4H), 1.27 (d, J=6.8 Hz, 6H).

KSC-335-006

1-(4-(tert-butyl)phenyl)-5-(4-(hydroxydiphenylmethyl)piperidin-1-yl)pentan-1-one Method A: diphenyl(piperidin-4-yl)methanol (0.544 g, 2.035 mmol), 1-(4-(tert-butyl)phenyl)-5-chloropentan-1-one (0.490 g, 1.938 mmol), sodium bicarbonate (0.195 g, 2.326 mmol) with water:2-butanone (18 mL, 1:5) to produce pure 1-(4-(tert-butyl)phenyl)-5-(4-(hydroxydiphenylmethyl)piperidin-1-yl)pentan-1-one (0.600 g, 1.240 mmol, 64.0% yield) as a colorless oil. $^1$H NMR (500 MHz, CDCl$_3$): δ 7.89 (d, J=8.4 Hz, 2H), 7.49-7.45 (m, 6H), 7.32-7.26 (m, 4H), 7.20-7.14 (m, 2H), 2.98-2.92 (m, 4H), 2.48-2.32 (m, 3H), 2.14 (br s, 1H), 1.99-1.89 (m, 2H), 1.77-1.62 (m, 2H), 1.60-1.42 (m, 6H), 1.34 (s, 9H).

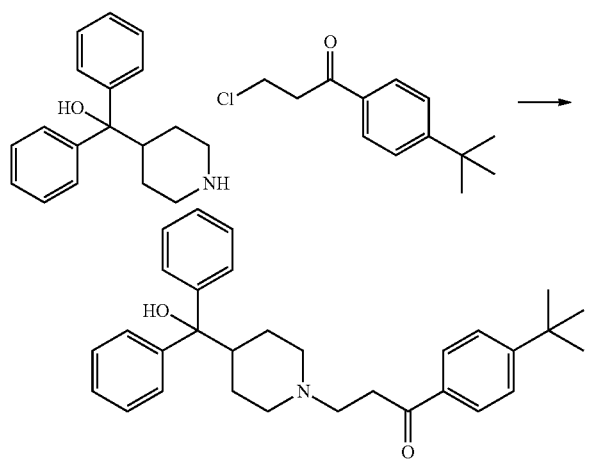

1-(4-(tert-butyl)phenyl)-3-(4-(hydroxydiphenylmethyl)piperidin-1-yl)propan-1-one Method A: diphenyl(piperidin-4-yl)methanol (0.543 g, 2.032 mmol), 1-(4-(tert-butyl)phenyl)-3-chloropropan-1-one (0.435 g, 1.936 mmol), sodium bicarbonate (0.195 g, 2.323 mmol) with water:2-butanone (18 mL, 1:5) to produce pure 1-(4-(tert-butyl)phenyl)-3-(4-(hydroxydiphenylmethyl)piperidin-1-yl)propan-1-one (0.838 g, 1.84 mmol, 95% yield) as a colorless oil. $^1$H NMR (500 MHz, CDCl$_3$): δ 7.89 (d, J=8.4 Hz, 2H), 7.50-7.45 (m, 6H), 7.32-7.25 (m, 4H), 7.21-7.14 (m, 2H), 3.15 (t, J=7.1 Hz, 2H), 3.01-2.96 (m, 2H), 2.81 (t, J=7.1 Hz, 2H), 2.49-2.42 (m, 1H), 2.15-2.04 (m, 3H), 1.56-1.46 (m, 4H), 1.33 (s, 9H). $^{13}$C NMR (125 MHz, CDCl$_3$): δ 198.9, 171.1, 156.8, 145.8, 134.3, 128.2, 128.0, 126.5, 125.8, 125.5, 79.4, 60.4, 54.2, 53.4, 44.0, 36.3, 35.1, 31.1, 26.4, 21.1, 14.2. LCMS Retention time: 3.968 min. LCMS purity 98.1%. HRMS (ESI): m/z calcd for C$_{31}$H$_{37}$NO$_2$ [M+H]$^+$ 456.2824, found 456.2897.

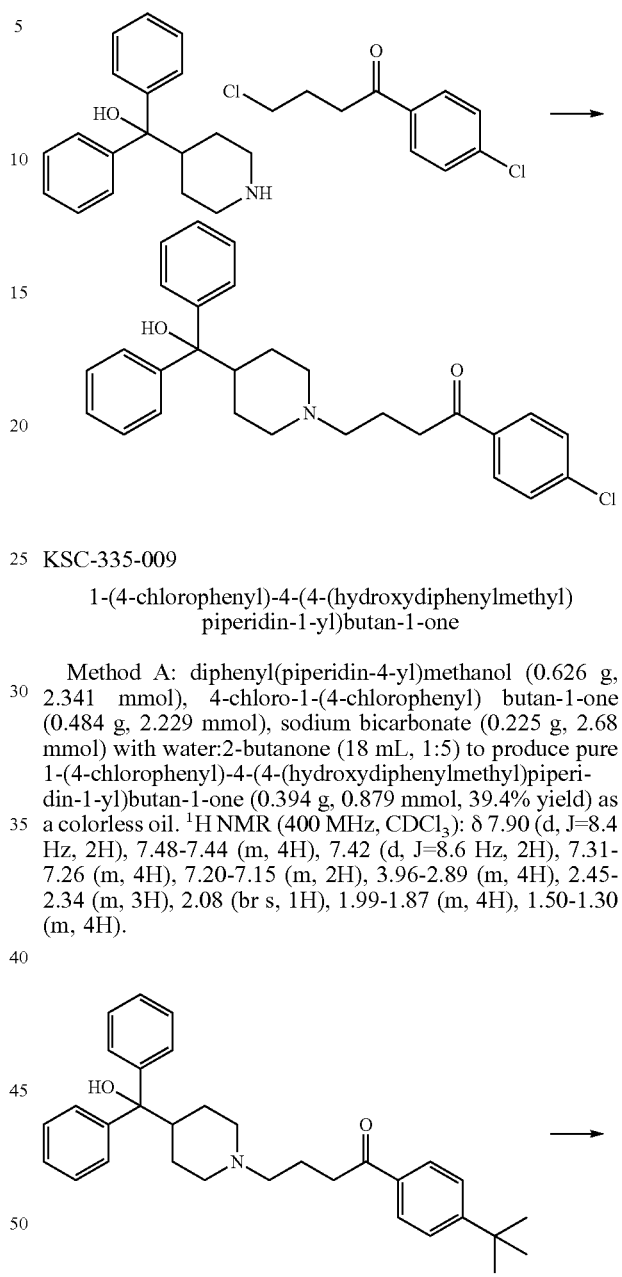

KSC-335-009

1-(4-chlorophenyl)-4-(4-(hydroxydiphenylmethyl)piperidin-1-yl)butan-1-one

Method A: diphenyl(piperidin-4-yl)methanol (0.626 g, 2.341 mmol), 4-chloro-1-(4-chlorophenyl) butan-1-one (0.484 g, 2.229 mmol), sodium bicarbonate (0.225 g, 2.68 mmol) with water:2-butanone (18 mL, 1:5) to produce pure 1-(4-chlorophenyl)-4-(4-(hydroxydiphenylmethyl)piperidin-1-yl)butan-1-one (0.394 g, 0.879 mmol, 39.4% yield) as a colorless oil. $^1$H NMR (400 MHz, CDCl$_3$): δ 7.90 (d, J=8.4 Hz, 2H), 7.48-7.44 (m, 4H), 7.42 (d, J=8.6 Hz, 2H), 7.31-7.26 (m, 4H), 7.20-7.15 (m, 2H), 3.96-2.89 (m, 4H), 2.45-2.34 (m, 3H), 2.08 (br s, 1H), 1.99-1.87 (m, 4H), 1.50-1.30 (m, 4H).

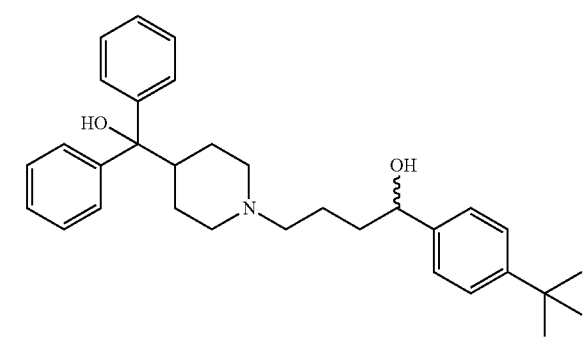

General Method B

KSC-335-014, Terfenadine 1-(4-(tert-butyl)phenyl)-4-(4-(hydroxydiphenylmethyl) piperidin-1-yl)butan-1-ol. To a vial was added the 1-(4-(tert-butyl)phenyl)-4-(4-(hydroxydiphenylmethyl)piperidin-1-yl) butan-1-one (KSC-335-007 (0.198 g, 0.422 mmol) and MeOH (2 mL). The sodium borohydride (0.032 g, 0.844 mmol) was then added and the reaction stirred at rt for 3 h. The reaction was concentrated to dryness, water (5 mL) was added and a white precipitate formed. The precipitate was filtered out and then dissolved in DCM (10 mL), dried with $MgSO_4$, filtered and concentrated to produce pure 1-(4-(tert-butyl)phenyl)-4-(4-(hydroxydiphenylmethyl)piperidin-1-yl) butan-1-ol (0.151 g, 0.320 mmol, 76% yield) as on oil. $^1$H NMR (400 MHz, $CDCl_3$): δ 7.52-7.46 (m, 4H), 7.33-7.25 (m, 8H), 7.21-7.15 (m, 2H), 4.61-4.56 (m, 1H), 3.16-3.11 (br m, 1H), 3.00-2.94 (m, 1H), 2.51-2.34 (m, 4H), 2.10-1.88 (m, 4H), 1.83-1.75 (m, 1H), 1.70-1.45 (m, 6H), 1.30 (s, 9H). $^{13}$C NMR (125 MHz, $CDCl_3$): δ 149.4, 146.1, 146.0, 142.7, 128.2, 128.1, 126.4, 126.3, 125.7, 125.6, 125.3, 125.0, 79.2, 73.4, 58.9, 54.7, 53.3, 44.2, 39.7, 34.4, 31.4, 26.0, 25.9, 24.1. LCMS Retention time: 4.137 min. LCMS purity 97.5%. HRMS (ESI): m/z calcd for $C_{32}H_{41}NO_2$ $[M+H]^+$ 472.3144, found 472.3219.

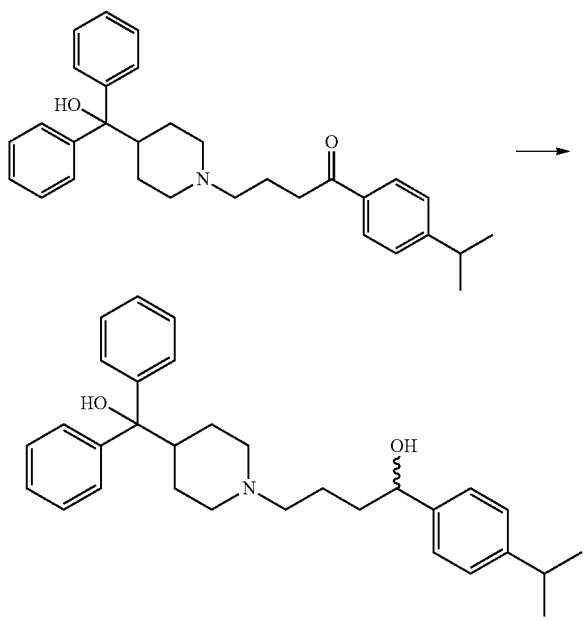

KSC-335-012

4-(4-(hydroxydiphenylmethyl)piperidin-1-yl)-1-(4-isopropylphenyl)butan-1-ol

Method B: 4-(4-(hydroxydiphenylmethyl)piperidin-1-yl)-1-(4-isopropylphenyl)butan-1-one (KSC-335-005) (0.154 g, 0.338 mmol) and MeOH (2 mL) sodium borohydride (0.026 g, 0.676 mmol) to produce pure 4-(4-(hydroxydiphenylmethyl)piperidin-1-yl)-1-(4-isopropylphenyl)butan-1-ol (0.146 g, 0.319 mmol, 94% yield) as on oil. $^1$H NMR (400 MHz, $CDCl_3$): δ 7.52-7.46 (m, 4H), 7.32-7.23 (m, 6H), 7.20-7.14 (m, 4H), 4.61-4.58 (m, 1H), 3.18-3.11 (br m, 1H), 3.00-2.94 (br m, 1H), 2.87 (septet, J=6.9 Hz, 1H), 2.50-2.33 (m, 3H), 2.29 (br s, 1H), 2.10-1.89 (m, 3H), 1.82-1.44 (m, 8H), 1.22 (d, J=6.9 Hz, 6H). $^{13}$C NMR (125 MHz, $CDCl_3$): δ 147.2, 146.1, 146.0, 128.2, 128.1, 126.5, 126.4, 126.1, 125.7, 125.7, 79.2, 73.5, 58.9, 54.7, 53.3, 44.2, 39.9, 33.7, 26.0, 25.9, 24.2, 24.1, 24.0. LCMS Retention time: 4.056 min. LCMS purity 98.6%. HRMS (ESI): m/z calcd for $C_{31}H_{39}NO_2$ $[M+H]^+$ 458.2986, found 458.3062.

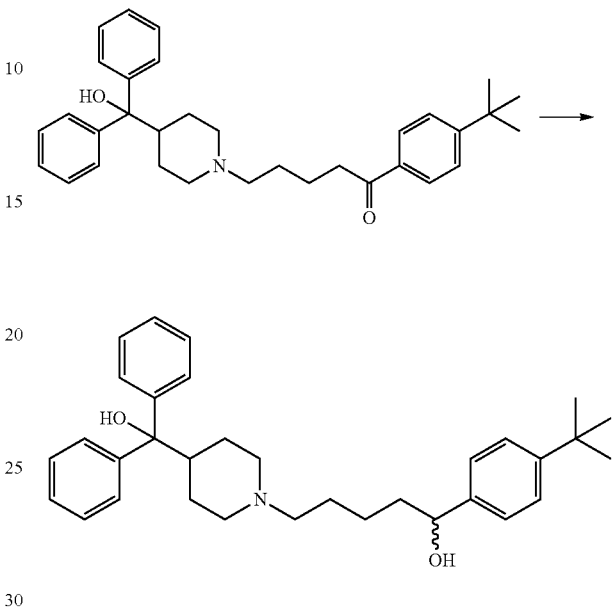

KSC-335-013

1-(4-(tert-butyl)phenyl)-5-(4-(hydroxydiphenylmethyl)piperidin-1-yl)pentan-1-ol

Method B: 1-(4-(tert-butyl)phenyl)-5-(4-(hydroxydiphenylmethyl)piperidin-1-yl)pentan-1-one (KSC-335-006) (0.204 g, 0.422 mmol) and MeOH (2 mL) and sodium borohydride (0.032 g, 0.844 mmol) to produce pure 1-(4-(tert-butyl)phenyl)-5-(4-(hydroxydiphenylmethyl)piperidin-1-yl)pentan-1-ol (0.156 g, 0.321 mmol, 76% yield) as on oil. $^1$H NMR (400 MHz, $CDCl_3$): δ 7.50-7.45 (m, 4H), 7.36 (d, J=8.4 Hz, 2H), 7.31-7.24 (m, 6H), 7.19-7.14 (m, 2H), 4.65-4.60 (m, 1H), 2.98-2.90 (br m, 1H), 2.48-2.38 (m, 1H), 2.30 (t, J=7.2 Hz, 2H), 2.23 (br s, 1H), 1.97-1.87 (m, 2H), 1.84-1.60 (m, 4H), 1.55-1.35 (m, 8H), 1.31 (s, 9H). $^{13}$C NMR (125 MHz, $CDCl_3$): δ 150.3, 146.0, 142.0, 128.1, 126.4, 125.8, 125.5, 125.3, 79.4, 74.1, 58.4, 54.1, 54.0, 44.2, 38.5, 34.5, 31.4, 31.3, 26.5, 26.3, 26.2, 23.7. LCMS Retention time: 4.254 min. LCMS purity 96.4%. HRMS (ESI): m/z calcd for $C_{33}H_{43}NO_2$ $[M+H]^+$ 486.3294, found 486.3370.

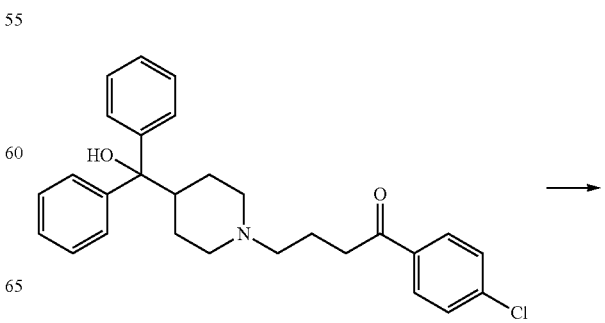

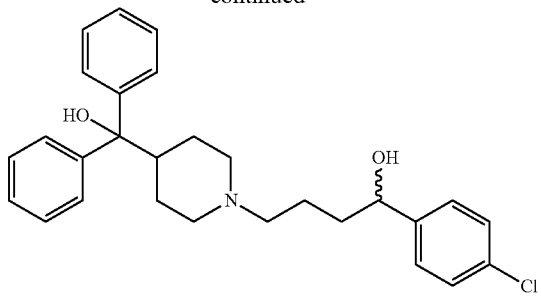

KSC-335-015

1-(4-chlorophenyl)-4-(4-(hydroxydiphenylmethyl)piperidin-1-yl)butan-1-ol

Method B: 1-(4-chlorophenyl)-4-(4-(hydroxydiphenylmethyl)piperidin-1-yl)butan-1-one (KSC-335-009) (0.156 g, 0.348 mmol) and MeOH (2 mL) sodium borohydride (0.026 g, 0.696 mmol) to produce pure 1-(4-chlorophenyl)-4-(4-(hydroxydiphenylmethyl)piperidin-1-yl)butan-1-ol (0.118 g, 0.262 mmol, 75% yield) as on oil. $^1$H NMR (400 MHz, CDCl$_3$): δ 7.51-7.46 (m, 4H), 7.32-7.24 (m, 8H), 7.20-7.15 (m, 2H), 4.61-4.56 (m, 1H), 3.16-3.10 (br m, 1H), 2.97-2.91 (m, 1H), 2.51-2.33 (m, 4H), 2.12-1.88 (m, 3H), 1.83-1.75 (m, 1H), 1.78-1.46 (m, 8H). $^{13}$C NMR (125 MHz, CDCl$_3$): δ 146.0, 145.9, 144.5, 139.1, 128.19, 128.18, 128.1, 127.1, 126.49, 126.45, 125.62, 125.57, 79.2, 72.9, 58.8, 54.7, 53.2, 44.2, 40.2, 26.0, 25.9, 24.1. LCMS Retention time: 3.845 min. LCMS purity 98.4%. HRMS (ESI): m/z calcd for C$_{28}$H$_{32}$ClNO$_2$ [M+H]$^+$ 450.2122, found 450.2194.

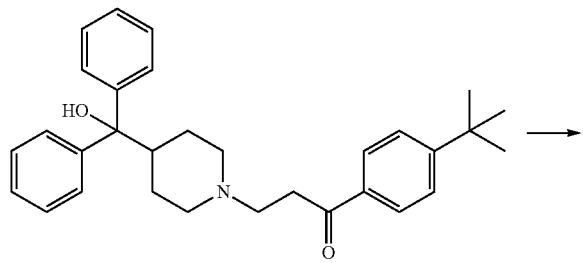

KSC-335-016

1-(4-(tert-butyl)phenyl)-3-(4-(hydroxydiphenylmethyl)piperidin-1-yl)propan-1-ol

Method B: 1-(4-(tert-butyl)phenyl)-3-(4-(hydroxydiphenylmethyl)piperidin-1-yl)propan-1-one (KSC-335-008) (0.116 g, 0.255 mmol) and MeOH (2 mL) and sodium borohydride (0.019 g, 0.509 mmol) to produce pure 1-(4-(tert-butyl)phenyl)-3-(4-(hydroxydiphenylmethyl)piperidin-1-yl)propan-1-ol (0.106 g, 0.232 mmol, 91% yield) as on oil.

$^1$H NMR (400 MHz, CDCl$_3$): δ 7.49-7.44 (m, 4H), 7.36-7.25 (m, 8H), 7.22-7.16 (m, 2H), 6.72 (br s, 1H), 4.90-4.85 (m, 1H), 3.21-3.15 (br m, 1H), 3.11-3.05 (br m, 1H), 2.70-2.62 (m, 1H), 2.57-2.40 (m, 2H), 2.14-2.06 (m, 2H), 1.91-1.79 (m, 3H), 1.57-1.45 (m, 4H), 1.31 (s, 9H). $^{13}$C NMR (125 MHz, CDCl$_3$): δ 149.6, 145.8, 145.7, 141.9, 128.2, 128.1, 126.6, 126.5, 125.8, 125.7, 125.2, 125.0, 79.4, 75.3, 57.3, 55.2, 53.2, 44.1, 34.4, 33.7, 31.4, 26.7, 26.4. LCMS Retention time: 4.006 min. LCMS purity 97.7%. HRMS (ESI): m/z calcd for C$_{31}$H$_{39}$NO$_2$ [M+H]$^+$ 458.2991, found 458.3066.

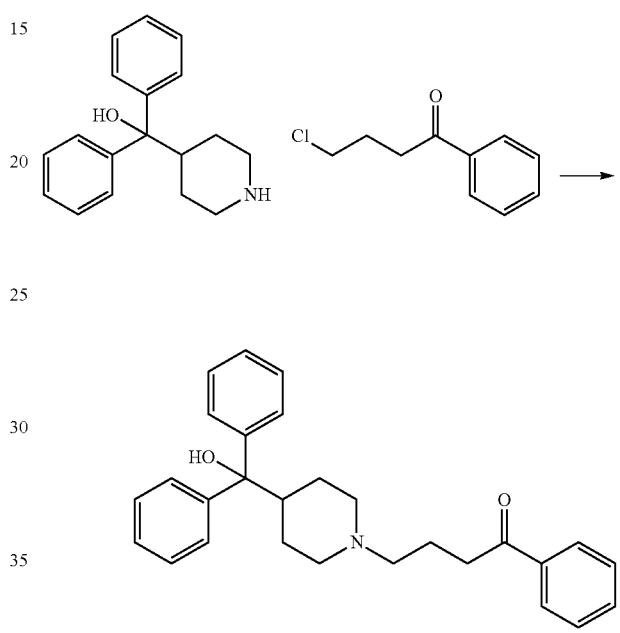

KSC-335-018

4-(4-(hydroxydiphenylmethyl)piperidin-1-yl)-1-phenylbutan-1-one

Method A: diphenyl(piperidin-4-yl)methanol (0.524 g, 1.961 mmol), 4-chloro-1-phenylbutan-1-one (0.300 ml, 1.868 mmol), sodium bicarbonate (0.188 g, 2.241 mmol) with water:2-butanone (18 mL, 1:5) to produce pure 4-(4-(hydroxydiphenylmethyl)piperidin-1l-yl)-1-phenylbutan-1-one (0.177 g, 0.428 mmol, 23% yield) as a colorless oil. $^1$H NMR (500 MHz, CDCl$_3$): δ 7.98-7.94 (m, 2H), 7.57-7.52 (m, 1H), 7.49-7.42 (m, 6H), 7.32-7.26 (m, 4H), 7.20-7.15 (m, 2H), 3.00-2.90 (m, 4H), 2.46-2.35 (m, 3H), 2.09 (br s, 1H), 2.00-1.87 (m, 4H), 1.50-1.33 (m, 4H).

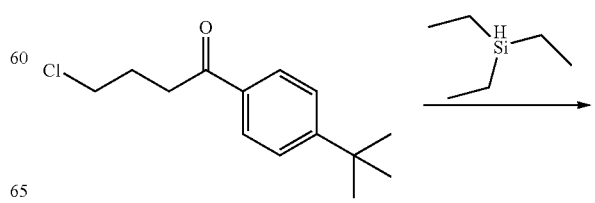

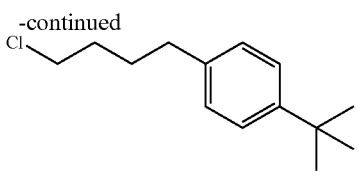

KSC-335-020

1-(tert-butyl)-4-(4-chlorobutyl)benzene

To a vial was added the 1-(4-(tert-butyl)phenyl)-4-chlorobutan-1-one (0.266 g, 1.114 mmol) and triethylsilane (0.518 g, 0.712 ml, 4.46 mmol) with TFA (4 mL). The reaction stirred at 75° C. for 18 h, was cooled to rt and concentrated in vacuo. The residue was then dissolved in DCM (5 mL) and washed with water (4 mL). The DCM layer was collected and washed with water (1×5 mL), dried with MgSO$_4$, filtered and adsorbed to silica and purified by Teledyne ISCO Combiflash chromatography (20 min, 0-40% EtOAc:Hex) and fractions 4 and 5 were collected to produce pure 1-(tert-butyl)-4-(4-chlorobutyl)benzene (0.155 g, 0.690 mmol, 61.9% yield) as an oil. $^1$H NMR (400 MHz, CDCl$_3$): δ 7.32 (d, J=7.6 Hz, 2H), 7.12 (d, J=7.6 Hz, 2H), 3.56 (t, J=6.5 Hz, 2H), 2.62 (t, J=7.5 Hz, 2H), 1.87-1.74 (m, 4H), 1.32 (s, 9H).

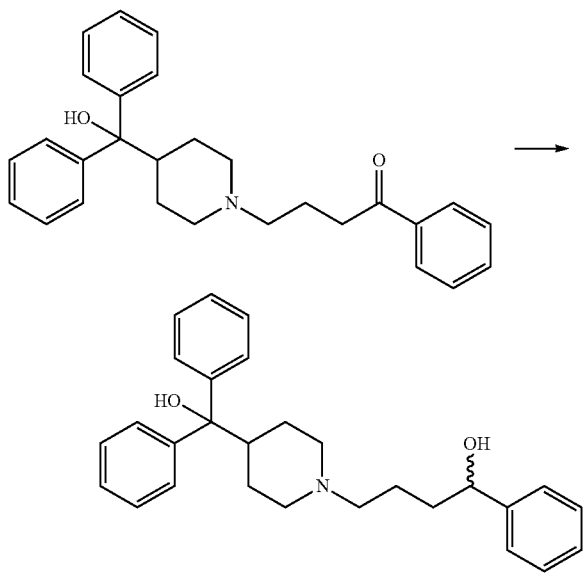

KSC-335-021

4-(4-(hydroxydiphenylmethyl)piperidin-1-yl)-1-phenylbutan-1-ol

Method B: 4-(4-(hydroxydiphenylmethyl)piperidin-1-yl)-1-phenylbutan-1-one (KSC-335-018) (0.065 g, 0.157 mmol) and MeOH (2 mL) and sodium borohydride (0.012 g, 0.314 mmol) to produce pure 4-(4-(hydroxydiphenylmethyl) piperidin-1-yl)-1-phenylbutan-1-ol (0.048 g, 0.116 mmol, 73% yield) as on oil. $^1$H NMR (400 MHz, CDCl$_3$): δ 7.51-7.46 (m, 4H), 7.37-7.33 (m, 2H), 7.32-7.26 (m, 5H), 7.23-7.14 (m, 3H), 4.65-4.61 (m, 1H), 3.15 (d, J=11.7 Hz, 1H), 2.96 (d, J=11.7 Hz, 1H), 2.52-2.31 (m, 4H), 2.11-1.90 (m, 3H), 1.84-1.74 (m, 2H), 1.70-1.44 (m, 7H). $^{13}$C NMR (125 MHz, CDCl$_3$): δ 146.0, 145.9, 145.8, 128.2, 128.1, 128.0, 126.6, 126.5, 126.4, 125.6, 125.6, 79.2, 73.6, 58.9, 54.7, 53.3, 44.2, 40.1, 26.0, 25.9, 24.1. LCMS Retention time: 3.711 min. LCMS purity 99.8%. HRMS (ESI): m/z calcd for C$_{28}$H$_{33}$NO$_2$ [M+H]$^+$ 416.2517, found 416.2592.

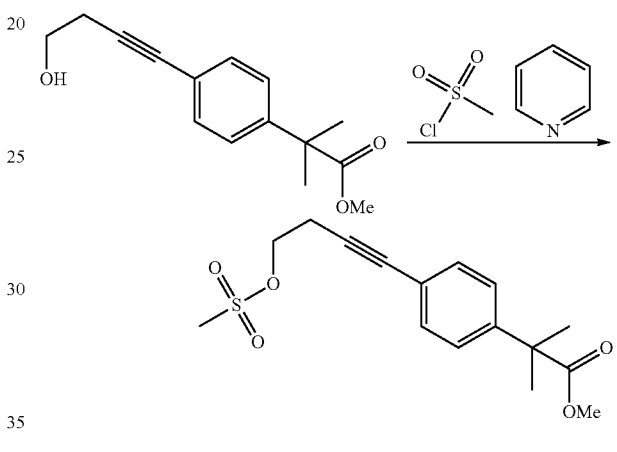

KSC-335-022

Methyl 2-methyl-2-(4-(4-((methylsulfonyl)oxy)but-1-yn-1-yl)phenyl)propanoate

To a vial was added the methyl 2-(4-(4-hydroxybut-1-yn-1-yl)phenyl)-2-methylpropanoate (0.051 g, 0.207 mmol) and dry DCM (2 mL). The methanesulfonyl chloride (0.047 g, 0.032 mL, 0.414 mmol) and pyridine (0.147 g, 0.151 mL, 1.864 mmol) were each added and the reaction and stirred at rt for 16 h. The reaction was then diluted with DCM (5 mL) and washed with 1% w/v sulfuric acid in water (3×7 mL), saturated NaHCO$_3$ (7 mL) and brine (7 mL). The organic layer was dried with MgSO$_4$, filtered and concentrated to produce methyl 2-methyl-2-(4-(4-((methylsulfonyl) oxy)but-1-yn-1-yl)phenyl)propanoate (0.063 g, 0.194 mmol, 94% yield). $^1$H NMR (400 MHz, CDCl$_3$): δ 7.35 (d, J=8.6 Hz, 2H), 7.26 (d, J=8.6 Hz, 2H), 4.38 (t, J=6.8 Hz, 2H), 3.64 (s, 3H), 3.06 (s, 3H), 2.87 (t, J=6.8 Hz, 2H), 1.56 (s, 6H).

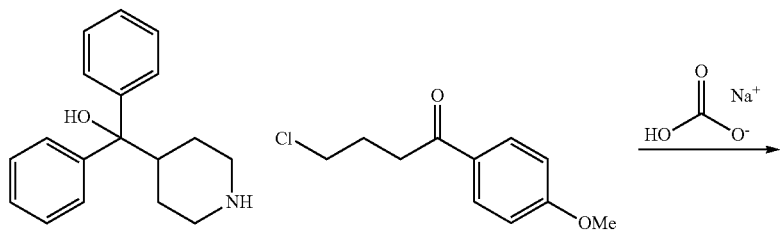

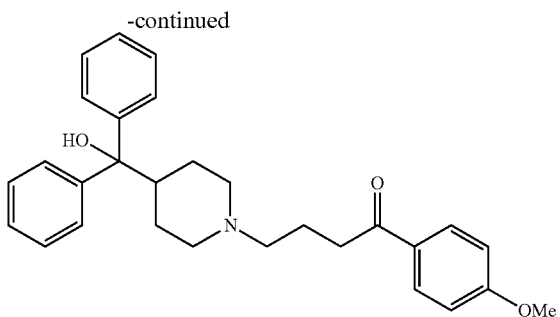

KSC-335-023

4-(4-(hydroxydiphenylmethyl)piperidin-1-yl)-1-(4-methoxyphenyl)butan-1-one

Method A: diphenyl(piperidin-4-yl)methanol (0.490 g, 1.832 mmol), 4-chloro-1-(4-methoxyphenyl)butan-1-one (0.371 g, 1.744 mmol), sodium bicarbonate (0.176 g, 2.093 mmol) with water (3 mL) and 2-butanone (15 mL) to produce pure 4-(4-(hydroxydi phenylmethyl)piperidin-1-yl)-1-(4-methoxyphenyl)butan-1-one (0.282 g, 0.636 mmol, 36% yield) as a colorless oil. $^1$H NMR (400 MHz, CDCl$_3$): δ 7.94 (d, J=9.0 Hz, 2H), 7.49-7.45 (m, 4H), 7.31-7.26 (m, 4H), 7.17 (tt, J$_1$=7.3 Hz, J$_2$=1.3 Hz, 2H), 6.92 (d, J=8.9 Hz, 2H), 3.87 (s, 3H), 2.97 (br s, 1H), 2.93 (t, J=7.3 Hz, 2H), 2.48-2.35 (m, 3H), 2.02-1.88 (m, 4H), 1.63-1.40 (m, 4H).

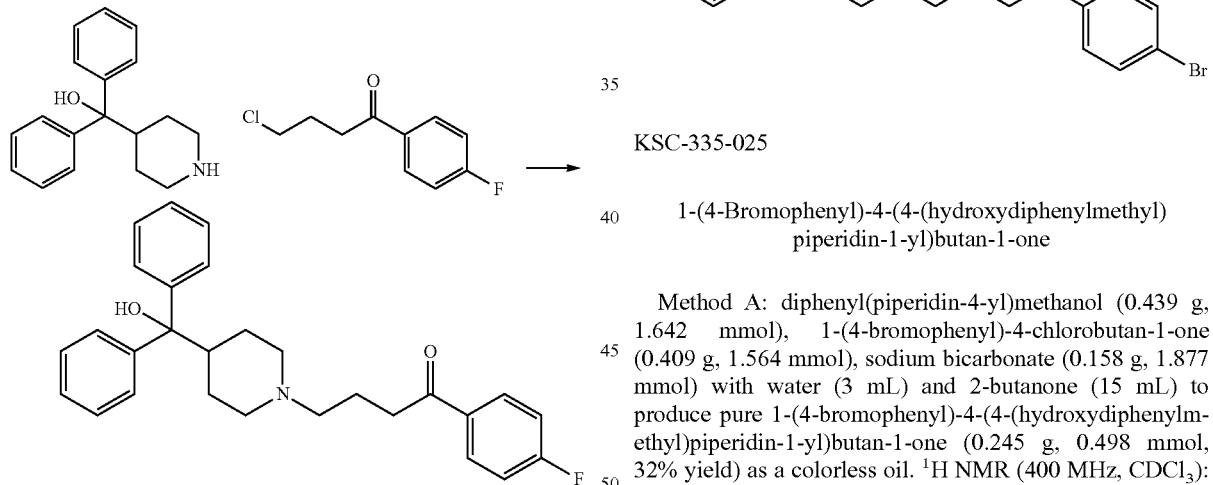

KSC-335-024

1-(4-Fluorophenyl)-4-(4-(hydroxydiphenylmethyl)piperidin-1-yl)butan-1-one

Method A: diphenyl(piperidin-4-yl)methanol (0.385 g, 1.439 mmol), 4-chloro-1-(4-fluorophenyl)butan-1-one (0.275 g, 1.371 mmol), sodium bicarbonate (0.138 g, 1.645 mmol) with water (3 mL) and 2-butanone (15 mL) to produce pure 1-(4-fluorophenyl)-4-(4-(hydroxydiphenylmethyl)piperidin-1-yl)butan-1-one (0.174 g, 0.403 mmol, 29% yield) as a colorless oil. $^1$H NMR (400 MHz, CDCl$_3$): δ 8.00-7.96 (m, 2H), 7.48-7.44 (m, 4H), 7.31-7.26 (m, 4H), 7.20-7.15 (m, 2H), 7.14-7.08 (m, 2H), 2.97-2.94 (m, 4H), 2.46-2.36 (m, 3H), 2.15 (br s, 1H), 2.01-1.88 (m, 4H), 1.52-1.35 (m, 4H).

KSC-335-025

1-(4-Bromophenyl)-4-(4-(hydroxydiphenylmethyl)piperidin-1-yl)butan-1-one

Method A: diphenyl(piperidin-4-yl)methanol (0.439 g, 1.642 mmol), 1-(4-bromophenyl)-4-chlorobutan-1-one (0.409 g, 1.564 mmol), sodium bicarbonate (0.158 g, 1.877 mmol) with water (3 mL) and 2-butanone (15 mL) to produce pure 1-(4-bromophenyl)-4-(4-(hydroxydiphenylmethyl)piperidin-1-yl)butan-1-one (0.245 g, 0.498 mmol, 32% yield) as a colorless oil. $^1$H NMR (400 MHz, CDCl$_3$): δ 7.83-7.79 (m, 2H), 7.60-7.56 (m, 2H), 7.48-7.45 (m, 4H), 7.31-7.26 (m, 4H), 7.20-7.15 (m, 2H), 2.95-2.90 (m, 4H), 2.45-2.35 (m, 3H), 2.17 (br s, 1H), 2.00-1.88 (m, 4H), 1.51-1.33 (m, 4H).

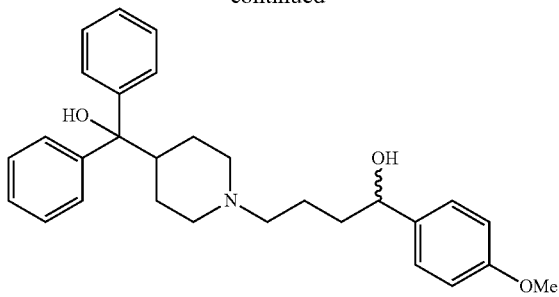

KSC-335-030

4-(4-(hydroxydiphenylmethyl)piperidin-1-yl)-1-(4-methoxyphenyl)butan-1-ol

Method B: 4-(4-(hydroxydiphenylmethyl)piperidin-1-yl)-1-(4-methoxyphenyl)butan-1-one (KSC-335-023) (0.113 g, 0.255 mmol) and MeOH (2 mL) and sodium borohydride (0.019 g, 0.509 mmol) to produce pure 4-(4-(hydroxydiphenylmethyl)piperidin-1-yl)-1-(4-methoxyphenyl)butan-1-ol (0.062 g, 0.139 mmol, 55% yield) as on oil. $^1$H NMR (400 MHz, CDCl$_3$): δ 7.51-7.46 (m, 4H), 7.32-7.24 (m, 6H), 7.20-7.15 (m, 2H), 6.84 (d, J=7.0 Hz, 2H), 4.60-4.56 (m, 1H), 3.78 (s, 3H), 3.14 (d, J=11.7 Hz, 1H), 2.95 (d, J=11.7 Hz, 1H), 2.50-2.35 (m, 4H), 2.10-2.02 (m, 1H), 1.99-1.86 (m, 2H), 1.80-1.73 (m, 1H), 1.69-1.45 (m, 7H). $^{13}$C NMR (125 MHz, CDCl$_3$): δ 158.3, 146.1, 146.0, 138.1, 128.1, 128.1, 126.7, 126.4, 126.4, 125.7, 125.6, 113.5, 79.2, 73.2, 58.9, 55.2, 54.7, 53.2, 44.2, 40.0, 26.0, 25.9, 24.1. LCMS Retention time: 3.620 min. LCMS purity 98.3%. HRMS (ESI): m/z calcd for C$_{29}$H$_{35}$NO$_3$ [M+H]$^+$ 446.2652, found 446.2728.

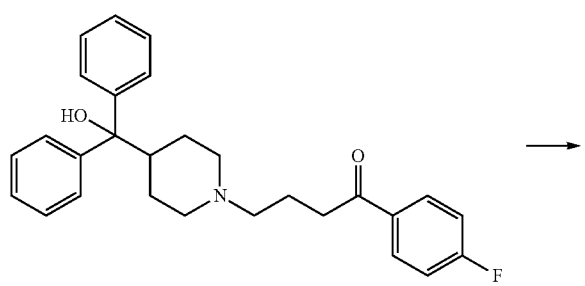

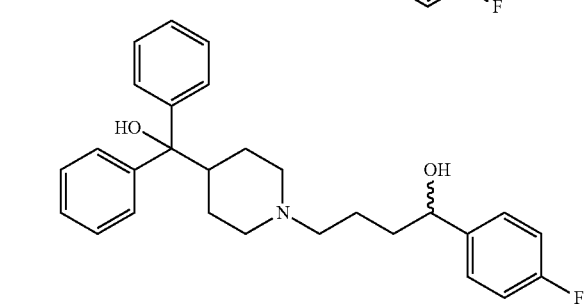

KSC-335-031

1-(4-fluorophenyl)-4-(4-(hydroxydiphenylmethyl)piperidin-1-yl)butan-1-ol

Method B: 1-(4-fluorophenyl)-4-(4-(hydroxydiphenylmethyl)piperidin-1-yl)butan-1-one (KSC-335-024) (0.064 g, 0.148 mmol) and MeOH (2 mL) and sodium borohydride (0.011 g, 0.297 mmol) to produce pure 1-(4-fluorophenyl)-4-(4-(hydroxydiphenylmethyl)piperidin-1-yl)butan-1-ol (0.059 g, 0.136 mmol, 92% yield) as on oil. $^1$H NMR (400 MHz, CDCl$_3$): δ 7.51-7.46 (m, 4H), 7.33-7.25 (m, 6H), 7.20-7.14 (m, 2H), 6.96 (t, J=8.8 Hz, 2H), 4.61-4.57 (m, 1H), 3.14 (d, J=11.7 Hz, 1H), 2.94 (d, J=11.7 Hz, 1H), 2.51-2.35 (m, 4H), 2.13-2.02 (m, 1H), 2.02-1.86 (m, 2H), 1.78-1.45 (m, 7H). $^{13}$C NMR (125 MHz, CDCl$_3$): δ 162.6, 160.7, 146.0, 145.9, 141.7, 141.6, 128.2, 128.1, 127.2, 127.1, 126.5, 126.4, 125.6, 125.5, 114.9, 114.7, 79.2, 73.0, 58.8, 54.8, 53.1, 44.2, 40.3, 30.9, 26.0, 25.9, 24.1. LCMS Retention time: 3.691 min. LCMS purity 98.5%. HRMS (ESI): m/z calcd for C$_{28}$H$_{32}$FNO$_2$ [M+H]$^+$ 434.2406, found 434.2482.

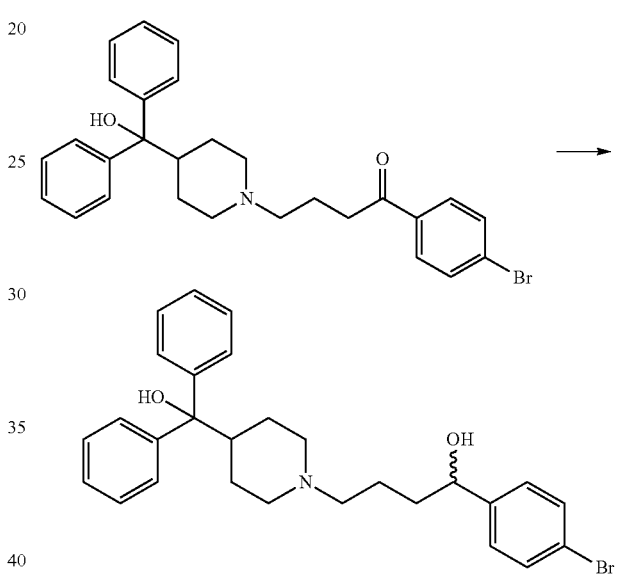

KSC-335-032

1-(4-bromophenyl)-4-(4-(hydroxydiphenylmethyl)piperidin-1-yl)butan-1-ol

Method B: 1-(4-bromophenyl)-4-(4-(hydroxydiphenylmethyl)piperidin-1-yl)butan-1-one (KSC-335-025) (0.083 g, 0.169 mmol) and MeOH (2 mL) and sodium borohydride (0.013 g, 0.337 mmol) to produce pure 1-(4-bromophenyl)-4-(4-(hydroxydiphenylmethyl)piperidin-1-yl)butan-1-ol (0.053 g, 0.107 mmol, 63.6% yield) as on oil. $^1$H NMR (400 MHz, CDCl$_3$): δ 7.51-7.46 (m, 4H), 7.41 (d, J=6.8 Hz, 2H), 7.32-7.26 (m, 4H), 7.22 (d, J=6.6 Hz, 2H), 7.20-7.15 (m, 2H), 4.60-4.56 (m, 1H), 3.14 (d, J=11.7 Hz, 1H), 2.93 (d, J=11.7 Hz, 1H), 2.50-2.42 (m, 1H), 2.41-2.34 (m, 2H), 2.11-2.05 (m, 1H), 2.01-1.95 (m, 1H), 1.94-1.86 (m, 1H), 1.78-1.45 (m, 8H). $^{13}$C NMR (125 MHz, CDCl$_3$): δ 146.0, 145.9, 145.1, 131.1, 128.2, 128.1, 127.5, 126.5, 126.4, 125.6, 125.6, 120.2, 79.2, 72.9, 58.8, 54.7, 53.2, 44.1, 40.1, 26.0, 25.9, 24.1. LCMS Retention time: 3.902 min. LCMS purity 99.1%. HRMS (ESI): m/z calcd for C$_{28}$H$_{32}$BrNO$_2$ [M+H]$^+$ 494.1614, found 494.1673.

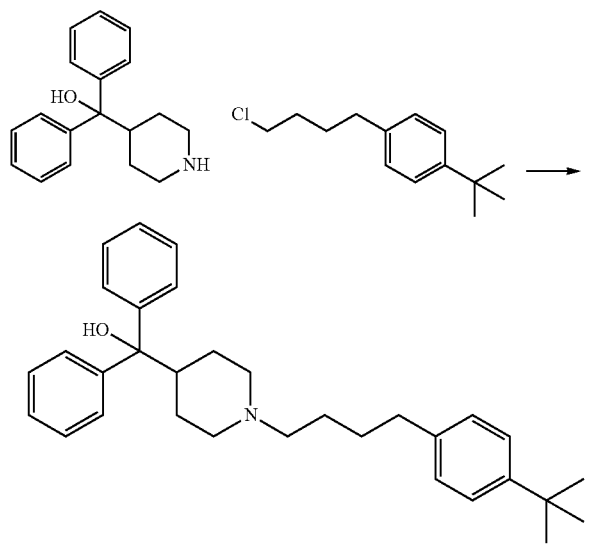

KSC-335-041

(1-(4-(4-(tert-butyl)phenyl)butyl)piperidin-4-yl)diphenylmethanol

To a vial was added the diphenyl(piperidin-4-yl)methanol (0.153 g, 0.571 mmol), 1-(tert-butyl)-4-(4-chlorobutyl)benzene (KSC-335-020) (0.154 g, 0.685 mmol) and potassium carbonate (0.473 g, 3.43 mmol) in acetonitrile. The reaction stirred overnight at 85° C. and for 18 h and was then cooled to rt and filtered. The filtrate was then diluted with brine and extracted with diethyl ether (3×15 mL). The ether layers were combined, dried with MgSO$_4$, filtered and purified by reverse-phase MPLC (20 min, 10-100% MeCN:H$_2$O) to produce pure (1-(4-(4-(tert-butyl)phenyl)butyl)piperidin-4-yl)diphenylmethanol (0.180 g, 0.395 mmol, 69% yield) as an oil. $^1$H NMR (400 MHz, CDCl$_3$): δ 7.38-7.34 (m, 4H), 7.19-7.14 (m, 6H), 7.07-7.02 (m, 2H), 6.99-6.95 (m, 2H), 2.86-2.80 (m, 2H), 2.45 (t, J=7.3 Hz, 2H), 2.35-2.26 (m, 1H), 2.22-2.17 (m, 2H), 1.84-1.76 (m, 3H), 1.52-1.30 (m, 8H), 1.18 (s, 9H). $^{13}$C NMR (125 MHz, CDCl$_3$): δ 171.1, 148.4, 146.0, 139.4, 128.1, 128.0, 126.4, 125.8, 125.1, 79.5, 60.4, 58.8, 54.1, 44.2, 35.2, 34.3, 31.4, 29.5, 26.8, 26.4, 21.0, 14.2. LCMS Retention time: 3.928 min. LCMS purity 97.8%. HRMS (ESI): m/z calcd for C$_{32}$H$_{41}$NO [M+H]$^+$ 456.3188, found 456.3261.

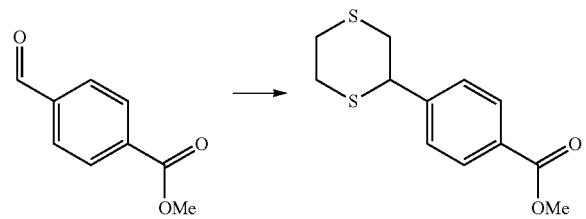 [SMILES: COC(=O)c1ccc(C=O)cc1 ; COC(=O)c1ccc(C2CSCCS2)cc1]

KSC-335-053
Methyl 4-(1,3-dithian-2-yl)benzoate. A flame dried vial was evaporated 3 times with argon and methyl 4-formylbenzoate (0.50 g, 3.05 mmol) was added with anhydrous DCM (8.70 mL) followed by 1,3-propanedithiol (0.339 mL, 3.35 mmol). The reaction began to stir at rt for 1.5 h. The reaction was then cooled to 0° C. and the BF3.OEt$_2$ (0.425 ml, 3.35 mmol) was added dropwise. The reaction was then warmed slowly to rt and stirred overnight. The reaction was then diluted with DCM (15 mL) and quenched with saturated NaHCO$_3$ (15 mL) and the DCM layer was dried with MgSO$_4$, filtered and adsorbed to silica and purified by MPLC (20 min, 0-35% EtOAc:Hex) to produce methyl 4-(1,3-dithian-2-yl)benzoate (0.669 g, 2.63 mmol, 86% yield). $^1$H NMR (400 MHz, CDCl$_3$): δ 8.01 (d, J=8.4 Hz, 2H), 7.54 (d, J=8.3 Hz, 2H), 3.91 (s, 3H), 3.12-3.03 (m, 2H), 2.96-2.90 (m, 2H), 2.23-2.16 (m, 1H), 2.01-1.89 (m, 1H), 1.55 (s, 2H).

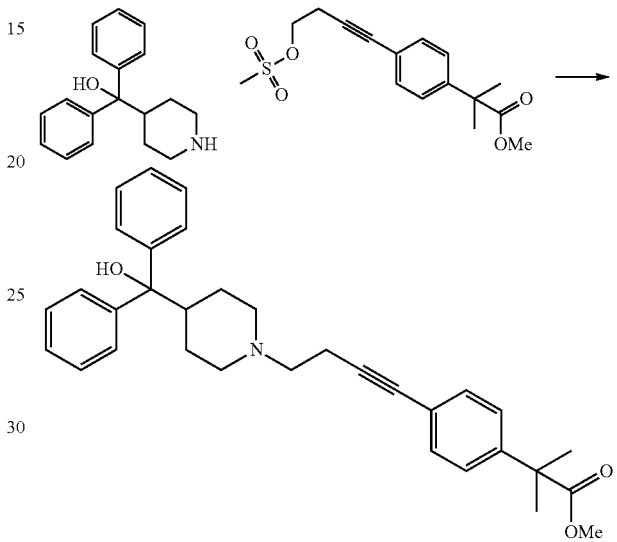

KSC-335-054

Methyl 2-(4-(4-(4-(hydroxydiphenylmethyl)piperidin-1-yl)but-1-yn-1-yl)phenyl)-2-methylpropanoate To a vial was added the diphenyl(piperidin-4-yl)methanol (0.528 g, 1.974 mmol), methyl 2-methyl-2-(4-(4-((methylsulfonyl)oxy)but-1-yn-1-yl)phenyl)propanoate (KSC-335-022) (0.582 g, 1.794 mmol) and potassium carbonate (0.744 g, 5.38 mmol) with acetonitrile (10 mL). The reaction stirred at 70° C. for 18 h and cooled to rt and filtered to remove the potassium carbonate. The filtrate was adsorbed to silica gel and purified by reverse-phase MPLC (20 min, 10-100% MeCN:H$_2$O) to produce pure methyl 2-(4-(4-(4-(hydroxydiphenylmethyl) piperidin-1-yl)but-1-yn-1-yl)phenyl)-2-methylpropanoate (0.434 g, 0.876 mmol, 49% yield). $^1$H NMR (400 MHz, CDCl$_3$): δ 7.49-7.46 (m, 4H), 7.34-7.27 (m, 6H), 7.25-7.15 (m, 4H), 3.64 (s, 3H), 3.03-2.97 (m, 2H), 2.68-2.63 (m, 2H), 2.59-2.54 (m, 2H), 2.48-2.40 (m, 1H), 2.14-2.06 (m, 2H), 1.63 (br s, 1H), 1.55 (s, 6H), 1.55-1.45 (m, 4H).

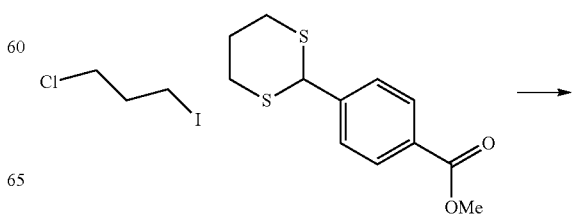

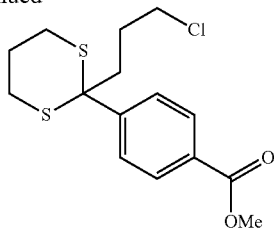

KSC-335-056

Methyl 4-(2-(3-chloropropyl)-1,3-dithian-2-yl)benzoate

To a dry vial was added the methyl 4-(1,3-dithian-2-yl)benzoate (KSC-335-053) (0.256 g, 1.01 mmol) and this was evacuated with argon 3 times. The dry THF (7 mL) was added and the reaction was cooled to −78° C. at and the NaHMDS (1.258 mL, 1.258 mmol) was added. After 30 minutes the 1-chloro-3-iodopropane (0.531 mL, 5.03 mmol) was added. The reaction was then allowed to warm to rt overnight. The mixture was quenched with the addition of saturated NH$_4$Cl (10 mL) at and diluted with EtOAc (15 mL) and shaken. The EtOAc layer was collected, dried with MgSO$_4$, filtered and adsorbed to silica and purified by MPLC (20 min, ~25% EtOAc:Hex) to produce pure methyl 4-(2-(3-chloropropyl)-1,3-dithian-2-yl)benzoate (0.102 g, 0.308 mmol, 31% yield). $^1$H NMR (400 MHz, CDCl$_3$): δ 8.07-8.03 (m, 2H), 8.01-7.98 (m, 2H), 3.93 (s, 3H), 3.41 (t, J=6.4 Hz, 2H), 2.74-2.62 (m, 4H), 2.19-2.13 (m, 2H), 1.99-1.92 (m, 2H), 1.78-1.70 (m, 2H).

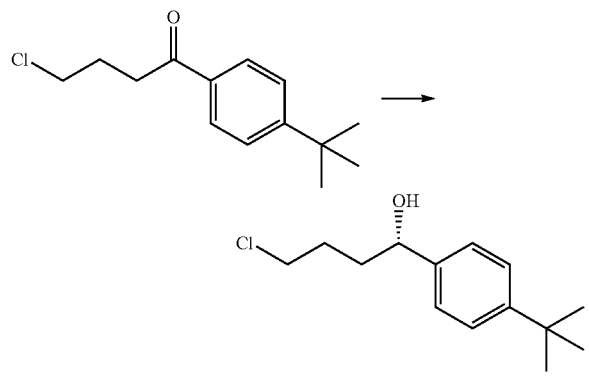

KSC-335-059

(S)-1-(4-(tert-butyl)phenyl)-4-chlorobutan-1-ol

To a flame-dried vial was added dry THF (2 mL) and then cooled to 0° C. The 1.0 M R-5,5-Diphenyl-2-methyl-3,4-propano-1,3,2-oxazaborlidine (0.105 mL, 0.105 mmol) in THF was added followed by the 2.0 M borane-methyl sulfide complex (0.654 mL, 1.309 mmol) in THF. The reaction began to stir at 0° C. for 30 minutes. To another flame-dried vial was added the 1-(4-(tert-butyl)phenyl)-4-chlorobutan-1-one (0.250 g, 1.047 mmol) and this was evacuated with argon 3 times then dissolved in dry THF (5 mL) and the oxazaborlidine solution was added dropwise at 0° C. and the reaction was allowed to warm to rt stirred for 2 h. The reaction was quenched with MeOH (10 mL) extracted with EtOAc (20 mL) then was washed with 1.0 M HCl (3×25 mL). The EtOAc layer was dried with MgSO$_4$, filtered and concentrated to produce pure (S)-1-(4-(tert-butyl)phenyl)-4-chlorobutan-1-ol (0.248 g, 1.030 mmol, 98% yield). [alpha]$^{25}$589=−24.0° (c=10 in CHCl$_3$). $^1$H NMR (400 MHz, CDCl$_3$): δ 7.38 (d, J=8.4 Hz, 2H), 7.28 (d, J=8.4, 2H), 4.71-4.67 (m, 1H), 3.61-3.53 (m, 2H), 1.98-1.79 (m, 4H), 1.32 (s, 9H).

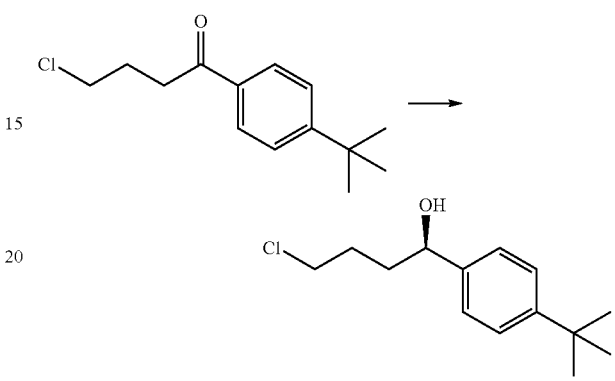

KSC-335-060

(R)-1-(4-(tert-butyl)phenyl)-4-chlorobutan-1-ol

Prepared the same as KSC-335-059 with 1.0 M (S)-5,5-diphenyl-2-methyl-3,4-propano-1,3,2-oxazaborlidine (0.105 ml, 0.105 mmol), 2.0 M Borane-methyl sulfide complex (0.654 ml, 1.309 mmol) and 1-(4-(tert-butyl)phenyl)-4-chlorobutan-1-one (0.250 g, 1.047 mmol) to produce pure (R)-1-(4-(tert-butyl)phenyl)-4-chlorobutan-1-ol (0.216 g, 0.897 mmol, 86% yield). [alpha]$^{25}$589=+23.1° (c=10 in CHCl$_3$). $^1$H NMR (400 MHz, CDCl$_3$): δ 7.38 (d, J=8.4 Hz, 2H), 7.28 (d, J=8.4, 2H), 4.71-4.67 (m, 1H), 3.61-3.53 (m, 2H), 1.98-1.79 (m, 4H), 1.32 (s, 9H).

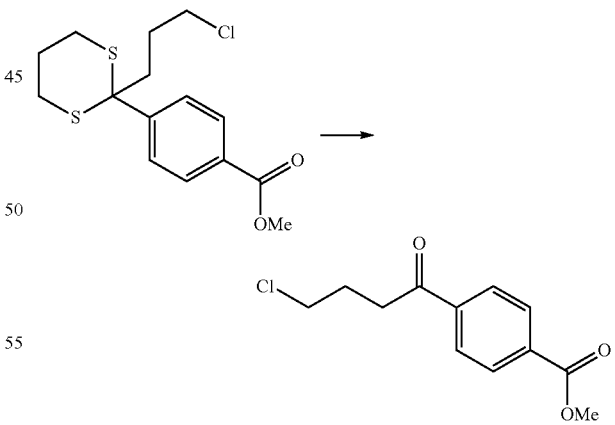

KSC-335-061

Methyl 4-(4-chlorobutanoyl)benzoate

To a vial was added the methyl 4-(2-(3-chloropropyl)-1,3-dithian-2-yl)benzoate (KSC-335-056) (0.102 g, 0.308 mmol) and acetonitrile (1.5 mL) with water (0.2 mL). The (bis(trifluoroacetoxy)iodo)benzene (0.199 g, 0.462 mmol)

was then added and the reaction stirred at rt for 1 h. The reaction was quenched with saturated NaHCO$_3$ (7 mL) then diluted with EtOAc (10 mL) and extracted. The EtOAc was collected and washed with water (2×8 mL) and then dried with MgSO$_4$, filtered and adsorbed to silica and purified by MPLC (20 min, 0-25% EtOAc:hex to produce pure methyl 4-(4-chlorobutanoyl)benzoate (0.0512 g, 0.213 mmol, 69% yield). $^1$H NMR (400 MHz, CDCl$_3$): δ 8.11 (d, J=8.00 Hz, 2H), 8.00 (d, J=8.6 Hz, 2H), 3.93 (s, 3H), 3.67 (t, J=6.1 Hz, 2H), 3.19 (t, J=6.1 Hz, 2H), 2.22 (quintet, J=6.3 Hz, 2H).

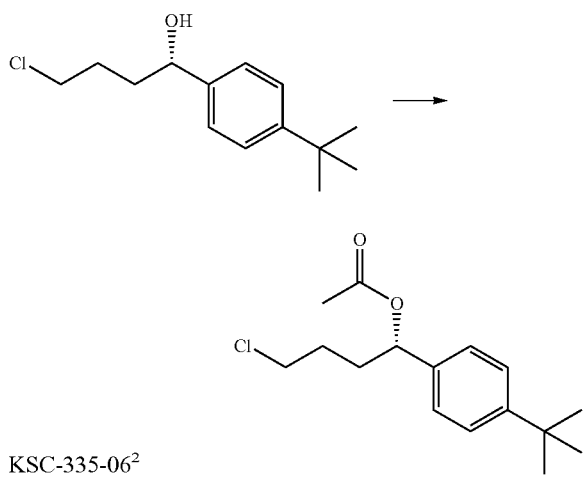

KSC-335-06$^2$ (S)-1-(4-(tert-butyl)phenyl)-4-chlorobutyl acetate

To a vial was added the (S)-1-(4-(tert-butyl)phenyl)-4-chlorobutan-1-ol (KSC-335-059) (0.248 g, 1.030 mmol) and diethyl ether (5.15 ml). The TEA (0.215 mL, 1.545 mmol) was added followed by the acetyl chloride (0.073 mL, 1.030 mmol) and the reaction began to stir at rt for 2 h. A white precipitate formed immediately. Water (5 mL) was added the reaction after 2 h and the ether layer was extracted. The aqueous was extracted again with more ether and the combined organics were dried with MgSO$_4$, filtered and concentrated to produce pure (S)-1-(4-(tert-butyl)phenyl)-4-chlorobutyl acetate (0.250 g, 0.884 mmol, 86% yield). [alpha]$^{25}$589=−42.11, (c=10, CH$_2$Cl$_2$). $^1$H NMR (400 MHz, CDCl$_3$): δ 7.36 (d, J=8.4 Hz, 2H), 7.25 (d, J=8.4 Hz, 2H), 5.78-5.73 (m, 1H), 3.53 (t, J=6.4 Hz, 2H), 2.06 (s, 3H), 2.02-1.68 (m, 4H), 1.31 (s, 9H).

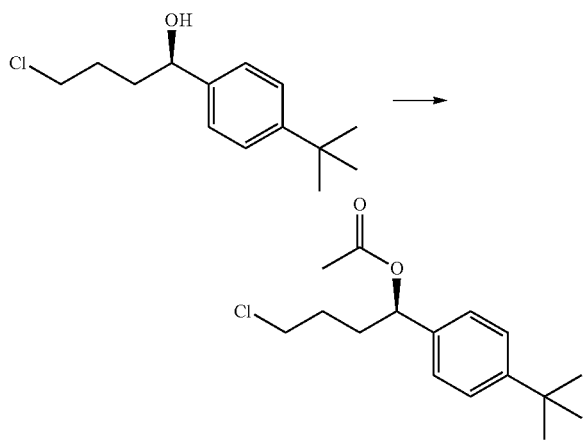

KSC-336-063

(R)-1-(4-(tert-butyl)phenyl)-4-chlorobutyl acetate

Prepared the same as KSC-335-062 with (R)-1-(4-(tert-butyl)phenyl)-4-chlorobutan-1-ol (KSC-335-060) (0.216 g, 0.897 mmol) and diethyl ether (4.5 mL), TEA (0.188 ml, 1.346 mmol) and acetyl chloride (0.064 ml, 0.897 mmol) to produce pure (R)-1-(4-(tert-butyl)phenyl)-4-chlorobutyl acetate (0.249 g, 0.880 mmol, 98% yield). [alpha]$^{25}$589=+54.57, (c=10, CH$_2$Cl$_2$). H NMR (400 MHz, CDCl$_3$): δ 7.36 (d, J=8.4 Hz, 2H), 7.25 (d, J=8.4 Hz, 2H), 5.78-5.73 (m, 1H), 3.53 (t, J=6.4 Hz, 2H), 2.06 (s, 3H), 2.02-1.68 (m, 4H), 1.31 (s, 9H).

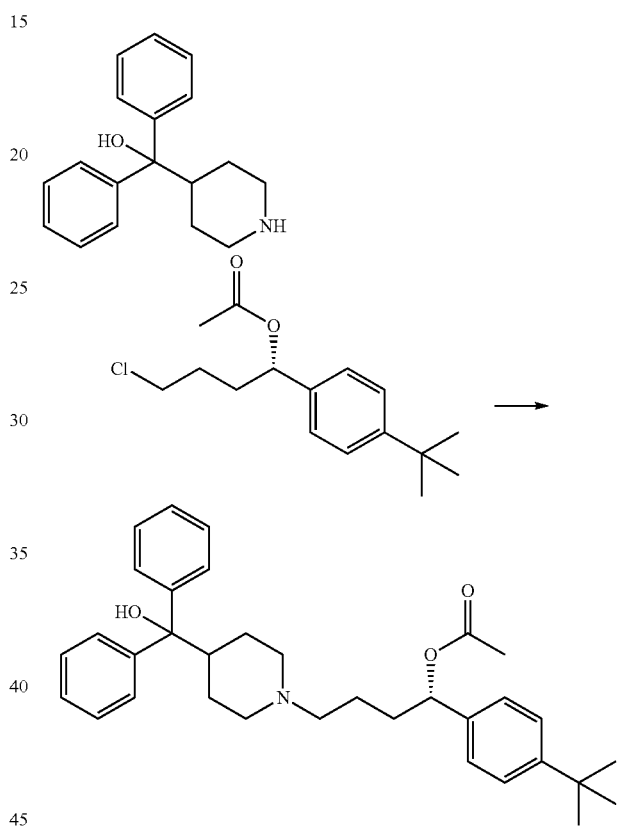

KSC-335-064

(S)-1-(4-(tert-butyl)phenyl)-4-(4-(hydroxydiphenylmethyl)piperidin-1-yl)butyl acetate To a vial was added the diphenyl(piperidin-4-yl)methanol (0.154 g, 0.578 mmol), (S)-1-(4-(tert-butyl)phenyl)-4-chlorobutyl acetate (0.196 g, 0.693 mmol) (KSC-335-062) and potassium carbonate (0.319 g, 2.310 mmol) in acetonitrile (10 mL). The reaction stirred overnight at 70° C. for 18 h and was then cooled to rt and filtered. The filtrate was then diluted with DCM and washed with water (10 mL) and brine (10 mL). The DCM layers were combined, dried with MgSO$_4$, filtered and purified by reverse-phase MPLC (20 min, 10-100% MeCN:water) to produce pure (S)-1-(4-(tert-butyl)phenyl)-4-(4-(hydroxydiphenylmethyl)piperidin-1-yl) butyl acetate (0.135 g, 0.263 mmol, 46% yield) as a brown oil. $^1$H NMR (400 MHz, CDCl$_3$): δ 7.48-7.45 (m, 4H), 7.35-7.14 (m, 10H), 5.73-5.68 (m, 1H), 2.93-2.87 (m, 2H), 2.46-2.37 (m, 1H), 2.87 (t, J=7.7 Hz, 2H), 2.11 (br s, 1H), 2.04 (s, 3H), 1.95-1.84 (m, 3H), 1.80-1.72 (m, 1H), 1.53-1.38 (m, 6H), 1.29 (s, 9H).

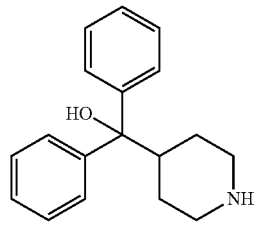

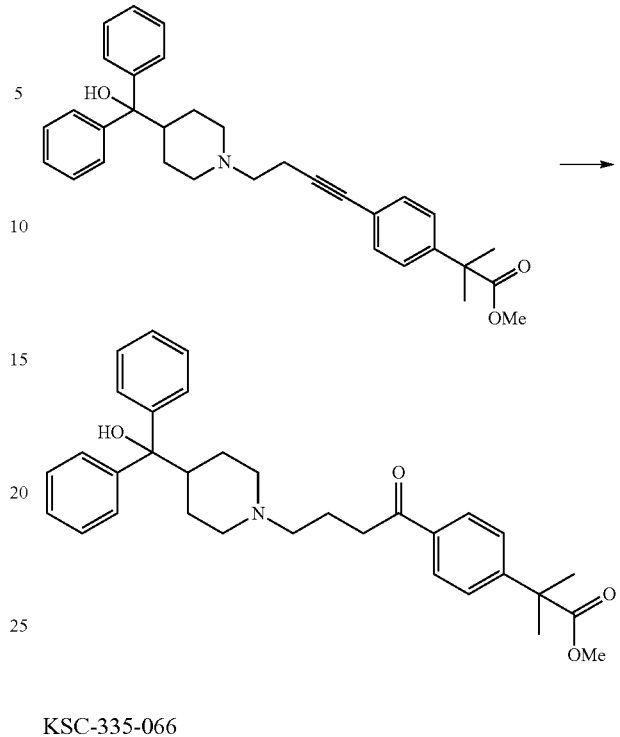

KSC-335-066

Methyl 2-(4-(4-(4-(hydroxydiphenylmethyl)piperidin-1-yl)butanoyl)phenyl)-2-methylpropanoate To a vial was added the methyl 2-(4-(4-(4-(hydroxydiphenylmethyl)piperidin-1-yl)but-1-yn-1-yl)phenyl)-2-methylpropanoate (KSC-335-054) (0.074 g, 0.149 mmol). The mercuric oxide (1.493 ml, 0.045 mmol) was made into a 0.03 M solution in 4% w/v sulfuric acid and added to the starting material then heated to 55° C. and stirred for 3.5 h. The reaction turned a milky white color upon addition of the mercuric oxide solution. The reaction was removed from heat and diluted with saturated NaHCO$_3$ (10 mL) and extracted with DCM (3×10 mL). The DCM layers were combined and dried with MgSO$_4$, filtered and concentrated then purified by reverse-phase MPLC (10-100% MeCN: water) to produce methyl 2-(4-(4-(4-(hydroxydiphenylmethyl) piperidin-1-yl)butanoyl)phenyl)-2-methylpropanoate (0.0217 g, 0.042 mmol, 28.3% yield). $^1$H NMR (400 MHz, CDCl$_3$): δ 7.93-7.91 (m, 2H), 7.48-7.45 (m, 4H), 7.42-7.39 (m, 2H), 7.30-7.26 (m, 4H), 7.19-7.14 (m, 2H), 3.63 (s, 3H), 2.96-2.88 (m, 4H), 2.44-2.34 (m, 3H), 2.08 (br s, 1H), 1.60 (s, 6H), 1.62-1.56 (m, 4H), 1.46-1.30 (m, 4H).

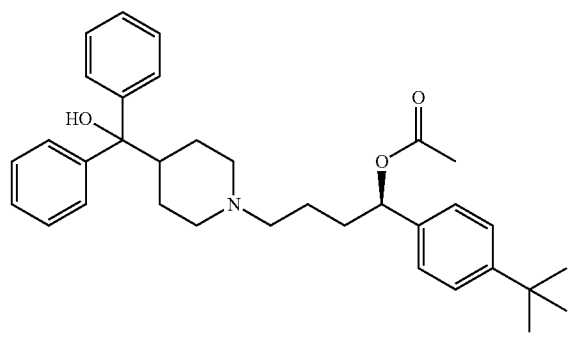

KSC-335-065

(R)-1-(4-(tert-butyl)phenyl)-4-(4-(hydroxydiphenylmethyl)piperidin-1-yl)butyl acetate Prepared the same way as KSC-335-064 with diphenyl (piperidin-4-yl)methanol (0.196 g, 0.734 mmol), (R)-1-(4-(tert-butyl)phenyl)-4-chlorobutyl acetate (KSC-335-063) (0.249 g, 0.880 mmol) and potassium carbonate (0.406 g, 2.93 mmol) in acetonitrile to produce pure (R)-1-(4-(tert-butyl)phenyl)-4-(4-(hydroxydiphenylmethyl)piperidin-1-yl) butyl acetate (0.237 g, 0.461 mmol, 63% yield) as a brown oil. $^1$H NMR (400 MHz, CDCl$_3$): δ 7.48-7.45 (m, 4H), 7.35-7.14 (m, 10H), 5.73-5.68 (m, 1H), 2.93-2.87 (m, 2H), 2.46-2.37 (m, 1H), 2.87 (t, J=7.7 Hz, 2H), 2.11 (br s, 1H), 2.04 (s, 3H), 1.95-1.84 (m, 3H), 1.80-1.72 (m, 1H), 1.53-1.38 (m, 6H), 1.29 (s, 9H).

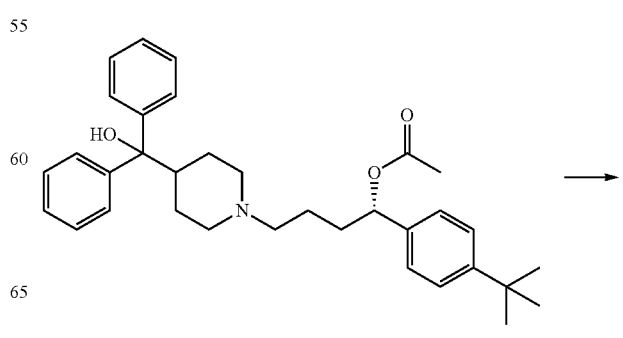

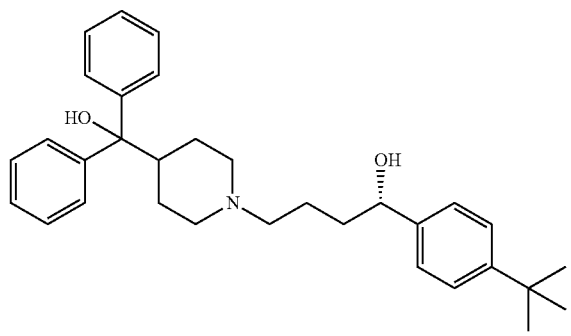

KSC-335-069

(S)-1-(4-(tert-butyl)phenyl)-4-(4-(hydroxydiphenyl-methyl)piperidin-1-yl)butan-1-ol To a vial was added the (S)-1-(4-(tert-butyl)phenyl)-4-(4-(hydroxydiphenylmethyl)piperidin-1-yl)butyl acetate (0.135 g, 0.263 mmol) and this vial was evacuated with nitrogen 3 times. The dry THF (9 mL) was then added. The 1.0 M lithium aluminum hydride (0.263 mL, 0.263 mmol) in THF was added dropwise at rt and the reaction stirred for 5 h. The reaction was quenched slowly with water (10 mL) and then extracted with diethyl ether (2×10 mL). The ether layer was dried with MgSO$_4$, filtered, concentrated and purified by reverse-phase MPLC (20 min, 10-100%, MeCN:H$_2$O) to produce pure (S)-1-(4-(tert-butyl)phenyl)-4-(4-(hydroxydiphenylmethyl)piperidin-1-yl)butan-1-ol (0.100 g, 0.212 mmol, 81% yield). [alpha]$^{25}$589=−38.8. $^1$H NMR (400 MHz, CDCl$_3$): δ 7.51-7.46 (m, 4H), 7.33-7.24 (m, 8H), 7.20-7.14 (m, 2H), 4.59 (dd, J=8.2 Hz, 2.8 Hz, 1H), 3.13 (br d, J=11.2 Hz, 1H), 2.97 (br d, J=11.2 Hz, 1H), 2.50-2.34 (m, 3H), 2.10-1.88 (m, 4H), 1.84-1.74 (m, 1H), 1.68-1.44 (m, 6H), 1.30 (s, 9H). $^{13}$C NMR (125 MHz, CDCl$_3$): δ 149.4, 146.1, 146.0, 142.7, 128.2, 128.1, 126.45, 126.43, 125.7, 125.6, 125.4, 125.0, 79.3, 73.4, 58.9, 54.7, 53.3, 44.2, 39.7, 34.4, 31.4, 26.1, 26.0, 24.1. LCMS Retention time: 4.159 min. LCMS purity 99.7%. HRMS (ESI): m/z calcd for C$_{32}$H$_{41}$NO$_2$ [M+H]$^+$ 472.3137, found 472.3210.

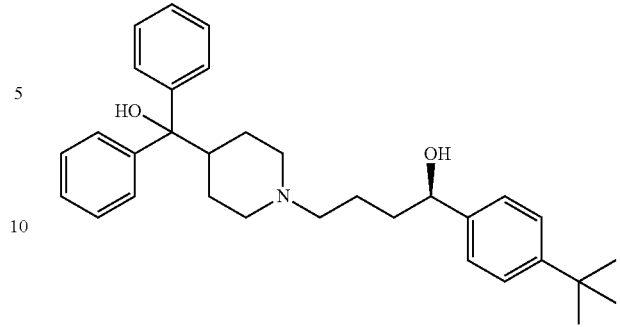

KSC-335-070

(R)-1-(4-(tert-butyl)phenyl)-4-(4-(hydroxydiphenyl-methyl)piperidin-1-yl)butan-1-ol To a vial was added the (R)-1-(4-(tert-butyl)phenyl)-4-(4-(hydroxydiphenylmethyl)piperidin-1-yl)butyl acetate (0.237 g, 0.461 mmol) and this vial was evacuated with nitrogen 3 times. The dry THF (Volume: 4.61 ml) was added and then the 1.0 M lithium aluminum hydride (0.461 mL, 0.461 mmol) in THF was added portionwise at rt for 5 h. The reaction was quenched slowly with water (10 mL) and then extracted with diethyl ether (2×10 mL). The ether layer was dried with MgSO$_4$, filtered, concentrated and purified by reverse-phase MPLC (20 min, 10-100%, MeCN:H$_2$O) to produce pure (R)-1-(4-(tert-butyl)phenyl)-4-(4-(hydroxydiphenylmethyl) piperidin-1-yl)butan-1-ol (0.116 g, 0.246 mmol, 53% yield). [alpha]$^{25}$589=+38.60. $^1$H NMR (400 MHz, CDCl$_3$): δ 7.51-7.46 (m, 4H), 7.33-7.24 (m, 8H), 7.20-7.14 (m, 2H), 4.59 (dd, J=8.2 Hz, 2.8 Hz, 1H), 3.13 (br d, J=11.2 Hz, 1H), 2.97 (br d, J=11.2 Hz, 1H), 2.50-2.34 (m, 3H), 2.10-1.88 (m, 4H), 1.84-1.74 (m, 1H), 1.68-1.44 (m, 6H), 1.30 (s, 9H). $^{13}$C NMR (125 MHz, CDCl$_3$): δ 149.4, 146.1, 146.0, 142.7, 128.2, 128.1, 126.45, 126.43, 125.7, 125.6, 125.4, 125.0, 79.3, 73.4, 58.9, 54.7, 53.3, 44.2, 39.7, 34.4, 31.4, 26.1, 26.0, 24.1. LCMS Retention time: 4.156 min. LCMS purity 97.8%. HRMS (ESI): m/z calcd for C$_{32}$H$_{41}$NO$_2$ [M+H]$^+$ 472.3137, found 472.3210.

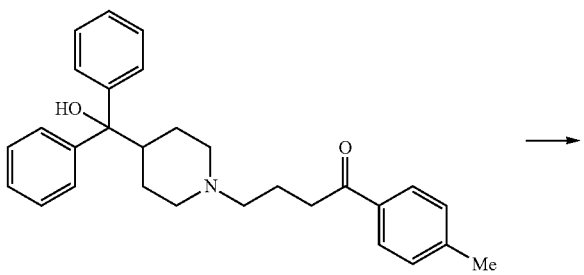

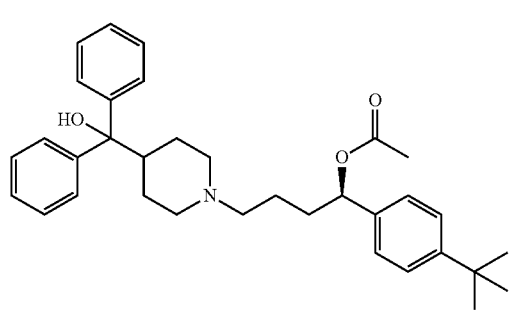

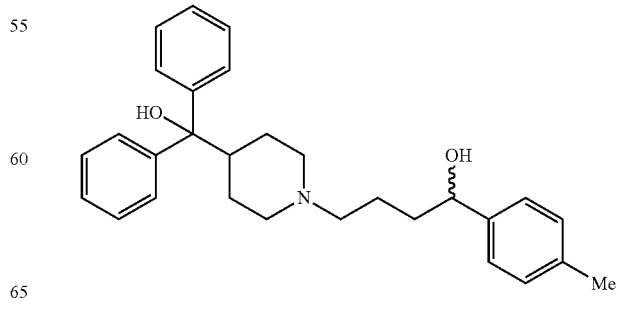

KSC-335-077

4-(4-(hydroxydiphenylmethyl)piperidin-1-yl)-1-(p-tolyl)butan-1-ol

Method B: 4-(4-(hydroxydiphenylmethyl)piperidin-1-yl)-1-(p-tolyl)butan-1-one (0.073 g, 0.171 mmol) and MeOH (Volume: 2 mL) and SODIUM BOROHYDRIDE (0.013 g, 0.341 mmol) to produce pure 4-(4-(hydroxydiphenylmethyl)piperidin-1-yl)-1-(p-tolyl)butan-1-ol (0.070 g, 0.163 mmol, 95% yield) as on oil. $^1$H NMR (400 MHz, CDCl$_3$): δ 7.51-7.46 (m, 4H), 7.32-7.09 (m, 10H), 4.59 (dd, J=8.0, 2.8 Hz, 1H), 3.15-3.09 (m, 1H), 2.99-2.92 (m, 1H), 2.52-2.32 (m, 6H), 2.32 (s, 3H), 2.09-1.87 (m, 3H), 1.82-1.73 (m, 1H), 1.68-1.44 (m, 6H). $^{13}$C NMR (125 MHz, CDCl$_3$): δ 146.1, 146.0, 142.9, 136.0, 128.7, 128.11, 128.10, 128.06, 126.39, 126.37, 125.7, 125.6, 125.5, 79.2, 73.3, 58.9, 54.6, 53.4, 53.3, 44.2, 39.9, 30.9, 26.0, 25.9, 26.0, 21.0. LCMS Retention time: 3.809 min. LCMS purity 94.1%. HRMS (ESI): m/z calcd for C$_{29}$H$_{35}$NO$_2$ [M+H]$^+$ 430.2668, found 430.2741.

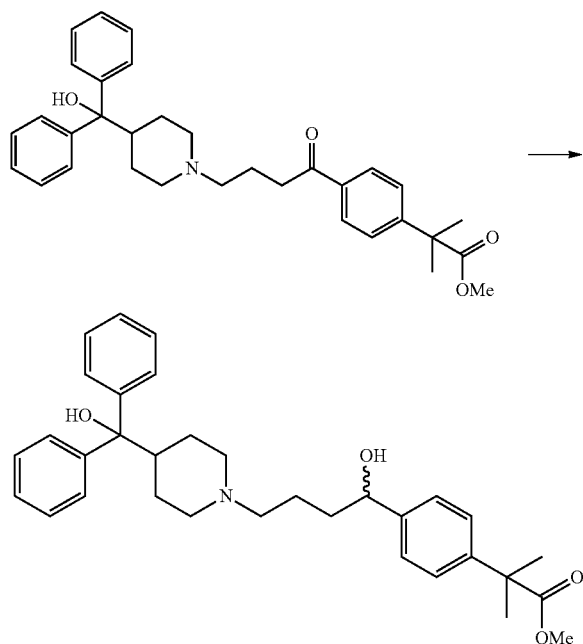

KSC-335-080

Methyl 2-(4-(1-hydroxy-4-(4-(hydroxydiphenylmethyl)piperidin-1-yl)butyl)phenyl)-2-methylpropanoate Method B: methyl 2-(4-(4-(4-(hydroxydiphenylmethyl)piperidin-1-yl)butanoyl)phenyl)-2-methylpropanoate (KSC-335-066)(0.148 g, 0.288 mmol) and MeOH (1 mL) and sodium borohydride (0.016 g, 0.432 mmol) to produce pure methyl 2-(4-(1-hydroxy-4-(4-(hydroxydiphenylmethyl)piperidin-1-yl)butyl)phenyl)-2-methylpropanoate (0.108 g, 0.209 mmol, 73% yield). $^1$H NMR (400 MHz, CDCl$_3$): δ 7.54-7.49 (m, 4H), 7.35-7.27 (m, 8H), 7.23-7.17 (m, 2H), 4.62 (dd, J=8.0, 2.8 Hz, 1H), 3.65 (s, 3H), 3.16 (d, J=11.7 Hz, 1H), 2.98 (d, J=11.7 Hz, 1H), 2.53-2.40 (m, 3H), 2.29 (br s, 1H), 2.14-2.06 (m, 1H), 2.01-1.93 (m, 2H), 1.84-1.50 (m, 14H). LCMS Retention time: 3.786 min. LCMS purity 98.2%. HRMS (ESI): m/z calcd for C$_{33}$H$_{41}$NO$_4$ [M+H]$^+$ 516.3036, found 516.3108.

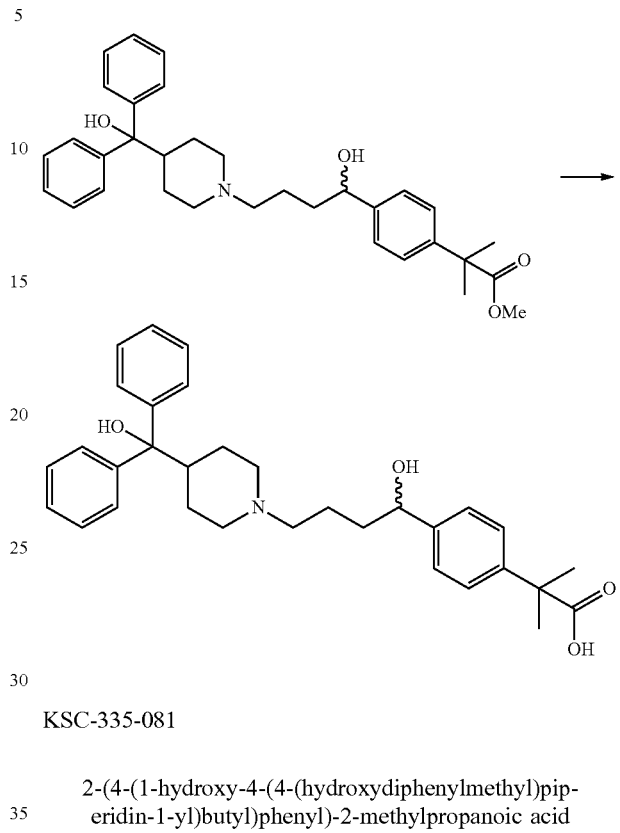

KSC-335-081

2-(4-(1-hydroxy-4-(4-(hydroxydiphenylmethyl)piperidin-1-yl)butyl)phenyl)-2-methylpropanoic acid To a vial was added the methyl 2-(4-(1-hydroxy-4-(4-(hydroxydiphenylmethyl)piperidin-1-yl)butyl)phenyl)-2-methylpropanoate (KSC-335-080) (0.094 g, 0.182 mmol) and THF (Volume: 3 mL,). The LiOH (0.022 g, 0.911 mmol) was dissolved in water (3.00 mL) and then added to the reaction stirred at 80° C. for 18 h. The reaction was removed from heat and cooled to rt and 1.0 M HCl in water was added to adjust to pH to 4 and a gummy off-white solid formed. DCM (5 mL) was added to the mixture and it was sonicated to break up the solid. The DCM layer was removed and the aqueous was extracted with DCM (2×5 mL). The DCM layer was concentrated and the residue was purified by reverse-phase MPLC (20 min, 10-100% MeCN:water) to produce the product with impurities. This was submitted to the purification core. The pure sample was recovered to produce 2-(4-(1-hydroxy-4-(4-(hydroxydiphenylmethyl)piperidin-1-yl)butyl)phenyl)-2-methylpropanoic acid (0.0378 g, 0.075 mmol, 41% yield). $^1$H NMR (400 MHz, DMSO-d$_6$): δ 8.22 (s, 1H), 7.52-7.49 (m, 4H), 7.29-7.26 (m, 8H), 7.15-7.10 (m, 2H), 4.47 (t, J=5.9 Hz, 1H), 2.94-2.86 (m, 3H), 2.35-2.30 (m, 2H), 2.05-1.95 (m, 2H), 1.60-1.35 (m, 12H), 1.28-1.22 (m, 2H). $^{13}$C NMR (125 MHz, CDCl$_3$): δ 177.7, 163.7, 147.2, 144.4, 143.4, 127.8, 125.8, 125.7, 125.6, 125.1, 78.4, 71.8, 57.7, 53.4, 53.2, 45.5, 43.1, 37.3, 26.5, 25.6, 22.6. LCMS Retention time: 2.612 min. LCMS purity 100%. HRMS (ESI): m/z calcd for C$_{32}$H$_{39}$NO$_4$ [M+H]$^+$ 502.2879, found 502.2952.

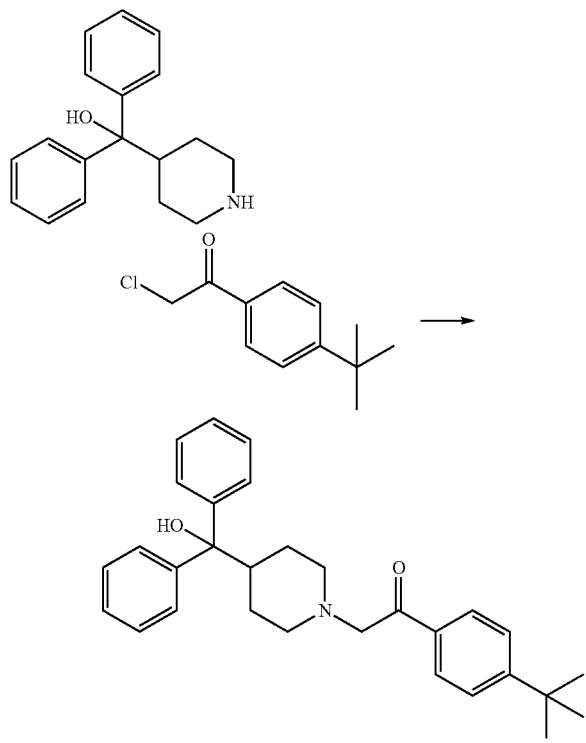

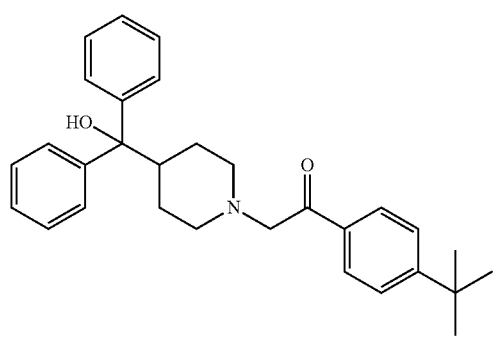

KSC-342-006

1-(4-(tert-butyl)phenyl)-2-(4-(hydroxydiphenylm-ethyl)piperidin-1-yl)ethanone

Method A: diphenyl(piperidin-4-yl)methanol (0.4 g, 1.496 mmol), 1-(4-(tert-butyl)phenyl)-2-chloroethanone (0.300 g, 1.425 mmol), sodium bicarbonate (0.144 g, 1.710 mmol) with water (3 mL) and 2-butanone (Volume: 15 mL) to produce pure 1-(4-(tert-butyl)phenyl)-2-(4-(hydroxydi-phenylmethyl)piperidin-1-yl)ethanone (0.452 g, 1.024 mmol, 71.8% yield) as a colorless oil. $^1$H NMR (500 MHz, CDCl$_3$): δ 7.93 (d, J=8.6 Hz, 2H), 7.50-7.43 (m, 6H), 7.32-7.26 (m, 4H), 7.20-7.15 (m, 2H), 3.78 (s, 2H), 3.07-3.01 (m, 2H), 2.47 (tt, J=11.8 Hz, 3.5 Hz, 1H), 2.26-2.18 (m, 2H), 1.66-1.45 (m, 5H), 1.33 (s, 9H). $^{13}$C NMR (125 MHz, CDCl$_3$): δ 196.1, 157.0, 145.8, 133.5, 129.8, 128.2, 128.0, 126.5, 125.8, 125.5, 125.1, 79.5, 64.2, 54.2, 43.8, 35.1, 31.2, 31.0, 26.2. LCMS Retention time: 3.987 min. LCMS purity 98.8%. HRMS (ESI): m/z calcd for C$_{30}$H$_{35}$NO$_2$ [M+H]$^+$ 442.2668, found 442.2741.

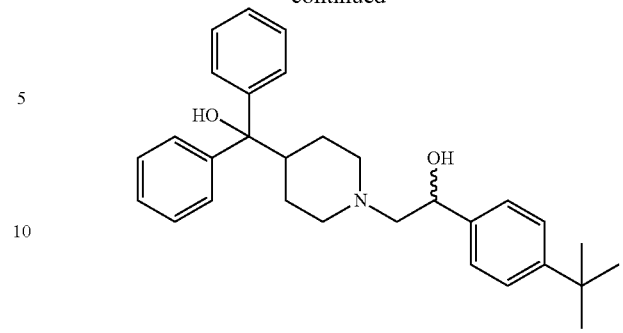

KSC-342-010

1-(4-(tert-butyl)phenyl)-2-(4-(hydroxydiphenylm-ethyl)piperidin-1-yl)ethanol

Method B: 1-(4-(tert-butyl)phenyl)-2-(4-(hydroxydiphe-nylmethyl)piperidin-1-yl)ethanone (0.113 g, 0.256 mmol) and MeOH (1 mL) and SODIUM BOROHYDRIDE (0.019 g, 0.512 mmol) to produce pure 1-(4-(tert-butyl)phenyl)-2-(4-(hydroxydiphenylmethyl)piperidin-1-yl)ethanol (0.106 g, 0.239 mmol, 93% yield) as a solid. $^1$H NMR (400 MHz, CDCl$_3$): δ 7.50-7.46 (m, 4H), 7.37-7.26 (m, 8H), 7.22-7.17 (M, 2H), 4.67 (m, 1H), 4.01 (br s, 1H), 3.20 (m, 1H), 2.86 (m, 1H), 2.50-2.45 (m, 3H), 2.37-2.30 (m, 1H), 2.10-2.02 (m, 1H), 1.60-1.45 (m, 5H), 1.31 (s, 9H). $^{13}$C NMR (125 MHz, CDCl$_3$): δ 150.3, 145.82, 145.78, 139.1, 128.20, 128.19, 126.59, 126.57, 125.7, 125.6, 125.2, 79.5, 68.6, 66.3, 55.8, 53.4, 52.2, 44.1, 34.5, 31.3, 26.8, 26.5. LCMS Retention time: 4.083 min. LCMS purity 94.2%. HRMS (ESI): m/z calcd for C$_{30}$H$_{37}$NO$_2$ [M+H]$^+$ 444.2824, found 444.2897.

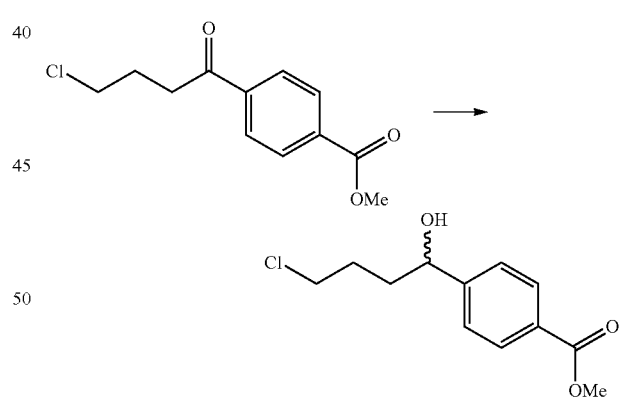

KSC-342-014

Methyl 4-(4-chloro-1-hydroxybutyl)benzoate

Method B: methyl 4-(4-chlorobutanoyl)benzoate (KSC-335-061) (0.042 g, 0.175 mmol) and MeOH with sodium borohydride (0.013 g, 0.349 mmol). to produce methyl 4-(4-chloro-1-hydroxybutyl)benzoate (0.037 g, 0.152 mmol, 87% yield). $^1$H NMR (400 MHz, CDCl$_3$): δ 8.00 (d, J=8.4 Hz, 2H), 7.40 (d, J=8.2 Hz, 2H), 4.8-4.6 (m, 1H), 3.90 (s, 3H), 3.58-3.52 (m, 2H), 2.19 (br s, 1H), 1.96-1.78 (m, 4H)

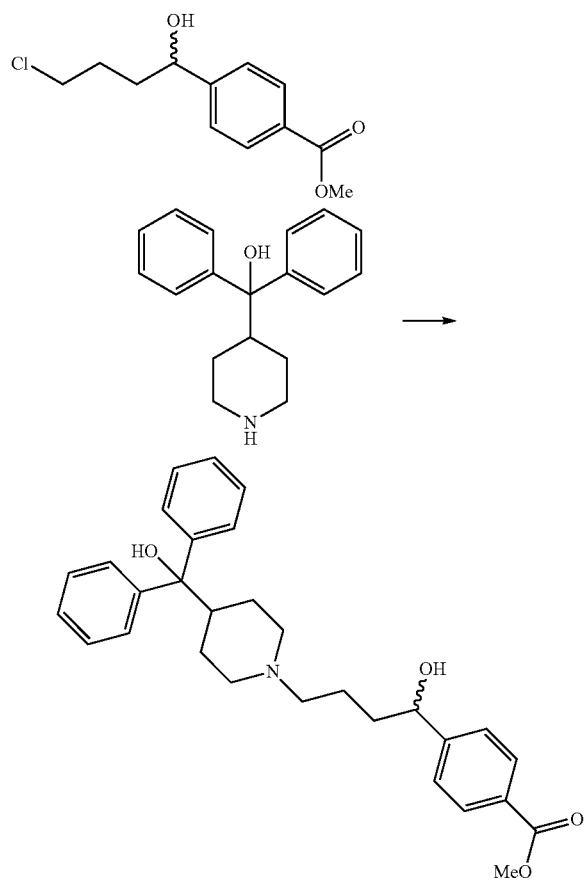

KSC-342-017

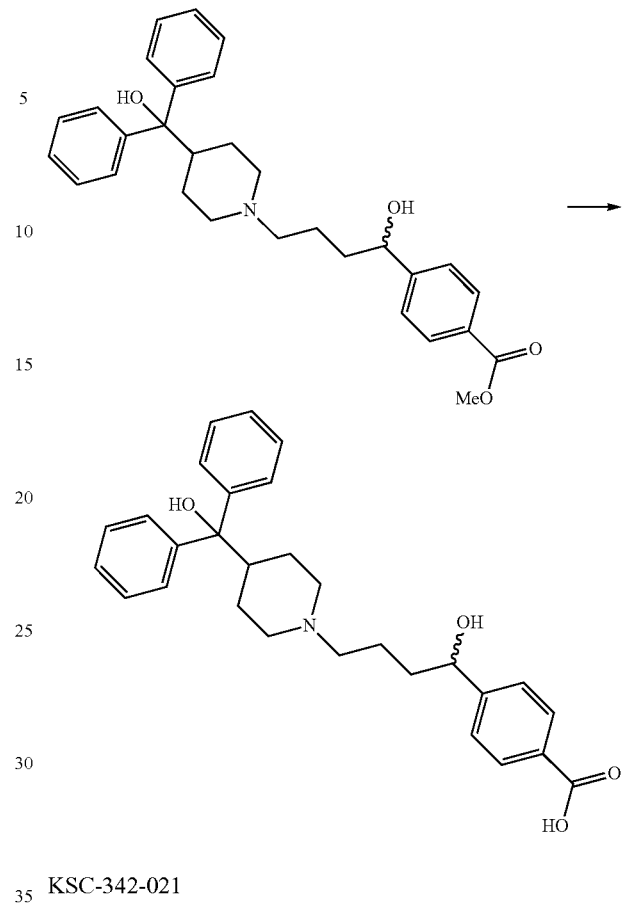

KSC-342-021

4-(1-hydroxy-4-(4-(hydroxydiphenylmethyl)piperidin-1-yl)butyl)benzoic acid

Methyl 4-(1-hydroxy-4-(4-(hydroxydiphenylmethyl)piperidin-1-yl)butyl)benzoate

To a vial was added the methyl 4-(4-chloro-1-hydroxybutyl)benzoate (KSC-342-014) (0.037 g, 0.152 mmol), diphenyl(piperidin-4-yl)methanol (0.122 g, 0.457 mmol), SODIUM BICARBONATE (0.026 g, 0.305 mmol), SODIUM IODIDE (1.143 mg, 7.62 μmol) and the vial was evacuated with argon 3 times. Dry acetonitrile (2 ml) was added and the reaction stirred overnight at reflux and was then cooled to rt after 18 h and the solvent was concentrated. The residue was dissolved in DCM (5 mL) and washed with 0.1 N HCl (5 mL), water (5 mL) and brine (5 mL). The product was purified by MPLC (0-10% MeOH:DCM) to produce pure methyl 4-(1-hydroxy-4-(4-(hydroxydiphenylmethyl)piperidin-1-yl)butyl)benzoate (0.0268 g, 0.057 mmol, 37% yield). $^1$H NMR (400 MHz, CDCl$_3$): δ 7.97 (d, J=8.4 Hz, 2H), 7.52-7.47 (m, 4H), 7.42 (d, J=7.9 Hz, 2H), 7.32-7.29 (m, 4H), 7.20-7.14 (m, 2H), 4.66 (m, 1H), 3.90 (s, 3H), 3.14 (m, 1H), 2.94 (m, 1H), 2.78 (br s, 1H), 2.52-2.43 (m, 1H), 2.39 (t, J=4.8 Hz, 2H), 2.13-2.06 (m, 1H), 2.04-1.92 (m, 2H), 1.77-1.47 (m, 8H). $^{13}$C NMR (125 MHz, CDCl$_3$): δ 167.2, 151.4, 146.0, 145.9, 129.5, 128.4, 128.2, 128.2, 126.51, 126.48, 125.64, 125.59, 79.2, 73.2, 58.8, 54.7, 51.9, 44.2, 40.0, 26.0, 25.9, 24.0. LCMS Retention time: 3.652 min. LCMS purity 100%. HRMS (ESI): m/z calcd for C$_{30}$H$_{35}$NO$_4$ [M+H]$^+$ 474.2566, found 474.2639.

To a vial was added the methyl 4-(1-hydroxy-4-(4-(hydroxydiphenylmethyl)piperidin-1-yl)butyl)benzoate (0.0195 g, 0.041 mmol) and THF (1 mL). The LiOH (6.90 mg, 0.288 mmol) was dissolved in water (1 mL) and added to the reaction. The reaction stirred at overnight and was then acidified with 1.0 M HCl to pH 2-3 then extracted with DCM (3×5 mL). The DCM layer was concentrated and purified by reverse-phase MPLC (10-100% MeCN:water) to produce pure 4-(1-hydroxy-4-(4-(hydroxydiphenylmethyl)piperidin-1-yl)butyl)benzoic acid (0.009 g, 0.020 mmol, 47% yield). $^1$H NMR (400 MHz, CD$_3$OD): δ 7.85 (d, J=8.2 Hz, 2H), 7.53-7.49 (m, 4H), 7.34-7.26 (m, 6H), 7.19-7.14 (m, 2H), 4.70 (m, 1H), 3.46 (m, 1H), 3.35 (s, 2H), 3.01-2.96 (m, 2H), 2.92-2.77 (m, 3H), 1.84-1.64 (m, 8H). $^{13}$C NMR (125 MHz, CD$_3$OD): δ 174.7, 148.2, 147.2, 137.6, 130.4, 129.1, 127.6, 127.0, 126.4, 79.9, 74.0, 53.9, 49.8, 36.9, 25.5, 21.8. LCMS Retention time: 2.490 min. LCMS purity 100%. HRMS (ESI): m/z calcd for C$_{29}$H$_{33}$NO$_4$ [M+H]$^+$ 460.2410, found 460.2482.

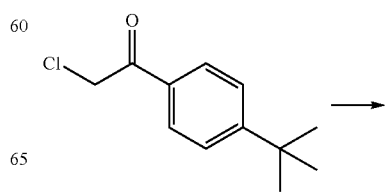

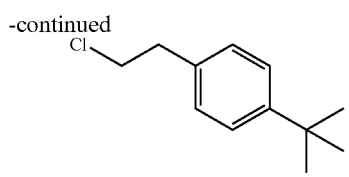

KSC-342-074

1-(Tert-butyl)-4-(2-chloroethyl)benzene

To a vial was added the 1-(4-(tert-butyl)phenyl)-2-chloroethanone (0.171 g, 0.812 mmol) and triethylsilane (0.519 mL, 3.25 mmol) with TFA (4 mL). The reaction stirred at 75° C. for 17 h and was then concentrated in vacuo. The residue was dissolved in DCM (5 mL) and washed with water (4 mL). The DCM layer was collected and washed with water (1×5 mL), dried with MgSO$_4$, filtered and adsorbed to silica and purified by MPLC (20 min, 0-40% EtOAc:hex) to produce pure 1-(tert-butyl)-4-(2-chloroethyl)benzene (0.114 g, 0.580 mmol, 71% yield). $^1$H NMR (400 MHz, CDCl$_3$): δ 7.34 (d, J=8.3 Hz, 2H), 7.16 (d, J=8.3 Hz, 2H), 3.71 (t, J=7.5 Hz, 2H), 3.05 (t, J=7.6 Hz, 2H), 1.32 (s, 9H).

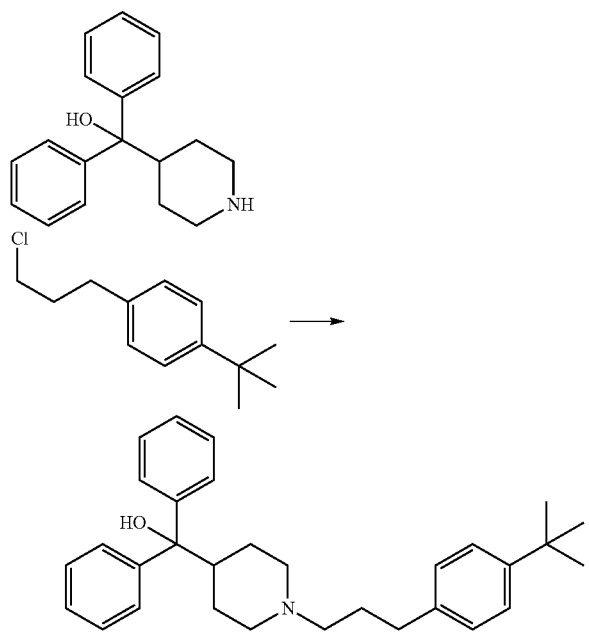

KSC-342-080

(1-(3-(4-(Tert-butyl)phenyl)propyl)piperidin-4-yl)diphenylmethanol

To a vial was added the diphenyl(piperidin-4-yl)methanol (0.142 g, 0.530 mmol), 1-(tert-butyl)-4-(3-chloropropyl)benzene (0.134 g, 0.636 mmol) and POTASSIUM CARBONATE (0.439 g, 3.18 mmol) in acetonitrile. The reaction stirred overnight at 85° C. for 18 h and then filtered. The filtrate was then diluted with brine and extracted with diethyl ether (3×15 mL). The ether layers were combined, dried with MgSO$_4$, filtered and purified by reverse-phase MPLC (20 min, 10-100% MeCN:water) to produce pure (1-(3-(4-(tert-butyl)phenyl)propyl)piperidin-4-yl)diphenylmethanol (0.152 g, 0.344 mmol, 65% yield) as an oil. $^1$H NMR (400 MHz, CDCl$_3$): δ 7.49-7.45 (m, 4H), 7.31-7.24 (m, 6H), 7.19-7.14 (m, 2H), 7.11-7.08 (m, 2H), 2.96 (m, 2H), 2.57 (t, J=7.7 Hz, 2H), 2.48-2.32 (m, 3H), 2.22 (br s, 1H), 1.97-1.90 (m, 2H), 1.83-1.75 (m, 2H), 1.53-1.45 (m, 4H), 1.29 (s, 9H). LCMS Retention time: 2.965 min. LCMS purity 97.2%. HRMS (ESI): m/z calcd for C$_{31}$H$_{39}$NO [M+H]$^+$ 442.3032, found 442.3104.

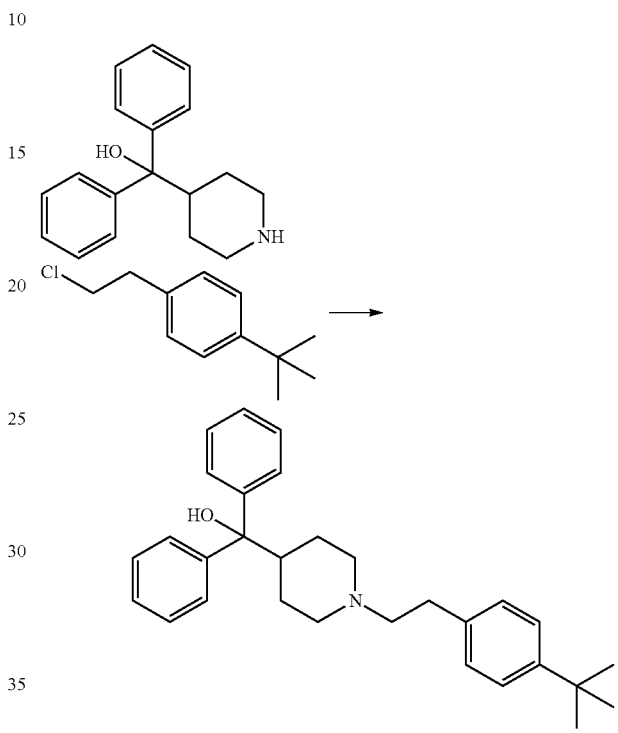

KSC-342-081

(1-(4-(Tert-butyl)phenethyl)piperidin-4-yl)diphenylmethanol

To a vial was added the diphenyl(piperidin-4-yl)methanol (0.150 g, 0.561 mmol), 1-(tert-butyl)-4-(2-chloroethyl)benzene (KSC-342-074) (0.110 g, 0.561 mmol) and potassium carbonate (0.465 g, 3.37 mmol) in acetonitrile. The reaction stirred overnight at 85° C. for 18 h and then filtered. The filtrate was then diluted with brine and extracted with diethyl ether (3×15 mL). The ether layers were combined, dried with MgSO$_4$, filtered and purified by reverse-phase MPLC (20 min, 10-100% MeCN:water) to produce pure (1-(4-(tert-butyl)phenethyl)piperidin-4-yl)diphenylmethanol (0.180 g, 0.421 mmol, 75% yield) as an oil. $^1$H NMR (400 MHz, CDCl$_3$): δ 7.51-7.47 (m, 4H), 7.33-7.27 (m, 6H), 7.21-7.16 (m, 2H), 7.14-7.11 (m, 2H), 3.09-3.03 (m, 2H), 2.80-2.74 (m, 2H), 2.60-2.55 (m, 2H), 2.51-2.42 (m, 1H), 2.28 (br s, 1H), 2.08-2.00 (m, 2H), 1.57-1.50 (m, 4H), 1.30 (s, 9H). $^{13}$C NMR (125 MHz, CDCl$_3$): δ 148.8, 145.9, 137.3, 128.3, 128.1, 126.5, 125.8, 125.2, 79.5, 60.8, 54.0, 44.2, 40.9, 34.3, 33.1, 31.4, 26.4. LCMS Retention time: 4.384 min. LCMS purity 99.7%. HRMS (ESI): m/z calcd for C$_{30}$H$_{37}$NO [M+H]$^+$ 428.2875, found 428.2948.

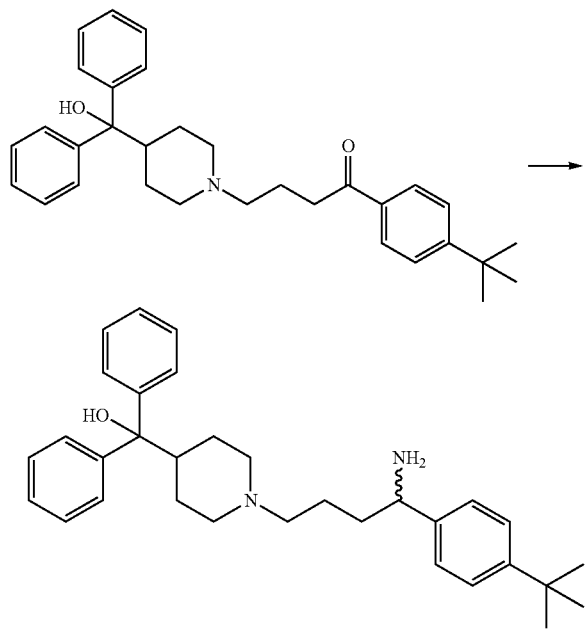

KSC-342-088

(1-(4-amino-4-(4-(tert-butyl)phenyl)butyl)piperidin-4-yl)diphenylmethanol

To a vial was added the 1-(4-(tert-butyl)phenyl)-4-(4-(hydroxydiphenylmethyl)piperidin-1-yl)butan-1-one (0.200 g, 0.426 mmol), Ammonium acetate (0.328 g, 4.26 mmol) and Sodium cyanoborohydride (0.040 g, 0.639 mmol) with MeOH (Volume: 4 ml). The reaction stirred at rt at 2:56:22 PM. The reaction was stirred overnight and then concentrated and diluted with dilute aqueous ammonium hydroxide and extracted with DCM. The DCM layer was concentrated and the crude NMR showed product and starting material. The reaction then purified by reverse-phase Teledyne ISCO Combiflash chromatography (10-100% MeCN:basic water) and fractions 5 and 6 were collected. These were then subjected to normal phase purification (0-10% MeOH (5% NH$_3$OH):DCM) to produce pure (1-(4-amino-4-(4-(tert-butyl)phenyl)butyl)piperidin-4-yl)diphenylmethanol (0.010 g, 0.021 mmol, 5% yield). $^1$H NMR (400 MHz, CDCl$_3$): δ 7.48-7.44 (m, 4H), 7.34-7.26 (m, 6H), 7.22-7.14 (m, 4H), 3.84 (t, J=6.7 Hz, 1H), 2.95-2.87 (m, 2H), 2.46-2.37 (m, 1H), 2.28 (t, J=7.6 Hz, 2H), 1.95-1.85 (m, 2H), 1.70-1.60 (m, 5H), 1.55-1.40 (m, 6H), 1.30 (s, 9H). $^{13}$C NMR (125 MHz, CDCl$_3$): δ 149.7, 146.0, 143.3, 128.1, 126.5, 125.9, 125.8, 125.3, 79.5, 58.7, 55.8, 54.2, 54.0, 44.2, 37.5, 34.4, 31.4, 26.4, 24.2. LCMS Retention time: 2.397 min. LCMS purity 100%. HRMS (ESI): m/z calcd for C$_{32}$H$_{42}$N$_2$O [M+H]$^+$ 471.3297, found 471.3370.

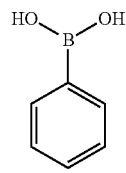

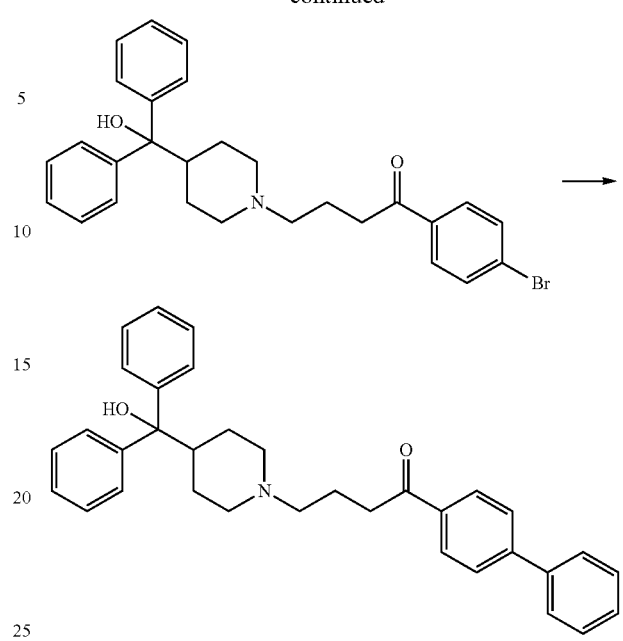

KSC-348-001

1-([1,1'-Biphenyl]-4-yl)-4-(4-(hydroxydiphenylmethyl)piperidin-1-yl)butan-1-one

To a vial was added the 1-(4-bromophenyl)-4-(4-(hydroxydiphenylmethyl)piperidin-1-yl)butan-1-one (0.098 g, 0.199 mmol), 1,1'-bis(di-t-butylphosphino)ferrocene palladium dichloride, (2.71 mg, 3.98 μmol) and phenylboronic acid (0.029 g, 0.239 mmol) followed by acetonitrile (1.5 mL). The potassium carbonate (0.041 g, 0.299 mmol) was dissolved in water (1.5 mL) and added the reaction. The reaction stirred at 60° C. for 18 h. The reaction was stopped and the organic layer was diluted with EtOAc and extracted then washed with brine. The EtOAc layer was collected, dried with MgSO$_4$, filtered and purified by reverse-phase MPLC (10-100% MeCN:water) to produce the desired 1-([1,1'-biphenyl]-4-yl)-4-(4-(hydroxydiphenylmethyl)piperidin-1-yl)butan-1-one (0.035 g, 0.071 mmol, 36% yield). $^1$H NMR (400 MHz, CDCl$_3$): δ 8.03 (d, J=8.6 Hz, 2H), 7.67 (d, J=8.4 Hz, 2H), 7.64-7.61 (m, 2H), 7.50-7.45 (m, 6H), 7.42-7.38 (m, 1H), 7.31-7.26 (m, 4H), 7.19-7.14 (m, 2H), 3.02-2.91 (m, 4H), 2.46-2.37 (m, 3H), 2.10 (br s, 1H), 1.97-1.92 (m, 4H), 1.50-1.35 (m, 4H).

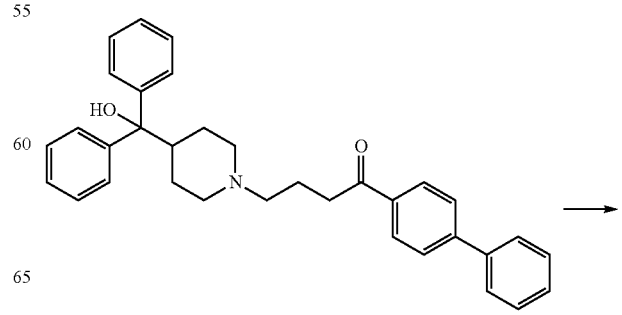

-continued

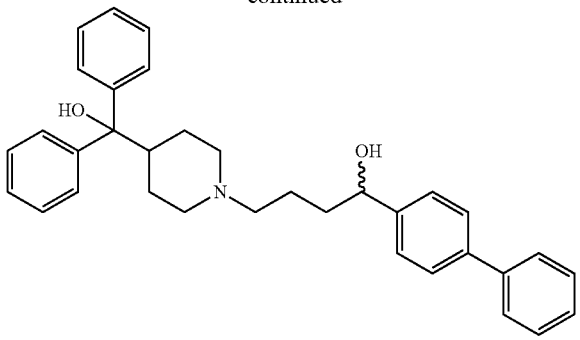

KSC-348-002

1-([1,1'-biphenyl]-4-yl)-4-(4-(hydroxydiphenylmethyl)piperidin-1-yl)butan-1-ol

Method B: 1-([1,1'-biphenyl]-4-yl)-4-(4-(hydroxydiphenylmethyl)piperidin-1-yl)butan-1-one (KSC-348-001) (0.035 g, 0.071 mmol) and MeOH (2 mL) and sodium borohydride (5.41 mg, 0.143 mmol) to produce pure 1-([1,1'-biphenyl]-4-yl)-4-(4-(hydroxydiphenylmethyl)piperidin-1-yl)butan-1-ol (0.033 g, 0.067 mmol, 94% yield) as on oil. $^1$H NMR (400 MHz, CDCl$_3$): δ 7.59-7.55 (m, 2H), 7.53-7.46 (m, 6H), 7.43-7.38 (m, 4H), 7.34-7.25 (m, 5H), 7.19-7.13 (m, 2H), 4.65 (dd, J=8.2 Hz, 2.7 Hz, 1H), 3.16-3.10 (m, 1H), 2.99-2.93 (m, 1H), 2.56 (br s, 1H), 2.50-2.34 (m, 3H), 2.10-1.92 (m, 3H), 1.86-1.76 (m, 1H), 1.70-1.45 (m, 6H).). $^{13}$C NMR (125 MHz, CDCl$_3$): δ 146.1, 146.0, 145.0, 141.1, 139.4, 128.6, 128.2, 128.1, 127.01, 126.96, 126.8, 126.44, 126.41, 126.1, 125.7, 125.6, 79.2, 73.3, 58.9, 54.7, 53.3, 44.2, 40.0, 26.0, 25.9, 24.1. LCMS Retention time: 4.049 min. LCMS purity 97.6%. HRMS (ESI): m/z calcd for C$_{34}$H$_{37}$NO$_2$ [M+H]$^+$ 492.2824, found 492.2897.

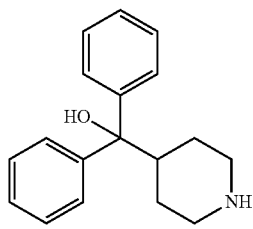

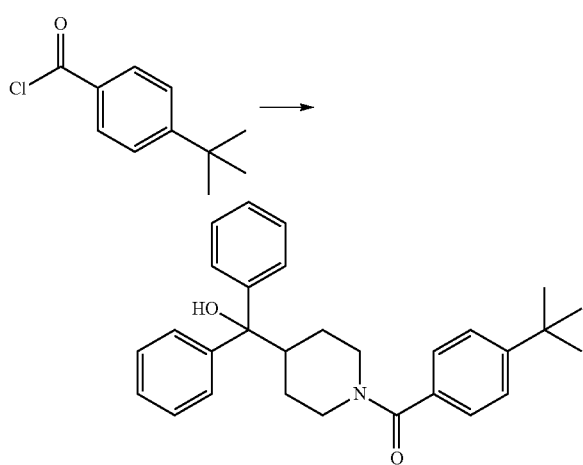

KSC-348-049

(4-(tert-butyl)phenyl)(4-(hydroxydiphenylmethyl)piperidin-1-yl)methanone

To a vial was added the diphenyl(piperidin-4-yl)methanol (0.232 g, 0.868 mmol), acetonitrile (3 mL) and TEA (0.181 ml, 1.30 mmol). The 4-(tert-butyl)benzoyl chloride (0.173 mL, 0.954 mmol) was added and the reaction stirred at 70° C. for 6 h and was diluted with EtOAc (15 mL) and washed with saturated NaHCO$_3$ (15 mL). The EtOAc was collected, dried with MgSO$_4$, filtered and adsorbed to silica and purified by MPLC (20 min, 0-30% EtOAc:Hex) to produce pure (4-(tert-butyl)phenyl)(4-(hydroxydiphenylmethyl)piperidin-1-yl)methanone (0.304 g, 0.711 mmol, 82% yield) as a white solid. $^1$H NMR (400 MHz, CDCl$_3$): δ 7.50-7.44 (m, 4H), 7.38-7.14 (m, 10H), 4.77 (br s, 1H), 3.84 (br s, 1H), 3.05-2.63 (m, 3H), 2.25-2.17 (m, 1H), 1.75-1.35 (m, 4H), 1.29 (s, 9H). $^{13}$C NMR (125 MHz, CDCl$_3$): δ 170.4, 152.7, 145.4, 133.2, 128.3, 126.7, 125.7, 125.2, 79.5, 44.5, 34.7, 31.2. LCMS Retention time: 3.774 min. LCMS purity 100%. HRMS (ESI): m/z calcd for C$_{29}$H$_{33}$NO$_2$ [M+H]$^+$ 428.2511, found 428.2584.

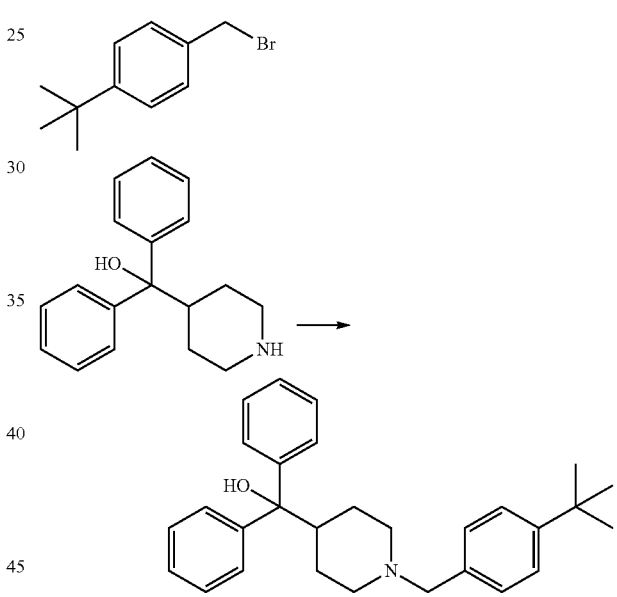

KSC-348-050

(1-(4-(tert-butyl)benzyl)piperidin-4-yl)diphenylmethanol

To a vial was added the diphenyl(piperidin-4-yl)methanol (0.085 ml, 0.393 mmol), acetonitrile (2 mL) and TEA (0.082 ml, 0.589 mmol). The p-tert-butylbenzyl bromide (0.098 g, 0.432 mmol) was then added and the reaction stirred at 70° C. and stirred for 5 h then diluted with EtOAc (15 mL) and washed with saturated NaHCO$_3$ (15 mL). The EtOAc was collected, dried with MgSO$_4$, filtered and adsorbed to silica and purified by reverse phase MPLC (20 min, 10-100% MeCN:water) to produce pure (1-(4-(tert-butyl)benzyl)piperidin-4-yl)diphenylmethanol (0.131 g, 0.317 mmol, 81% yield) as a brown oil. $^1$H NMR (400 MHz, CDCl$_3$): δ 7.48-7.45 (m, 4H), 7.32-7.25 (m, 6H), 7.22-7.14 (m, 4H), 3.47 (s, 2H), 2.96-2.90 (m, 2H), 2.46-2.38 (m, 1H), 2.02-1.95 (m, 1H), 1.51-1.44 (m, 4H), 1.30 (s, 9H). $^{13}$C NMR (125 MHz, CDCl₃): δ 149.8, 146.0, 135.1, 128.9, 128.1, 126.4, 125.8, 125.0, 79.5, 62.8, 53.9, 44.2, 34.4, 31.4, 26.5, 21.0. LCMS Retention time: 4.186 min. LCMS purity 99.7%. HRMS (ESI): m/z calcd for $C_{29}H_{35}NO$ [M+H]⁺ 414.2719, found 414.2791.

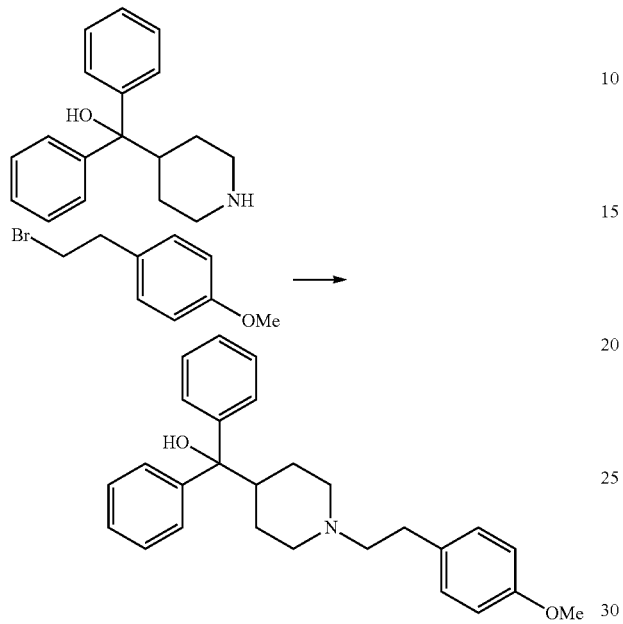

KSC-348-058

(1-(4-methoxyphenethyl)piperidin-4-yl)diphenyl-methanol

To a vial was added the diphenyl(piperidin-4-yl)methanol (0.381 g, 1.425 mmol), acetonitrile (5 mL) and TEA (0.298 ml, 2.138 mmol). The 1-(2-bromoethyl)-4-methoxybenzene (0.245 ml, 1.568 mmol) was then added and the reaction stirred at 75° C. and the stirred for 16 h then was quenched with saturated NaHCO₃, extracted with EtOAc, dried with MgSO₄, filtered and adsorbed to silica. The product was purified by MPLC (20 min, 0-10% MeOH:DCM) to produce pure (1-(4methoxyphenethyl) piperidin-4-yl)diphenyl-methanol (0.289 g, 0.720 mmol, 50% yield) as a sticky solid. ¹H NMR (400 MHz, CDCl₃): δ 7.49-7.46 (m, 4H), 7.32-7.28 (m, 4H), 7.19 (tt, J=7.3 Hz, 1.9 Hz, 2H), 7.12 (d, J=8.6 Hz, 2H), 6.82 (d, J=8.5 Hz, 2H), 3.77 (s, 3H), 3.29-3.24 (m, 2H), 2.95-2.90 (m, 2H), 2.80-2.75 (m, 2H), 2.58-2.50 (m, 1H), 2.42-2.30 (m, 3H), 1.90-1.77 (m, 2H), 1.65-1.57 (m, 2H). ¹³C NMR (125 MHz, CDCl₃): δ 158.3, 145.5, 129.6, 128.3, 126.7, 125.6, 114.0, 79.3, 55.3, 53.6, 53.4, 43.4, 31.5, 25.1. LCMS Retention time: 3.695 min. LCMS purity 100%. HRMS (ESI): m/z calcd for $C_{27}H_{31}NO_2$ [M+H]⁺ 402.2355, found 402.2353.

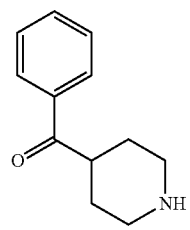

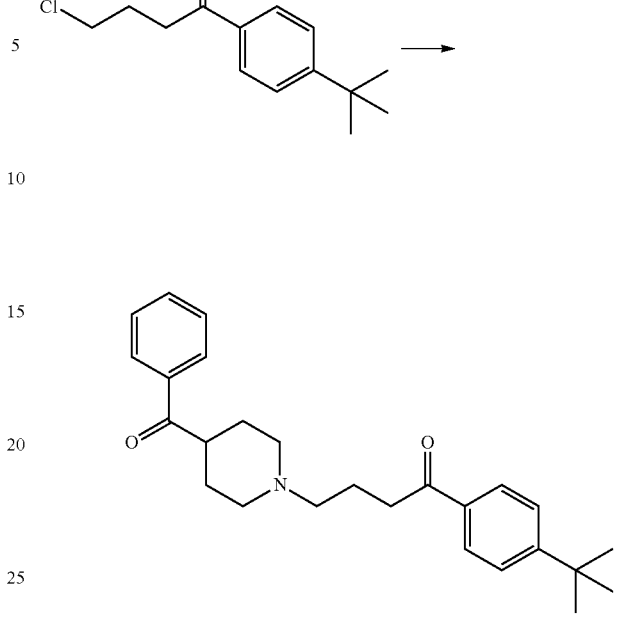

KSC-352-055

4-(4-Benzoylpiperidin-1-yl)-1-(4-(tert-butyl)phenyl)butan-1-one

To a vial was added the 1-(4-(tert-butyl)phenyl)-4-chlorobutan-1-one (0.060 g, 0.252 mmol) and potassium iodide (0.063 g, 0.377 mmol) with acetonitrile (2 mL). The reaction stirred at 85° C. for 1 h then the phenyl(piperidin-4-yl)methanone (0.050 g, 0.264 mmol) along with potassium carbonate (0.052 g, 0.377 mmol) was added. The reaction was then heated back to 85° C. for 48 h. The reaction was cooled to rt and diluted with water then extracted with EtOAc (3×15 mL). The EtOAc layer was dried with MgSO₄, filtered and adsorbed to silica. The product was purified by reverse-phase MPLC (20 min, 10-100% MeCN:water) to produce 4-(4-benzoylpiperidin-1-yl)-1-(4-(tert-butyl)phenyl)butan-1-one (0.026 g, 0.066 mmol, 26% yield). ¹H NMR (400 MHz, CDCl₃): δ 7.95-7.90 (m, 4H), 7.57-7.53 (m, 1H), 7.49-7.44 (m, 4H), 3.27-3.18 (m, 1H), 3.03-2.96 (m, 4H), 2.44 (t, J=7.04 Hz, 2H), 2.13-2.06 (m, 2H), 1.98-1.91 (m, 2H), 1.85-1.76 (m, 4H), 1.34 (s, 9H).

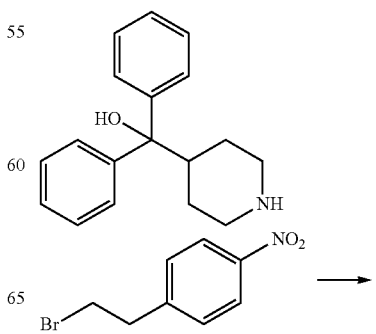

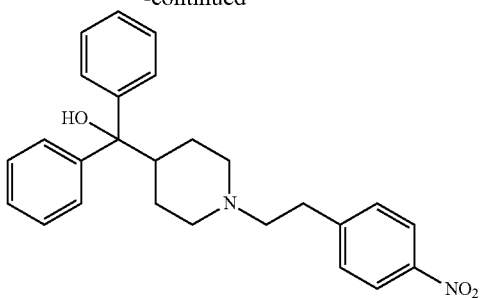

KSC-352-060

(1-(4-nitrophenethyl)piperidin-4-yl)diphenylmethanol

To a vial was added the diphenyl(piperidin-4-yl)methanol (0.513 g, 1.919 mmol), 1-(2-bromoethyl)-4-nitrobenzene (0.401 g, 1.744 mmol) and acetonitrile (10 mL). The TEA (0.365 ml, 2.62 mmol) was then added and the reaction stirred at 85° C. for 18 h then cooled to rt. The reaction was diluted with water and extracted with EtOAc (3×15 mL). The EtOAc layer was collected and dried with MgSO$_4$, filtered and adsorbed to silica then purified by MPLC (15 min, 0-10% MeOH:DCM). to produce pure (1-(4-nitrophenethyl)piperidin-4-yl)diphenylmethanol (0.145 g, 0.348 mmol, 20% yield). $^1$H NMR (400 MHz, CDCl$_3$): δ 8.13 (d, J=8.7 Hz, 2H), 7.49-7.46 (m, 4H), 7.35 (d, J=8.7 Hz, 2H), 7.32-7.27 (m, 4H), 7.21-7.16 (m, 2H), 3.11-3.05 (m, 2H), 2.97-2.91 (m, 2H), 2.69-2.63 (m, 2H), 2.52-2.43 (m, 1H), 2.25 (br s, 1H), 2.20-2.10 (m, 2H), 1.63-1.53 (m, 4H). $^{13}$C NMR (125 MHz, CDCl$_3$): δ 147.9, 146.5, 145.7, 129.5, 128.2, 126.6, 125.7, 123.7, 79.4, 59.4, 53.9, 43.9, 33.2, 26.1, 21.1. LCMS Retention time: 3.654 min. LCMS purity 98.8%. HRMS (ESI): m/z calcd for C$_{26}$H$_{28}$N$_2$O$_3$ [M+H]$^+$ 417.2162, found 417.2173.

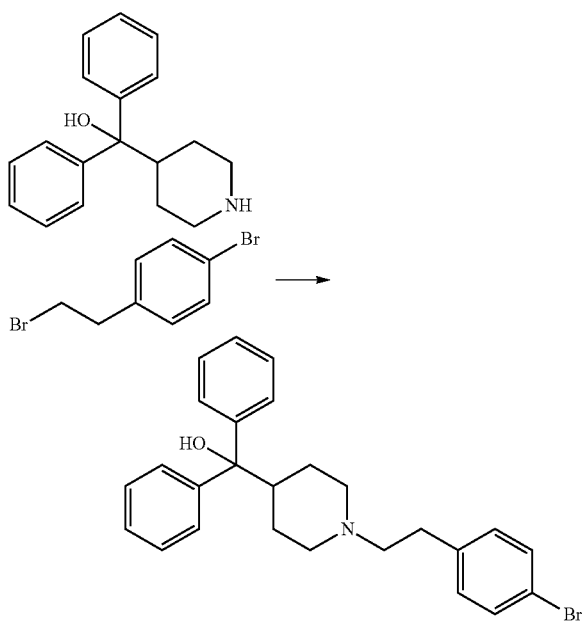

KSC-352-061

(1-(4-bromophenethyl)piperidin-4-yl)diphenylmethanol

To a vial was added the diphenyl(piperidin-4-yl)methanol (0.496 g, 1.855 mmol), 1-bromo-4-(2-bromoethyl)benzene (0.258 ml, 1.69 mmol) and acetonitrile (10 mL). The TEA (0.353 mL, 2.53 mmol) was then added and the reaction stirred at 85° C. for 18 h then cooled to rt. The reaction was diluted with water and extracted with EtOAc (3×15 mL). The EtOAc layer was collected and dried with MgSO$_4$, filtered and adsorbed to silica then purified by MPLC (15 min, 0-10% MeOH:DCM). to produce pure (1-(4-bromophenethyl)piperidin-4-yl)diphenylmethanol (0.488 g, 1.083 mmol, 64% yield). $^1$H NMR (400 MHz, CDCl$_3$): δ 7.50-7.46 (m, 4H), 7.38 (d, J=8.3 Hz, 2H), 7.34-7.27 (m, 4H), 7.18 (tt, J=7.3 Hz, 1.8 Hz, 2H), 7.06 (d, J=8.4 Hz, 2H), 3.06-3.00 (m, 2H), 2.77-2.72 (m, 2H), 2.58-2.52 (m, 2H), 2.50-2.41 (m, 1H), 2.15-2.00 (m, 3H), 1.56-1.49 (m, 4H). $^{13}$C NMR (125 MHz, CDCl$_3$): δ 145.8, 139.3, 131.4, 130.4, 128.2, 126.6, 125.8, 119.8, 79.5, 60.4, 54.0, 44.1, 33.1, 26.4, 21.1 LCMS Retention time: 3.969 min. LCMS purity 99.8%. HRMS (ESI): m/z calcd for C$_{26}$H$_{28}$BrNO [M+H]$^+$ 450.1354, found 450.1427.

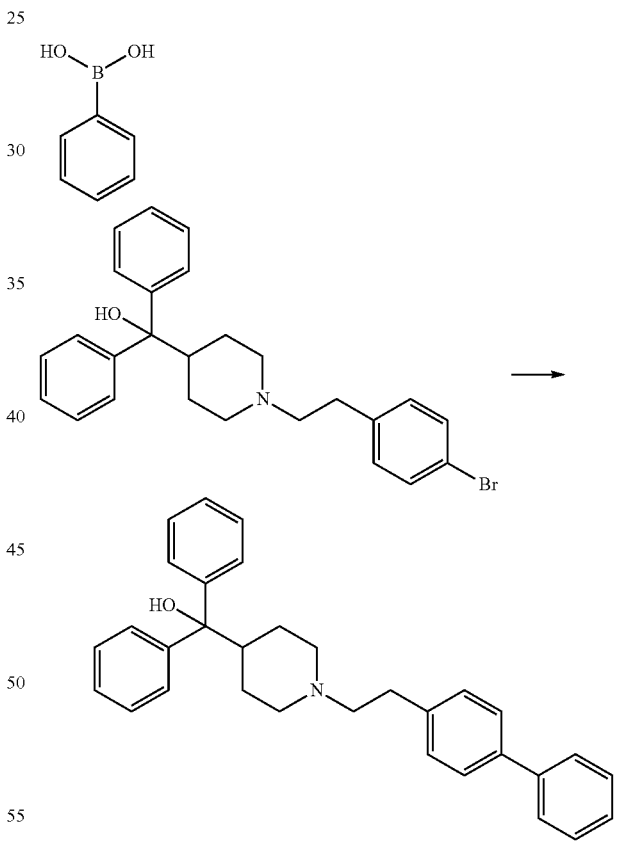

KSC-352-063

(1-(2-([1,1'-biphenyl]-4-yl)ethyl)piperidin-4-yl)diphenylmethanol

To a vial was added the phenylboronic acid (0.019 g, 0.152 mmol), 1,1'-bis(di-tert-butylphosphino)ferrocene palladium dichloride (4.12 mg, 6.33 µmol), (1-(4-bromophenethyl)piperidin-4-yl)diphenylmethanol (KSC-352-061) (0.057 g, 0.127 mmol) and potassium carbonate (0.035 g, 0.253 mmol). The vial was then evacuated with argon 3 times and acetonitrile (1 mL) was added followed by water (1 mL). The reaction then stirred at 60° C. for 18 h then was diluted with EtOAc (5 mL) and saturated NaHCO₃ (5 mL). The EtOAc layer was collected and the aqueous layer was extracted with more EtOAc (2×5 mL). The EtOAc layers were combined and dried with MgSO₄, filtered and concentrated. The reaction was purified by MPLC (10-100% MeCN:water) to produce pure (1-(2-([1,1'-biphenyl]-4-yl)ethyl)piperidin-4-yl)diphenylmethanol (0.045 g, 0.101 mmol, 79% yield) as a clear oil. ¹H NMR (400 MHz, CDCl₃): δ 7.59-7.45 (m, 2H), 7.53-7.48 (m, 6H), 7.45-7.40 (m, 2H), 7.35-7.25 (m, 7H), 7.22-7.16 (m, 2H), 3.11-3.05 (m, 2H), 2.87-2.81 (m, 2H), 2.65-2.59 (m, 2H), 2.53-2.44 (m, 1H), 2.22 (br s, 1H), 2.12-2.04 (m, 2H), 1.59-1.52 (m, 4H). ¹³C NMR (125 MHz, CDCl₃): δ 145.9, 141.0, 139.5, 139.0, 129.1, 128.7, 128.2, 127.1, 127.03, 126.96, 126.5, 125.8, 79.5, 60.7, 54.0, 50.8, 44.2, 33.3, 26.4. LCMS Retention time: 4.086 min. LCMS purity 99%. HRMS (ESI): m/z calcd for $C_{32}H_{33}NO$ [M+H]⁺ 448.2562, found 448.2635.

cooled to rt and diluted with EtOAc (5 mL) and saturated NaHCO₃ (5 mL). The EtOAc layer was collected and the aqueous layer was extracted with more EtOAc (2×5 mL). The EtOAc layers were combined and dried with MgSO₄, filtered and concentrated. The reaction was purified by reverse-phase MPLC (10-100% MeCN:water) to produce pure diphenyl(1-(4-(pyridin-4-yl)phenethyl)piperidin-4-yl)methanol (0.015 g, 0.033 mmol, 30% yield) as an oil. ¹H NMR (400 MHz, CDCl₃): δ 8.64-8.62 (m, 2H), 7.60 (d, J=8.2 Hz, 2H), 7.51-7.46 (m, 6H), 7.32-7.28 (m, 6H), 7.18 (tt, J=7.3 Hz, 1.8 Hz, 2H), 3.10-3.04 (m, 2H), 2.88-2.82 (m, 2H), 2.65-2.58 (m, 2H), 2.51-2.43 (m, 1H), 2.19 (br s, 1H), 2.12-2.03 (m, 2H), 1.58-1.51 (m, 4H). ¹³C NMR (125 MHz, CDCl₃): δ 150.2, 148.1, 145.9, 141.7, 135.8, 129.5, 128.2, 127.0, 126.5, 125.8, 121.4, 79.5, 60.5, 54.1, 44.1, 41.0, 33.4, 26.4. LCMS Retention time: 3.585 min. LCMS purity 93.3%. HRMS (ESI): m/z calcd for $C_{31}H_{32}N_2O$ [M+H]⁺ 449.2515, found 449.2587.

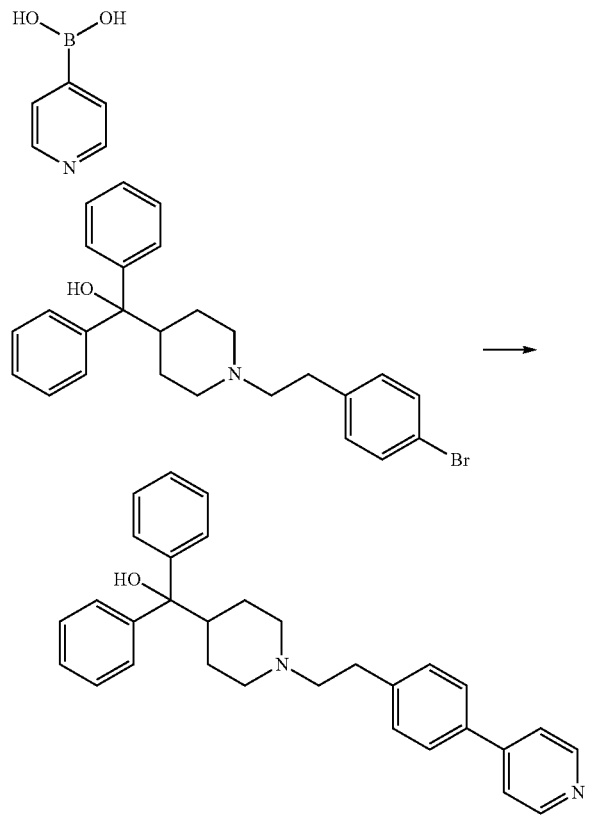

KSC-352-064

Diphenyl(1-(4-(pyridin-4-yl)phenethyl)piperidin-4-yl)methanol

To a vial was added the (1-(4-bromophenethyl)piperidin-4-yl)diphenylmethanol (KSC-352-061) (0.050 g, 0.111 mmol), pyridin-4-ylboronic acid (0.018 g, 0.133 mmol), 1,1'-bis(di-tert-butylphosphino)ferrocene palladium dichloride (3.62 mg, 5.55 µmol) and potassium carbonate (0.031 g, 0.222 mmol). The vial was evacuated 3 times with argon and then acetonitrile (1 mL) followed by water (1 mL) was added. The reaction stirred at 60° C. for 18 h and was then

KSC-352-065

Diphenyl(1-(4-(pyridin-3-yl)phenethyl)piperidin-4-yl)methanol

To a vial was added the (1-(4-bromophenethyl)piperidin-4-yl)diphenylmethanol (0.057 g, 0.127 mmol), pyridin-3-ylboronic acid (0.019 g, 0.152 mmol), 1,1'-Bis(di-tert-butylphosphino)ferrocene palladium dichloride (4.12 mg, 6.33 µmol) and potassium carbonate (0.035 g, 0.253 mmol). The vial was evacuated with argon 3 times and then acetonitrile (1 mL) followed by water (1 mL) was added. The reaction stirred at 60° C. for 18 h and then cooled to rt and diluted with EtOAc (5 mL) and saturated NaHCO₃ (5 mL). The EtOAc layer was collected and the aqueous layer was extracted with more EtOAc (2×5 mL). The EtOAc layers were combined and dried with MgSO$_4$, filtered and concentrated. The reaction was purified by RP MPLC (10-100% MeCN:water) to produce pure diphenyl(1-(4-(pyridin-3-yl)phenethyl)piperidin-4-yl)methanol (0.05 g, 0.111 mmol, 88% yield) as an oil. 1H NMR (400 MHz, CDCl$_3$): δ 8.79 (dd, J=2.4 Hz, 0.9 Hz, 1H), 8.53 (dd, J=4.8 Hz, 1.6 Hz, 1H), 7.86-7.83 (m, 1H), 7.51-7.47 (m, 6H), 7.36-7.27 (m, 7H), 7.20-7.15 (m, 2H), 3.10-3.03 (m, 2H), 2.87-2.81 (m, 2H), 2.71 (br s, 1H), 2.63-2.58 (m, 2H), 2.51-2.43 (m, 1H), 2.11-2.03 (m, 2H), 1.58-1.52 (m, 4H). $^{13}$C NMR (125 MHz, CDCl$_3$): δ 148.04, 147.97, 146.0, 140.5, 136.5, 135.5, 134.3, 129.4, 128.1, 127.1, 126.4, 125.8, 123.5, 79.4, 60.5, 54.1, 44.1, 33.2, 26.2. LCMS Retention time: 3.582 min. LCMS purity 98.8%. HRMS (ESI): m/z calcd for C$_{31}$H$_{32}$N$_2$O [M+H]$^+$ 449.2515, found 449.2587.

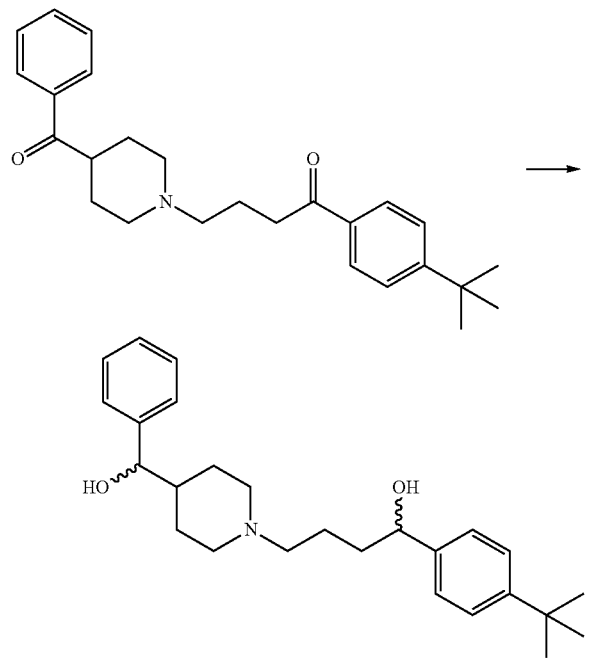

KSC-352-066

1-(4-(tert-butyl)phenyl)-4-(4-(hydroxy(phenyl)methyl)piperidin-1-yl)butan-1-ol

Method B: 4-(4-benzoylpiperidin-1-yl)-1-(4-(tert-butyl)phenyl)butan-1-one (KSC-352-055) (0.026 g, 0.066 mmol) and MeOH (2 mL) and sodium borohydride (10.05 mg, 0.266 mmol) to produce pure 1-(4-(tert-butyl)phenyl)-4-(4-(hydroxy(phenyl)methyl)piperidin-1-yl)butan-1-ol (0.019 g, 0.048 mmol, 72% yield) as a mixture of diastereomers. $^1$H NMR (400 MHz, CDCl$_3$): δ 7.36-7.24 (m, 9H), 4.63-4.57 (m, 1H), 4.33 (d, J=7.6 Hz, 1H), 3.23-2.83 (m, 2H), 2.42-2.35 (m, 2H), 2.13-1.89 (m, 3H), 1.86-1.52 (m, 6H), 1.46-1.16 (m, 4H), 1.31 (s, 9H). $^{13}$C NMR (125 MHz, CDCl$_3$): δ 149.4, 143.4, 142.8, 128.3, 127.63, 127.61, 126.6, 125.4, 125.0, 78.74, 78.67, 73.4, 58.9, 54.30, 54.26, 52.8, 52.7, 43.21, 43.2, 39.9, 34.4, 31.4, 28.4, 28.3, 28.2, 24.2, 24.1. LCMS Retention time: 3.707 min. LCMS purity 97.1%. HRMS (ESI): m/z calcd for C$_{26}$H$_{37}$NO$_2$ [M+H]$^+$ 396.2824, found 396.2897.

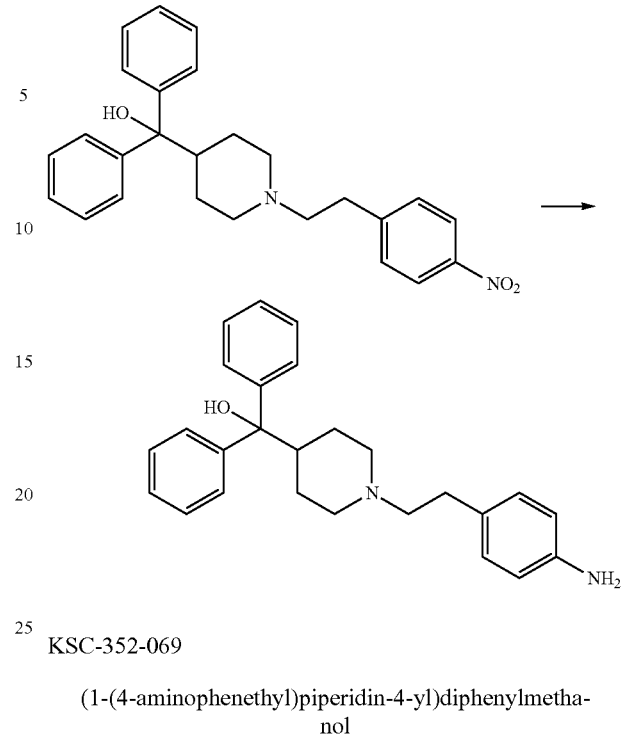

KSC-352-069

(1-(4-aminophenethyl)piperidin-4-yl)diphenylmethanol

To a vial was added the (1-(4-nitrophenethyl)piperidin-4-yl)diphenylmethanol (KSC-352-060) (0.135 g, 0.324 mmol) with MeOH (1 mL) and DCM (1 mL). The reaction was cooled to 0° C. and the Raney Nickel (1.902 mg, 0.032 mmol) was added. The sodium borohydride (0.031 g, 0.810 mmol) was then added portionwise and the reaction stirred at rt for 28 h and the Raney Nickel filtered through celite. The reaction was diluted with DCM and washed with water and the DCM layer was dried with MgSO$_4$, filtered and adsorbed to silica then purified by MPLC (0-15% MeOH:DCM) to produce pure (1-(4-aminophenethyl)piperidin-4-yl)diphenylmethanol (0.077 g, 0.199 mmol, 61% yield). H NMR (400 MHz, CDCl$_3$): δ 7.51-7.47 (m, 4H), 7.32-7.27 (m, 4H), 7.18 (tt, J=7.3 Hz, 1.8 Hz, 2H), 6.97 (d, J=8.3 Hz, 2H), 6.61 (d, J=8.3 Hz, 2H), 3.52 (br s, 2H), 3.07-3.01 (m, 2H), 2.70-2.65 (m, 2H), 2.54-2.41 (m, 3H), 2.22 (br s, 1H), 2.07-1.98 (m, 2H), 1.56-1.49 (m, 4H). $^{13}$C NMR (125 MHz, CDCl$_3$): δ 145.9, 144.4, 130.4, 129.4, 128.1, 126.5, 125.8, 115.2, 79.5, 61.2, 54.1, 44.2, 32.8, 26.4, 21.0. LCMS Retention time: 3.328 min. LCMS purity 93.1%. HRMS (ESI): m/z calcd for C$_{26}$H$_{30}$N$_2$O [M+H]$^+$ 387.2358, found 387.2431.

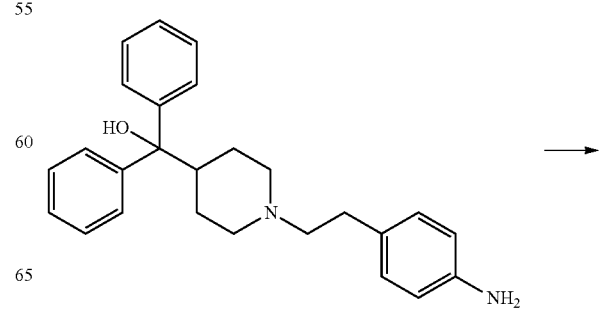

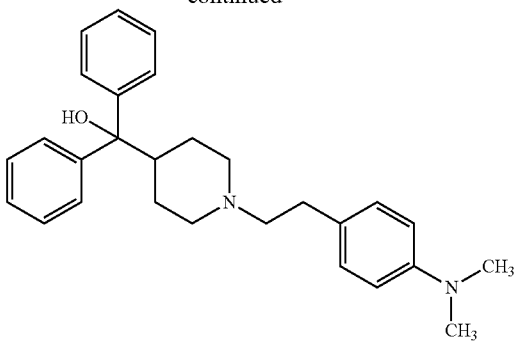

KSC-352-075

(1-(4-(Dimethylamino)phenethyl)piperidin-4-yl)diphenylmethanol

To a vial was added the (1-(4-aminophenethyl)piperidin-4-yl)diphenylmethanol (KSC-352-069) (0.030 g, 0.078 mmol) and acetic acid (1 mL). The paraformaldehyde (0.058 mL, 0.776 mmol) solution in water followed by sodium cyanoborohydride (0.015 g, 0.233 mmol) was then added and the reaction stirred at rt for 20 h. The reaction was concentrated and diluted with saturated NaHCO$_3$ and extracted with EtOAc (3×5 mL). The EtOAc layer was dried with MgSO$_4$, filtered and concentrated. The product was purified by reverse-phase MPLC (10-100% MeCN:water) to produce (1-(4-(dimethylamino)phenethyl)piperidin-4-yl)diphenylmethanol (0.027 g, 0.065 mmol, 84% yield). $^1$H NMR (400 MHz, CDCl$_3$): δ 7.50-7.46 (m, 4H), 7.31-7.26 (m, 4H), 7.17 (tt, J=7.3 Hz, 1.8 Hz, 2H), 7.06 (d, J=8.3 Hz, 2H), 6.68 (d, J=8.3 Hz, 2H), 3.08-3.02 (m, 2H), 2.90 (s, 6H), 2.72-2.67 (m, 2H), 2.56-2.50 (m, 2H), 2.48-2.42 (m, 1H), 2.30 (br s, 1H), 2.07-2.00 (m, 2H), 1.56-1.51 (m, 4H). $^{13}$C NMR (125 MHz, CDCl$_3$): δ 149.1, 146.0, 129.2, 128.4, 128.1, 126.4, 125.8, 112.9, 79.4, 61.1, 54.0, 44.2, 41.0, 40.8, 32.6, 26.4. LCMS Retention time: 2.50 min. LCMS purity 96.1%. HRMS (ESI): m/z calcd for C$_{28}$H$_{34}$N$_2$O [M+H]$^+$ 415.2671, found 415.2744.

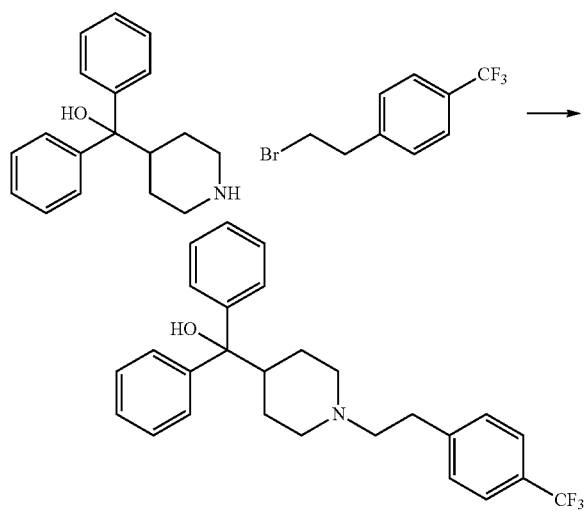

KSC-352-082

Diphenyl(1-(4-(trifluoromethyl)phenethyl)piperidin-4-yl)methanol

To a vial was added the diphenyl(piperidin-4-yl)methanol (0.100 g, 0.374 mmol), 1-(2-bromoethyl)-4-(trifluoromethyl)benzene (0.057 ml, 0.340 mmol) and acetonitrile (10 mL). The TEA (0.071 mL, 0.510 mmol) was then added and the reaction stirred at 85° C. for 18 h. The reaction was diluted with water and extracted with EtOAc (3×15 mL). The EtOAc layer was collected and dried with MgSO$_4$, filtered and adsorbed to silica then purified by MPLC (15 min, 0-10% MeOH:DCM) to produce pure diphenyl(1-(4-(trifluoromethyl)phenethyl)piperidin-4-yl)methanol (0.074 g, 0.168 mmol, 49% yield) as an oil. $^1$H NMR (400 MHz, CDCl$_3$): δ 7.54-7.47 (m, 4H), 7.33-7.27 (m, 6H), 7.19 (tt, J=7.3 Hz, 1.8 Hz, 2H), 3.06-3.00 (m, 2H), 2.86-2.80 (m, 2H), 2.60-2.55 (m, 2H), 2.51-2.42 (m, 1H), 2.14 (br s, 1H), 2.10-2.03 (m, 2H), 1.57-1.47 (m, 4H). $^{13}$C NMR (125 MHz, CDCl$_3$): δ 145.9, 144.6, 129.0, 128.3 (q, J=32 Hz), 128.2, 126.5, 125.8, 125.2 (q, 3.8 Hz), 124.2 (q, J=271.8 Hz), 79.5, 60.2, 54.1, 44.1, 33.6, 26.4, 21.0. LCMS Retention time: 3.877 min. LCMS purity 99.1%. HRMS (ESI): m/z calcd for C$_{27}$H$_{28}$F$_3$NO [M+H]$^+$ 440.2123, found 440.2196.

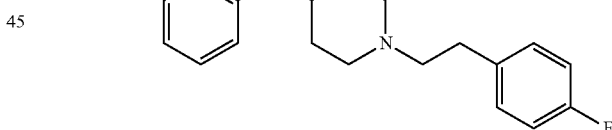

KSC-352-088

(1-(4-Fluorophenethyl)piperidin-4-yl)diphenylmethanol

To a vial was added the diphenyl(piperidin-4-yl)methanol (0.099 g, 0.370 mmol), 1-(2-bromoethyl)-4-fluorobenzene (0.047 mL, 0.337 mmol) and acetonitrile (10 mL). The TEA (0.070 mL, 0.505 mmol) was then added and the reaction stirred at 85° C. at for 19 h and was cooled to rt. The reaction was diluted with water and extracted with EtOAc (3×15 mL). The EtOAc layer was collected and dried with MgSO$_4$, filtered and adsorbed to silica then purified by MPLC (15 min, 0-10% MeOH:DCM) to produce pure (1-(4-fluorophenethyl)piperidin-4-yl)diphenylmethanol (0.123 g, 0.316 mmol, 94% yield). ¹H NMR (400 MHz, CDCl₃): δ 7.51-7.47 (m, 4H), 7.32-7.27 (m, 4H), 7.21-7.11 (m, 4H), 6.98-6.92 (m, 2H), 3.06-3.00 (m, 2H), 2.78-2.72 (m, 2H), 2.56-2.51 (m, 2H), 2.50-2.42 (m, 1H), 2.21 (br s, 1H), 2.08-1.99 (m, 2H), 1.57-1.48 (m, 4H). ¹³C NMR (125 MHz, CDCl₃): δ 161.2 (d, J=243.6 Hz), 145.9, 136.5 (d, J=3.2 Hz), 129.9 (d, J=7.9 Hz), 128.1, 126.5, 125.8, 115.0 (d, J=21.2 Hz), 79.5, 60.8, 54.1, 44.2, 33.0, 26.4, 21.0. LCMS Retention time: 3.733 min. LCMS purity 96.8%. HRMS (ESI): m/z calcd for C₂₆H₂₈FNO [M+H]⁺ 390.2155, found 390.2228.

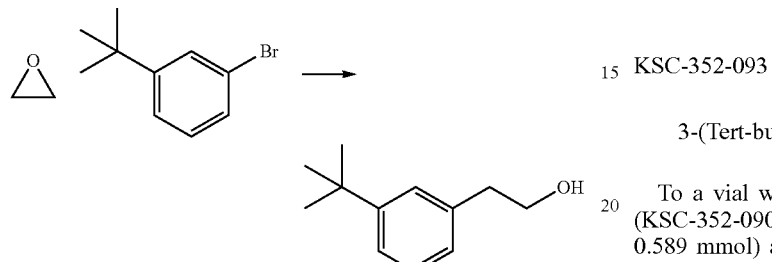

KSC-352-090

2-(3-(Tert-butyl)phenyl)ethanol

To a vial was added the 1-bromo-3-(tert-butyl)benzene (0.107 g, 0.502 mmol) and dry THF. The reaction was then cooled to −78° C. and the BuLi (0.221 mL, 0.552 mmol) (2.5 M in hexanes) was added dropwise and the reaction stirred for 30 min at −78° C. and then ethylene oxide (0.502 mL, 1.255 mmol) (2.5-3.3M solution in THF) was added dropwise and the reaction stirred for 10 minutes at −78° C. then warmed to rt and stirred for 1 h. The reaction was then quenched with 1.0 M HCl (2 mL) and extracted with EtOAc (3×5 mL). The EtOAc layer was combined, concentrated and purified by reverse-phase MPLC (10-100% MeCN:water) to produce pure 2-(3-(tert-butyl)phenyl)ethanol (0.035 g, 0.196 mmol, 39% yield). ¹H NMR (400 MHz, CDCl₃): δ 7.31-7.27 (m, 3H), 7.10-7.07 (m, 1H), 3.90 (t, J=6.6 Hz, 2H), 2.91 (t, J=6.5 Hz, 2H), 1.52 (br s, 1H), 1.36 (s, 9H).

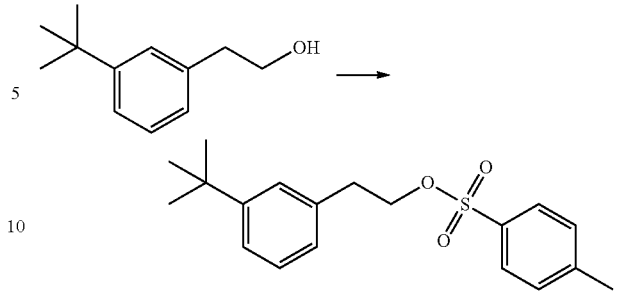

KSC-352-093

3-(Tert-butyl)phenethyl 4-methylbenzenesulfonate

To a vial was added the 2-(3-(tert-butyl)phenyl)ethanol (KSC-352-090) (0.035 g, 0.196 mmol), TEA (0.082 mL, 0.589 mmol) and DCM (2 mL) followed by p-toluenesulfonyl chloride (0.056 g, 0.294 mmol). The reaction began to stir at rt for 20 h and was then diluted with saturated NaHCO₃ and extracted with EtOAc. The EtOAc was then dried with MgSO₄, filtered and concentrated then purified by reverse-phase MPLC (10-100% MeCN:water) to provide pure 3-(tert-butyl)phenethyl 4-methylbenzenesulfonate (0.060 g, 0.180 mmol, 92% yield). ¹H NMR (400 MHz, CDCl₃): δ 7.70 (d, J=8.4 Hz, 2H), 7.30-7.24 (m, 3H), 7.19 (t, J=7.52 Hz, 1H), 7.14-7.12 (m, 1H), 4.22 (t, J=7.2 Hz, 2H), 2.96 (t, J=7.2 Hz, 2H), 2.43 (s, 3H), 1.29 (s, 9H).

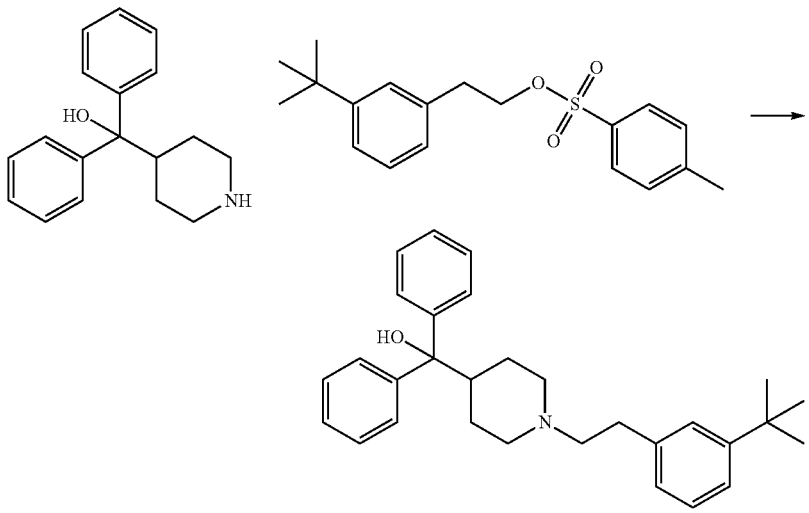

KSC-352-097

(1-(3-(Tert-butyl)phenethyl)piperidin-4-yl)diphenylmethanol

To a vial was added the 3-(tert-butyl)phenethyl 4-methylbenzenesulfonate (KSC-352-093) (0.060 g, 0.180 mmol), diphenyl(piperidin-4-yl)methanol (0.048 g, 0.180 mmol) and acetonitrile (1 mL). The TEA (0.038 mL, 0.271 mmol) was added and the reaction stirred at 85° C. for 18 h and was cooled to rt then diluted with water and extracted with EtOAc. The EtOAc layer was concentrated and the crude product was purified by reverse-phase MPLC (10-100% MeCN:water) to produce the pure (1-(3-(tert-butyl)phenethyl)piperidin-4-yl)diphenylmethanol (0.065 g, 0.152 mmol, 84% yield). $^1$H NMR (400 MHz, CDCl$_3$): δ 7.51-7.47 (m, 4H), 7.32-7.27 (m, 4H), 7.23-7.16 (m, 5H), 7.01-6.98 (m, 1H), 3.09-3.04 (m, 2H), 2.81-2.76 (m, 2H), 2.61-2.55 (m, 2H), 2.51-2.43 (m, 1H), 2.28 (br s, 1H), 2.10-2.02 (m, 2H), 1.30 (s, 9H), 1.32-1.26 (m, 4H). $^{13}$C NMR (125 MHz, CDCl$_3$): δ 151.2, 145.9, 140.0, 128.1, 128.0, 126.5, 125.8, 125.71, 125.68, 123.0, 79.5, 54.1, 44.2, 34.6, 34.0, 31.6, 31.4, 26.4, 22.6. LCMS Retention time: 4.214 min. LCMS purity 96.4%. HRMS (ESI): m/z calcd for C$_{30}$H$_{37}$NO [M+H]$^+$ 428.2875, found 428.2948.

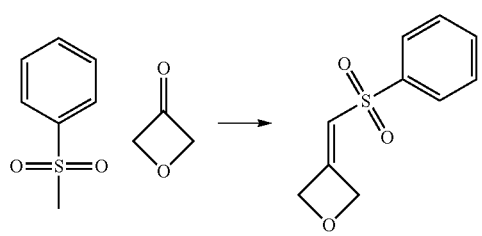

KSC-352-099

3-((Phenylsulfonyl)methylene)oxetane

To an oven-dried vial was added (methylsulfonyl)benzene (0.570 g, 3.65 mmol) and the vial was evacuated with argon 3 times. The dry THF (17 mL) was added and the reaction was cooled to 0° C. The 2.5 M BuLi in hexanes (3.21 mL, 8.03 mmol) was added dropwise and the reaction began to stir at 0° C. and stirred for 45 minutes. The diethyl chlorophosphate (0.528 mL, 3.65 mmol) was then added at 0° C. and the reaction stirred for 30 minutes. The reaction was then cooled to −78° C. and the oxetan-3-one (0.330 mL, 5.15 mmol) was then added dropwise and the reaction stirred for 2 h. The reaction was then warmed to rt and filtered through a silica plug. The reaction was then concentrated onto silica and purified by MPLC (20 min, 0-40% EtOAc:hex) to provide pure 3-((phenylsulfonyl)methylene)oxetane (0.579 g, 2.75 mmol, 75% yield). $^1$H NMR (400 MHz, CDCl$_3$): δ 7.91-7.87 (m, 2H), 7.69-7.64 (m, 1H), 7.60-7.55 (m, 2H), 6.12 (quintet, J=2.3 Hz, 1H), 5.66-5.63 (m, 2H), 5.30-5.27 (m, 2H).

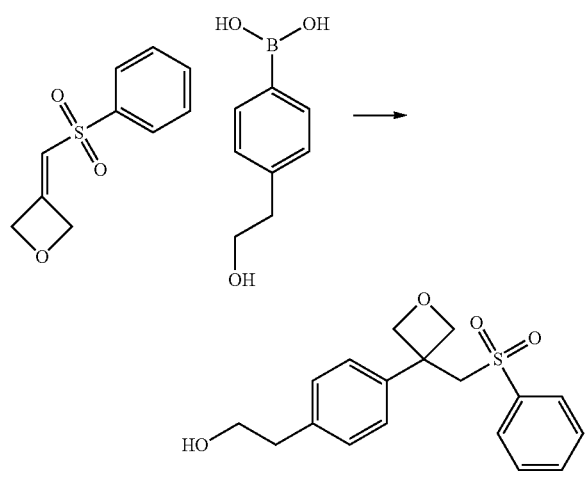

KSC-367-003

2-(4-(3-((Phenylsulfonyl)methyl)oxetan-3-yl)phenyl)ethanol

To a vial was added the chloro(1,5-cyclooctadiene)rhodium(I), dimer (0.012 g, 0.025 mmol) and 1,4-dioxane (10 mL). The 1.5 M aqueous KOH (0.496 mL, 0.745 mmol) was then added and the reaction stirred for 1 minute at rt. Then the (4-(2-hydroxyethyl)phenyl)boronic acid (0.103 g, 0.621 mmol) and 3-((phenylsulfonyl)methylene)oxetane (KSC-352-099) (0.052 g, 0.248 mmol) in 1 mL dioxane was added and the reaction stirred for 30 minutes at 100° C. in waves. The reaction was then cooled to rt and diluted with EtOAc and washed with 1.0 M HCl. The water layer was extracted with EtOAc (3×15 mL). The EtOAc layer was collected and the water was extracted with EtOAc again. The EtOAc layers were combined and dried with MgSO$_4$, filtered and concentrated then purified by reverse-phase MPLC (30 min, 10-100% MeCN:water) to produce pure 2-(4-(3-((phenylsulfonyl)methyl) oxetan-3-yl)phenyl)ethanol (0.063 g, 0.190 mmol, 76% yield). $^1$H NMR (400 MHz, CDCl$_3$): δ 7.55-7.52 (m, 2H), 7.50-7.46 (m, 1H), 7.36-7.31 (m, 2H), 7.09 (d, J=8.4 Hz, 2H), 7.01 (d, J=8.3 Hz, 2H), 5.03 (d, J=6.4 Hz, 2H), 4.93 (d, J=6.4 Hz, 2H), 4.03 (s, 2H), 3.82 (t, J=7.3 Hz, 2H), 2.80 (t, J=7.3 Hz, 2H).

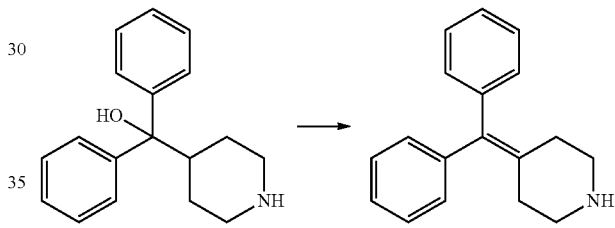

KSC-367-027

4-(diphenylmethylene)piperidine

To a vial was added the diphenyl(piperidin-4-yl)methanol (0.514 g, 1.922 mmol) and TFA (4 mL). The reaction stirred at 75° C. at for 24 h and was concentrated in vacuo. The residue was then dissolved in DCM (5 mL) and washed with water (4 mL). The DCM layer was collected and washed with water (1×5 mL), dried with MgSO$_4$, filtered concentrated then purified by reverse-phase MPLC (10-100% MeCN:Hex) to produce pure 4-(diphenylmethylene)piperidine (0.296 g, 1.187 mmol, 62% yield). $^1$H NMR (400 MHz, CDCl$_3$): δ 7.34-7.28 (m, 4H), 7.25-7.20 (m, 2H), 7.18-7.14 (m, 4H), 2.96-2.92 (m, 4H), 2.37-2.33 (m, 4H), 1.75 (br s, 1H).

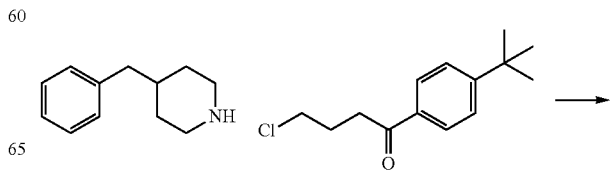

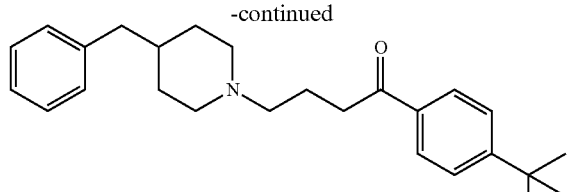

KSC-367-032

4-(4-Benzylpiperidin-1-yl)-1-(4-(tert-butyl)phenyl)butan-1-one

To a vial was added the 4-benzylpiperidine (0.25 ml, 1.422 mmol), 1-(4-(tert-butyl)phenyl)-4-chlorobutan-1-one (0.407 g, 1.707 mmol), acetonitrile and TEA (0.297 mL, 2.133 mmol). The reaction stirred at 85° C. for 17 h. The reaction was cooled to rt and diluted with saturated NaHCO$_3$ then extracted with EtOAc. The EtOAc was dried with MgSO$_4$, filtered and concentrated. The crude material was purified by reverse-phase MPLC (10-100% MeCN:water) to produce 4-(4-benzylpiperidin-1-yl)-1-(4-(tert-butyl)phenyl)butan-1-one (0.291 g, 0.771 mmol, 54% yield). $^1$H NMR (400 MHz, CDCl$_3$): δ 7.91 (d, J=8.6 Hz, 2H), 7.47 (d, J=8.5 Hz, 2H), 7.29-7.24 (m, 2H), 7.20-7.16 (m, 1H), 7.14-7.11 (m, 2H), 2.96 (t, J=7.2 Hz, 2H), 2.90-2.84 (m, 2H), 2.50 (d, J=7.0 Hz, 2H), 2.36 (t, J=7.3 Hz, 2H), 1.96-1.82 (m, 4H), 1.63-1.56 (m, 2H), 1.53-1.46 (m, 1H), 1.34 (s, 9H), 1.28-1.18 (m, 2H).

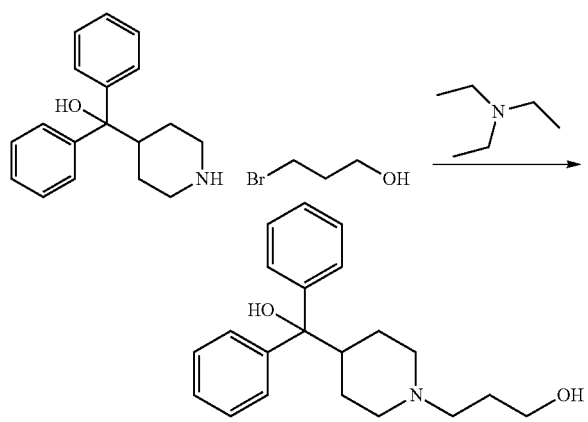

KSC-367-033

3-(4-(Hydroxydiphenylmethyl)piperidin-1-yl)propan-1-ol

To a vial was added the diphenyl(piperidin-4-yl)methanol (0.502 g, 1.878 mmol), 3-bromopropan-1-ol (0.204 mL, 2.253 mmol), acetonitrile and TEA (0.393 mL, 2.82 mmol). The reaction stirred at 85° C. for 3 h. The reaction was cooled to rt and diluted with saturated NaHCO$_3$ and extracted with EtOAc. The EtOAc layer was concentrated and purified by reverse-phase MPLC (10-100% MeCN:water) to provide 3-(4-(hydroxydiphenylmethyl)piperidin-1-yl)propan-1-ol (0.395 g, 1.214 mmol, 65% yield) as a white solid. $^1$H NMR (400 MHz, CDCl$_3$): δ 7.48-7.44 (m, 4H), 7.31-7.27 (m, 4H), 7.20-7.15 (m, 2H), 5.45 (br s, 1H), 3.75 (t, J=5.2 Hz, 2H), 3.12-3.06 (m, 2H), 2.57 (t, J=5.7 Hz, 2H), 2.47-2.36 (m, 1H), 1.98-1.91 (m, 2H), 1.70-1.65 (m, 3H), 1.54-1.42 (m, 4H).

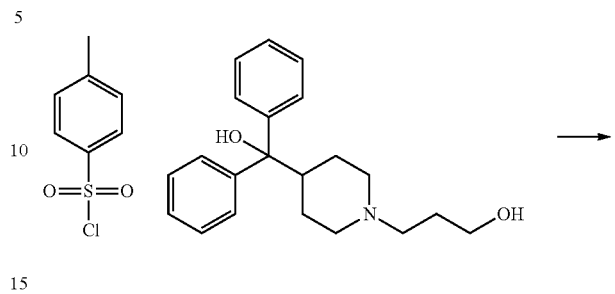

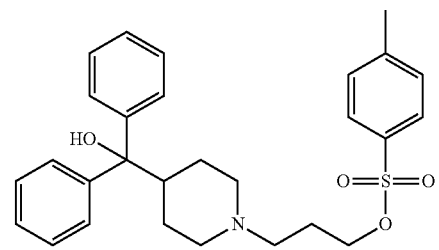

KSC-367-036

3-(4-(Hydroxydiphenylmethyl)piperidin-1-yl)propyl 4-methylbenzenesulfonate

Prepared with same method at KSC-352-093 using 3-(4-(hydroxydiphenylmethyl)piperidin-1-yl)propan-1-ol (KSC-367-033) (0.395 g, 1.214 mmol), 4-methylbenzene-1-sulfonyl chloride (0.347 g, 1.821 mmol), DCM (5 mL) and TEA (0.508 mL, 3.64 mmol) to produce pure 3-(4-(hydroxydiphenylmethyl)piperidin-1-yl)propyl 4-methylbenzenesulfonate (0.193 g, 0.402 mmol, 33% yield). $^1$H NMR (400 MHz, CDCl$_3$): δ 7.69-7.66 (m, 2H), 7.46-7.41 (m, 4H), 7.24-7.19 (m, 4H), 7.15-7.05 (m, 4H), 4.26-4.12 (m, 4H), 3.73-3.65 (m, 2H), 3.27-3.18 (m, 2H), 2.68-2.60 (m, 1H), 2.47-2.37 (m, 2H), 2.30 (s, 3H), 1.88-1.76 (m, 2H), 1.52-1.43 (m, 2H).

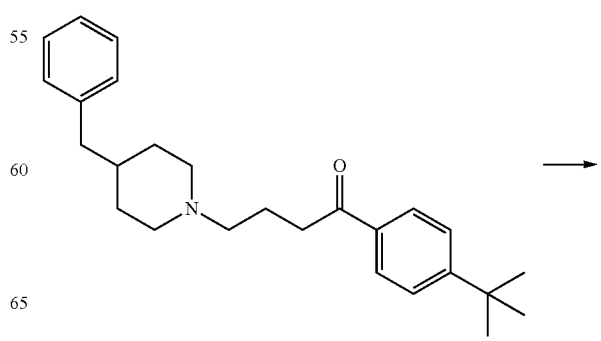

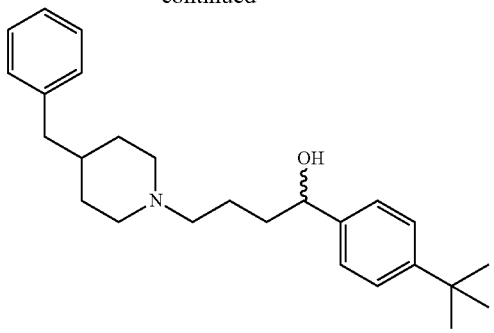

KSC-367-039

4-(4-Benzylpiperidin-1-yl)-1-(4-(tert-butyl)phenyl)butan-1-ol

Method B: 4-(4-benzylpiperidin-1-yl)-1-(4-(tert-butyl)phenyl)butan-1-one (KSC-367-032) (0.291 g, 0.771 mmol) and MeOH (5 mL) and sodium borohydride (0.117 g, 3.08 mmol) to produce pure 4-(4-benzylpiperidin-1-yl)-1-(4-(tert-butyl)phenyl)butan-1-ol (0.232 g, 0.611 mmol, 79% yield). $^1$H NMR (400 MHz, CDCl$_3$): δ 7.35-7.25 (m, 6H), 7.21-7.12 (m, 3H), 4.64-4.60 (m, 1H), 3.13-3.07 (m, 1H), 2.94-2.88 (m, 1H), 2.54 (d, J=7.0 Hz, 2H), 2.44-2.34 (m, 2H), 2.03-1.93 (m, 2H), 1.90-1.38 (m, 10H), 1.31 (s, 9H). $^{13}$C NMR (125 MHz, CDCl$_3$): δ 149.4, 142.9, 140.7, 129.1, 128.2, 125.8, 125.4, 125.0, 73.5, 59.0, 54.6, 52.9, 42.9, 40.1, 38.0, 34.4, 31.8, 31.6, 31.4, 24.3. LCMS Retention time: 4.330 min. LCMS purity 99.1%. HRMS (ESI): m/z calcd for C$_{26}$H$_{37}$NO [M+H]$^+$ 380.2875, found 380.2948.

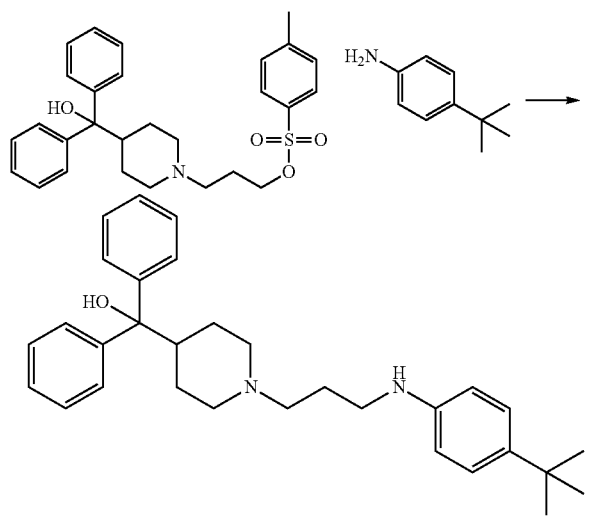

KSC-367-043

(1-(3-((4-(Tert-butyl)phenyl)amino)propyl)piperidin-4-yl)diphenylmethanol

To a vial was added the 3-(4-(hydroxydiphenylmethyl)piperidin-1-yl)propyl 4-methylbenzenesulfonate (KSC-367-036) (0.088 g, 0.183 mmol), 4-(tert-butyl)aniline (0.035 mL, 0.220 mmol) and TEA (0.038 mL, 0.275 mmol) with acetonitrile (3 mL). The reaction began to stir at 85° C. for 18 h and was then cooled to rt and diluted with saturated NaHCO$_3$ then extracted with EtOAc. The EtOAc was concentrated and purified by reverse-phase MPLC (10-100% MeCN:water) to produce pure (1-(3-((4-(tert-butyl)phenyl)amino) propyl)piperidin-4-yl)diphenylmethanol (0.038 g, 0.083 mmol, 45% yield). $^1$H NMR (400 MHz, CDCl$_3$): δ 7.50-7.46 (m, 4H), 7.33-7.28 (m, 4H), 7.21-7.16 (m, 4H), 6.51 (d, J=8.7 Hz, 2H), 3.13 (t, J=6.4 Hz, 2H), 3.02-2.96 (m, 2H), 2.49-2.41 (m, 3H), 2.15 (br s, 1H), 2.00-1.93 (m, 2H), 1.80-1.73 (m, 2H), 1.57-1.43 (m, 5H), 1.27 (s, 9H). $^{13}$C NMR (125 MHz, CDCl$_3$): δ 146.4, 145.9, 139.7, 128.2, 126.5, 125.9, 125.8, 112.4, 79.6, 57.4, 54.2, 44.2, 43.7, 33.8, 31.5, 26.6, 26.2. LCMS Retention time: 4.208 min. LCMS purity 100%. HRMS (ESI): m/z calcd for C$_{30}$H$_{38}$N$_2$O [M+H]$^+$ 457.6620, found 457.3194.

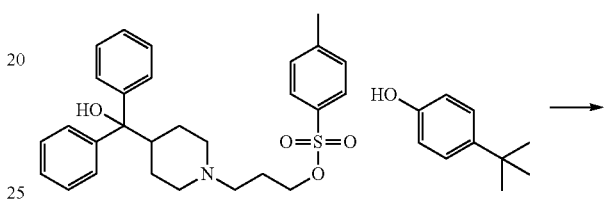

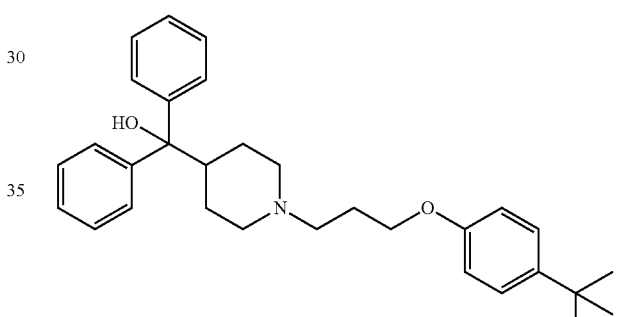

KSC-367-044

(1-(3-(4-(Tert-butyl)phenoxy)propyl)piperidin-4-yl)diphenylmethanol

To a vial was added the 3-(4-(hydroxydiphenylmethyl)piperidin-1-yl)propyl 4-methylbenzenesulfonate (KSC-367-036) (0.105 g, 0.219 mmol), 4-(tert-butyl)phenol (0.039 g, 0.263 mmol) and TEA (0.046 mL, 0.328 mmol) with acetonitrile (3 mL). The reaction stirred at 85° C. for 18 h then diluted with saturated NaHCO$_3$ and extracted with EtOAc. The EtOAc layer was concentrated and purified by RP MPLC (10-100% MeCN:water) to produce pure (1-(3-(4-(tert-butyl)phenoxy)propyl)piperidin-4-yl)diphenylmethanol (0.015 g, 0.033 mmol, 15% yield). $^1$H NMR (400 MHz, CDCl$_3$): δ 7.49-7.46 (m, 4H), 7.31-7.26 (m, 6H), 7.19-7.14 (m, 2H), 6.81 (d, J=8.8 Hz, 2H), 3.96 (t, J=6.4 Hz, 2H), 3.01-2.94 (m, 2H), 2.51-2.40 (m, 3H), 1.99-1.89 (m, 5H), 1.52-1.45 (m, 4H), 1.28 (s, 9H). $^{13}$C NMR (125 MHz, CDCl$_3$): δ 156.7, 145.9, 143.2, 128.1, 126.5, 126.1, 125.7, 116.3, 113.9, 79.5, 66.3, 60.4, 55.4, 54.1, 44.1, 34.0, 31.5, 29.7, 27.0, 26.4. LCMS Retention time: 4.293 min. LCMS purity 95.2%. HRMS (ESI): m/z calcd for C$_{30}$H37NO$_2$ [M+H]$^+$ 458.6470, found 458.3068.

175

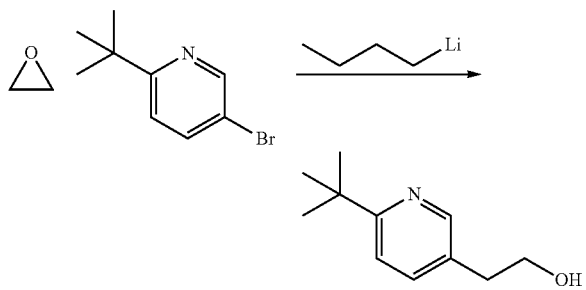

KSC-367-047

2-(6-(tert-butyl)pyridin-3-yl)ethanol

Prepared by same method as KSC-352-090 with 5-bromo-2-(tert-butyl)pyridine (0.303 g, 1.415 mmol), dry THF (10 mL), 2.5 M BuLi in hexanes (0.623 mL, 1.557 mmol) and ethylene oxide (1.415 ml, 3.54 mmol) (2.5-3.3M solution in THF) to produce pure 2-(6-(tert-butyl)pyridin-3-yl)ethanol (0.211 g, 1.177 mmol, 83% yield). $^1$H NMR (400 MHz, CDCl$_3$): δ 8.40 (br d, J=2.4 Hz, 1H), 7.48 (dd, J=8.2 Hz, 2.4 Hz, 1H), 7.26 (dd, J=8.2 Hz, 0.8 Hz, 1H), 3.85 (br t, J=6.0 Hz, 2H), 2.82 (t, J=6.5 Hz, 2H), 2.29 (br s, 1H), 1.33 (s, 9H).

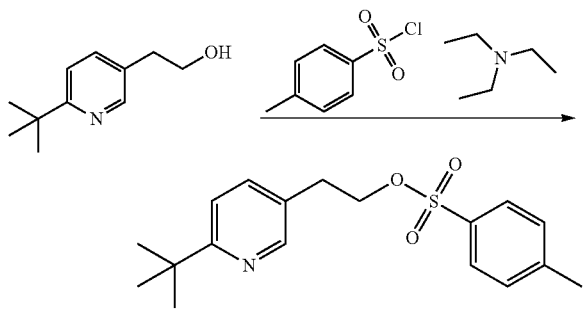

KSC-367-049

176

2-(6-(tert-butyl)pyridin-3-yl)ethyl 4-methylbenzenesulfonate

Prepared by same method at KSC-352-093 with 2-(6-(tert-butyl)pyridin-3-yl)ethanol (KSC-367-047) (0.211 g, 1.177 mmol), TEA (0.492 mL, 3.53 mmol) and DCM (2 mL) followed by p-toluenesulfonyl chloride (0.337 g, 1.766 mmol) to provide pure 2-(6-(tert-butyl)pyridin-3-yl)ethyl 4-methylbenzenesulfonate (0.260 g, 0.780 mmol, 66% yield). $^1$H NMR (400 MHz, CDCl$_3$): δ 8.29 (br d, J=2.4 Hz, 1H), 7.69 (d, J=8.3 Hz, 2H), 7.40 (dd, J=8.2 Hz, 2.4 Hz, 1H), 7.30-7.27 (m, 2H), 7.23 (dd, J=8.2 Hz, 0.8 Hz, 1H), 4.19 (t, J=6.9 Hz, 2H), 2.92 (t, J=6.8 Hz, 2H), 2.43 (s, 3H), 1.34 (s, 9H).

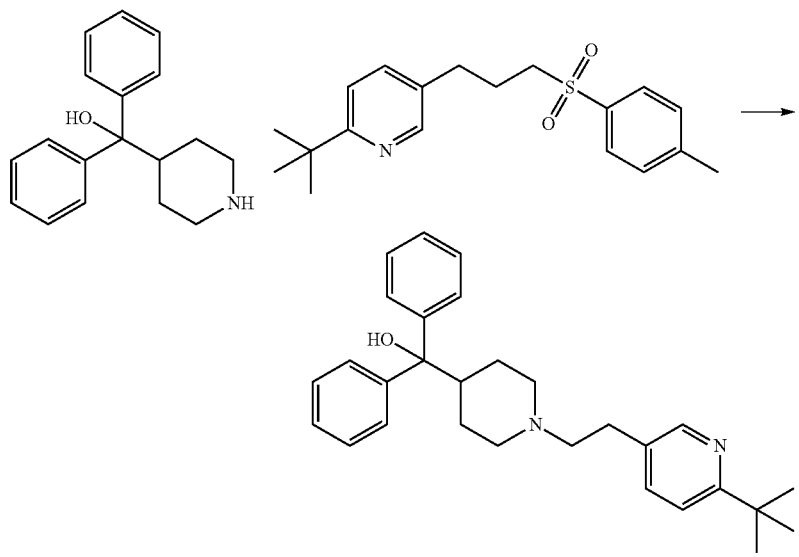

KSC-367-052

(1-(2-(6-(Tert-butyl)pyridin-3-yl)ethyl)piperidin-4-yl)diphenylmethanol

To a vial was added the diphenyl(piperidin-4-yl)methanol (0.250 g, 0.936 mmol), 2-(6-(tert-butyl)pyridin-3-yl)ethyl 4-methylbenzenesulfonate (KSC-367-049) (0.260 g, 0.780 mmol) and acetonitrile (5 mL). The TEA (0.163 mL, 1.170 mmol) was then added and the reaction stirred at 50° C. for 20 h and was then cooled to rt and diluted with saturated NaHCO$_3$ then extracted with DCM. The DCM layer was concentrated and purified by reverse-phase MPLC (10-100% MeCN:water) to produce pure (1-(2-(6-(tert-butyl)pyridin-3-yl)ethyl)piperidin-4-yl)diphenylmethanol (0.308 g, 0.719 mmol, 92% yield). $^1$H NMR (400 MHz, CDCl$_3$): δ 8.39-8.38 (m, 1H), 7.51-7.48 (m, 4H), 7.42 (dd, J=8.1 Hz, 2.4 Hz, 1H), 7.32-7.27 (m, 4H), 7.25-7.22 (m, 1H), 7.20-7.15 (m, 2H), 3.07-3.01 (m, 2H), 2.76-2.71 (m, 2H), 2.57-2.52 (m, 2H), 2.50-2.42 (m, 1H), 2.31 (br s, 1H), 2.09-2.01 (m, 2H), 1.57-1.48 (m, 4H), 1.35 (s, 9H). $^{13}$C NMR (125 MHz, CDCl$_3$): δ 166.9, 148.7, 145.9, 136.3, 132.3, 128.1, 126.5, 125.8, 118.6, 79.4, 60.2, 54.0, 44.1, 37.0, 30.3, 30.2, 26.4. LCMS Retention time: 3.802 min. LCMS purity 99.5%. HRMS (ESI): m/i calcd for C$_{29}$H$_{36}$N$_2$O [M+H]$^+$ 429.2828, found 429.2900.

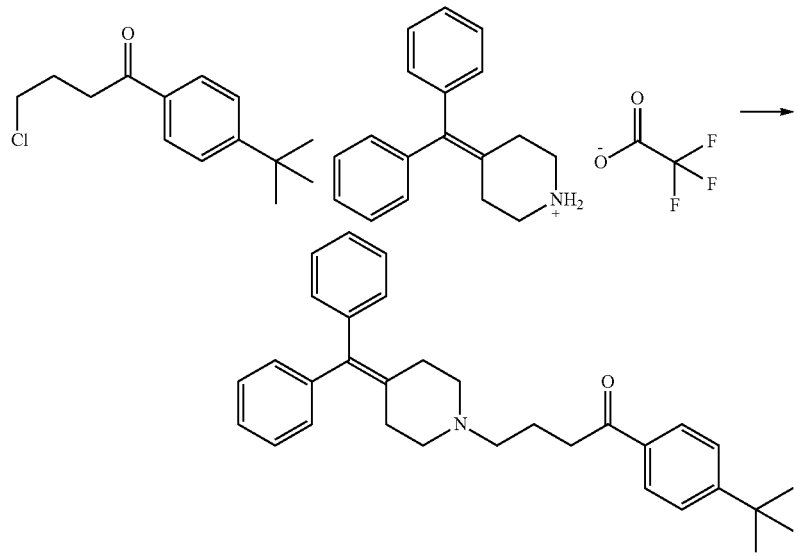

KSC-367-053

1-(4-(Tert-butyl)phenyl)-4-(4-(diphenylmethylene)piperidin-1-yl)butan-1-one

To a vial was added the 4-(diphenylmethylene)piperidin-1-ium 2,2,2-trifluoroacetate (KSC-367-027) (0.0475 g, 0.131 mmol), 1-(4-(tert-butyl)phenyl)-4-chlorobutan-1-one (0.037 g, 0.157 mmol) and TEA (0.046 mL, 0.327 mmol) in acetonitrile. The reaction stirred at 75° C. for 20 h. The reaction was removed from heat and diluted with saturated NaHCO$_3$, extracted with EtOAc. The EtOAc layer was concentrated and purified by reverse-phase MPLC (10-100% MeCN:water) to produce pure 1-(4-(tert-butyl)phenyl)-4-(4-(diphenylmethylene)piperidin-1-yl)butan-1-one (0.019 g, 0.042 mmol, 32% yield). $^1$H NMR (400 MHz, CDCl$_3$): δ 7.91 (d, J=8.2 Hz, 2H), 7.46 (d, J=8.3 Hz, 2H), 7.30-7.25 (m, 4H), 7.21-7.17 (m, 2H), 7.13-7.10 (m, 4H), 2.99 (t, J=7.2 Hz, 2H), 2.51-2.32 (m, 10H), 1.98-1.91 (m, 2H), 1.34 (s, 9H).

(1-(4-Chlorophenethyl)piperidin-4-yl)diphenylmethanol

To a vial was added the diphenyl(piperidin-4-yl)methanol (0.221 g, 0.827 mmol), 1-(2-bromoethyl)-4-chlorobenzene (0.165 g, 0.752 mmol), acetonitrile (4 mL) and TEA (0.157 mL, 1.128 mmol). The reaction stirred at 75° C. for 18 h then was cooled to rt and diluted with saturated NaHCO$_3$ and extracted with EtOAc. The EtOAc layer was concentrated and purified by reverse-phase MPLC (10-100% MeCN:water) to produce pure (1-(4-chlorophenethyl)piperidin-4-yl)diphenylmethanol (0.224 g, 0.552 mmol, 73% yield). $^1$H NMR (400 MHz, CDCl$_3$): δ 7.39-7.36 (m, 4H), 7.20-7.15 (m, 4H), 7.12-7.09 (m, 2H), 7.08-7.03 (m, 2H), 6.99-6.96 (m, 2H), 2.92-2.87 (m, 2H), 2.64-2.58 (m, 2H), 2.43-2.38 (m, 2H), 2.37-2.30 (m, 1H), 2.22 (br s, 1H), 1.95-1.88 (m, 2H), 1.44-1.35 (m, 4H). $^{13}$C NMR (125 MHz, CDCl$_3$): δ 145.9, 145.8, 138.9, 131.6, 129.9, 128.3, 128.0, 126.4, 125.7, 79.4, 79.3, 60.4, 57.0, 44.1, 33.0, 26.4. LCMS Retention time: 3.903 min. LCMS purity 99.6%. HRMS (ESI): m/z calcd for C$_{26}$H$_{28}$ClNO [M+H]$^+$ 406.1859, found 406.1932.

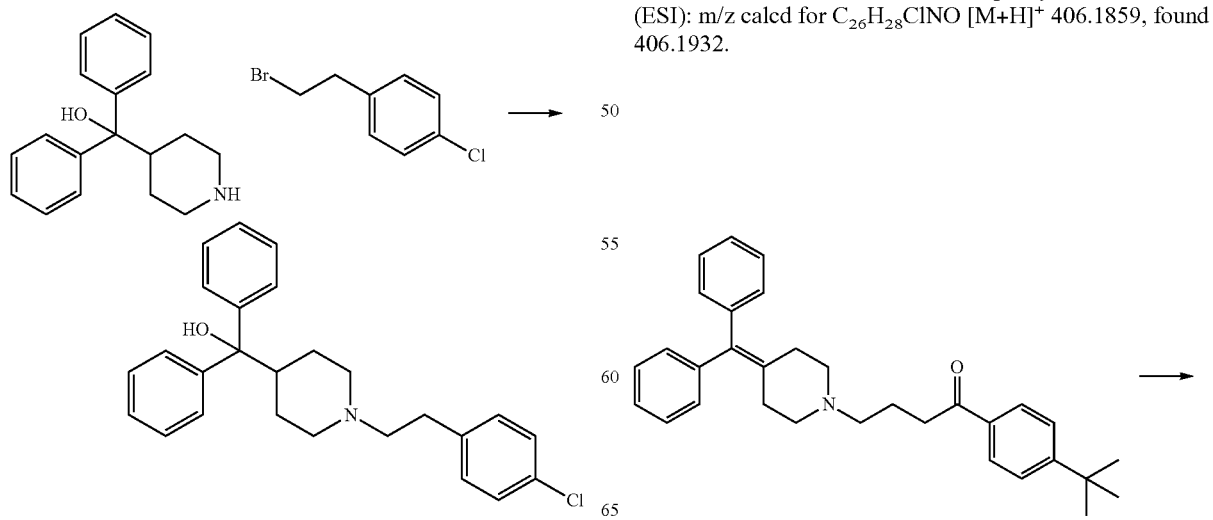

KSC-367-055

179

-continued

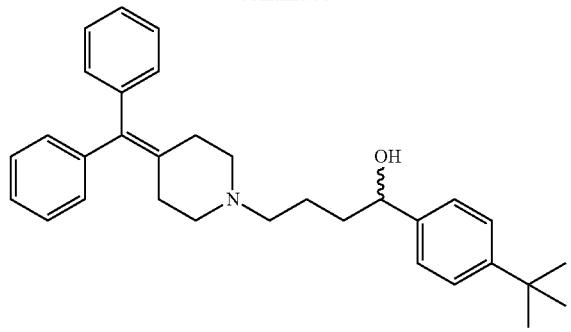

KSC-367-058

1-(4-(Tert-butyl)phenyl)-4-(4-(diphenylmethylene)piperidin-1-yl)butan-1-ol

Method B: 1-(4-(tert-butyl)phenyl)-4-(4-(diphenylmethylene)piperidin-1-yl)butan-1-one (KSC-367-053) (0.019 g, 0.042 mmol) and sodium borohydride (6.37 mg, 0.168 mmol) to produce pure 1-(4-(tert-butyl)phenyl)-4-(4-(diphenylmethylene)piperidin-1-yl)butan-1-ol (0.010 g, 0.022 mmol, 52% yield). $^1$H NMR (400 MHz, CDCl$_3$): δ 7.35-7.26 (m, 8H), 7.23-7.18 (m, 2H), 7.13-7.10 (m, 4H), 4.68-4.65 (m, 1H), 2.66-2.60 (m, 2H), 2.55-2.42 (m, 8H), 2.00-1.94 (m, 1H), 1.90-1.81 (m, 1H), 1.73-1.63 (m, 3H), 1.30 (s, 9H). $^{13}$C NMR (125 MHz, CDCl$_3$): δ 149.5, 142.7, 142.3, 136.4, 134.6, 129.7, 128.0, 126.4, 125.3, 125.0, 73.3, 58.7, 55.0, 39.6, 34.4, 31.6, 31.4, 31.1, 24.0, 22.6. LCMS Retention time: 4.454 min. LCMS purity 97.1%. HRMS (ESI): m/z calcd for C$_{32}$H$_{39}$NO [M+H]$^+$ 454.3032, found 454.3104.

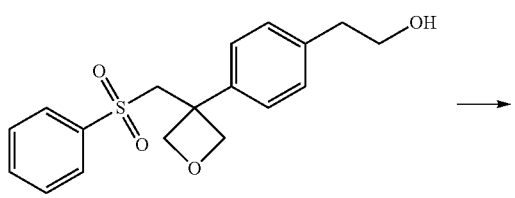

180

-continued

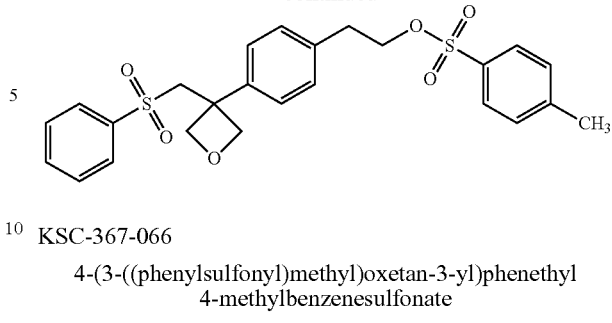

KSC-367-066

4-(3-((phenylsulfonyl)methyl)oxetan-3-yl)phenethyl 4-methylbenzenesulfonate

Prepared by the same method as KSC-352-093 with 2-(4-(3-((phenylsulfonyl)methyl)oxetan-3-yl)phenyl)ethanol (KSC-367-003) (0.104 g, 0.313 mmol), TEA (0.131 mL, 0.939 mmol) and DCM (2 mL) followed by p-toluenesulfonyl chloride (0.089 g, 0.469 mmol) to produce 4-(3-((phenylsulfonyl)methyl)oxetan-3-yl)phenethyl 4-methylbenzenesulfonate (0.041 g, 0.084 mmol, 27% yield). $^1$H NMR (400 MHz, CDCl$_3$): δ 7.75 (d, J=8.3 Hz, 2H), 7.57-7.46 (m, 4H), 7.36-7.32 (m, 4H), 7.02-6.96 (m, 3H), 5.00 (d, J=6.4 Hz, 2H), 4.93 (d, J=6.4 Hz, 2H), 4.17 (t, J=7.0 Hz, 2H), 4.01 (s, 2H), 2.90 (t, J=7.0 Hz, 2H), 2.45 (s, 3H).

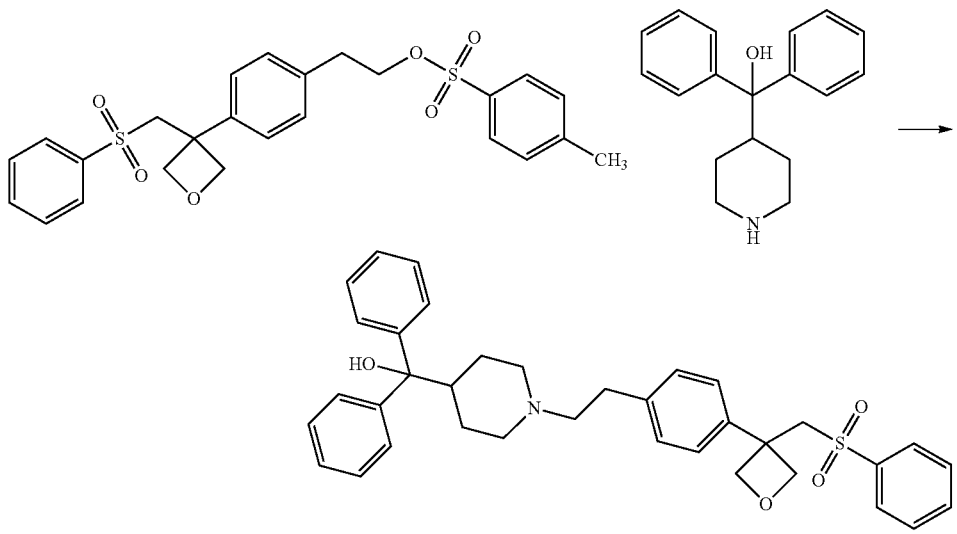

KSC-367-069

Diphenyl(1-(4-(3-((phenylsulfonyl)methyl)oxetan-3-yl)phenethyl)piperidin-4-yl)methanol To a vial was added the 4-(3-((phenylsulfonyl)methyl) oxetan-3-yl)phenethyl 4-methylbenzenesulfonate (KSC-367-066) (0.041 g, 0.084 mmol) and diphenyl(piperidin-4-yl)methanol (0.025 g, 0.093 mmol) in acetonitrile. The TEA (0.018 ml, 0.126 mmol) was then added and the reaction stirred at 50° C. for 18 h. The reaction was removed from heat and cooled to rt then diluted with saturated NaHCO$_3$. The reaction was then extracted with EtOAc (3×5 mL) and the EtOAc layer was dried with MgSO$_4$, filtered and concentrated. The crude residue was purified by reverse-phase MPLC (15 min, 10-100% MeCN:water) to produce diphenyl (1-(4-(3 ((phenylsulfonyl) methyl)oxetan-3-yl)phenethyl)piperidin-4-yl)methanol (0.024 g, 0.041 mmol, 49% yield). $^1$H NMR (400 MHz, CDCl$_3$): δ 7.53-7.43 (m, 6H), 7.33-7.27

(m, 7H), 7.21-7.16 (m, 2H), 7.04 (d, J=8.2 Hz, 2H), 6.96 (d, J=8.2 Hz, 2H), 5.02 (d, J=6.4 Hz, 2H), 4.92 (d, J=6.4 Hz, 2H), 4.01 (s, 2H), 3.08-3.02 (m, 2H), 2.74-2.69 (m, 2H), 2.56-2.44 (m, 3H), 2.10-2.02 (m, 2H), 1.60-1.50 (m, 5H).

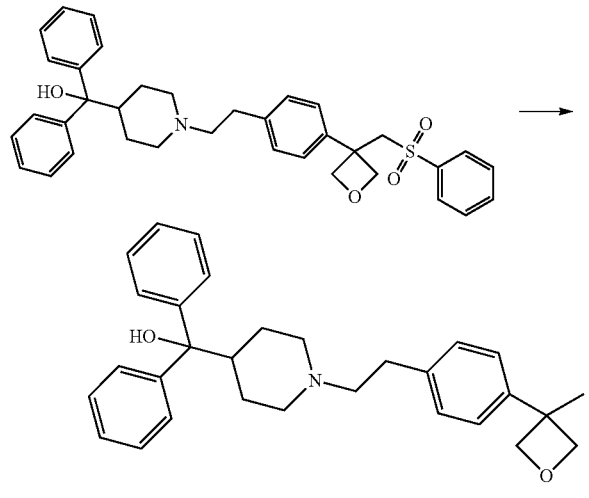

KSC-367-072

(1-(4-(3-Methyloxetan-3-yl)phenethyl)piperidin-4-yl)diphenylmethanol

To a vial was added the diphenyl(1-(4-(3-((phenylsulfonyl)methyl)oxetan-3-yl)phenethyl)piperidin-4-yl)methanol (KSC-367-069) (0.024 g, 0.041 mmol) and MeOH (10 mL) and the reaction as heated to 50° C. The magnesium was added in 3 additions (0.016 g, 0.066 mmol, 16 equiv) 1.5 h apart. The reaction was removed from heat 1.5 h after the final magnesium addition, cooled to rt and poured into 1.0 M HCl with ice. The aqueous layer was then extracted with DCM (3×10 mL) and the organic layers were combined and dried with MgSO$_4$, filtered and concentrated then purified by reverse-phase MPLC (15 min, 10-100% MeCN:water). To produce (1-(4-(3-methyloxetan-3-yl)phenethyl)piperidin-4-yl)diphenylmethanol (0.0045 g, 10.19 µmol, 24.70% yield) as a light brown solid. $^1$H NMR (400 MHz, CDCl$_3$): δ 7.51-7.47 (m, 4H), 7.32-7.27 (m, 4H), 7.21-7.16 (m, 4H), 7.13-7.10 (m, 2H), 4.95 (d, J=5.5 Hz, 2H), 4.61 (d, J=5.5 Hz, 2H), 3.09-3.02 (m, 2H), 2.81-2.75 (m, 2H), 2.59-2.54 (m, 2H), 2.50-2.42 (m, 1H), 2.16 (br s, 1H), 2.09-2.00 (m, 2H), 1.71 (s, 3H), 1.56-1.48 (m, 4H). $^{13}$C NMR (125 MHz, CDCl$_3$): δ 145.9, 144.1, 138.4, 128.8, 128.2, 126.5, 125.8, 125.1, 83.8, 79.5, 60.7, 54.1, 44.1, 43.1, 33.3, 27.8, 26.4. LCMS Retention time: 3.652 min. LCMS purity 97.9%. HRMS (ESI): m/z calcd for C$_{30}$H$_{35}$NO$_2$ [M+H]$^+$ 442.2668, found 442.2741.

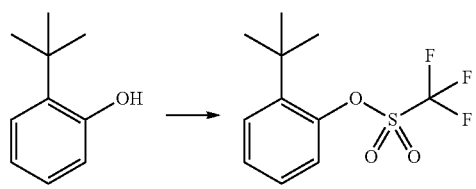 [SMILES: CC(C)(C)c1ccccc1O ; CC(C)(C)c1ccccc1OS(=O)(=O)C(F)(F)F]

KSC-367-088

2-(Tert-butyl)phenyl trifluoromethanesulfonate

To a vial was added the 2-(tert-butyl)phenol (1.0 ml, 6.51 mmol) and DCM (4 mL) followed by pyridine (1.053 mL, 13.02 mmol). The reaction was then cooled to 0° C. and the triflic anhydride (1.320 mL, 7.81 mmol) was added dropwise and the reaction stirred for 2 h. The reaction was then allowed to warm to rt and was diluted with DCM and quenched with 1.0 M HCl. The DCM layer was collected and washed with saturated NaHCO$_3$ and brine. The organic layer was then dried (MgSO$_4$), filtered and adsorbed to silica and purified by MPLC (0-25% EtOAc:hex) to produce pure 2-(tert-butyl)phenyl trifluoromethanesulfonate (1.66 g, 5.88 mmol, 90% yield). $^1$H NMR (400 MHz, CDCl$_3$): δ 7.49-7.46 (m, 1H), 7.37-7.34 (m, 1H), 7.31-7.27 (m, 2H), 1.43 (s, 9H).

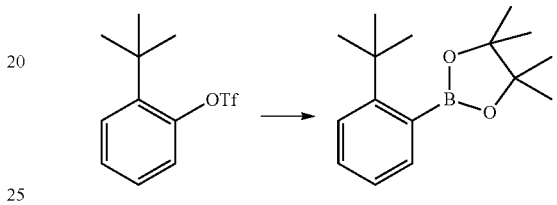

KSC-381-009

2-(2-(Tert-butyl)phenyl)-4,4,5,5-tetramethyl-1,3,2-dioxaborolane

To a flame-dried vial was added molecular sieves and 2-(tert-butyl)phenyl trifluoromethanesulfonate (KSC-367-088) (0.475 g, 1.683 mmol) and 1,1'-Bis(diphenylphosphino)ferrocenedichloropalladium(II) (0.042 g, 0.050 mmol). The vial was evacuated with argon 3 times and then dioxane (1 mL), TEA (0.704 mL, 5.05 mmol) and 4,4,5,5-tetramethyl-1,3,2-dioxaborolane (0.732 mL, 5.05 mmol) were added via syringe. The reaction stirred at reflux (100° C.) for 2 h. The reaction was then removed from heat and diluted with water then extracted with DCM (3×5 mL). The DCM layer was then washed again with water (3×10 mL). The DCM layer was dried with MgSO$_4$, filtered and concentrated. The residue was diluted with hexanes and filtered through MgSO$_4$ to remove the residual Pd complex. The hexanes layer was then concentrated to produce pure 2-(2-(tert-butyl)phenyl)-4,4,5,5-tetramethyl-1,3,2-dioxaborolane (0.093 g, 0.357 mmol, 86% yield). $^1$H NMR (400 MHz, CDCl$_3$): δ 7.45 (dd, J=7.2 Hz, 1.2 Hz, 1H), 7.41-7.39 (m, 1H), 7.29 (td, J=7.6 Hz, 2.0 Hz, 1H), 7.14 (td, J=7.6 Hz, 2.0 Hz, 1H), 1.41 (s, 9H), 1.38 (s, 12H).

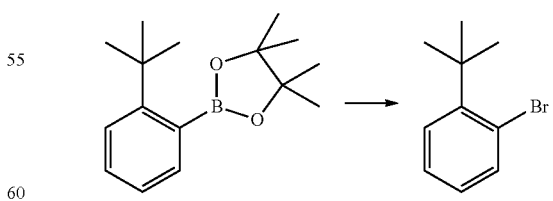

KSC-381-011

1-Bromo-2-(tert-butyl)benzene

To a vial was added the 2-(2-(tert-butyl)phenyl)-4,4,5,5-tetramethyl-1,3,2-dioxaborolane (KSC-381-009) (0.180 g, 0.692 mmol) and MeOH (1.5 mL). The copper (II) bromide (0.464 g, 2.075 mmol) was then dissolved in water and added to the reaction then stirred at 80° C. for 24 h. The reaction was then removed from heat and diluted with water and extracted with EtOAc. The EtOAc was dried with MgSO$_4$, filtered and concentrated to produce 1-bromo-2-(tert-butyl)benzene (0.103 g, 0.483 mmol, 70% yield) as a brown liquid. $^1$H NMR (400 MHz, CDCl$_3$): δ 7.59 (dd, J=8.0 Hz, 1.6 Hz, 1H), 7.44 (dd, J=8.0 Hz, 1.6 Hz, 1H), 7.24 (td, J=7.6 Hz, 2.0 Hz, 1H), 7.02 (td, J=7.6 Hz, 2.0 Hz, 1H), 1.51 (s, 9H).

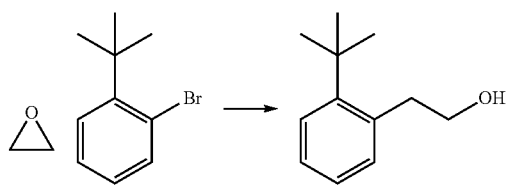

KSC-381-015

2-(2-(Tert-butyl)phenyl)ethanol

Prepared by same method as KSC-352-090 with 1-bromo-2-(tert-butyl)benzene (KSC-381-011) (0.147 g, 0.690 mmol), dry THF, 2.5 M BuLi in hexanes (0.303 ml, 0.759 mmol) and then ethylene oxide (0.690 ml, 1.724 mmol) (2.5-3.3M solution in THF) to produce pure 2-(2-(tert-butyl)phenyl)ethanol (0.018 g, 0.101 mmol, 14.64% yield) as a clear oil. $^1$H NMR (400 MHz, CDCl$_3$): δ 7.43-7.37 (m, 1H), 7.23-7.19 (m, 1H), 7.18-7.14 (m, 2H), 3.90 (t, J=7.6 Hz, 2H), 3.19 (t, J=7.6 Hz, 2H), 1.44 (s, 9H).

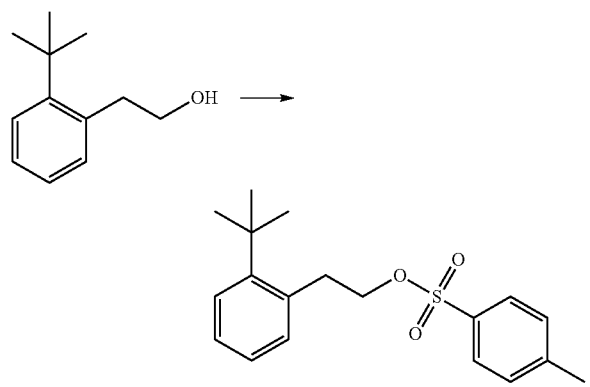

KSC-381-018

2-(Tert-butyl)phenethyl 4-methylbenzenesulfonate

Prepared according to same procedure as KSC-352-093 with 2-(2-(tert-butyl)phenyl)ethanol (KSC-381-015) (0.018 g, 0.101 mmol), TEA (0.042 mL, 0.303 mmol) and DCM (2 mL) followed by p-toluenesulfonyl chloride (0.029 g, 0.151 mmol) to provide pure 2-(tert-butyl)phenethyl 4-methylbenzenesulfonate (0.022 g, 0.066 mmol, 66% yield) and a clear oil. $^1$H NMR (400 MHz, CDCl$_3$): δ 7.76 (d, J=8.0 Hz, 2H), 7.37-7.31 (m, 3H), 7.17-7.04 (m, 3H), 4.19 (t, J=7.6 Hz, 2H), 3.25 (t, J=7.6 Hz, 2H), 2.44 (s, 3H), 1.33 (s, 9H).

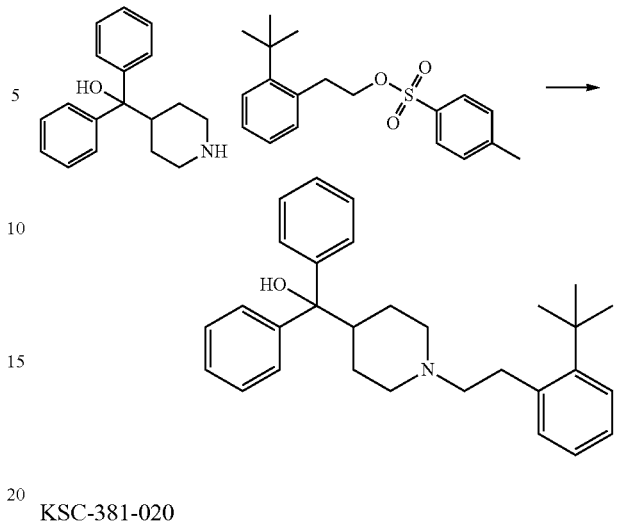

KSC-381-020

(1-(2-(Tert-butyl)phenethyl)piperidin-4-yl)diphenylmethanol

To a vial was added the 2-(tert-butyl)phenethyl 4-methylbenzenesulfonate (KSC-381-018) (0.022 g, 0.066 mmol), diphenyl(piperidin-4-yl)methanol (0.018 g, 0.066 mmol) and acetonitrile. The TEA (0.014 mL, 0.099 mmol) was added and the reaction stirred at 85° C. for 20 h. The reaction was cooled to rt and diluted with water then extracted with EtOAc. The EtOAc layer was concentrated and the crude product was purified by reverse-phase MPLC (10-100% MeCN:water) to produce the pure (1-(2-(tert-butyl)phenethyl) piperidin-4-yl)diphenylmethanol (0.013 g, 0.030 mmol, 46% yield). $^1$H NMR (400 MHz, CDCl$_3$): δ 7.51-7.48 (m, 4H), 7.37-7.28 (m, 5H), 7.21-7.09 (m, 5H), 3.15-3.04 (m, 4H), 2.65-2.60 (m, 2H), 2.52-2.42 (m, 1H), 2.17-2.08 (m, 3H), 1.60-1.53 (m, 4H), 1.41 (s, 9H). $^{13}$C NMR (125 MHz, CDCl$_3$): δ 147.7, 145.9, 138.5, 132.1, 128.2, 126.5, 126.1, 125.9, 125.84, 125.79, 79.5, 61.7, 54.2, 44.2, 35.7, 31.7, 29.7, 26.4. LCMS Retention time: 4.200 min. LCMS purity 99.3%. HRMS (ESI): m/z calcd for C$_{30}$H$_{37}$NO [M+H]$^+$ 428.2875, found 428.2948.

Bacterial Strains and Conditions

All strains used to evaluate the antimicrobial activity of terfenadine and corresponding structural derivatives are shown below in Table 5. S. aureus strain UAMS-1 is an osteomyelitis clinical isolate (Gillaspy et al. "Role of the accessory gene regulator (agr) in pathogenesis of staphylococcal osteomyelitis. Infect. Immun. 63:3373-3380 (1995)), whereas ciprofloxacin-resistant strains CRC118 and CRC61 are spontaneous ciprofloxacin-resistant derivatives of UAMS-1 that were selected by growth on Mueller-Hinton agar (MHA) (Becton, Dickinson & Company, Franklin Lakes, N.J.) at 1.5×MIC ciprofloxacin (0.75 μg/ml).

TABLE 5

| Bacterial Strains Used in Terfenadine Study | | |
|---|---|---|
| Species | Strain | Source |
| S. aureus | UAMS-1 | 1 |
|  | CRC61 | Dunman Lab, URMC |
|  | CRC118 | Dunman Lab, URMC |

Minimum Inhibitory Concentration (MIC) Testing

Minimum Inhibitory Concentration (MIC) testing was performed to determine the minimum concentration of test compound that is necessary to inhibit visible growth of bacteria according to Clinical and Laboratory Standards (CLSI) guidelines (Clinical and Laboratory Standards Institute (CLSI). Methods for Dilution Antimicrobial Susceptibility Tests for Bacteria That Grow Aerobically; Approved Standard—Ninth Edition. CLSI document M07-A9. 2012. Clinical and Laboratory Standards Institute, 940 West Valley Road, Suite 1400, Wayne, Pa. 19087-1898 USA.) To do so, $10^5$ colony forming units of an overnight bacterial culture were seeded into individual wells of 96-well round-bottom microtiter plates containing 88 µl of MHB medium. To the first column, 2 µl of the test compound's corresponding solvent was also added to each well (negative control). To the next ten columns, 2 µl of the test compound (dissolved in DMSO for terfenadine and its derivatives or sterile water for ciprofloxacin) was added in increasing 2-fold increments of 0.5 µg/ml to 256 µg/ml to each successive well. Each test compound was evaluated in duplicate. Plates were incubated at 37° C. incubator for 16 h at which point the minimum inhibitory concentration was determined to be the lowest concentration of test compound that inhibited bacterial growth, as judged by the unaided eye.

S. aureus DNA Gyrase Supercoiling Assay (TopoGEN)

The gyrase supercoiling assays were performed to determine if test compounds interfered with S. aureus DNA gyrase activity, following the manufacturer's recommendations (TopoGEN). Reactions (20 µl) contained kit provided assay buffer, ATP, potassium glutamate, relaxed plasmid DNA (0.4 µg/ml), 2 Units of S. aureus DNA gyrase, and various amounts of test compound. Reactions were incubated at 37° C. for 30 min and then stopped by the addition of 10% SDS, filtered through 0.025 µm Millipore membrane filters in a 10 mM Tris-HCl buffer (pH 8), and electrophoresed in a 1% agarose TAE gel. Gels were stained with 0.5 µg/ml ethidium bromide and images were analyzed using densitometry (Image J, NIH). The $IC_{50}$ values for each test compound was determined to be the compound concentration that inhibited S. aureus DNA gyrase activity by 50%.

S. aureus Topoisomerase IV Decatenation Assay (Inspiralis)

A Topoisomerase IV assay was performed on test compounds to determine if they interfered with the ability of S. aureus topoisomerase IV to decatenate kDNA, according to the recommendations of the manufacturer (Inspiralis). To do so, 0.25 U S. aureus topoisomerase IV enzyme was mixed with 200 ng kDNA in kit provided reaction buffer, in the absence or presence of various concentrations of test compounds at 37° C. for 30 min. The reaction was stopped by the addition of STEB stop buffer and 30 µl of 24:1 chlorform: isoamyl alcohol (total volume 90 µl). Reaction products then electrophoresed in a 1% agarose TAE gel, stained with 0.5 µg/ml ethidium bromide and images were analyzed using densitometry (Image J, NIH). The $IC_{50}$ value for each test compound was determined as the compound concentration that inhibited S. aureus topoisomerase IV activity by 50%.

The results are set forth in Table 6.

TABLE 6

| Compound # | KUC Registry Number | Molecular Weight (g/mol) | Structure | MIC (µg/mL) | Gyrase IC50 (µg/mL) | Topoisomerase iv IC50 (µg/mM) |
|---|---|---|---|---|---|---|
| Terfenadine | N/Ac | 471.673 | 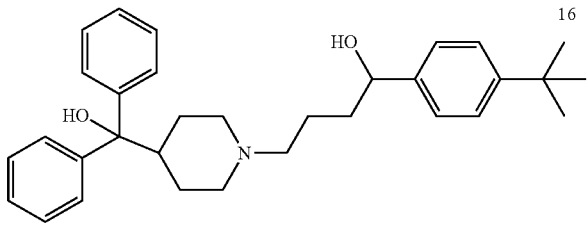 [SMILES: CC(C)(C)c1ccc(C(O)CCCN2CCC(C(O)(c3ccccc3)c3ccccc3)CC2)cc1] | 16 | 190.00 | 206.67 |
| 1 | KSC-335-012 | 457.647 | 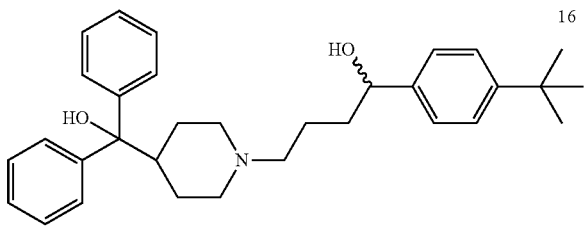 [SMILES: CC(C)(C)c1ccc(C(O)CCCN2CCC(C(O)(c3ccccc3)c3ccccc3)CC2)cc1] | 16 | 126.67 | 273.33 |
| 2 | KSC-335-013 | 485.7 | 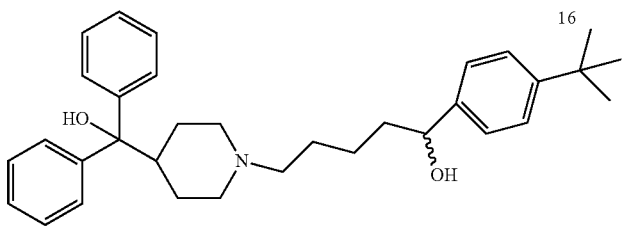 [SMILES: CC(C)(C)c1ccc(C(O)CCCCN2CCC(C(O)(c3ccccc3)c3ccccc3)CC2)cc1] | 16 | 100.00 | 133.33 |

TABLE 6-continued

| Compound # | KUC Registry Number | Molecular Weight (g/mol) | Structure | MIC (μg/mL) | Gyrase IC50 (μg/mL) | Topoisomerase iv IC50 (μg/mM) |
|---|---|---|---|---|---|---|
| 3 | KSC-335-014 | 471.673 | 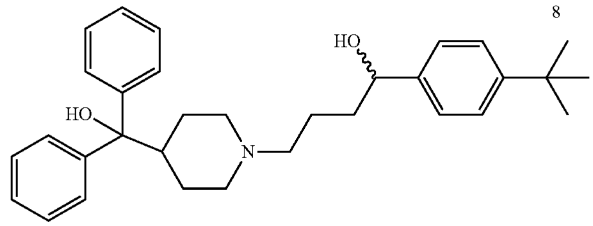 [SMILES: CC(C)(C)c1ccc(C(O)CCCN2CCC(C(O)(c3ccccc3)c3ccccc3)CC2)cc1] | 8 | 330.00 | 103.33 |
| 4 | KSC-335-015 | 450.012 | 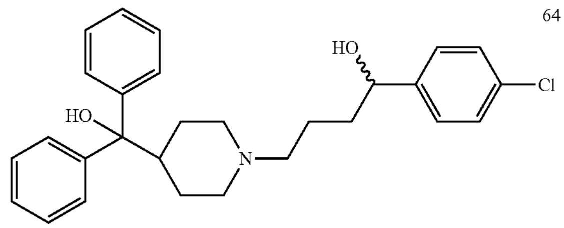 | 64 | 133.33 | >333 |
| 5 | KSC-335-016 | 457.647 | 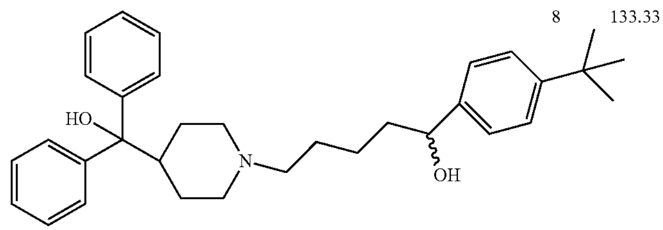 | 8 | 133.33 | 333.00 |
| 6 | KSC-335-021 | 415.567 | 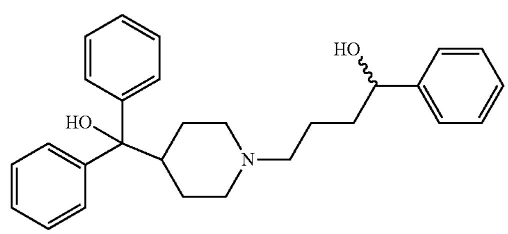 [SMILES: OC(CCCN1CCC(C(O)(c2ccccc2)c2ccccc2)CC1)c1ccccc1] | 256 | >500 | >333 |
| 7 | KSC-335-030 | 445.593 | 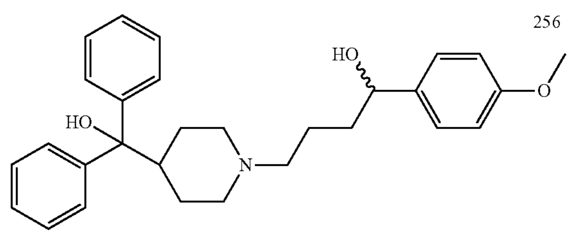 [SMILES: COc1ccc(C(O)CCCN2CCC(C(O)(c3ccccc3)c3ccccc3)CC2)cc1] | 256 | >500 | >333 |
| 8 | KSC-335-031 | 433.558 | 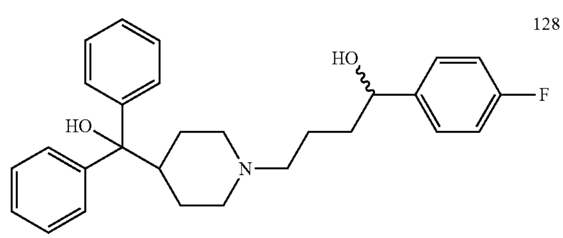 | 128 | >500 | >333 |

TABLE 6-continued

| Compound # | KUC Registry Number | Molecular Weight (g/mol) | Structure | MIC (μg/mL) | Gyrase IC50 (μg/mL) | Topoisomerase iv IC50 (μg/mM) |
|---|---|---|---|---|---|---|
| 9 | KSC-335-032 | 494.463 | 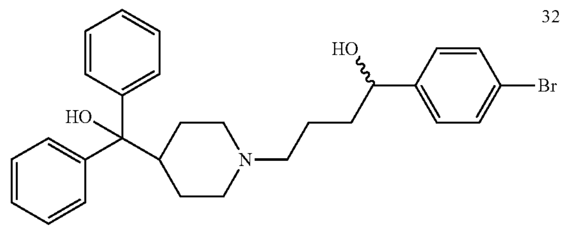 [SMILES: OC(CCCN1CCC(C(O)(c2ccccc2)c2ccccc2)CC1)c1ccc(Br)cc1] | 32 | >500 | >333 |
| 10 | KSC-335-041 | 455.674 | 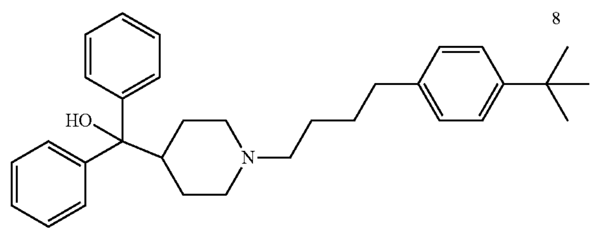 [SMILES: CC(C)(C)c1ccc(CCCCN2CCC(C(O)(c3ccccc3)c3ccccc3)CC2)cc1] | 8 | 93.33 | 320.00 |
| 11 | KSC-335-007 | 469.658 | 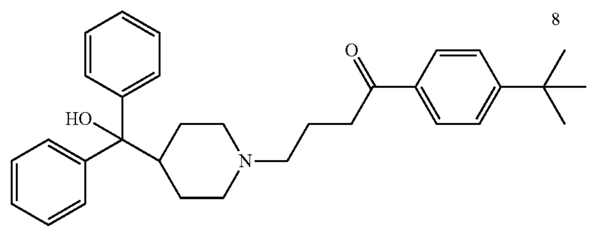 | 8 | 93.33 | 110.00 |
| 12 | KSC-337-069 | 471.673 | 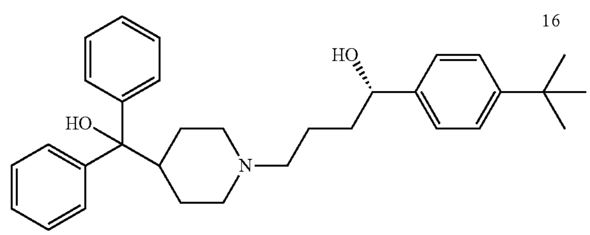 [SMILES: CC(C)(C)c1ccc([C@@H](O)CCCN2CCC(C(O)(c3ccccc3)c3ccccc3)CC2)cc1] | 16 | 126.67 | 100.00 |
| 13 | KSC-335-070 | 471.673 | 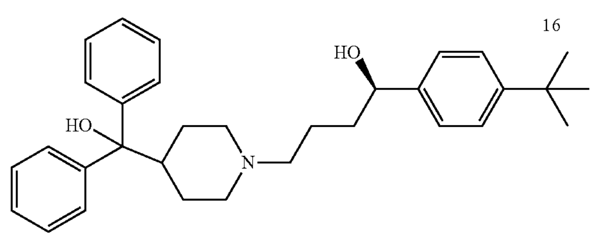 | 16 | 410.00 | 110.00 |
| 14 | KSC-335-077 | 529.594 | 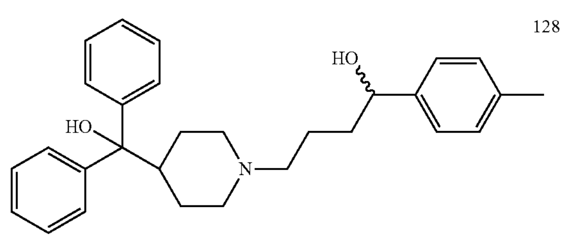 | 128 | >500 | >333 |

TABLE 6-continued

| Compound # | KUC Registry Number | Molecular Weight (g/mol) | Structure | MIC (μg/mL) | Gyrase IC50 (μg/mL) | Topoisomerase iv IC50 (μg/mM) |
|---|---|---|---|---|---|---|
| 15 | KSC-335-080 | 515.683 | 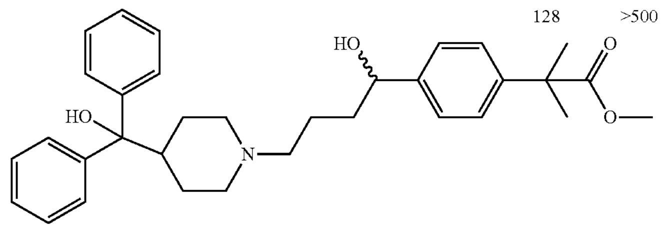 [SMILES: COC(=O)C(C)(C)c1ccc(C(O)CCCN2CCC(C(O)(c3ccccc3)c3ccccc3)CC2)cc1] | 128 | >500 | >333 |
| 16 | KSC-335-081 | 501.656c | 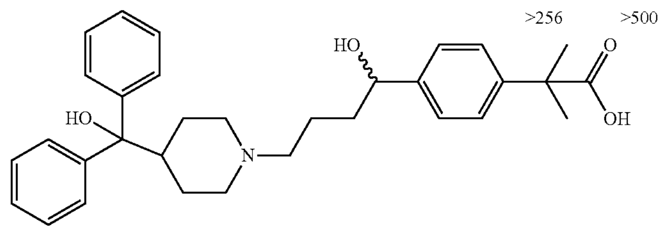 | >256 | >500 | >333 |
| 17 | KSC-342-010 | 443.62 | 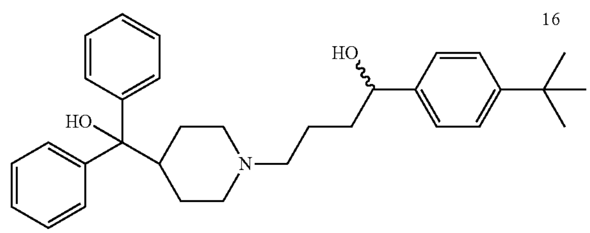 | 16 | 73.33 | 100.00 |
| 18 | KSC-342-017 | 473.603 | 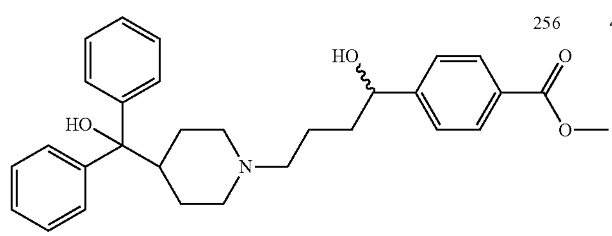 [SMILES: COC(=O)c1ccc(C(O)CCCN2CCC(C(O)(c3ccccc3)c3ccccc3)CC2)cc1] | 256 | 440.00 | 333 |
| 19 | KSC-342-021 | 459.577 | 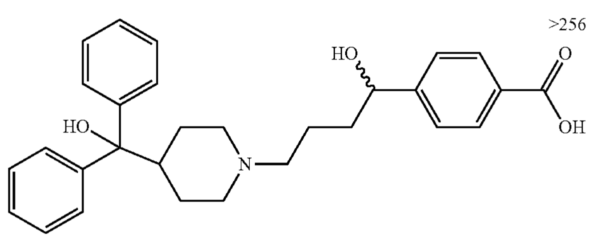 [SMILES: O=C(O)c1ccc(C(O)CCCN2CCC(C(O)(c3ccccc3)c3ccccc3)CC2)cc1] | >256 | >500 | >333 |
| 20 | KSC-342-006 | 441.604 | 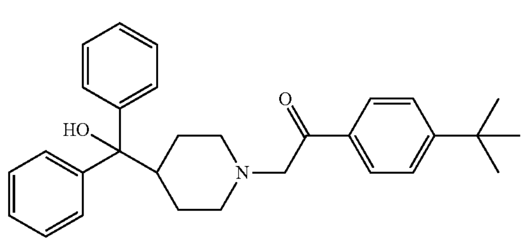 [SMILES: CC(C)(C)c1ccc(C(=O)CN2CCC(C(O)(c3ccccc3)c3ccccc3)CC2)cc1] | >256 | 73.33 | 246.67 |

TABLE 6-continued

| Compound # | KUC Registry Number | Molecular Weight (g/mol) | Structure | MIC (µg/mL) | Gyrase IC50 (µg/mL) | Topoisomerase iv IC50 (µg/mM) |
|---|---|---|---|---|---|---|
| 21 | KSC-335-008 | 455.631 | 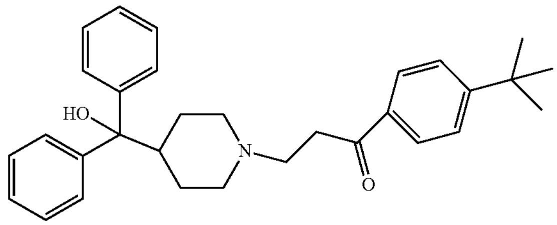 [SMILES: CC(C)(C)c1ccc(C(=O)CCN2CCC(C(O)(c3ccccc3)c3ccccc3)CC2)cc1] | 32 | 90.00 | 133.33 |
| 22 | KSC-342-080 | 441.647 | 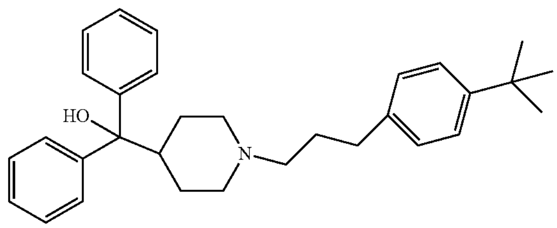 [SMILES: CC(C)(C)c1ccc(CCCN2CCC(C(O)(c3ccccc3)c3ccccc3)CC2)cc1] | 8 | 93.33 | 100.00 |
| 23 | KSC-342-081 | 427.621 | 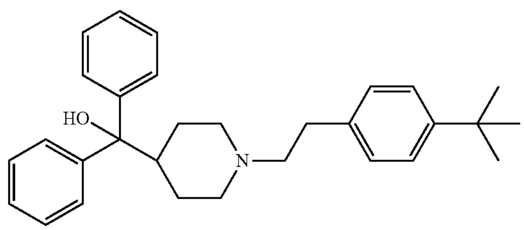 [SMILES: CC(C)(C)c1ccc(CCN2CCC(C(O)(c3ccccc3)c3ccccc3)CC2)cc1] | 8 | 93.33 | 146.67 |
| 24 | KSC-342-088 | 470.689 | 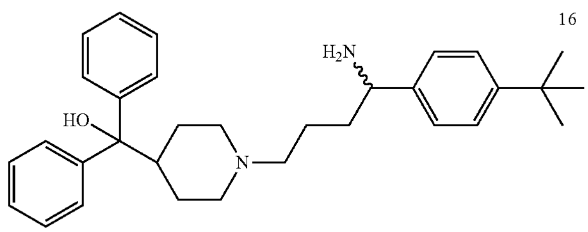 | 16 | >500 | 333 |
| 25 | KSC-348-002 | 491.633 | 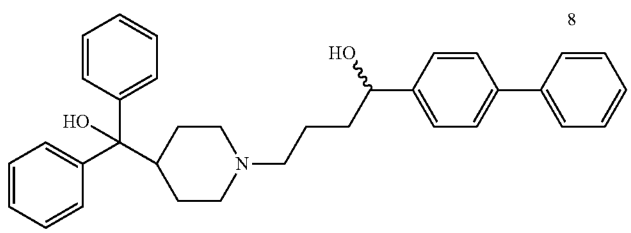 [SMILES: OC(CCCN1CCC(C(O)(c2ccccc2)c2ccccc2)CC1)c1ccc(-c2ccccc2)cc1] | 8 | 13.33 | 100.00 |
| 26 | KSC-348-050 | 413.594 | 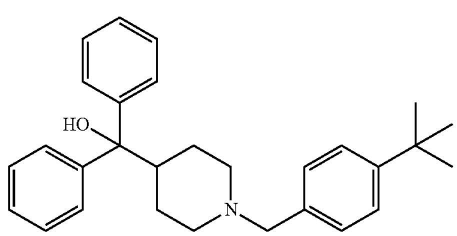 [SMILES: CC(C)(C)c1ccc(CN2CCC(C(O)(c3ccccc3)c3ccccc3)CC2)cc1] | 8 | 90.00 | 213.33 |

TABLE 6-continued

| Compound # | KUC Registry Number | Molecular Weight (g/mol) | Structure | MIC (µg/mL) | Gyrase IC50 (µg/mL) | Topoisomerase iv IC50 (µg/mM) |
|---|---|---|---|---|---|---|
| 27 | KSC-348-049 | 427.578 | 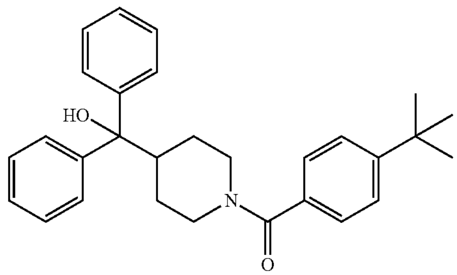 [SMILES: CC(C)(C)c1ccc(C(=O)N2CCC(C(O)(c3ccccc3)c3ccccc3)CC2)cc1] | >256 | 93.33 | >333 |
| 28 | KSC-348-058 | 401.541 | 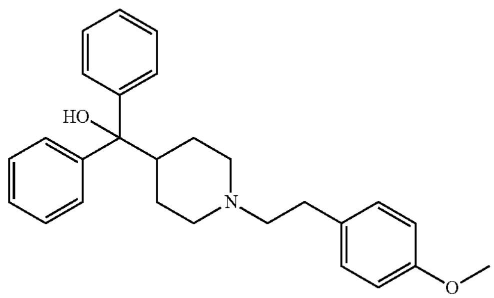 [SMILES: COc1ccc(CCN2CCC(C(O)(c3ccccc3)c3ccccc3)CC2)cc1] | 256 | >333 | >333 |
| 29 | KSC-352-060 | 416.512 | 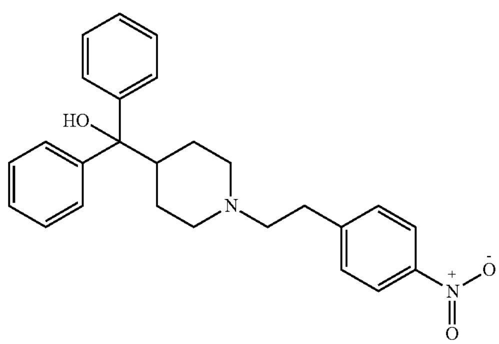 | 64 | 263.33 | >333 |
| 30 | KSC-352-061 | 450.411 | 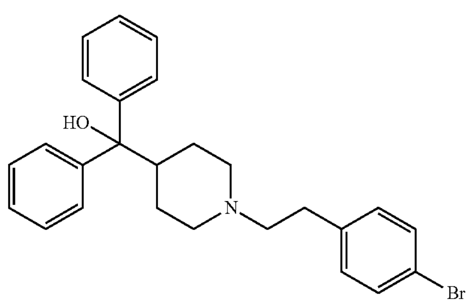 [SMILES: OC(c1ccccc1)(c1ccccc1)C1CCN(CCc2ccc(Br)cc2)CC1] | 16 | 246.67 | 260.00 |
| 31 | KSC-352-066 | 395.577 | 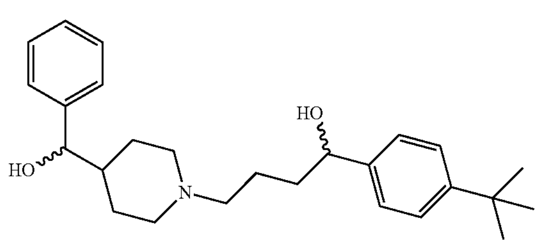 [SMILES: CC(C)(C)c1ccc(C(O)CCCN2CCC(C(O)c3ccccc3)CC2)cc1] | 128 | 333 | 333 |

TABLE 6-continued

| Compound # | KUC Registry Number | Molecular Weight (g/mol) | Structure | MIC (µg/mL) | Gyrase IC50 (µg/mL) | Topoisomerase iv IC50 (µg/mM) |
|---|---|---|---|---|---|---|
| 32 | KSC-352-063 | 447.611 | 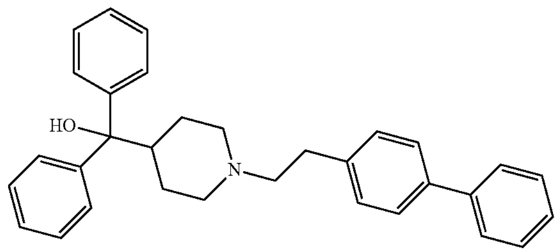 [SMILES: OC(c1ccccc1)(c1ccccc1)C1CCN(CCc2ccc(-c3ccccc3)cc2)CC1] | 8 | 80.00 | 133.33 |
| 33 | KSC-352-064 | 448.599 | 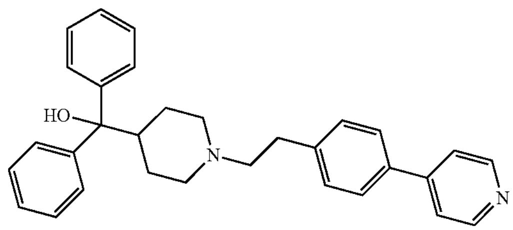 [SMILES: OC(c1ccccc1)(c1ccccc1)C1CCN(CCc2ccc(-c3ccncc3)cc2)CC1] | 32 | 93.33 | 226.67 |
| 34 | KSC-352-069 | 386.529 | 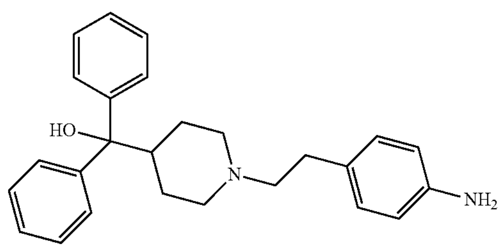 [SMILES: Nc1ccc(CCN2CCC(C(O)(c3ccccc3)c3ccccc3)CC2)cc1] | 256 | 93.33 | >333 |
| 35 | KSC-352-065 | 448.599 | 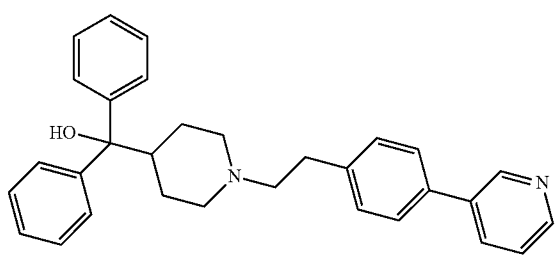 [SMILES: OC(c1ccccc1)(c1ccccc1)C1CCN(CCc2ccc(-c3cccnc3)cc2)CC1] | 32 | 250.00 | 280.00 |
| 36 | KSC-352-075 | 414.582 | 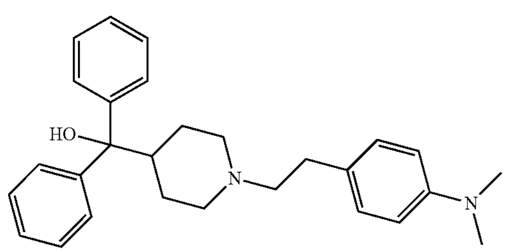 [SMILES: CN(C)c1ccc(CCN2CCC(C(O)(c3ccccc3)c3ccccc3)CC2)cc1] | 256 | >333 | >333 |
| 37 | KSC-352-082 | 439.513 | 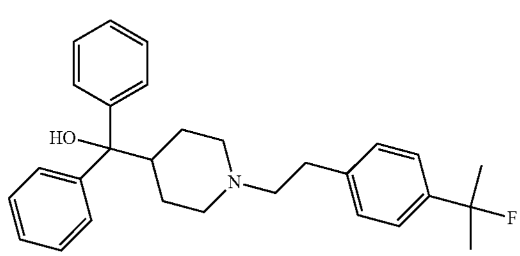 [SMILES: CC(C)(F)c1ccc(CCN2CCC(C(O)(c3ccccc3)c3ccccc3)CC2)cc1] | 16 | 16.67 | >333 |

TABLE 6-continued
| Compound # | KUC Registry Number | Molecular Weight (g/mol) | Structure | MIC (μg/mL) | Gyrase IC50 (μg/mL) | Topoisomerase iv IC50 (μg/mM) |
|---|---|---|---|---|---|---|
| 38 | KSC-352-088 | 389.505 | 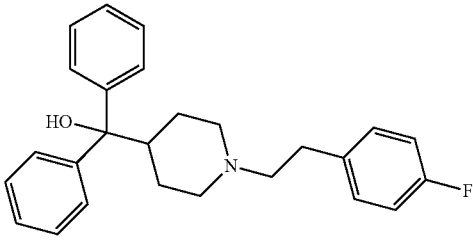 [SMILES: OC(c1ccccc1)(c1ccccc1)C1CCN(CCc2ccc(F)cc2)CC1] | 128 | >333 | >333 |
| 39 | KSC-352-097 | 427.621 | 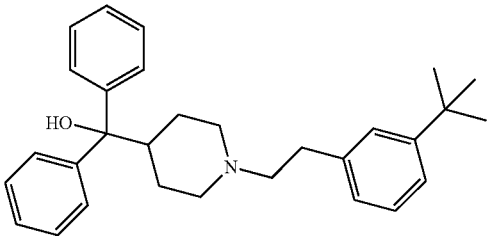 [SMILES: CC(C)(C)c1cccc(CCN2CCC(C(O)(c3ccccc3)c3ccccc3)CC2)c1] | 16 | 93.33 | >333 |
| 40 | KSC-367-039 | 379.578 | 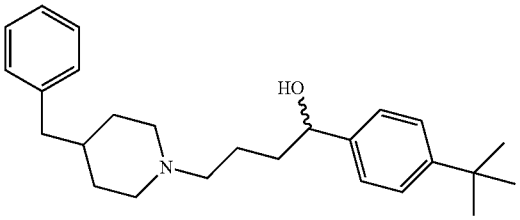 [SMILES: CC(C)(C)c1ccc(C(O)CCCN2CCC(Cc3ccccc3)CC2)cc1] | 64 | >333 | >333 |
| 41 | KSC-367-043 | 456.662 | 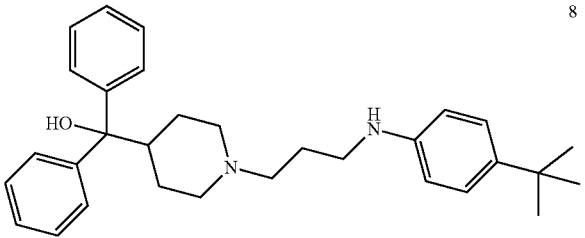 [SMILES: CC(C)(C)c1ccc(NCCCN2CCC(C(O)(c3ccccc3)c3ccccc3)CC2)cc1] | 8 | 193.33 | 250.00 |
| 42 | KSC-367-044 | 457.647 | 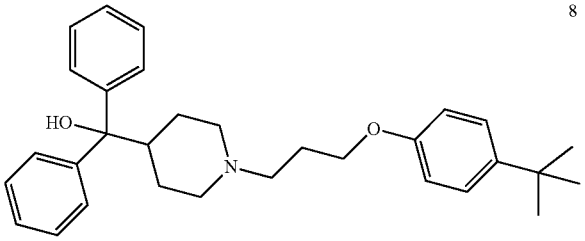 | 8 | 100.00 | >333 |
| 43 | KSC-367-052 | 428.609 | 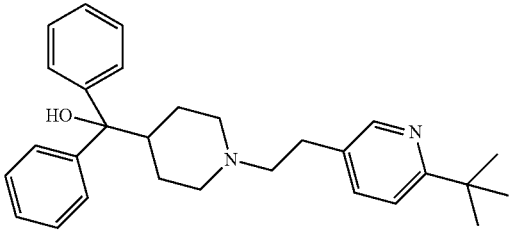 [SMILES: CC(C)(C)c1ccc(CCN2CCC(C(O)(c3ccccc3)c3ccccc3)CC2)cn1] | 64 | >333 | >333 |

TABLE 6-continued

| Compound # | KUC Registry Number | Molecular Weight (g/mol) | Structure | MIC (µg/mL) | Gyrase IC50 (µg/mL) | Topoisomerase iv IC50 (µg/mM) |
|---|---|---|---|---|---|---|
| 44 | KSC-367-055 | 405.96 | 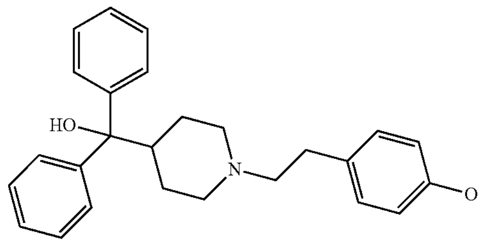 [SMILES: Oc1ccc(CCN2CCC(C(O)(c3ccccc3)c3ccccc3)CC2)cc1] | 32 | 260.00 | 266.67 |
| 45 | KSC-367-072 | 441.064 | 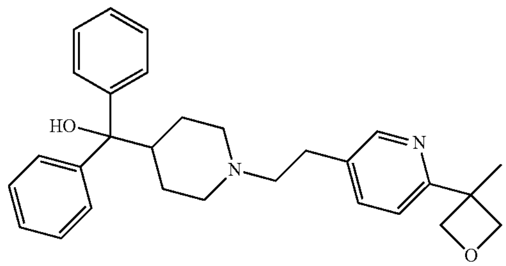 [SMILES: CC1(c2ccc(CCN3CCC(C(O)(c4ccccc4)c4ccccc4)CC3)cn2)COC1] | >256 | >333 | >333 |

What is claimed is:

1. A method of treating an enterococcal infection in a subject with an enterococcal infection, the method comprising administering to the subject an effective amount of a compound of Formula III

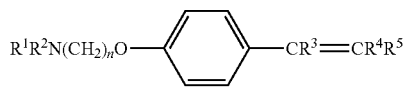

(III)

or a pharmaceutically acceptable salt thereof, wherein $R^1$ and $R^2$ are independently selected from ethyl or methyl, n is 1 or 2, $R^3$ and $R^4$ are both phenyl or substituted phenyl, wherein the substituent can be halo, hydroxyl, a lower alkyl or a substituted lower alkyl wherein the substituent can be halo, hydroxy, or lower alkoxy, and $R^5$ is hydrogen, a halogen, a lower alkyl from about 1 to 4 carbon atoms or a substituted alkyl wherein the substituent can be halo, hydroxy, or lower alkoxy.

2. The method of claim 1, wherein the enterococcal infection is a respiratory infection.

3. The method of claim 1, wherein the enterococcal infection is a gastrointestinal infection.

4. The method of claim 1, wherein the enterococcal infection is a skin infection.

5. The method of claim 1, wherein the enterococcal infection is an *Enterococcus faecium* infection.

6. The method of claim 1, wherein the enterococcal infection is a small colony variant bacterial infection.

7. The method of claim 1, wherein the compound is selected from the group consisting of clomiphene or a pharmaceutically acceptable salt thereof; tamoxifen or a pharmaceutically acceptable salt thereof; and 4-hydroxy tamoxifen or a pharmaceutically acceptable salt thereof.

* * * * *